United States Patent
Fowler et al.

(10) Patent No.: US 12,298,297 B2
(45) Date of Patent: May 13, 2025

(54) VISUAL CELL SORTING

(71) Applicant: University of Washington, Seattle, WA (US)

(72) Inventors: Douglas Fowler, Seattle, WA (US); Nicholas Hasle, Seattle, WA (US); Sriram Pendyala, Seattle, WA (US); Hyeon-Jin Kim, Seattle, WA (US)

(73) Assignee: University of Washington, Seattle, WA (US)

( * ) Notice: Subject to any disclaimer, the term of this patent is extended or adjusted under 35 U.S.C. 154(b) by 524 days.

(21) Appl. No.: 17/532,917

(22) Filed: Nov. 22, 2021

(65) Prior Publication Data

US 2022/0163513 A1     May 26, 2022

Related U.S. Application Data

(60) Provisional application No. 63/117,350, filed on Nov. 23, 2020.

(51) Int. Cl.
| | | |
|---|---|---|
| *G01N 33/50* | (2006.01) | |
| *G01N 15/10* | (2024.01) | |
| *G01N 33/58* | (2006.01) | |
| *G02B 21/26* | (2006.01) | |
| *G02B 21/36* | (2006.01) | |
| *G06T 7/00* | (2017.01) | |
| *G06T 7/70* | (2017.01) | |

(52) U.S. Cl.
CPC ..... *G01N 33/5026* (2013.01); *G01N 15/1023* (2024.01); *G01N 33/582* (2013.01); *G02B 21/26* (2013.01); *G02B 21/365* (2013.01); *G06T 7/0012* (2013.01); *G06T 7/70* (2017.01); *G01N 2015/1006* (2013.01); *G01N 2015/1028* (2024.01); *G06T 2207/10056* (2013.01); *G06T 2207/30024* (2013.01); *G06T 2207/30204* (2013.01)

(58) Field of Classification Search
None
See application file for complete search history.

(56) References Cited

U.S. PATENT DOCUMENTS

| | | |
|---|---|---|
| 9,291,628 B2 | 3/2016 | Leonard |
| 9,765,291 B2 | 9/2017 | Allbritton |
| 2019/0005304 A1 | 1/2019 | Adalsteinsson |

OTHER PUBLICATIONS

Lee J, Liu Z, Suzuki PH, Ahrens JF, Lai S, Lu X, Guan S, St-Pierre F. Versatile phenotype-activated cell sorting. Sci Adv. Oct. 23, 2020;6(43):eabb7438. doi: 10.1126/sciadv.abb7438. PMID: 33097540; PMCID: PMC7608836. (Year: 2020).*
Grimm JB, English BP, Choi H, Muthusamy AK, Mehl BP, Dong P, Brown TA, Lippincott-Schwartz J, Liu Z, Lionnet T, Lavis LD. Bright photoactivatable fluorophores for single-molecule imaging. Nat Methods. Dec. 2016;13(12):985-988. doi: 10.1038/nmeth.4034. Epub Oct. 24, 2016. PMID: 27776112. (Year: 2016).*
Katiyar A, Tocco VJ, Li Y, Aggarwal V, Tamashunas AC, Dickinson RB, Lele TP. Nuclear size changes caused by local motion of cell boundaries unfold the nuclear lamina and dilate chromatin and intranuclear bodies. Soft Matter. Dec. 7, 2019;15(45):9310-9317. (Year: 2019).*
Neely AE, Bao X. Nuclei Isolation Staining (NIS) Method for Imaging Chromatin-Associated Proteins in Difficult Cell Types. Curr Protoc Cell Biol. Sep. 2019;84(1):e94. doi: 10.1002/cpcb.94. PMID:31483111; PMCID: PMC6727977. (Year: 2019).*
Aldrich JL, Long DS. In situ fixation and subsequent collection of cultured endothelial cells in a shear flow. MethodsX. May 3, 2019;6:1164-1173. doi: 10.1016/j.mex.2019.05.001. PMID: 31193472; PMCID: PMC6531827. (Year: 2019).*
Alli, Elizabeth, et al. "Reversal of stathmin-mediated resistance to paclitaxel and vinblastine in human breast carcinoma cells." Molecular pharmacology 71.5 (2007): 1233-1240.
Binan, Loïc, et al. "Live single-cell laser tag." Nature communications 7.1 (2016): 1-8.
Binan, Loic, et al. "Opto-magnetic capture of individual cells based on visual phenotypes." elife 8 (2019): e45239.
Bloom, Jesse D. "An experimentally determined evolutionary model dramatically improves phylogenetic fit." Molecular Biology and Evolution 31.8 (2014): 1956-1978.
Boutros, Michael, Florian Heigwer, and Christina Laufer. "Microscopy-based high-content screening." Cell 163.6 (2015): 1314-1325.
Bray, Mark-Anthony, et al. "Cell Painting, a high-content image-based assay for morphological profiling using multiplexed fluorescent dyes." Nature protocols 11.9 (2016): 1757-1774.
Butler, Andrew, et al. "Integrating single-cell transcriptomic data across different conditions, technologies, and species." Nature biotechnology 36.5 (2018): 411-420.

(Continued)

*Primary Examiner* — Allison M Fox
*Assistant Examiner* — Qinhua Gu
(74) *Attorney, Agent, or Firm* — Christensen O'Connor Johnson Kindness PLLC

(57) ABSTRACT

The disclosure provides methods, systems and related software, for automated or semi-automated sorting and/or isolating cells with visually distinguishable phenotypes. In some embodiments, the methods comprise providing a plurality cells with a photo-activatable detectable marker in their respective nuclei. The plurality of cells are imaged and, based on the image, the status for one or more visually identifiable phenotypes are determined. Cells determined to have the desired phenotype status are specifically exposed to a light wavelength for a time sufficient to uniquely activate the photo-activatable detectable marker in the individual cells with the desired phenotype status. The cells are then sorted on the basis of the activated detectable marker. The disclosure also provides methods for preparation and isolation of nuclei from fixed, adherent cells for analysis.

14 Claims, 38 Drawing Sheets

Specification includes a Sequence Listing.

(56) References Cited

OTHER PUBLICATIONS

Cao, Junyue, et al. "Comprehensive single-cell transcriptional profiling of a multicellular organism." Science 357.6352 (2017): 661-667.
Chen, Kok Hao, et al. "Spatially resolved, highly multiplexed RNA profiling in single cells." Science 348.6233 (2015): aaa6090.
Chien, Miao-Ping, et al. "Photostick: a method for selective isolation of target cells from culture." Chemical science 6.3 (2015): 1701-1705.
Cho, J. H., et al. "Arginine methylation-dependent regulation of ASK1 signaling by PRMT1." Cell Death & Differentiation 19.5 (2012): 859-870.
Christiansen, Eric M., et al. "In silico labeling: predicting fluorescent labels in unlabeled images." Cell 173.3 (2018): 792-803.
Chudakov, Dmitriy M., Sergey Lukyanov, and Konstantin A. Lukyanov. "Tracking intracellular protein movements using photoswitchable fluorescent proteins PS-CFP2 and Dendra2." Nature protocols 2.8 (2007): 2024-2032.
Conacher, C. G., et al. "Real-time monitoring of population dynamics and physical interactions in a synthetic yeast ecosystem by use of multicolour flow cytometry." Applied Microbiology and Biotechnology 104.12 (2020): 5547-5562.
Dagkesamanskaya, Adilya, et al. "Use of photoswitchable fluorescent proteins for droplet-based microfluidic screening." Journal of microbiological methods 147 (2018): 59-65.
Medaglia, Chiara, et al. "Spatial reconstruction of immune niches by combining photoactivatable reporters and scRNA-seq." Science 358.6370 (2017): 1622-1626.
Di Michele, Michela, et al. "A proteomic approach to paclitaxel chemoresistance in ovarian cancer cell lines." Biochimica et Biophysica Acta (BBA)-Proteins and Proteomics 1794.2 (2009): 225-236.
Dorman, Stephanie N., et al. "Genomic signatures for paclitaxel and gemcitabine resistance in breast cancer derived by machine learning." Molecular oncology 10.1 (2016): 85-100.
Emanuel, George, Jeffrey R. Moffitt, and Xiaowei Zhuang. "High-throughput, image-based screening of pooled genetic-variant libraries." Nature methods 14.12 (2017): 1-18.
Eng, Chee-Huat Linus, et al. "Transcriptome-scale super-resolved imaging in tissues by RNA seqFish+." Nature 568.7751 (2019): 235-239.
Feldman, David, et al. "Optical pooled screens in human cells." Cell 179.3 (2019): 787-799.
Feldman, David, et al. "Pooled optical screens in human cells." Biorxiv (2018): 383943.
Gasic, Ivana, Sarah A. Boswell, and Timothy J. Mitchison. "Tubulin mRNA stability is sensitive to change in microtubule dynamics caused by multiple physiological and toxic cues." PLoS biology 17.4 (2019): e3000225.
Georges, Elias, Anne-Marie Bonneau, and Panagiotis Prinos. "RNAi-mediated knockdown of α-enolase increases the sensitivity of tumor cells to antitubulin chemotherapeutics." International Journal of Biochemistry and Molecular Biology 2.4 (2011): 303-308.
Gibson, Daniel G., et al. "Enzymatic assembly of DNA molecules up to several hundred kilobases." Nature methods 6.5 (2009): 343-345.
Taghverdi, Laleh, et al. "Batch effects in single-cell RNA-sequencing data are corrected by matching mutual nearest neighbors." Nature biotechnology 36.5 (2018): 421-427.
Isozaki, Akihiro, et al. "A practical guide to intelligent image-activated cell sorting." Nature protocols 14.8 (2019): 2370-2415.
Kalderon, Daniel, et al. "A short amino acid sequence able to specify nuclear location." Cell 39.3 (1984): 499-509.
Ke, Rongqin, et al. "In situ sequencing for RNA analysis in preserved tissue and cells." Nature methods 10.9 (2013): 857-860.
Kuo, Chun-Ting, et al. "Optical painting and fluorescence activated sorting of single adherent cells labelled with photoswitchable Pdots." Nature communications 7.1 (2016): 1-11.
Lee, Je Hyuk, et al. "Fluorescent in situ sequencing (FISSEQ) of RNA for gene expression profiling in intact cells and tissues." Nature protocols 10.3 (2015): 442-458.
Lee, Je Hyuk, et al. "Highly multiplexed subcellular RNA sequencing in situ." Science 343.6177 (2014): 1-12.
Li, Na, et al. "GRP78 regulates clusterin stability, retrotranslocation and mitochondrial localization under ER stress in prostate cancer." Oncogene 32.15 (2013): 1933-1942.
Liberzon, Arthur, et al. "The molecular signatures database hallmark gene set collection." Cell systems 1.6 (2015): 1-18.
Lin, Jhih-rong, and Jianjun Hu. "SeqNLS: nuclear localization signal prediction based on frequent pattern mining and linear motif scoring." PloS one 8.10 (2013): e76864.
Love, Michael I., Wolfgang Huber, and Simon Anders. "Moderated estimation of fold change and dispersion for RNA-seq data with DESeq2." Genome biology 15.550 (2014): 1-21.
Matreyek, Kenneth A., Jason J. Stephany, and Douglas M. Fowler. "A platform for functional assessment of large variant libraries in mammalian cells." Nucleic acids research 45.11 (2017): e102-e102.
Matreyek, Kenneth A., et al. "An improved platform for functional assessment of large protein libraries in mammalian cells." Nucleic acids research 48.1 (2020): e1-e1.
Matreyek, Kenneth A., et al. "Multiplex assessment of protein variant abundance by massively parallel sequencing." Nature genetics 50.6 (2018): 874-882.
McInnes, Leland, John Healy, and James Melville. "Umap: Uniform manifold approximation and projection for dimension reduction." arXiv:1802.03426v3 [stat.ML] Sep. 18, 2020.
Moffitt, Jeffrey R., et al. "High-throughput single-cell gene-expression profiling with multiplexed error-robust fluorescence in situ hybridization." Proceedings of the National Academy of Sciences 113.39 (2016): 11046-11051.
Nguyen Ba, Alex N., et al. "NLStradamus: a simple Hidden Markov Model for nuclear localization signal prediction." BMC bioinformatics 10.202 (2009): 1-11.
Ooe, Asako, Kikuya Kato, and Shinzaburo Noguchi. "Possible involvement of CCT5, RGS3, and YKT6 genes up-regulated in p53-mutated tumors in resistance to docetaxel in human breast cancers." Breast cancer research and treatment 101.3 (2007): 305-315.
Ounkomol, Chawin, et al. "Label-free prediction of three-dimensional fluorescence images from transmitted-light microscopy." (2018). Allen Institute for Cell Science, Seattle, WA.
Parasido, Erika, et al. "The sustained induction of c-MYC drives nab-paclitaxel resistance in primary pancreatic ductal carcinoma cells." Molecular Cancer Research 17.9 (2019): 1-26.
Qiu, Xiaojie, et al. "Single-cell mRNA quantification and differential analysis with Census." Nature methods 14.3 (2017): 309-315.
Rohban, Mohammad Hossein, et al. "Systematic morphological profiling of human gene and allele function via Cell Painting." Elife 6 (2017): e24060.
Rowinsky, Eric K., et al. "Taxol: the first of the taxanes, an important new class of antitumor agents." Seminars in oncology. vol. 19. No. 6. 1992.
Rubin, Alan F., et al. "A statistical framework for analyzing deep mutational scanning data." Genome biology 18.1 (2017): 1-15.
Shafer, Aaron, et al. "Rapamycin potentiates the effects of paclitaxel in endometrial cancer cells through inhibition of cell proliferation and induction of apoptosis." International journal of cancer 126.5 (2010): 1-22.
Shcherbakova, Daria M., et al. "Bright monomeric near-infrared fluorescent proteins as tags and biosensors for multiscale imaging." Nature communications 7.1 (2016): 1-12.
Su, Dan, et al. "Stathmin and tubulin expression and survival of ovarian cancer patients receiving platinum treatment with and without paclitaxel." Cancer 115.11 (2009): 2453-2463.
Subramanian, Aravind, et al. "Gene set enrichment analysis: a knowledge-based approach for interpreting genome-wide expression profiles." Proceedings of the National Academy of Sciences 102.43 (2005): 15545-15550.
Sugimura, Masaki, et al. "Mechanisms of paclitaxel-induced apoptosis in an ovarian cancer cell line and its paclitaxel-resistant clone." Oncology 66.1 (2004): 53-61.

(56) References Cited

OTHER PUBLICATIONS

Theodoropoulos, Panayiotis A., et al. "Taxol affects nuclear lamina and pore complex organization and inhibits import of karyophilic proteins into the cell nucleus." Cancer research 59.18 (1999): 4625-4633.

Thul, Peter J., et al. "A subcellular map of the human proteome." Science 356.6340 (2017): eaal3321.

Trapnell, Cole, et al. "The dynamics and regulators of cell fate decisions are revealed by pseudotemporal ordering of single cells." Nature biotechnology 32.4 (2014): 381-391.

Trielli, Marc O., et al. "Differential Taxol-dependent arrest of transformed and nontransformed cells in the G1 phase of the cell cycle, and specific-related mortality of transformed cells." The Journal of cell biology 135.3 (1996): 689-700.

Väremo, Leif, Jens Nielsen, and Intawat Nookaew. "Enriching the gene set analysis of genome-wide data by Incorporating directionality of gene expression and combining statistical hypotheses and methods." Nucleic acids research 41.8 (2013): 4378-4391.

Wang, Chong, et al. "Imaging-based pooled CRISPR screening reveals regulators of lncRNA localization." Proceedings of the National Academy of Sciences 116.22 (2019): 10842-10851.

Yang, Jie, et al. "mBeRFP, an improved large stokes shift red fluorescent protein." PLoS One 8.6 (2013): e64849.

Young, Matthew D., and Sam Behjati. "SoupX removes ambient RNA contamination from droplet-based single-cell RNA sequencing data." Gigascience (2020): 1-16.

Zhang, Jiajie, et al. "PEAR: a fast and accurate Illumina Paired-End reAd mergeR." Bioinformatics 30.5 (2014): 614-620.

Zhou, Ming, et al. "Warburg effect in chemosensitivity: targeting lactate dehydrogenase-A re-sensitizes taxol-resistant cancer cells to taxol." Molecular cancer 9.33 (2010): 1-12.

Zigon, Eric S., et al. "A rapid single cell sorting verification method using plate-based image cytometry." Cytometry Part A 93.10 (2018): 1060-1065.

\* cited by examiner

VISUAL CELL SORTING

CROSS-REFERENCE TO RELATED APPLICATION

This application claims the benefit of Provisional Application No. 63/117,350, filed Nov. 23, 2020, the disclosure of which is incorporated herein by reference in its entirety.

STATEMENT OF GOVERNMENT LICENSE RIGHTS

This invention was made with Government support under Grant Nos. F30 CA236335, R01 GM109110, and RM1 HG010461, awarded by the National Institutes of Health. The Government has certain rights in the invention.

STATEMENT REGARDING SEQUENCE LISTING

The sequence listing associated with this application is provided in text format in lieu of a paper copy and is hereby incorporated by reference into the specification. The name of the text file containing the sequence listing is 3915P1163USUW_Seq_List_20211116_ST25.txt. The text file is 100 KB; was created on Nov. 16, 2021; and is being submitted via EFS-Web with the filing of the specification.

BACKGROUND

High-content imaging, in situ sequencing methods, and other approaches have revolutionized the investigation of how genetic variants and gene expression programs dictate cellular morphology, organization and behavior. One important application of these methods is visual genetic screening, in which a library of genetic variants is introduced into cells and the effect of each variant on a visual phenotype is quantified. In a classical high content visual genetic screen, each genetic perturbation occupies a separate well. New in situ methods, which employ sequencing by repeated hybridization of fluorescent oligo probes or direct synthesis to visually read out nucleic acid barcodes, permit hundreds of perturbations to be assessed in a pooled format. For example, multiplexed fluorescent in-situ hybridization was used to assess the effect of 210 CRISPR sgRNAs on RNA localization in ~30,000 cultured human U-2 OS cells; and in situ sequencing was used to measure the effect of 963 gene knockouts on the localization of an NFkB reporter at a throughput of ~3 million cells. Visual phenotyping methods can also dissect non-genetic drivers of phenotypic heterogeneity. Here, characterization of cells with distinct visual phenotypes can reveal different cell states—such as signaling pathway activities and gene expression profiles—that are associated with different cellular morphologies. For example, the photoactivatable marker technology Single-Cell Magneto-Optical Capture has been used to isolate and sequence the transcriptomes of cells that successfully resolved ionizing radiation-induced DNA damage foci.

Despite their utility, current methods have limitations. Some, such as high-content imaging, require highly specialized or custom-built hardware. Others, like in situ sequencing, employ complex protocols, sophisticated computational pipelines, and expensive dye-based reagents. Methods that mark and sort for individual cells with a photoactivatable protein or compound are simpler and less expensive. However, these are either low-throughput (<1,000 cells per experiment) or lack single-cell specificity. Furthermore, they cannot investigate more than one or two phenotypes per experiment.

Despite the advances in the art, there remains a need for sensitive and facile technologies to assay and/or segregate cells based on observable phenotypes. The present disclosure addresses these and related needs.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In accordance with the foregoing, in one aspect the disclosure provides a method of high-throughput cell sorting. The method comprises: providing a plurality of cells with a photo-activatable detectable marker in their respective nuclei; imaging the plurality of cells; determining the phenotype status for one or more phenotypes of individual cells in the plurality of cells based on the imaging of the plurality of cells; exposing the individual cells exhibiting a desired phenotype status for the one or more phenotypes to a light wavelength for a time sufficient to uniquely activate the photo-activatable detectable marker in the individual cells with the desired phenotype status for the one or more phenotypes; and isolating individual cells or nuclei thereof with uniquely activated photo-activatable detectable marker.

In some embodiments, the photo-activatable detectable marker is a photo-activatable protein and the plurality of cells are engineered to express the photo-activatable protein. In some embodiments, the photo-activatable protein is Dendra2.

In some embodiments, the photo-activatable detectable marker is an affinity reagent conjugated to at least one dye and/or fluorophore, wherein the affinity reagent is optionally an antibody or antibody fragment or derivative. In some embodiments, the affinity reagent is conjugated to two dye(s) and/or fluorophore(s) that emit different light wavelengths upon exposure to the light wavelength in the exposing step. In some embodiments, the method further comprises contacting the plurality of cells with the affinity reagent.

In some embodiments, the plurality of cells are in culture. In one embodiment, the plurality of cells are fixed to a surface. In some embodiments, the method further comprises extracting intact nuclei from the fixed cells.

In some embodiments, the plurality of cells are primary cells obtained from a subject.

In some embodiments, the imaging, determining, and exposing steps are automated by a programmable microscope system containing instructions to discriminate phenotypic states for one or more phenotypes of interest. In some embodiments, the programmable microscope system is configured for z-stack imaging.

In some embodiments, the individual cells or nuclei thereof are isolated using fluorescence activated cell sorting (FACS). In some embodiments, the method comprises determining the phenotype status for a plurality of phenotypes. In some embodiments, the individual cells with each of the plurality of phenotypes has a uniquely activated photo-activatable detectable marker that emits a different detectable light wavelength.

In another aspect, the disclosure provides a system for high-throughput cell sorting. The system comprises:
a microscope device with at least one objective;
a light source; and
at least one computing device including a non-transitory computer-readable medium having instructions stored thereon, wherein the instructions are configured to cause the at least one computing device to provide:
an image processing engine configured to:
receive image signal from the microscope device representing one or more cells in a field of view and assess individual cell(s) in the field of view for a phenotype status for one or more phenotypes; and
assign a coordinate to each individual cell in the field of view determined to have the desired phenotype status; and
a cell tagging engine configured to provide the light source with instructions to apply a light wavelength to the coordinate assigned to each individual cell determined to have the desired phenotype status.

In some embodiments, the microscope device comprises a XY motorized stage coupled to a stage controller, wherein the instructions of at least one computing device are configured to provide a stage control engine configured to provide the stage controller instructions to move the XY motorized stage in X and Y directions. In some embodiments, the microscope device comprises a Z drive device, wherein the instructions of at least one computing device are configured to provide a Z drive control engine configured to provide the Z drive device instructions to move the at least one objective in a Z axis to allow capture of images of different planes in the field of view. In some embodiments, the non-transitory computer-readable medium further comprises instructions stored thereon configured to synchronize the microscope device and light source to control for latency.

In another aspect, the disclosure provides a non-transitory computer-readable medium having computer-executable instructions stored thereon. The instructions are configured, in response to one or more processors of at least one computing device, to cause the at least one computing device to perform actions for capturing and assessing microscopic images of cells, and exposing cells observed to have a phenotype status for one more phenotypes. The actions comprise:
receiving, by the computing device, image signal from the microscope device representing one or more cells in a field of view and assess individual cell(s) in the field of view for a phenotype status for one or more phenotypes;
assigning, by the computing device, a coordinate to each individual cell in the field of view determined to have the desired phenotype status; and
providing, by the computing device, instructions to a light source to apply a light wavelength to the coordinate assigned to each individual cell determined to have the desired phenotype status.

In another aspect, the disclosure provides a method of isolating nuclei from fixed adherent cells. The method comprises exposing fixed adherent cells to trypsin for a time that avoids nuclear lysis; applying sufficient force to dislodge the fixed adherent cells but that avoids nuclear lysis; and isolating the nuclei.

In some embodiments, the nuclei, or a portion thereof, are specifically tagged with a detectable marker. In some embodiments, the method further comprises tagging the nuclei of the fixed, adherent cells with a detectable marker. In some embodiments, the detectable marker is or comprises a photoactivated protein, a small molecule dye, a fluorescent label, and the like. In some embodiments, the dye or label is conjugated to an affinity reagent. In some embodiments, the affinity reagent is an antibody or antibody fragment or derivative thereof. In some embodiments, the photoactivated protein is Dendra2, or wherein the small molecule dye is PA-JF549. In some embodiments, the method comprises isolating the nuclei based on the presence of a detectable marker. In some embodiments, the nuclei are isolated using fluorescence activated cell sorting (FACS). In some embodiments, the method further comprises sequencing at least a portion of the DNA or RNA extracted from one or more isolated nuclei. In some embodiments, the trypsin is trypLE Express. In some embodiments, the fixed adherent cells are exposed to trypsin for less than 5 minutes. In some embodiments, the force is applied at least in part by scraping. In some embodiments, the force is applied at least in part by pipetting.

DESCRIPTION OF THE DRAWINGS

The foregoing aspects and many of the attendant advantages of this disclosure will become more readily appreciated as the same become better understood by reference to the following detailed description, when taken in conjunction with the accompanying drawings, wherein.

FIGS. 3A-3D. Visual Cell Sorting-derived variant scores accurately predict NLS function. (3A) Nine NLS variants were individually expressed in the CMPK-miRFP reporter in U-2 OS H3-Dendra2 cells. The median nucleus to cytoplasm (N:C) ratio of cells expressing each variant was measured by microscope and compared to its localization score derived by Visual Cell Sorting. n≥141 cells per variant per replicate. Bars, mean across at least three separate replicates. (3B) SV40 NLS variants that appeared to enhance nuclear localization were individually tested both alone and in combination. NLS variants with up to three amino acid changes were expressed in U-2 OS H3-Dendra2 cells and imaged; the median N:C ratio was quantified across cells in the same well. n≥527 cells per variant per replicate. (3C) Representative images from cells expressing the wild-type SV40 NLS or the optimized superNLS fused to the miRFP reporter. Scale bars=20 μm; highlighted letters, amino acid differences from wild-type. (3D) Nuclear localization scores derived from Visual Cell Sorting were used to generate a predictive model that was trained on UniProt NLS annotations. Precision/recall curves for the model and two other linear motif scoring models, NLStradamus (Nguyen Ba A N, et al. (2009) NLStradamus: A simple Hidden Markov Model for nuclear localization signal prediction. BMC Bioinformatics 10: 1-11) and SeqNLS (Lin J rong & Hu J (2013) SeqNLS: nuclear localization signal prediction based on frequent pattern mining and linear motif scoring. PLoS One 8.10:e76864), on a test dataset (n=30 NLSs) are shown.

Figure 11A:
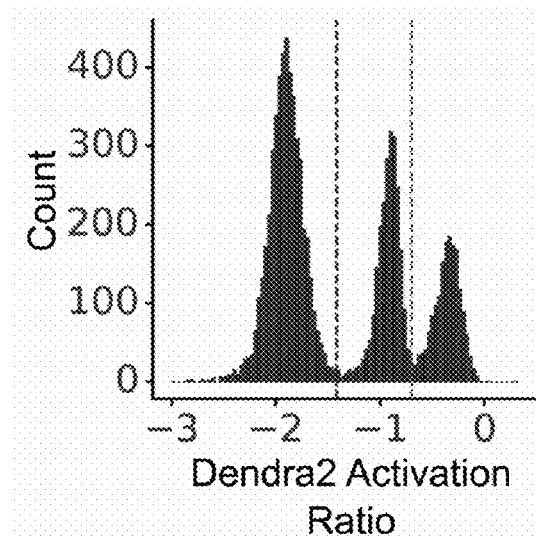
Figure 11B:
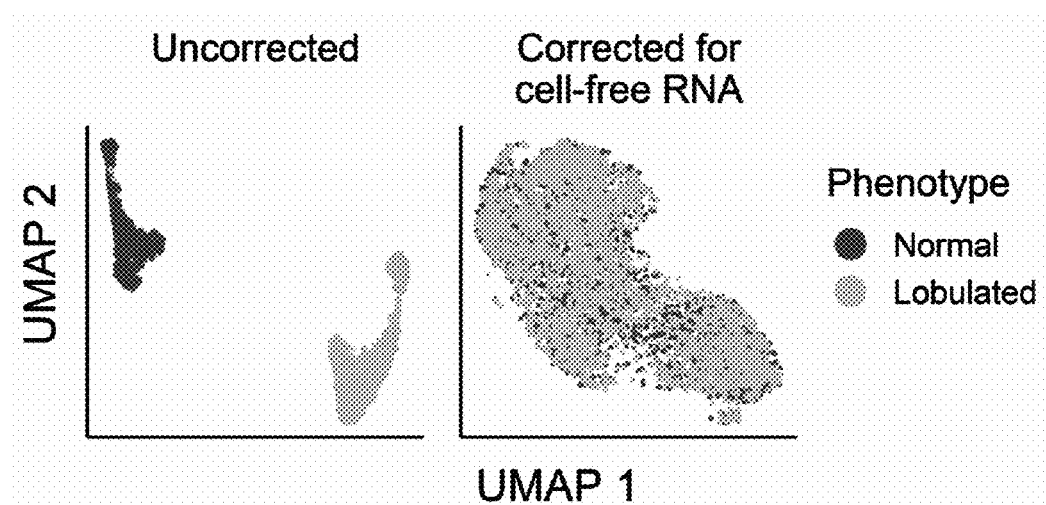
Figure 11C:
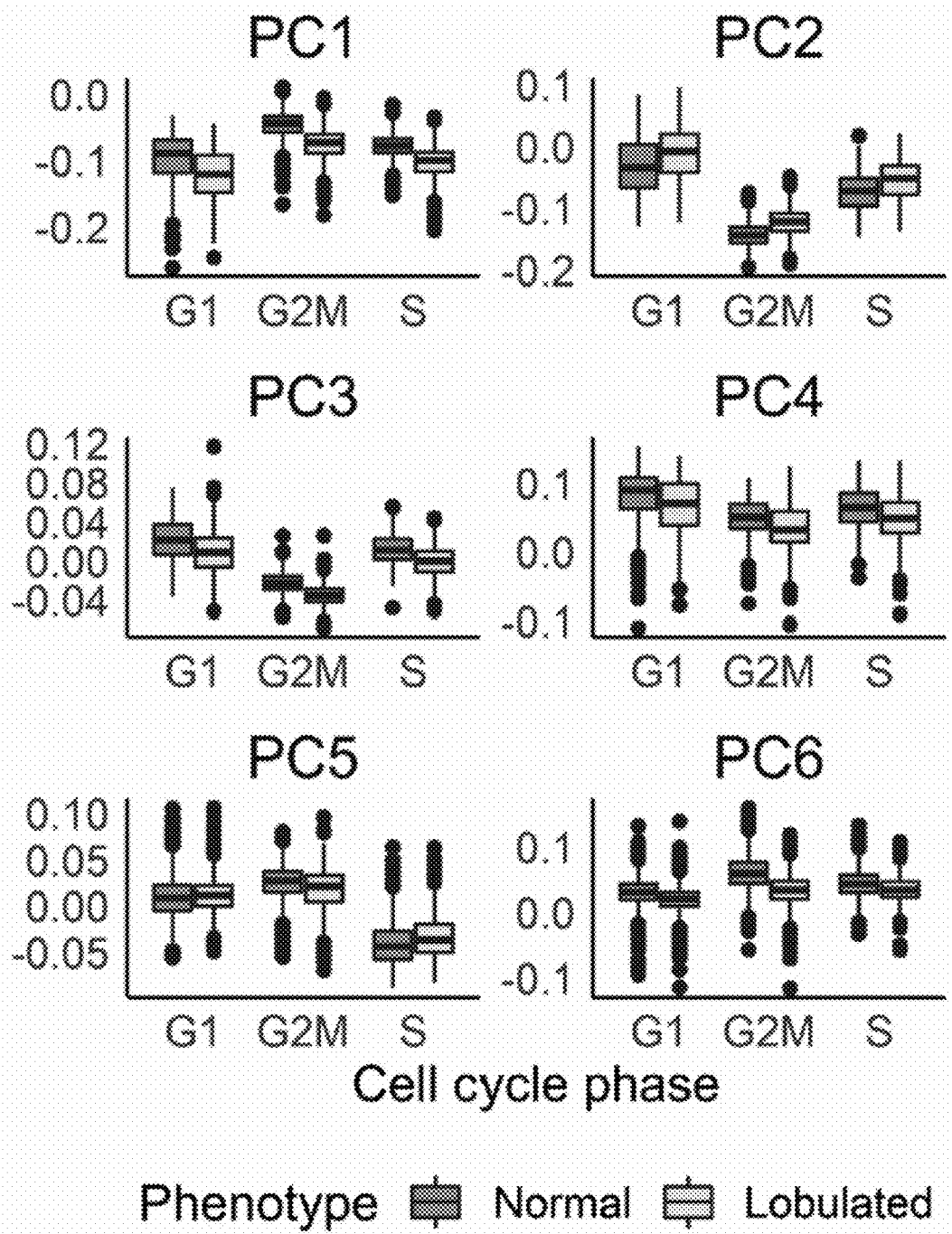
Figure 11D:
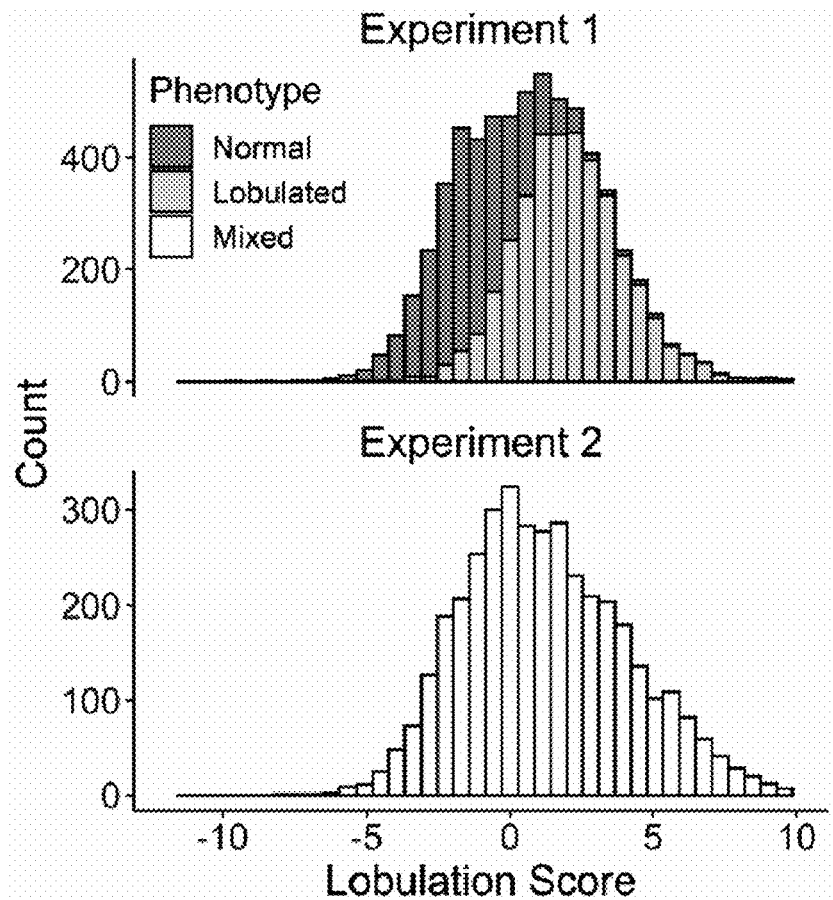

FIGS. 4A-4F. Visual Cell Sorting to dissect heterogeneous nuclear morphology following paclitaxel treatment. (4A) RPE-1 NLS-Dendra2×3 cells were treated for 24 hours with 0.25 nM paclitaxel or DMSO and imaged. The shape factor, which measures the degree of an object's circularity, was computed for each nucleus. One normal nucleus with a shape factor near one and one lobulated nucleus with a low shape factor are shown. The computationally determined boundaries of each nucleus are shown in blue; scale bar=10 (4B) Shape factor density plots for vehicle (DMSO) and 0.25 nM paclitaxel-treated RPE-1 cells (n≥3,914 cells per treatment). Dashed line, cutoff for lobulated nuclei (shape factor <0.65). (4C) RPE-1 cells were treated with 0.25 nM paclitaxel, then subjected to Visual Cell Sorting according to nuclear shape factor. Populations of cells with normal or lobulated nuclei were subjected separately to single cell RNA sequencing. (4D) UMAP analysis of single cell RNA sequencing results of paclitaxel-treated cells. Expression of cell-cycle related genes were used to annotate each cell as being in G1, S, or G2/M. (4E) A differential gene test was performed using as covariates cell cycle scores and a lobulation score, which is higher in lobulated cells compared to morphologically normal cells (FIG. 11D). Genes related to microtubule structure or various chaperone complexes are colored according to the expected $\log_2$ fold-change per unit increase in lobulation score (effect size); asterisks, genes associated with paclitaxel resistance. (4F) Expression counts for genes associated with c-Myc and mTORC1 signaling were aggregated across cells binned according to their lobulation score, then log-normalized and rescaled. Higher lobulation scores correspond to a higher likelihood of nuclear lobulation.

Figure 5A:
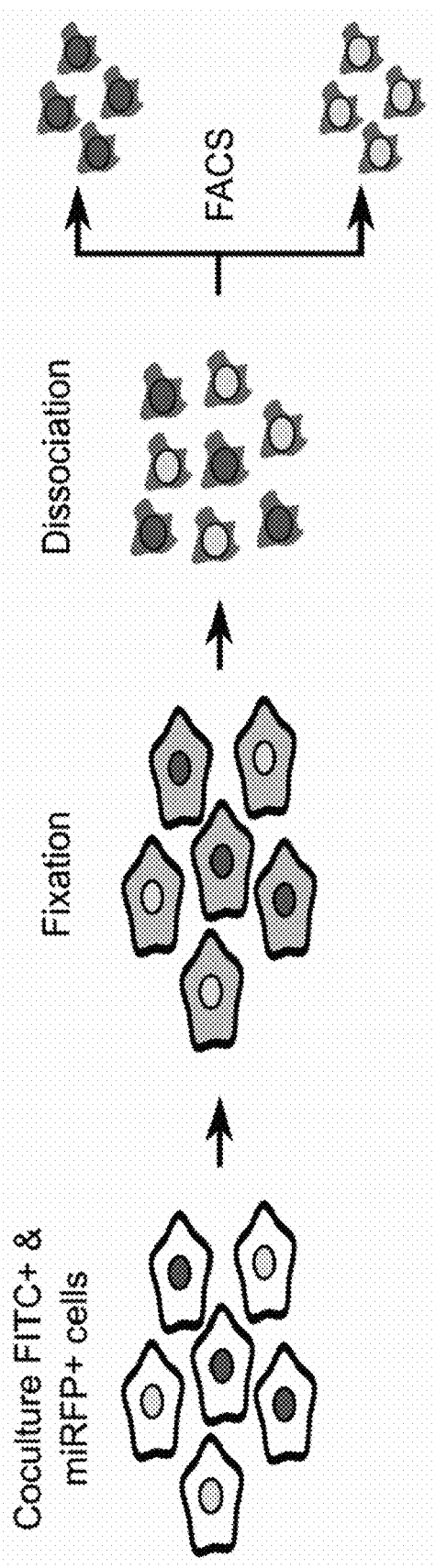
Figure 5B:
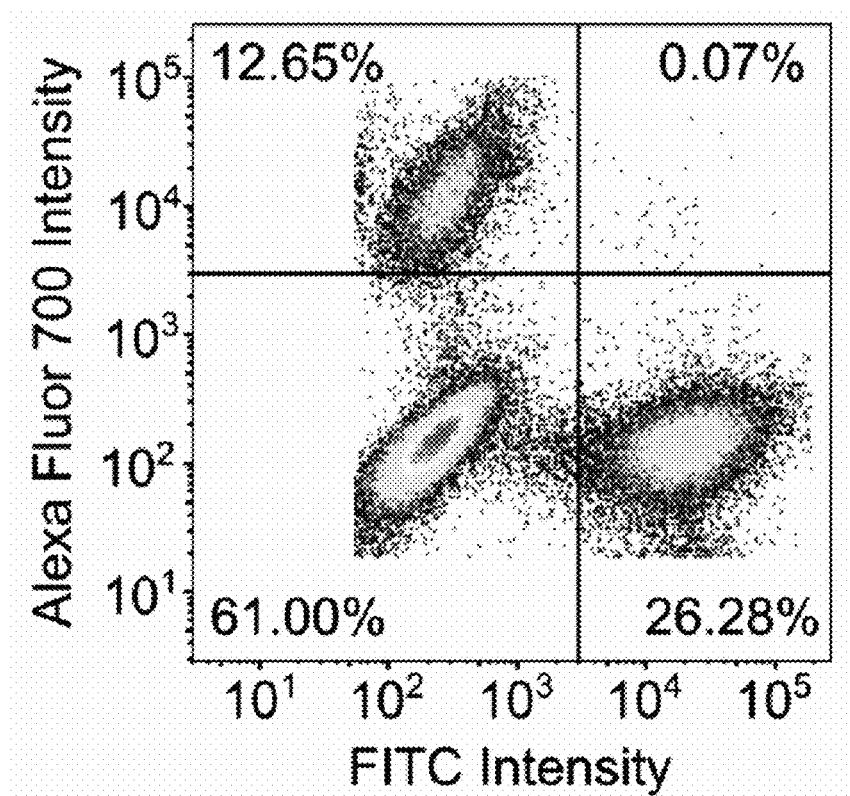
Figure 5C:
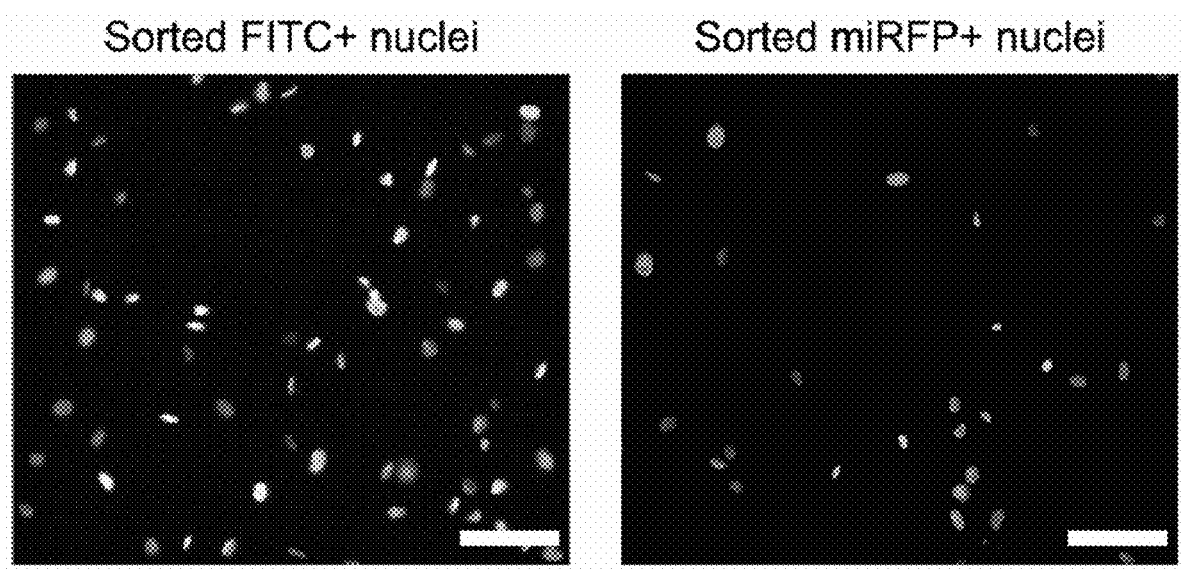

FIGS. 5A-5C. Validation of single nuclear suspensions obtained from fixed adherent cells. (5A) FITC+ and miRFP+ U-2 OS cells were co-cultured onto a 6-well plate, fixed with paraformaldehyde and dissociated with trypLE. The resulting single nuclear suspensions were validated via FACS. (5B) Of the single nuclear suspensions, 61% of cells had no marker expression (bottom left), 26% expressed the green marker (bottom right), 13% expressed the red marker (top left), and 0.07% were putative doublets (top right). (5C) Sorted FITC+(bottom right from FIG. 1C) and miRFP+ U-2 OS nuclei (top left from FIG. 1C) were visualized. Scale bar=100 um.

Figure 6A:
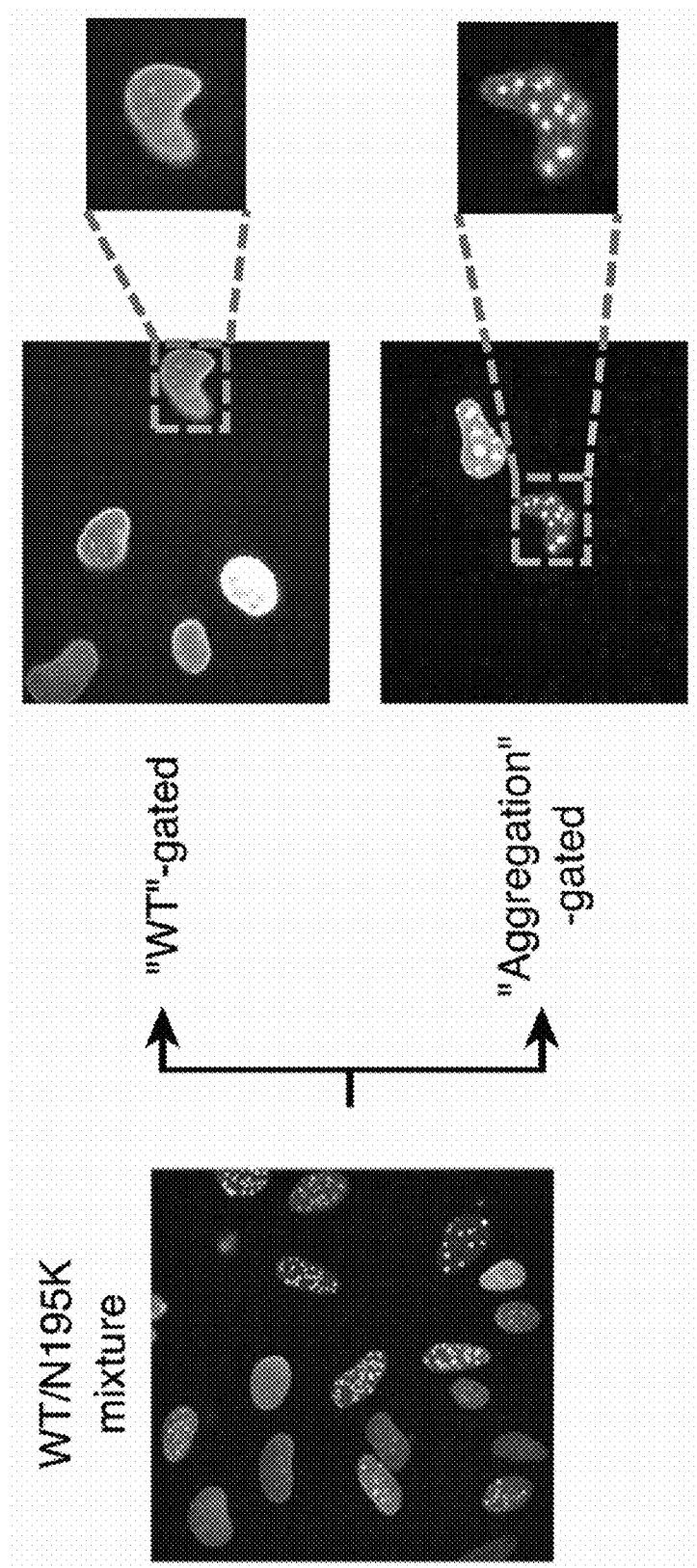
Figure 6B:
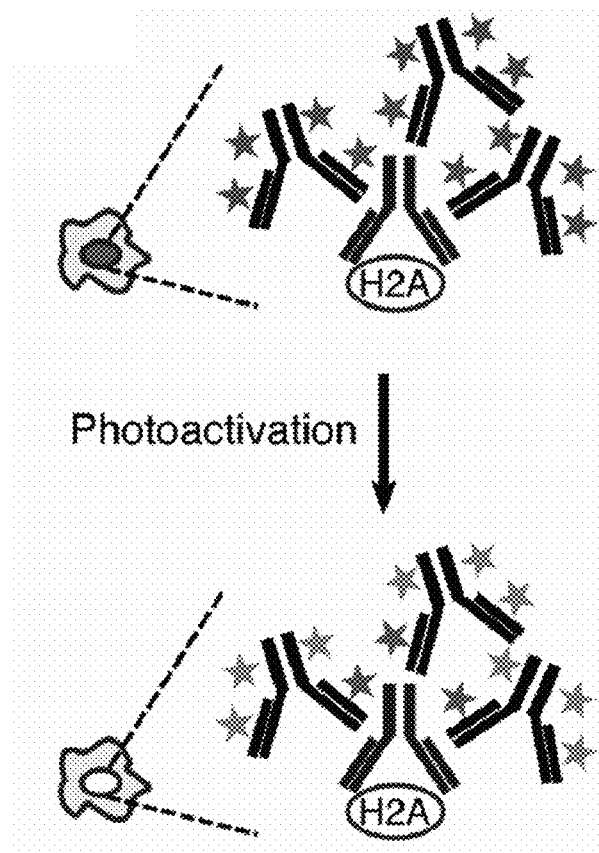
Figure 6C:
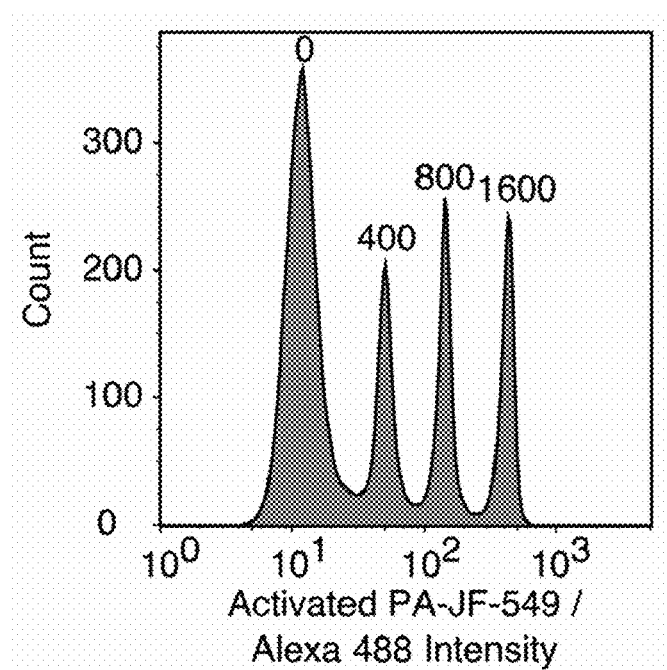

FIGS. 6A-6C. Visual Cell Sorting of fixed cells. (6A) VCS demixes nuclei of fixed U-2 OS cells expressing either WT LMNA (uniform) or N195K (punctate). (6B) Antibody co-conjugated with the photoactivatable PA-JF-549 (grey and red) and Alexa 488 (green) dyes enables VCS without transgenic Dendra2 expression. (6C) U-2 OS cells with no Dendra2 expression were separated into 4 distinct populations by VCS using an antibody tagged with PA-JF-549/Alexa 488. The numbers on the plot represent the duration of photoactivation.

Figure 7:
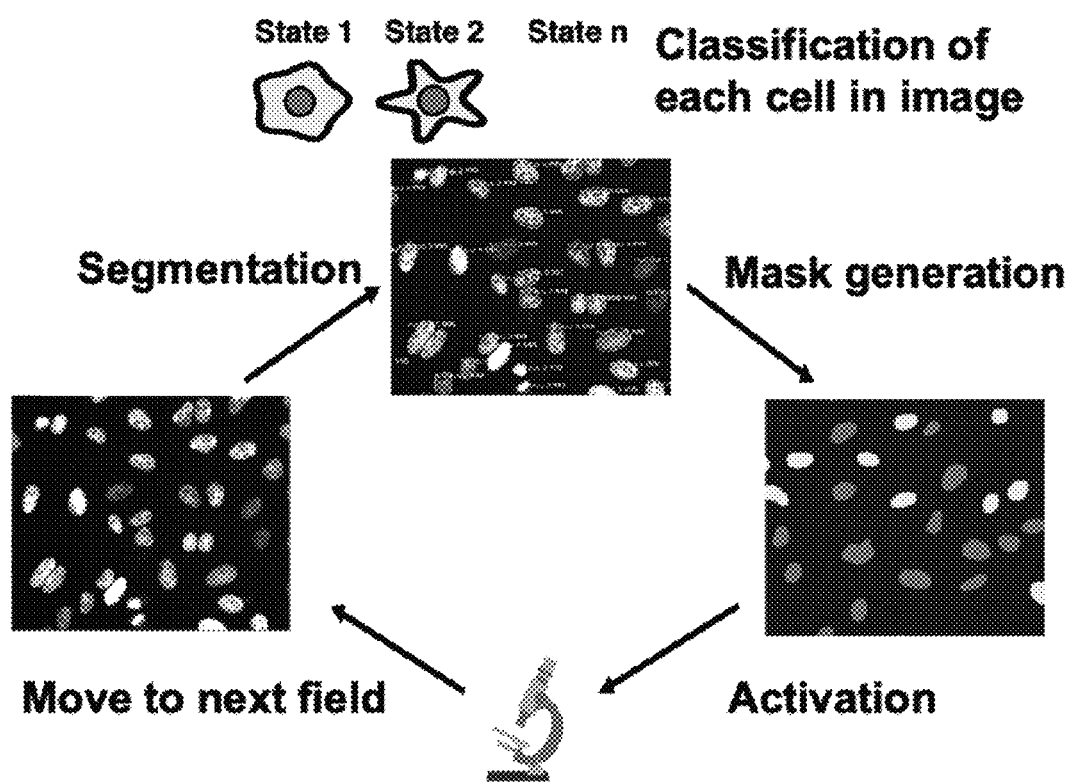

FIG. 7. Schematic diagram of an embodiment of the automated microscopy-based analysis, classification, and tagging of cells with visual phenotypes. Computational improvements were made to VCS that permit a broad range of cell phenotypes to be separated at a hundred-fold increased throughput than previously demonstrated. A pipeline was developed where microscope images are rapidly moved to a deep-learning environment where segmentation and phenotype classification for every cell in the image are carried out. Subsequently, activation decisions are relayed back to the microscope and targeted cells are photoactivated (see FIGS. 1A-1D). This pipeline is iterated through every field of view in the image. For segmentation of nuclei, recently published state-of-the-art deep-learning-based models were used (J. C. Caicedo et al. *Nat. Methods* 2019). For cell classification into activated and un-activated populations, off-the-shelf deep-learning-based classifiers were train on human annotation sets that can be cheaply and quickly produced. This new pipeline generalizes to any visual cell phenotype and can process hundreds of cells per second. When combined with cell fixation and fixed nuclei recovery up to millions of cells can be separated in a single experiment, enabling pooled reverse genetics experiments with large protein libraries or genome-scale CRISPR screens.

FIGS. 8A-8D. Visual Cell Sorting. (8A) RPE-I cells expressing NLS-Dendra2×3 were imaged in the unactivated and activated Dendra2 channels; then left unactivated or activated for 50, 200, or 800 ms; and re-imaged. Scale bar=100 μm. (8B) U-2 OS cells expressing H3-Dendra2 under the control of a doxycycline inducible promoter were activated with 405 nm light for 50, 200, or 800 ms; incubated for various lengths of time; and then subject to flow cytometry to determine the degree of activated Dendra2 (left panel). To examine whether shutting off Dendra2 expression before the experiment increases photoactivation ratio stability, the experiment was repeated, but doxycycline was removed from the media before cells were placed under the microscope (right panel). (8C) To examine the effect of Dendra2 photoactivation on cell viability, cells were activated for 800 ms and then apoptosis, necrosis, and death were assessed by flow cytometry using DAPI and Annexin-V (n=10,000 cells). Negative C, no photoactivation. Positive C, incubation of cells at 50 C for 10 min. The results of three independent replicates are shown. (8D) To test whether Dendra2 photoactivation affects gene expression, cells were activated for 800 ms, incubated for 0.5, 1.5, 2.5, 3.5, 4.5, or 6 hours and subsequently subject to bulk RNA seq. Samples were compared to two separate replicates of unactivated cells. Volcano plot of differentially expressed genes shown. Dotted line, adjusted p-value of 0.01.

FIGS. 9A-9D. Visual Cell Sorting for pooled, image-based genetic screening. (9A) Image analysis pipeline to calculate nucleus to cytoplasm (NC) ratio. Nuclei were segmented using the H3-Dendra2 signal. Cytoplasmic masks were created by dilating and then removing the nuclear mask. Mean miRFP intensity was measured within each mask and the nucleus to cytoplasm (N:C) ratio calculated. (9B) After selective photoactivation on the microscope based on N:C ratio, cells were subject to fluorescence-activated cell sorting and sorted according to their nuclear localization phenotype. Two days after sorting, cells from each sort bin were re-imaged in the miRFP channel and the nucleus to cytoplasm ratio reassessed (n=~1,500 per photoactivation bin). Center line, median; box limits, upper and lower quartiles; whiskers, 1.5× interquartile range; points, outliers. R1T2, recombination replicate 1, Visual Cell Sorting technical replicate 2. (9C) Representative images of sorted cells. (9D) Correlation plots of normalized scores calculated for each replicate. r^2, square of Pearson's correlation coefficient.

Figure 10A:
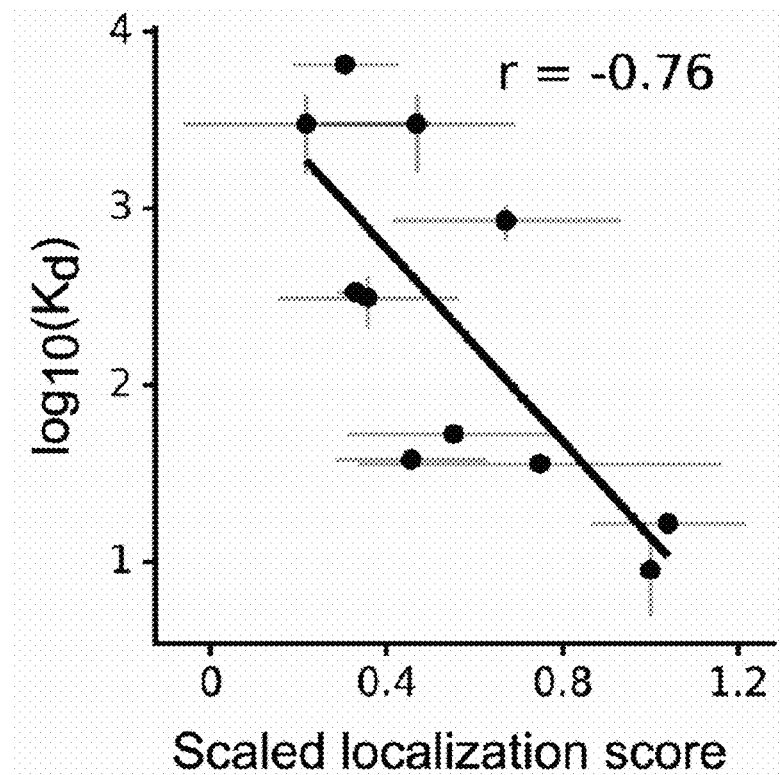
Figure 10B:
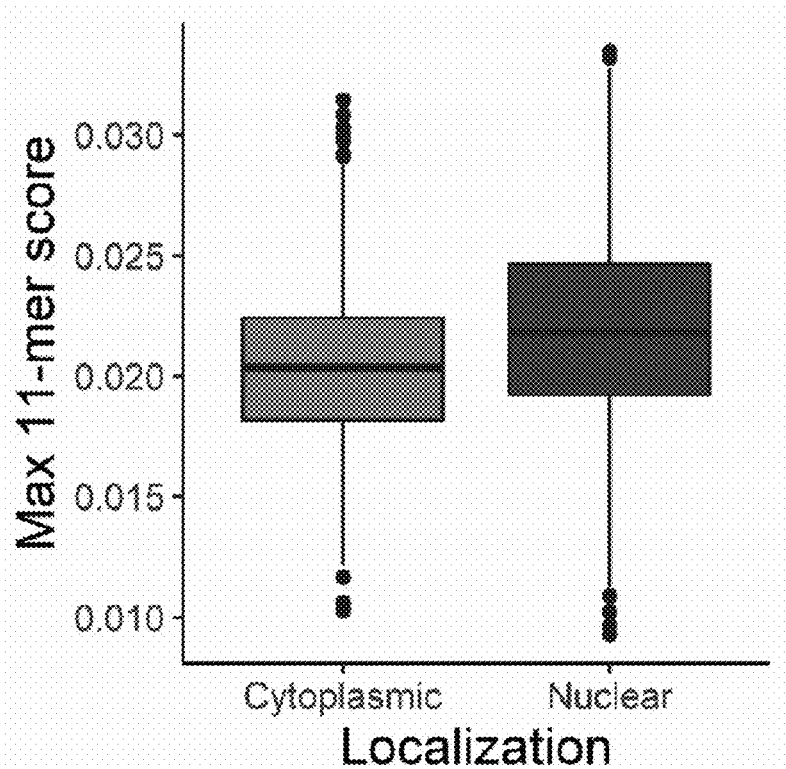
Figure 10C:
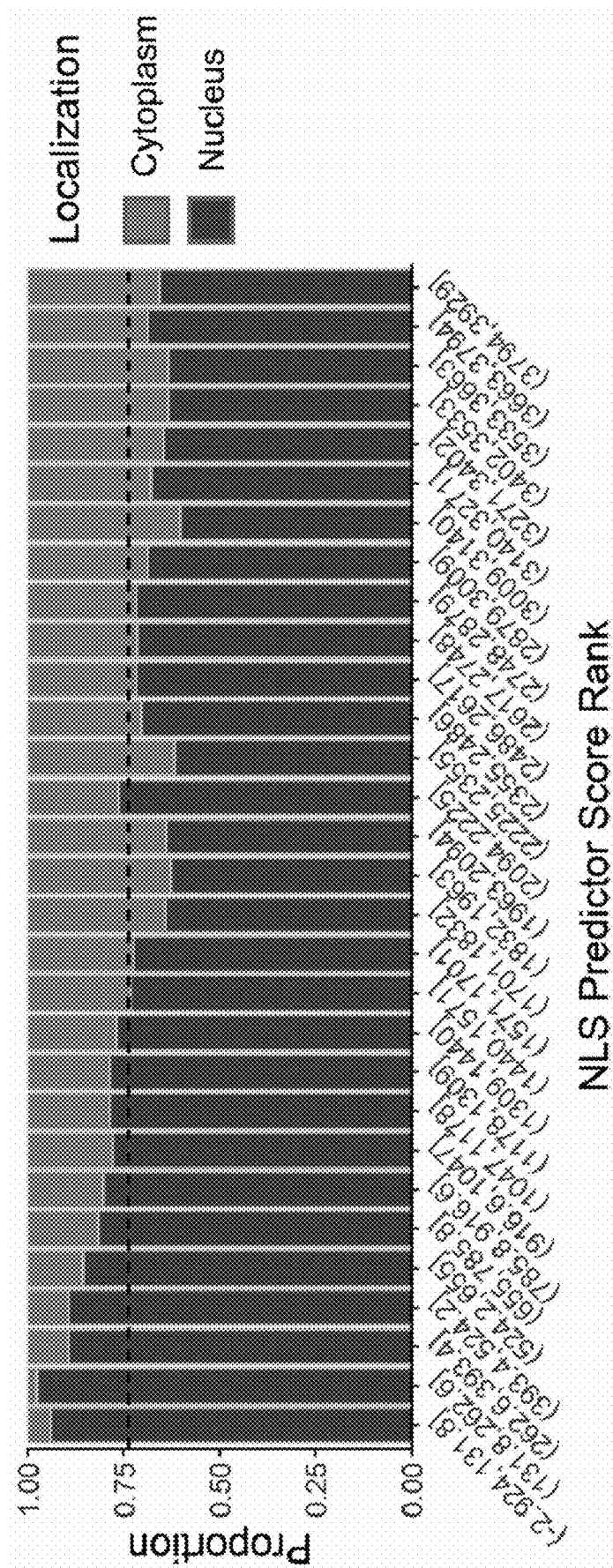

FIGS. 10A-10C. Visual Cell Sorting-derived variant scores accurately predict NLS function. (10A) Dissociation constants measuring binding between SV40 NLS variants and importin alpha, as reported by Hodel and colleagues (2001) were plotted against the variants' mean normalized scores. Grey bars, standard error from the mean. r, Pearson's correlation coefficient. (10B) All 11-mers in proteins annotated as exclusively cytoplasmic or exclusively nuclear by the Human Protein Atlas were subject to our NLS prediction model; the top-scoring 11-mer within each protein was extracted for each group (N=3,925 11-mers; Wilcoxon rank sum p value <$10^{-16}$). (10C) Each protein's top-scoring 11-mer was ranked and binned according to its score (n=131 proteins per bin). Dotted line, expected proportion of nuclear proteins per bin if the model has no predictive power.

FIGS. 11A-11F. (11A) Photoactivation gates for Visual Cell Sorting. Cells between the blue and red dotted lines represent putative normal nuclear shape factor cells activated with 405 nm light for 200 ms; and cells above the red dotted line represent putative low nuclear shape factor (lobulated) cells activated for 800 ms. Cells below the blue dotted line were not imaged or not activated. (11B) UMAP projection of the single cell transcriptomes derived from Visual Cell Sorting-separated lobulated and normal cells before and cell-free RNA correction with the algorithm used by SoupX (11C) Visual Cell Sorting-separated cells were aligned to an unseparated, paclitaxel-treated population with the mutual nearest neighbors algorithm. The first six principal components of the separated cells, subset by nuclear phenotype and cell cycle stage, are shown. (11D) Lobulation scores were generated using linear combinations of principal components 1-4. Top, Visual Cell Sorting experiment (N=6, 277 cells); bottom, unseparated cell population (N=3,859 cells. (11E) Volcano plot showing DEGs significantly correlated with the lobulation score in the unseparated, paclitaxel-treated population. Red points, significant DEGs with a $\log_2$ (Effect Size), which estimates the expected log 2 fold-change per unit increase in lobulation score, greater than 0.1 and a q-value less than 0.01. (11F) Raw gene counts of selected significant DEGs of cells in the unseparated, paclitaxel-treated population versus the cells' lobulation scores. Colored lines, negative binomial regression model stratified by cell cycle stage; ES, effect size, the expected fold change in gene expression per unit increase in lobulation score.

FIGS. 12A-12F. The gating scheme for selective photoactivation of cells expressing miRFP. Custom code using flowCore (v1.11.20) in R (v3.6.0) was used to gate the cells as follows. (12A) Debris was removed using a SSC.A vs FSC.A plot. (12B) and (12C) A Mahalanobis distance filter was used to identify live cells on a SSC.A vs FSC.A plot. (12D) and (12E) A Mahalanobis distance filter was used to identify single cells on a FSC.W vs FSC.A plot. (12F) Dendra2-positive cells were identified using a FITC plot.

FIGS. 13A-13E. The gating scheme for Visual Cell Sorting of cells expressing the SV40 NLS library. Using the BD FACSDiva software, cells were gated as follows. (13A) Live cells were identified using a SSC-A vs FSC-A plot. (13B) Single cells were gated using a FSC-W vs FSC-A plot. (13C) Cells expressing Dendra2 were gated using a FITC-A plot. (13D) Cells expressing miRFP were gated using an AlexaFluor 700-A plot. (13E) Cells were divided into four bins according to the ratio of activated/unactivated Dendra2.

FIGS. 14A-14D. The gating scheme for Visual Cell Sorting on cells treated with paclitaxel. Using the BD FACSDiva software, cells were gated as follows. (14A) Live cells were identified using a SSC-A vs FSC-A plot (14B) Single cells were gated using a FSC-W vs FSC-A plot. (14C) Cells expressing Dendra2 were gated using a FITC-A plot. (14D) Cells were divided into three bins (0 ms, 200 ms, and 800 ms) according to the ratio of activated/unactivated Dendra2. Cells in the 200 ms and 800 ms bins were sorted.

Figure 15B:
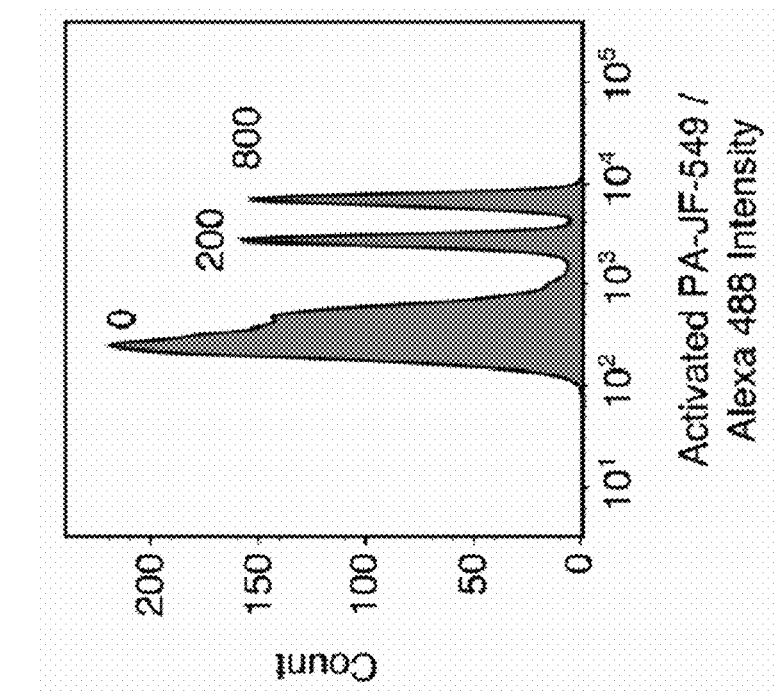
Figure 15A:
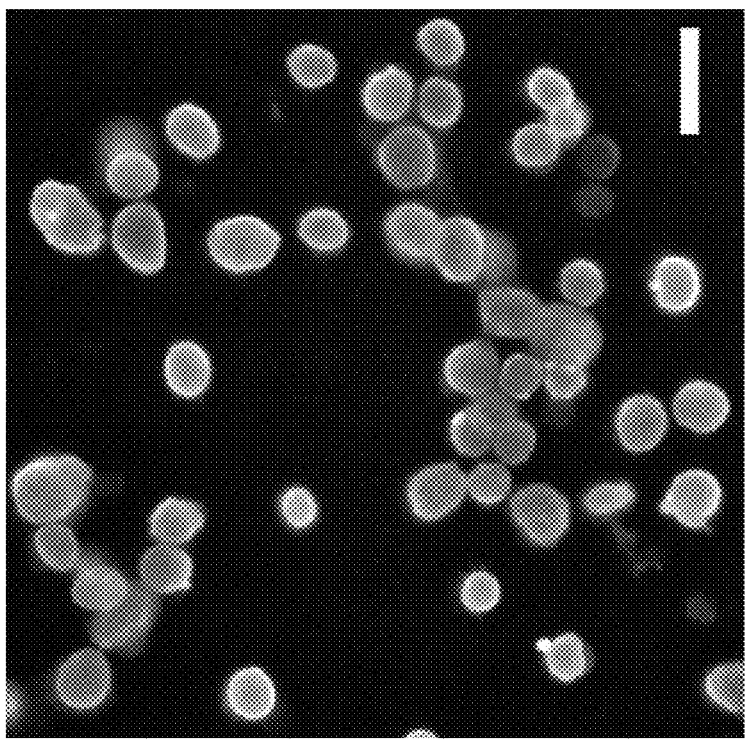

FIGS. 15A and 15B. Visual Cell Sorting on mouse embryonic stem cells. (15A) Mouse embryonic stem cells were stained for Histone 2B with a combination of primary anti-H2B antibody and secondary antibody labeled with photoactivatable PA-JF-549 and Alexa 488. Scale bar=20 um. The stained cells were mixed and imaged. (15B) Mouse embryonic stem cells from (15A) are separated via Visual Cell Sorting using the ratio of PA-JF-549 to Alexa 488 signal intensities. The numbers on the plot represent the duration in milliseconds of PA-JF-549 photoactivation used to produce each population.

DETAILED DESCRIPTION

Microscopy is a powerful tool for characterizing complex cellular phenotypes, but linking these phenotypes to genotype or RNA expression at scale remains challenging. This disclosure is based on the development of Visual Cell Sorting, a method that physically separates hundreds of thousands of live cells based on their visual phenotype. As described in more detail below, the inventors demonstrated automated imaging and phenotypic analysis directed selective illumination of a photoconvertible fluorescent protein (e.g., Dendra2) expressed in live cells. These photoactivated cells were then isolated using fluorescence-activated cell sorting (FACS). To extend the proof of concept, Visual Cell Sorting was used to assess hundreds of nuclear localization sequence variants in a pooled format, identifying variants that improve nuclear localization and enabling annotation of nuclear localization sequences in thousands of human proteins. In another assay, cells that retained normal nuclear morphologies after paclitaxel treatment were recovered, and their single cell transcriptomes were then derived to identify pathways associated with paclitaxel resistance in cancers. The methods have also been successfully applied to primary murine cells and not simply cultured cell lines, demonstrating the robustness of the technique. Unlike alternative methods, Visual Cell Sorting depends on inexpensive reagents and commercially available hardware. As such, it can be readily deployed to uncover the relationships between visual cellular phenotypes and internal states, including genotypes and gene expression programs. Additionally, the inventors developed a facile method to recover tagged nuclei from fixed, adherent cells, which can be later sorted and assayed.

In accordance with the foregoing, in one aspect, the disclosure provides a method of high-throughput cell sorting. The method comprises providing a plurality of cells with a photo-activatable detectable marker in their respective nuclei and imaging the plurality of cells. The phenotype status of the cells for one or more phenotypes is/are determined for the plurality of cells based on the images obtained of the cells. Cells that are determined to have a desired phenotype status for the one or more phenotypes are selectively exposed to a light wavelength for a time sufficient to uniquely activate the photo-activatable detectable marker in the individual cells with the desired phenotype status for the one or more phenotypes. In this regard, the term "selectively exposed" refers to the relevant exposure of light at a determined wavelength is exposed only to (or substantially only to) the cells that exhibit the desired phenotype status. Cells that do not exhibit the desired phenotype status are substantially avoided during the application of the light and, thus, the photo-activatable detectable marker in their nuclei is not activated. In some embodiments, the method also comprises isolating individual cells or nuclei thereof with uniquely activated photo-activatable detectable marker.

The phenotype status can be for any phenotype observed visually or optically from microscopy-based imaging of cells. The only criteria is that the phenotype status is observable visually in the microscopic field of view. Exemplary, non-limiting phenotypes include physical traits such as size, dimension (e.g., length, width, or ratios thereof), general shape or morphology (e.g., normal, elongated, lobulated, etc.) and cell behavioral phenotypes (e.g. motility, and the like). Furthermore, as described in more detail below, various stains and dyes can be used to expose, visualize, or otherwise represent morphological features or antigen expression (including antigen expression patterns) that can then be used as the visual phenotypes (e.g. immunofluorescent labeling of cell structures). The phenotype status can be the result of the cells' genetic background, gene expression patterns, and/or be influenced by reaction to a factor contacted to the cell (e.g., a drug). For example, a drug can be screened against a heterogeneous population of cells, and a subset of cells that have an altered morphology can be designated as having the desired phenotype status. Those cells can be specifically tagged by selective exposure to the light wavelength and subsequently sorted for further analysis.

In some embodiments, the phenotype status is a binary status, e.g., presence or absence of a trait, or the presence of one of two alternative phenotypes of a trait. For example, a cell can be determined to be round or lobulated. The cells would then be sorted into one of two bins accordingly. In other embodiments, the phenotype status can reflect a degree to which the cell exhibits a particular trait. For example, cells can be differentially tagged differently based on conformance to a measurement subrange, such as a cell diameter that is extra-small, small, large, and extra-large, etc. To illustrate, in the Examples below the inventors demonstrated an embodiment wherein the cells were exposed to excitatory light for different periods of time, resulting in different signal intensities from the photo-activatable detectable marker (e.g., Dendra2), which could be distinguished by the cell sorter. Thus, the cells can be exposed to varying intensities of the excitatory light depending on the cell diameter, resulting in four distinguishable signal intensities of the cell nucleus that can be sorted. In yet further embodiments, the cells can contain a plurality of different photo-activatable detectable markers in the nuclei that result in distinct signals upon activation. For optimal performance, in some embodiments each of the plurality of different photo-activatable detectable markers has a distinct excitatory wavelength to allow for selective activation. In some embodiments each of the plurality of different photo-activatable detectable markers also has a distinct emission wavelength such that they can be differentiated and sorted. To add power and sensitivity, at least one of the different photo-activatable detectable markers are capable of emitting distinguishable signal intensities from the cell nucleus based on the duration of light exposure during activation.

While the general discussion is in the context of assessing cells for the phenotype status of a single trait, the method can be multiplexed to assess the plurality of cells for the phenotype status of multiple traits, such as 2, 3, 4, 5, 6, 7, 8, or more traits. This can be implemented, for example, by use of a photo-activatable detectable marker that provides distinguishable emission intensities from the cell nucleus upon stimulation, e.g., stimulation for different lengths of time. Additionally or alternatively, this can be implemented by incorporation of a plurality of different photo-activatable detectable markers in the nuclei that result in distinct signals upon activation. As discussed above, the each of the plurality of different photo-activatable detectable markers has a distinct excitatory wavelength to allow for selective activation. Further, the different photo-activatable detectable markers are preferably selected to have distinct emission wavelengths upon activation. In some embodiments, one or more of the different photo-activatable detectable markers can be responsive to the duration of light stimulation, thus providing different and distinguishable intensities that can facilitate their mutual sorting. Thus, a single cell can emit multiple wavelength by the activation of multiple photo-activatable markers.

The term "photo-activatable detectable marker" refers to any moiety that is capable of emitting detectable light at a known wavelength after activation or excitation with application of light energy. A wide variety photo-activatable detectable markers are known and are encompassed by the present disclosure. In some embodiments, the photo-activatable detectable marker continues to emit the detectable light for a period of time after activation, such as at least about 1, 2, 3, 4, 5, 6, 12, 24 and hours. In some embodiments, the photo-activatable detectable marker is a photo-activatable protein. The photo-activatable protein can be characterized as a photoswitchable or photoconvertible protein. The photoactivation can be irreversible or reversible. Exemplary, nonlimiting photo-activatable proteins encompassed by the present disclosure include irreversible photo-activatable proteins such as photoactivatable (PA)-green fluorescent protein (GFP), PA-mCherry, PA-mRFP1, PS-CFP2, mEos, tdEos, Kaede, KikGr, mKiGr, derivatives thereof and the like. Exemplary, nonlimiting photo-activatable proteins encompassed by the present disclosure include reversible photo-activatable proteins such as photoactivatable Dronpa, Padron, rsCherry, rsCherryrev, and FP595, derivatives thereof, and the like. Additional examples of photo-activatable proteins are known and are encompassed by this disclosure. See, e.g., Fluorescent Proteins 101: A Desktop Resource (1st Edition). Tyler J. Ford and The Addgene Team|October, 2017, and references cited therein, each of which is incorporated herein by reference in its entirety.

An exemplary, nonlimiting example of the photo-activatable protein is Dendra2, which is an improved version of a green-to-red photoswitchable fluorescent protein Dendra. Dendra2 converts to a red fluorescent state in response to intense-blue-light irradiation at 460-500 nm. See Gurskaya N G, et al., 2006, Engineering of a monomeric green-to-red photoactivatable fluorescent protein induced by blue light. Nat Biotechnol. 24 (4):461-5, incorporated herein by reference in its entirety. Dendra2 exhibits prolonged red fluorescence after activation (i.e., photoconversion) allowing subsequent sorting steps to be performed as much as 12 hours later. However, a practical limit may be reaches as the signal starts to decay and/or cells continue to grow and divide. Dendra2 can be implemented in conjunction with other fluorescent protein markers that identify phenotype status. For example, mBeRFP, miRFP (Shcherbakova et al, 2016, Bright monomeric near-infrared fluorescent proteins as tags and biosensors for multiscale imaging. Nat Commun 7:1-12, incorporated herein by reference in its entirety), and mBeRFP (Yang et al, 2013, mBeRFP, an Improved Large Stokes Shift Red Fluorescent Protein. PLoS One 8:6-11, incorporated herein by reference in its entirety) are other exemplary fluorescent proteins encompassed by the present disclosure. Each of these emit wavelengths that avoid substantial overlap with that of Dendra2 and, thus, can be used in conjunction with Dendra2. These fluorescent markers can be integrated into (e.g., conjugated to) affinity reagents that are specific for an antigen of interest in or on the target cell or nucleus. Their presence, intensity, or distribution in or on the target cell or nucleus can visually represent a phenotype status, which can then result in photoactivation of the exemplary Dendra2 photo-activatable protein. A skilled practitioner will understand that myriad appropriate combinations of photo-activatable detectable markers (e.g., proteins) and/or fluorescent markers can be used in the disclosed method. Typically cover combinations are chosen to avoid neutral interference or overlap in emission and/or excitation signals. As described above, combinations of distinct photo-activatable detectable marker and fluorescent phenotypic markers typically are chosen to avoid significant overlap in emission wavelengths such that they can readily be distinguishable. Additional considerations can include having non-overlapping excitation wavelengths.

In some embodiments, the cell or cells are engineered to express the photo-activatable protein. For example, the cell or cells are engineered to comprise a nucleic acid encoding the photo-activatable protein operatively linked to an appropriate promoter and/or enhancer sequence(s) to facilitate expression of the photo-activatable protein. Amino acid sequences of appropriate photo-activatable detectable proteins are widely known and, therefore, encoding nucleic acid sequences can be routinely determined. In some embodiments, the photo-activatable protein comprises a nuclear localization sequence (NLS) to result in localization of the expressed photo-activatable protein in the nucleus of the cell(s). An exemplary NLS is set forth in SEQ ID NO:1, but others are widely known and are encompassed by this disclosure.

In some embodiments, the photo-activatable detectable marker comprises an affinity reagent conjugated to at least one dye and/or fluorophore. In some embodiments the affinity reagent is an antibody or antibody fragment or derivative, as described below in more detail. The affinity reagent can specifically bind to an antigen that exists in or on the cell, for example an antigen specifically expressed in or on the nucleus, such as histone proteins. In further embodiments, the affinity reagent is conjugated to two dye(s) and/or fluorophore(s) that emit different light wavelengths upon activation by exposure to the light in the exposing step. In some embodiments, the method further comprises contacting the cells with the affinity reagent to permit localization of the photo-activatable detectable marker to the nucleus.

The cells can be any starting population of cells that is heterogenous for at least one phenotype. For example, the plurality of cells can comprise a cultured cell line. Alternatively, the plurality of cells can be pooled cells from different experimental conditions (e.g., from a library screen). In some embodiments, the cultured cells can be fixed to a surface, such as in a flask, plate, well, or other tissue culture container. In alternative embodiments, the cells are primary cells obtained from a tissue, organ, or biological sample obtained from a subject (e.g., plant, animal, such as human, mouse, rat, pig, horse, cow, dog, cat, monkey, ape, and the like).

In some embodiments where the cells are fixed to a surface, the method can further comprise the step of extracting the intact nuclei from the fixed cells after the cells have been imaged, their phenotype status determined, and have been exposed to the light wavelength to activate the photo-activatable detectable marker in the individual cells' nuclei. The nuclei can be extracted according to the methodology described below so as to avoid rupture of the nuclei. This results in preserving the physical association of the genome of the cell with the induced detectable signal that is triggered due to determination of the cell's phenotype status.

After the exposing steps, the individual cells, or nuclei extracted from the individual cells, emit a detectable signal that is induced based on the determination of the desired phenotype status. The cells or nuclei extracted therefrom can then be sorted and collected for further analysis. Cell or nuclei sorting can be performed with any method available. One embodiment that is especially useful is sorting the cells or nuclei using fluorescence activated cell sorting (FACS). The genomic DNA and/or mRNA can be extracted from the sorted cells or nuclei and subjected to sequencing analysis, RNAseq analysis, ChIP analysis, chromatin accessibility, and myriad other assay platforms, to assess genomic, transcriptomic, epigenetic and other associations with the determined phenotype status.

In some embodiments, the imaging, determining, and light exposing steps are automated by a programmable microscope system containing instructions to discriminate phenotypic states for one or more phenotypes of interest. The system and related software is described in more detail below.

In another aspect, the disclosure provides a system for high-throughput cell sorting. The system comprises: a microscope device with at least one objective; a light source; and at least one computing device including a non-transitory computer-readable medium having instructions stored thereon. The instructions are configured to cause the at least one computing device to provide an image processing engine. The image processing engine is configured to: receive image signal from the microscope device representing one or more cells in a field of view and assess individual cell(s) in the field of view for a phenotype status for one or more phenotypes; and assign a coordinate to each individual cell in the field of view determined to have the desired phenotype status. The instructions are configured to cause the at least one computing device to provide the light source with instructions to apply a light wavelength to the coordinate assigned to each individual cell determined to have the desired phenotype status.

The microscope can be any standard or programmable microscope available that is configured for observation of cells. The microscope can comprise one or a plurality of objectives allowing for observation at various magnifications. The microscope device can incorporate an XY stage that facilitates movement of the stage, and consequently a container holding the plurality of cells mounted thereon, relative to the objective so as to shift the field of view along a plane perpendicular to the objective. The XY stage can be motorized and coupled to a stage controller that controls the movement of the XY stage along the X axis and Y axis. In such embodiments, the instructions of at least one computing device are configured to provide a stage control engine configured to provide the stage controller instructions to move the XY motorized stage in X and Y directions to control movement of stage in the plane perpendicular to the objective and, thus, move the observed field of view.

In some embodiments, the microscope device comprises a Z drive device, wherein the instructions of at least one computing device are configured to provide a Z drive control engine configured to provide the Z drive device instructions to controllably move the at least one objective or stage to increase or decrease the distance between the at least one objective and stage in a Z axis. Such movement allows capture of images of different planes in the field of view. For example, as described in Example 2 below, the inventors incorporated Piezo Z stage into the microscope set up to permit z-stacking of multiple images to provide a composite image with additional detail in a greater field of focus. Such z stacking can provide the system and method (as described above) with additional power and sensitivity for assessing and determining the desired phenotype status.

In some embodiments, the non-transitory computer-readable medium further comprises instructions stored thereon configured to synchronize the microscope device and light source to control for latency. For example, the instructions can implement a hardware trigger that coordinates instructions and inputs from the variously controlled hardware components of the microscope system to ensure minimal time gaps between image focus, capture (including capture of multiple images at various planes of focus in a single view), optional stacking/compilations into a composite image, assessment of the image, directed exposure to relevant light wavelengths and durations thereof for the observe phenotypic status, and optional movement of the stage to a new field of view to repeat the operation.

The at least one computing device can include any suitable computing devices, such as a desktop computing device, a server computing device, a rackmount computing device, an embedded computing device, a laptop computing device, and the like. In some embodiments, the at least one computing device is integrated into the microscope. The computing device is configured to provide an image processing engine and a cell tagging engine, and in some embodiments also a Z drive control engine and/or a Z drive control engine. In general, the word "engine," as used herein, refers to logic embodied in hardware or software instructions, which can be written in a programming language, such as C, C++, COBOL, JAVA™ PHP, Perl, HTML, CSS, JavaScript, VBScript, ASPX, Microsoft.NET™, and/or any other programming language. An engine may be compiled into executable programs or written in interpreted programming languages. Engines may be callable from other engines or from themselves. Generally, the engines described herein refer to logical modules that can be merged with other engines, or can be divided into sub-engines. The engines can be stored in any type of computer-readable medium or computer storage device and be stored on and executed by one or more general purpose computers, thus creating a special purpose computer configured to provide the engine(s).

The system can be configured to assess phenotype status in an automated fashion. Accordingly, in some embodiments, the computing device (e.g., as integrated into a programmable microscope) is configured to receive one or more images of a field of view from the microscope. The image or images can first be pre-processed to adjust image brightness, contrast, and/or other features. Then, the image is analyzed by a series of neural networks. A first neural network is used to identify individual cells, which are cropped from the image. A second neural network, trained to recognize cell phenotype status, is applied to cell crops, resulting in classification of cells according to their phenotype. These classifications, along with positional information from the original image, are used to create an activation bitmap. The bitmap instructs the light source to activate (i.e., illuminate) the particular cells having the phenotype(s) of interest at the appropriate coordinates in the field of view. In some embodiments, once all relevant cells are appropriate activated, the field of view can be adjusted (e.g., to a neighboring field of view) to repeat the imaging, analysis, and illumination process. This process can be repeated as many times as desired, e.g., until the cell plate has been entirely scanned.

In another aspect, the disclosure provides a non-transitory computer-readable medium having computer-executable instructions stored thereon. The instructions are configured, in response to one or more processors of the at least one computing device, to cause the at least one computing device to perform actions for capturing and assessing microscopic images of cells, and exposing cells observed to have a phenotype status for one more phenotypes, according to elements of the method described above. For example, the actions comprise receiving, by the computing device, image signal from the microscope device representing one or more cells in a field of view and assess individual cell(s) in the field of view for a phenotype status for one or more phenotypes. The actions also comprise assigning, by the computing device, a coordinate to each individual cell in the field of view determined to have the desired phenotype status. Finally, the actions also comprise providing, by the computing device, instructions to a light source to apply a light wavelength to the coordinate assigned to each individual cell determined to have the desired phenotype status.

As used herein, the term "computer-readable medium" includes volatile and non-volatile and removable and non-removable media implemented in any method or technology capable of storing information, such as computer readable instructions, data structures, program modules, or other data. In this regard, the system memory and storage medium are merely examples of computer-readable media.

Suitable implementations of computing devices, e.g., that include a processor, system memory, communication bus, storage medium, and network interface, are known and commercially available. The computing device may include input devices, such as a keyboard, keypad, mouse, microphone, touch input device, touch screen, tablet, and/or the like. Such input devices may be coupled to the computing device by wired or wireless connections including RF, infrared, serial, parallel, Bluetooth, USB, or other suitable connections protocols using wireless or physical connections. Similarly, the computing device may also include output devices such as a display, speakers, printer, etc. Since these devices are well known in the art, they are not illustrated or described further herein.

As described above in the context of the Visual Cell Sorting method, intact cells can be fixed to a surface for imaging purposes. However, the notwithstanding the fixed nature of the cells, the genetic material can still be functionally sorted and isolated by virtue of the extracting and sorting the nuclei based on the activated marker signal. Thus, in another aspect the disclosure provides a method of isolating nuclei from fixed adherent cells. The method comprises: exposing fixed, adherent cells to a proteinase, such as trypsin, for a time that avoids nuclear lysis; applying sufficient force to dislodge the fixed, adherent cells but that avoids nuclear lysis; and isolating the nuclei.

As described above, the nuclei, or a portion thereof, can be specifically tagged with a detectable marker. In some embodiments, the detectable marker is a protein, and the protein is expressed in the nuclei, thereby tagging the nuclei. In some embodiments the detectable marker is tethered to an affinity reagent, where in the affinity reagent is specifically bound to an antigen in or on the nucleus. Affinity reagents applicable to this aspect of the disclosure are described in more detail below. In some embodiments, the method comprises the step of actively tagging the nuclei of the fixed, adherent cells with a detectable marker. Depending on the nature of the detectable marker, the step of actively tagging the nuclei can comprise expressing a protein detectable marker in the cell, or contacting the cell with an affinity reagent that is tethered or conjugated to the detectable marker.

The detectable marker can be any moiety that provides a detectable signal and is not limited to any particular imaging or marker technology. For example, the detectable marker can be or comprise a photoactivated protein, a small molecule dye, a fluorescent label, and the like. In some embodiments, the detectable marker is a photo-activatable detectable marker, e.g., a photo-activatable protein, such as described above in more detail. For example, the detectable marker can be Dendra2. In another embodiment, the detectable marker is a small molecule dye, such as PA-JF549. A wide variety of detectable markers for the purpose of this aspect are known and can be readily selected and implemented by a skilled practitioner.

The fixed, adherent cells are contacted to a proteinase enzyme to facilitate breakdown of the outer cell membrane allowing access to the nucleus. In one embodiment, the proteinase is trypsin, such as trypLE Express or trypLE Select, although many other appropriate cell trypsins are known and are encompassed by this aspect. TrypLE is a useful trypsin embodiment as it is relatively gentle on the cells and reduces nuclear lysis during prolonged exposure times. Other dissociation regents are known and encompassed by this aspect, such as Accutase, StemPro Accutase, and the like)

Preferably, the cells are contacted with a concentration of protease (e.g., trypsin) at a concentration and time sufficient to facilitate rupture of the outer membrane but insufficient to rupture the nuclei. For example, the fixed, adherent cells can be exposed to the protease (e.g., trypsin) for less than 5 minutes, such as about 5, 4, 3, 2, and 1 minute. Exemplary concentrations of trypsin can be from about 0.01% to about 0.4% w/v, such as from about 0.05% to about 0.3% w/v, from about 0.05% to about 0.25% w/v, from about 0.1% to about 0.25% w/v, from about 0.15% to about 0.2% w/v, and any range therebetween. It will be understood that the time of exposure can be inversely related to the concentration of protease (e.g., trypsin) in the solution. Thus, the higher the concentration of protease (e.g., trypsin), the shorter the exposure time. Furthermore, the exposure time can be tuned accordingly based on the degree of cell fixation. Exposure to the protease (e.g., trypsin) is combined with application of force to dislodge the fixed, adherent cells. The force can be applied in any manner that detaches the cells but retains or substantially retains nucleus integrity. For example, the force can be applied at least in part by scraping and/or repeated pipetting action, and/or other gentle agitation action (e.g., swirling, shaking, rocking, etc.)

In some embodiments, the method comprises isolating the nuclei based on the presence of a detectable marker. For example, the nuclei can be isolated using fluorescence activated cell sorting (FACS).

After sorting and isolation, the nuclei can be subjected to further analysis. For example, the method can further comprise sequencing at least a portion of the DNA or RNA extracted from one or more isolated nuclei. Genomic DNA can be subjected to chromatin accessibility or ChIP analyses.

Additional Definitions

Unless specifically defined herein, all terms used herein have the same meaning as they would to one skilled in the art of the present invention. Practitioners are particularly directed to Sambrook J., et al. (eds.), *Molecular Cloning: A Laboratory Manual*, 3rd ed., Cold Spring Harbor Press, Plainsview, New York (2001); Ausubel, F. M., et al. (eds.), *Current Protocols in Molecular Biology*, John Wiley & Sons, New York (2010); Bonifacino, J. S., et al. (eds), *Current Protocols in Cell Biology*, John Wiley & Sons, New York (1999); and Radbruch, A. (ed.), *Flow Cytometry and Cell Sorting*, Springer-Verlag, Berlin (1992), for definitions and terms of art.

The use of the term "or" in the claims is used to mean "and/or" unless explicitly indicated to refer to alternatives only or the alternatives are mutually exclusive, although the disclosure supports a definition that refers to only alternatives and "and/or."

Following long-standing patent law, the words "a" and "an," when used in conjunction with the word "comprising" in the claims or specification, denotes one or more, unless specifically noted.

Unless the context clearly requires otherwise, throughout the description and the claims, the words "comprise," "comprising," and the like, are to be construed in an inclusive sense as opposed to an exclusive or exhaustive sense; that is to indicate, in the sense of "including, but not limited to." Words using the singular or plural number also include the plural and singular number, respectively. Additionally, the words "herein," "above," and "below," and words of similar import, when used in this application, shall refer to this application as a whole and not to any particular portions of the application. The word "about" indicates a number within range of minor variation above or below the stated reference number. For example, "about" can refer to a number within a range of 10%, 9%, 8%, 7%, 6%, 5%, 4%, 3%, 2%, or 1% above or below the indicated reference number.

As used herein, the terms "nucleic acid" or "polynucleic acid" refer to a polymer of nucleotide monomer units or "residues", typically DNA or RNA. The nucleotide monomer subunits, or residues, of the nucleic acids each contain a nitrogenous base (i.e., nucleobase) a five-carbon sugar, and a phosphate group. The identity of each residue is typically indicated herein with reference to the identity of the nucleobase (or nitrogenous base) structure of each residue. Canonical nucleobases include adenine (A), guanine (G), thymine (T), uracil (U) (in RNA instead of thymine (T) residues) and cytosine (C). However, the nucleic acids of the present disclosure can include any modified nucleobase, nucleobase analogs, and/or non-canonical nucleobase, as are well-known in the art.

As used herein, the term "polypeptide" or "protein" refers to a polymer in which the monomers are amino acid residues that are joined together through amide bonds. When the amino acids are alpha-amino acids, either the L-optical isomer or the D-optical isomer can be used, the L-isomers being preferred. The term polypeptide or protein as used herein encompasses any amino acid sequence and includes modified sequences such as glycoproteins. The term polypeptide is specifically intended to cover naturally occurring proteins, as well as those that are recombinantly or synthetically produced.

One of skill will recognize that individual substitutions, deletions or additions to a peptide, polypeptide, or protein sequence which alters, adds or deletes a single amino acid or a percentage of amino acids in the sequence is a "conservatively modified variant" where the alteration results in the substitution of an amino acid with a chemically similar amino acid. Conservative amino acid substitution tables providing functionally similar amino acids are well known to one of ordinary skill in the art. The following six groups are examples of amino acids that are considered to be conservative substitutions for one another:
 (1) Alanine (A), Serine (S), Threonine (T),
 (2) Aspartic acid (D), Glutamic acid (E),
 (3) Asparagine (N), Glutamine (Q),
 (4) Arginine (R), Lysine (K),
 (5) Isoleucine (I), Leucine (L), Methionine (M), Valine (V), and
 (6) Phenylalanine (F), Tyrosine (Y), Tryptophan (W).

Reference to sequence identity addresses the degree of similarity of two polymeric sequences, such as protein or nucleic acid sequences. Determination of sequence identity can be readily accomplished by persons of ordinary skill in the art using accepted algorithms and/or techniques. Sequence identity is typically determined by comparing two optimally aligned sequences over a comparison window, where the portion of the peptide or polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity. Various software driven algorithms are readily available, such as BLAST N or BLAST P to perform such comparisons.

The term "affinity reagent" refers to a macromolecule that specifically binds to a target antigen. The affinity reagent can be an antibody based molecule, including antibody fragments and derivatives. As used herein, the term "antibody" encompasses immunoglobulin molecules and antigen binding antibody derivatives and fragments thereof, derived from any antibody-producing mammal (e.g., mouse, rat, rabbit, and primate including human), that specifically bind to an antigen of interest. Exemplary antibodies include monoclonal antibodies, multi-specific antibodies (e.g., bispecific antibodies), chimeric antibodies (e.g., mouse-rabbit, mouse-human, mouse-primate, primate-human monoclonal antibodies), and humanized antibodies, as described in more detail below.

An antibody "derivative" encompasses fragments, modifications, fusions, or other antibody-related constructs that incorporate structure of at least part of an antibody molecule. An antigen-binding antibody derivative will typically contain at least a portion of the complementarity-determining regions (CDRs) of the original antibody sufficient to bind to the antigen of interest. An antibody "fragment" is a portion of a full-length antibody, preferably including the CDRs, antigen binding regions, and/or variable regions thereof necessary to permit binding to the antigen. Illustrative examples of antibody fragments and derivatives encompassed by the present disclosure include Fab, Fab', F(ab)$_2$, F(ab')$_2$ and Fv fragments, nanobodies (e.g., V$_H$H fragments and V$_{NAR}$ fragments), linear antibodies, single-chain antibody molecules, multi-specific antibodies formed from antibody fragments, and the like. Single-chain antibodies include single-chain variable fragments (scFv) and single-chain Fab fragments (scFab). A "single-chain Fv" or "scFv" antibody fragment, for example, comprises the V$_H$ and V$_L$ domains of an antibody, wherein these domains are present in a single polypeptide chain. The Fv polypeptide can further comprise a polypeptide linker between the V$_H$ and V$_L$ domains, which enables the scFv to form the desired structure for antigen binding. Single-chain antibodies can also include diabodies, triabodies, and the like. Antibody fragments can be produced recombinantly, or through enzymatic digestion.

Other derivatives can be chimeric antibodies, which combine parts of different source antibodies. For example, complementarity determining regions (CDRs) and potential entire variable regions can be derived from one source organism (e.g., mouse, human, etc.) and combined with other components, such as constant regions, of a different organism (e.g., human, mouse, rabbit, etc.) to produce the chimeric molecule that avoids stimulating immune responses in a subject. It will be understood that constant regions of other species, such as from human, can be similarly incorporated into such a chimeric construct. A "humanized antibody" is a chimeric antibody that comprises a minimal sequence that conforms to specific CDRs derived from non-human immunoglobulin that is transplanted into a human antibody framework. Humanized antibodies are typically recombinant proteins in which only the antibody CDRs are of non-human origin.

The antibodies, or antibody fragments or derivatives of the disclosure can be produced using any technique commonly known in the art. Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual* (Cold Spring Harbor Laboratory Press, 2nd ed. 1988); Hammerling et al., in: *Monoclonal Antibodies and T-Cell Hybridomas* 563-681 (Elsevier, N.Y., 1981), incorporated herein by reference in their entireties. The term "monoclonal antibody" refers to an antibody that is derived from a single clone, including any eukaryotic, prokaryotic, or phage clone, and not the method by which it is produced. Methods for producing and screening for specific antibodies using hybridoma technology are routine and well known in the art. Once a monoclonal antibody is identified, the encoding relevant binding domains can be cloned into an expression vector that also comprises nucleic acids encoding the other components of a derivative.

Antibody fragments that recognize specific epitopes can be generated by any technique known to those of skill in the art. For example, Fab and F(ab')$_2$ fragments of the invention can be produced by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the CHI domain of the heavy chain. Further, the antibodies of the present invention can also be generated using various phage display methods known in the art.

As used herein, the term "specifically binds" refers to an association or union of an affinity reagent (e.g., an antibody or antigen-binding derivative or fragment thereof), to a target molecule (e.g., a nucleus-specific antigen, such as a histone protein) with an affinity or $K_a$ (i.e., an equilibrium association constant of a particular binding interaction with units of 1/M) equal to or greater than $10^5$ M$^{-1}$, while not significantly associating with any other antigens. Antibodies or antibody derivatives can be classified as "high affinity" or "low affinity". "High affinity" refers to antibodies or antibody derivatives with a $K_a$ of at least $10^7$ M$^{-1}$, at least $10^8$ at least $10^9$ M$^{-1}$, at least $10^{10}$ M$^{-1}$, at least $10^{11}$ M$^{-1}$, at least $10^{12}$ M$^{-1}$, or at least $10^{13}$ M$^{-1}$. "Low affinity" refers to those antibodies or antibody derivatives with a $K_a$ of up to $10^7$ M$^{-1}$, up to $10^6$ M$^{-1}$, up to $10^5$ M$^{-1}$. Alternatively, affinity can be defined as an equilibrium dissociation constant (Kd) of a particular binding interaction with units of M (e.g., $10^{-5}$ M to $10^{-13}$ M). A variety of assays are known for identifying antibodies or antibody derivatives of the present disclosure that specifically bind to their intended antigen targets, as well as determining binding domain affinities, such as Western blot, ELISA, and Biacore® analysis (see also, e.g., Scatchard et al., *Ann. N.Y. Acad. Sci.* 51:660, 1949; and U.S. Pat. Nos. 5,283,173, 5,468,614, or the equivalent).

The affinity reagent disclosed herein can also be an aptamer. As used herein, the term "aptamer" refers to oligonucleic or peptide molecules that can bind to specific antigens of interest. Nucleic acid aptamers usually are short strands of oligonucleotides that exhibit specific binding properties. They are typically produced through several rounds of in vitro selection or systematic evolution by exponential enrichment protocols to select for the best binding properties, including avidity and selectivity. One type of useful nucleic acid aptamers are thioaptamers, in which some or all of the non-bridging oxygen atoms of phosphodiester bonds have been replaced with sulfur atoms, which increases binding energies with proteins and slows degradation caused by nuclease enzymes. In some embodiments, nucleic acid aptamers contain modified bases that possess altered side-chains that can facilitate the aptamer/target binding.

Peptide aptamers are protein molecules that often contain a peptide loop attached at both ends to a protamersein scaffold. The loop typically has between 10 and 20 amino acids long, and the scaffold is typically any protein that is soluble and compact. One example of the protein scaffold is Thioredoxin-A, wherein the loop structure can be inserted within the reducing active site. Peptide aptamers can be generated/selected from various types of libraries, such as phage display, mRNA display, ribosome display, bacterial display and yeast display libraries Disclosed are materials, compositions, and components that can be used for, can be used in conjunction with, can be used in preparation for, or are products of the disclosed methods and compositions. It is understood that, when combinations, subsets, interactions, groups, etc., of these materials are disclosed, each of various individual and collective combinations is specifically contemplated, even though specific reference to each and every single combination and permutation of these compounds may not be explicitly disclosed. This concept applies to all aspects of this disclosure including, but not limited to, steps in the described methods. Thus, specific elements of any foregoing embodiments can be combined or substituted for elements in other embodiments. For example, if there are a variety of additional steps that can be performed, it is understood that each of these additional steps can be performed with any specific method steps or combination of method steps of the disclosed methods, and that each such combination or subset of combinations is specifically contemplated and should be considered disclosed. Additionally, it is understood that the embodiments described herein can be implemented using any suitable material such as those described elsewhere herein or as known in the art.

Publications cited herein and the subject matter for which they are cited are hereby specifically incorporated by reference in their entireties.

EXAMPLES

The following examples are set forth so as to provide those of ordinary skill in the art with a complete disclosure and description of how to make and use the present invention, and are not intended to limit the scope of what the inventors regard as their invention nor are they intended to represent that the experiments below are all or the only experiments performed.

Example 1

Introduction

This example discloses the development of Visual Cell Sorting, a flexible and simple high-throughput method that uses commercial hardware to enable the investigation of cells according to visual phenotype, to address shortcomings in extant platforms. Visual Cell Sorting is an automated platform that directs a digital micromirror device to mark single live cells that express a nuclear photoactivatable fluorescent protein for subsequent physical separation by fluorescence activated cell sorting (FACS). It is demonstrated here that Visual Cell Sorting enables visual phenotypic sorting into 4 bins; increases the throughput of cellular separation by 1,000-fold compared to other single cell photoconversion-based technologies; and permits pooled genetic screening and transcriptomic profiling. For example, Visual Cell Sorting enabled the sorting of hundreds of thousands of cultured human cells according to the nuclear localization of a fluorescent reporter protein, and thus scoring of a library of nuclear localization sequence variants for function. In a second application, paclitaxel-treated cells with normal or lobulated nuclear morphologies were isolated and subjected each population to single cell RNA sequencing, revealing multiple pathways associated with paclitaxel resistance. Visual Cell Sorting requires simple, inexpensive, and commercially available widefield microscope hardware, routine genetic engineering, and a standard 4-laser FACS instrument to perform. As such, Visual Cell Sorting can readily be deployed to uncover the relationships between visual cellular phenotypes and their associated internal states, including genotype and gene expression programs.

Results

Physical Separation of Cells by Visual Phenotype

Figure 1A:
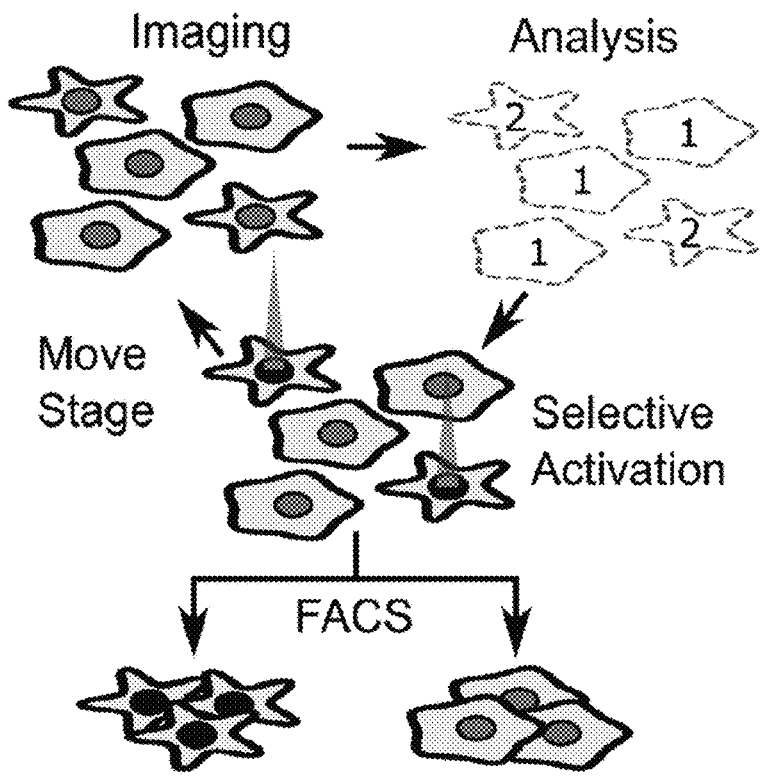
FIGS. 1A-1D. An illustrative embodiment of Visual Cell Sorting. (1A) In an automated fashion, cells in a field of view are imaged and their phenotype classified. Cells of interest are illuminated with 405 nm light, which irreversibly photoactivates Dendra2 from its green to its red fluorescent state. Alternatively, affinity reagents with photoconvertible dyes can be used. The microscope then moves to a new field of view. These steps are repeated across an entire culture well. Then, fluorescence-activated cell sorting based on Dendra2 photoactivation is used to physically recover cells of interest. (1B) To assess the photoactivation accuracy, U-2 OS cells expressing nuclear Dendra2 and miRFP, or nuclear Dendra2 alone, were co-cultured. The microscope was programmed to activate Dendra2 in cells expressing miRFP. Following photoactivation, miRFP expression and the ratio of activated to unactivated Dendra2 (left panel, n=18,766 cells) were assessed with flow cytometry. In a second co-culture, Dendra2 was unactivated (right panel, n=18,395 cells). Lines indicate gates for miRFP-positive cells and activated Dendra2 cells, with the percentage of cells appearing in each quadrant indicated. (1C) Same experiment as (1B), except cells were mixed such that 0.5%, 4%, 12%, or 50% were miRFP positive. Precision and recall were computed; large solid, mean (N=3 replicates); small points, individual replicate values; error bars, standard error from the mean. (1D) U-2 OS cells in one well were illuminated with 405 nm light for 0, 50, 200, or 800 ms (red; N=16,397). Cells in a second well were left unactivated (grey; N=8,497). The ratio of activated to unactivated Dendra2 was determined by flow cytometry.
Figure 8A:
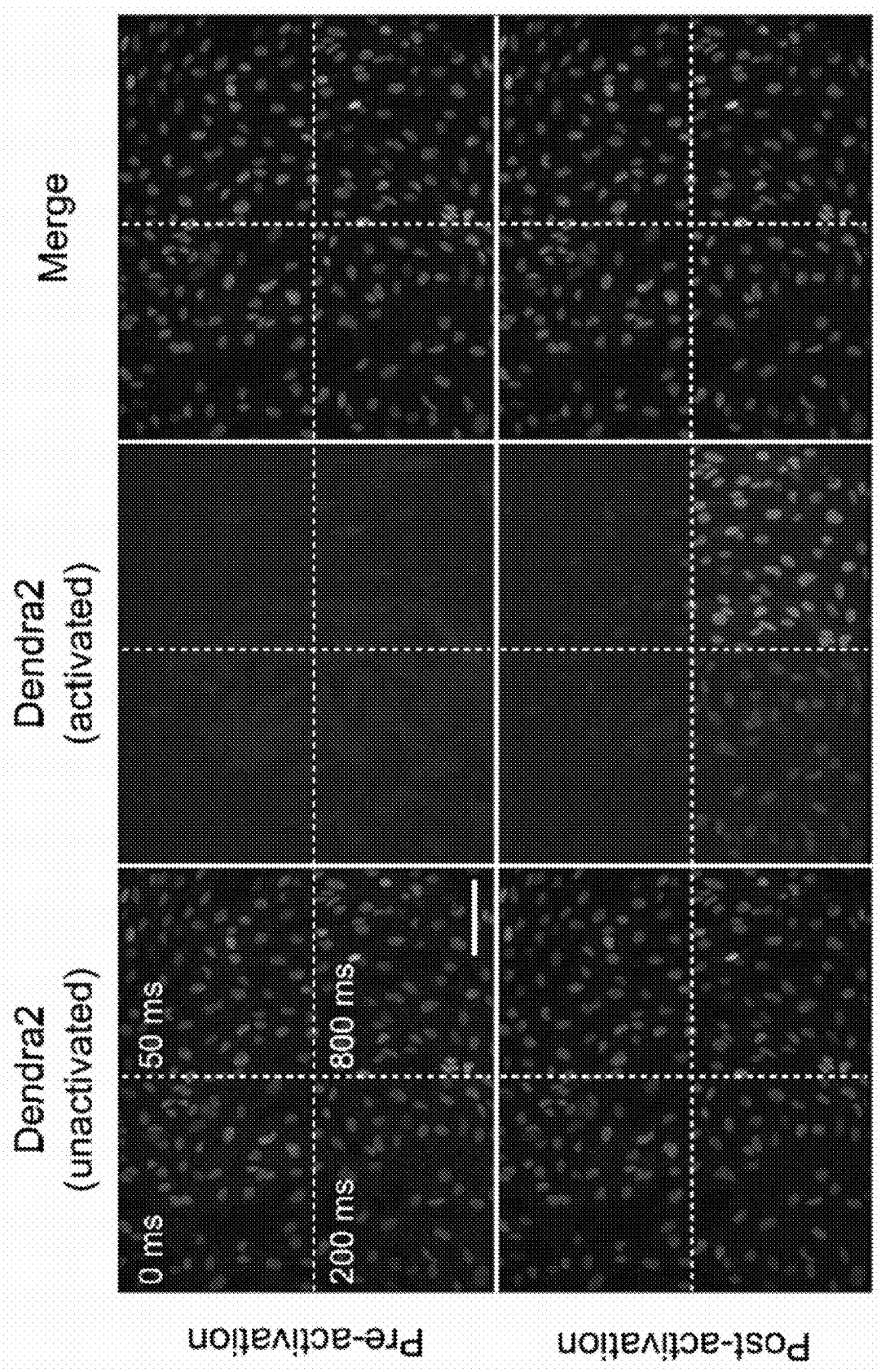

Visual Cell Sorting uses FACS to separate hundreds of thousands of cells by their visual phenotypes. Cells are first modified to express Dendra2, a green-to-red photoconvertible fluorescent protein (Chudakov et al, 2007, Tracking intracellular protein movements using photoswitchable fluorescent proteins PS-CFP2 and Dendra2. Nat. Protoc. 2: 2024-2032) that will act as a phenotypic marker and enable downstream FACS sorting. Next, cells are imaged on an automated microscope. In each field of view, cells are identified and analyzed for phenotypes of interest. According to their phenotype, cells are illuminated with 405 nm light for different lengths of time using a digital micromirror device, resulting in different levels of red Dendra2 fluorescence (FIG. 8A). The imaging, analysis, and photoactivation steps are performed at each field of view; and unlike previous photoactivatable marker-based methods, these steps are automated, allowing hundreds of thousands of cells to be assessed per experiment. Once all cells have been imaged, analyzed, and photoactivated, FACS is used to sort them into bins according to their level of Dendra2 photoactivation (FIG. 1A).

First, the single cell accuracy of Dendra2 photoactivation, and whether variable photoactivation states could be discerned by flow cytometry, were established. It was noted that similar technologies use photoactivatable dyes or proteins localized to the whole cell body. This localization strategy makes identifying the boundaries of the fluorescent signal difficult, which results in partial photoactivation or photoactivation of the marker in a cell adjacent to a cell of interest. With this in mind, Dendra2 was expressed in the nucleus either as a histone H3 fusion (H3-Dendra2) or with an upstream nuclear localization sequence (NLS-Dendra2×3). The boundaries of nuclear Dendra2 signal are easy to identify, permitting quantitative photoactivation of Dendra2 in the cells of interest; and the cytoplasm provides a spacer between the Dendra2 in different cells, reducing photoactivation of cells adjacent to the cells of interest.

Figure 1B:
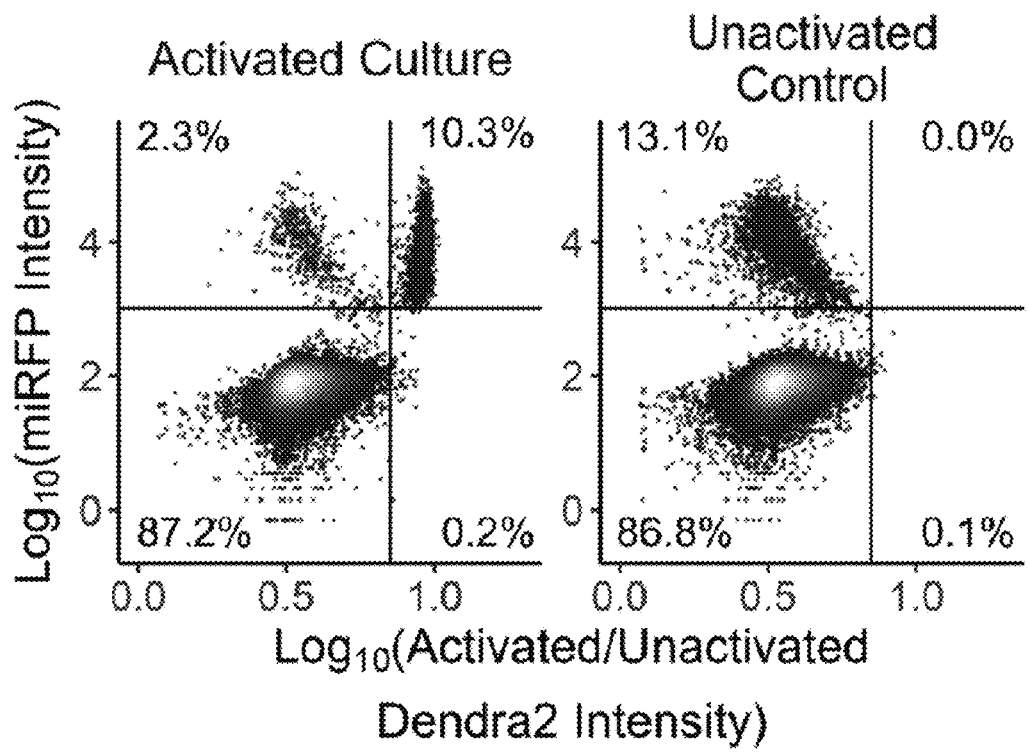
Figure 1C:
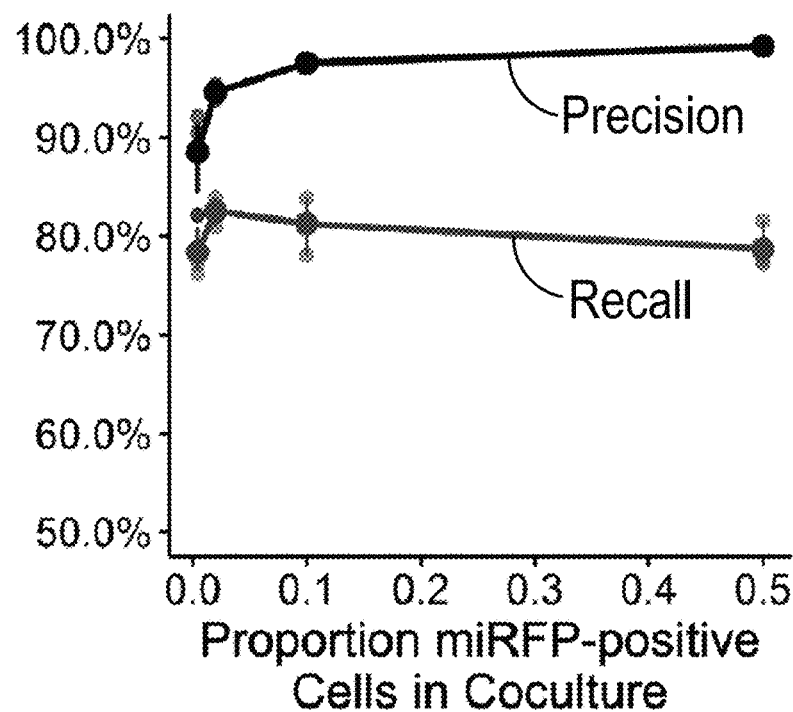

To measure photoactivation accuracy, H3-Dendra2 positive cells co-expressing H2B-miRFP (Shcherbakova et al, 2016, Bright monomeric near-infrared fluorescent proteins as tags and biosensors for multiscale imaging. Nat. Commun. 7: 1-12) were mixed with cells expressing H3-Dendra2 alone at decreasing ratios. The microscope was instructed to activate Dendra2 in cells harboring miRFP-positive nuclei, and then the co-occurrence of miRFP was quantified and Dendra2 florescence signals were activated using flow cytometry (FIG. 1B). The ratio of activated Dendra2 fluorescence to unactivated Dendra2 fluorescence (Dendra2 photoactivation ratio) accurately predicted whether a cell was miRFP-positive, even when the miRFP expressing cells were present at ~0.5% frequency, with average precision of 94% and recall of 80% (FIG. 1C).

Figure 1D:
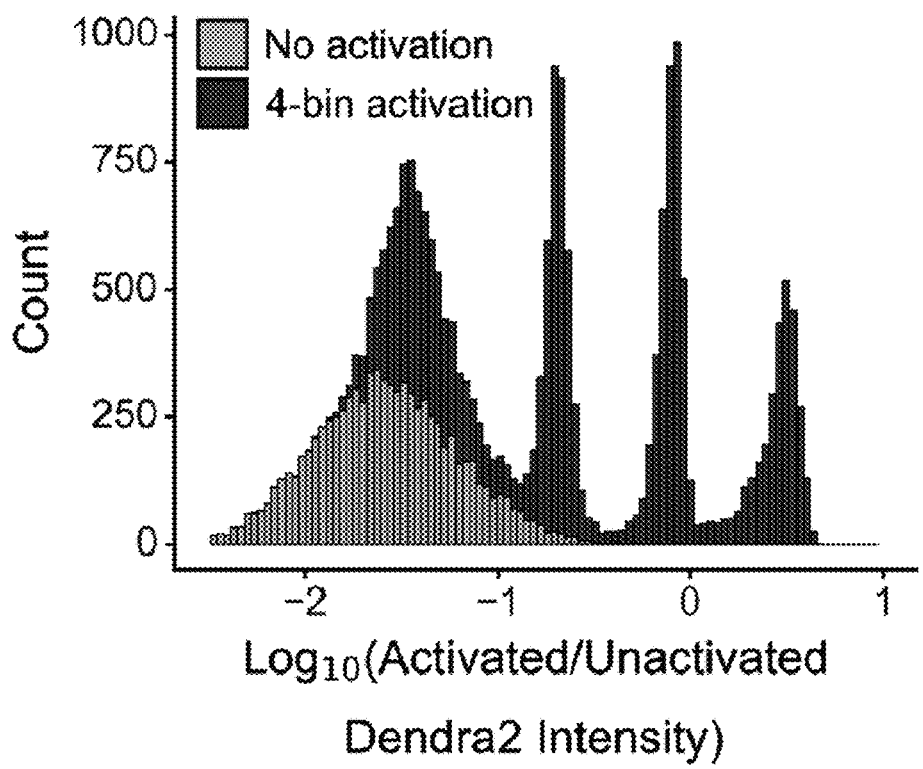
Figure 8B:
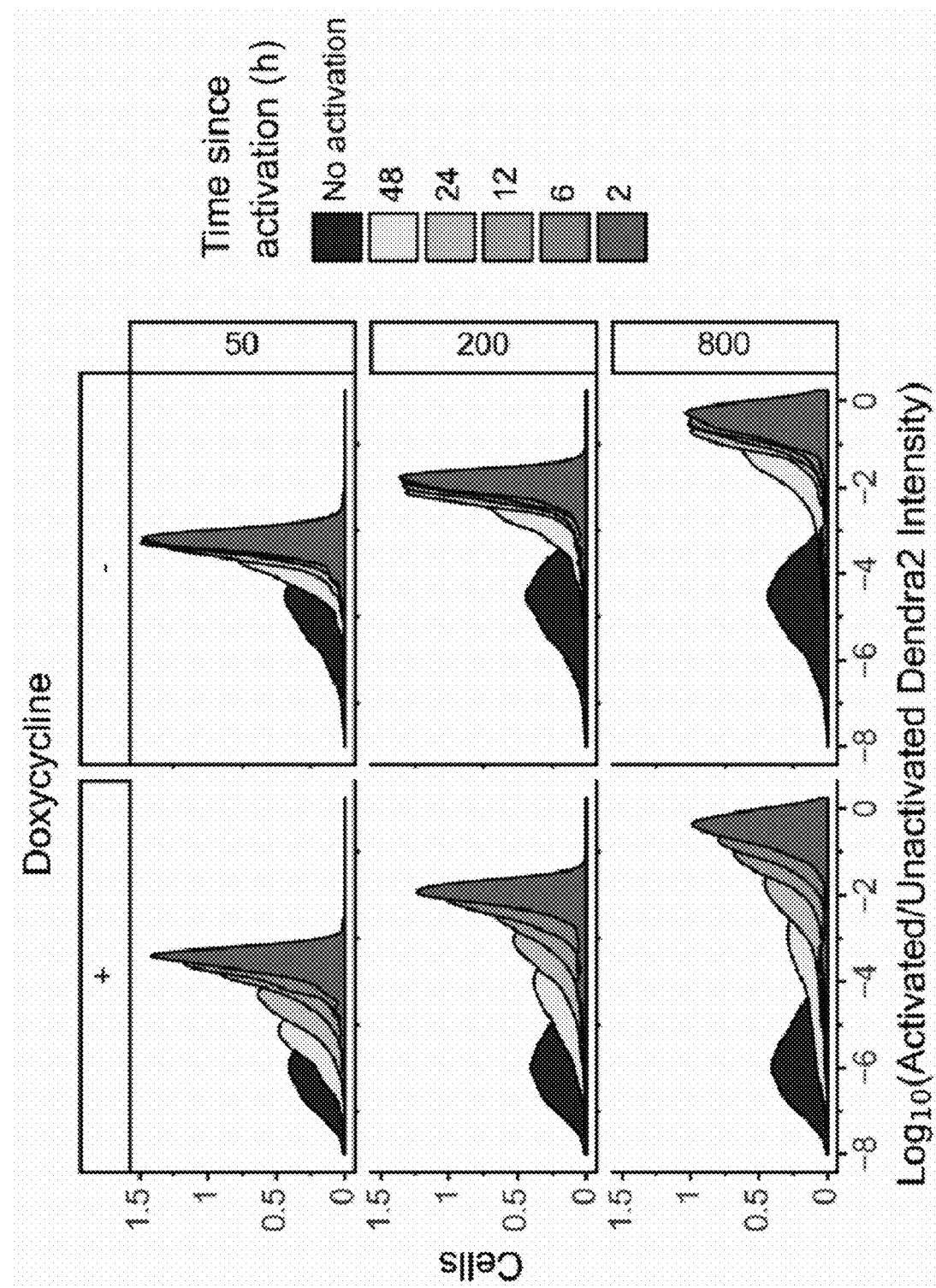
Figure 8C:
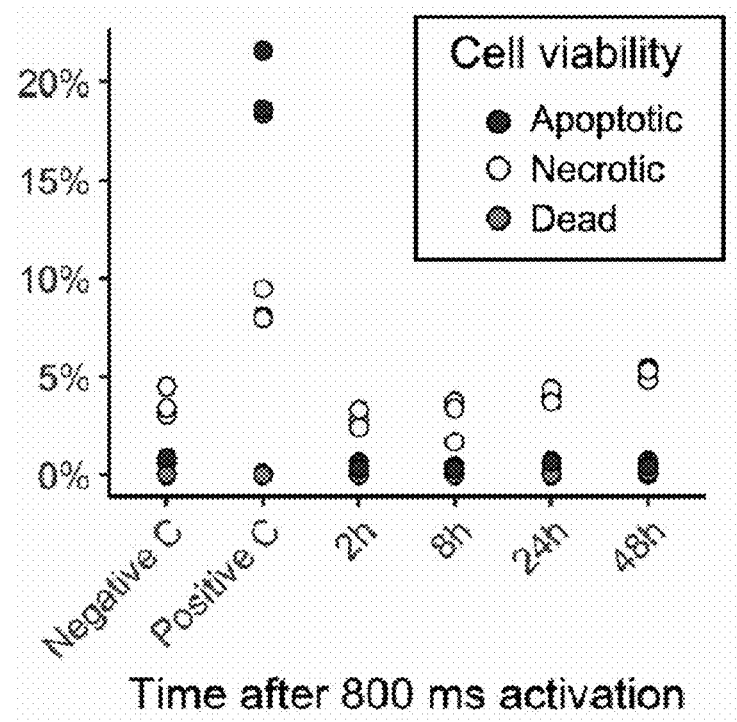
Figure 8D:
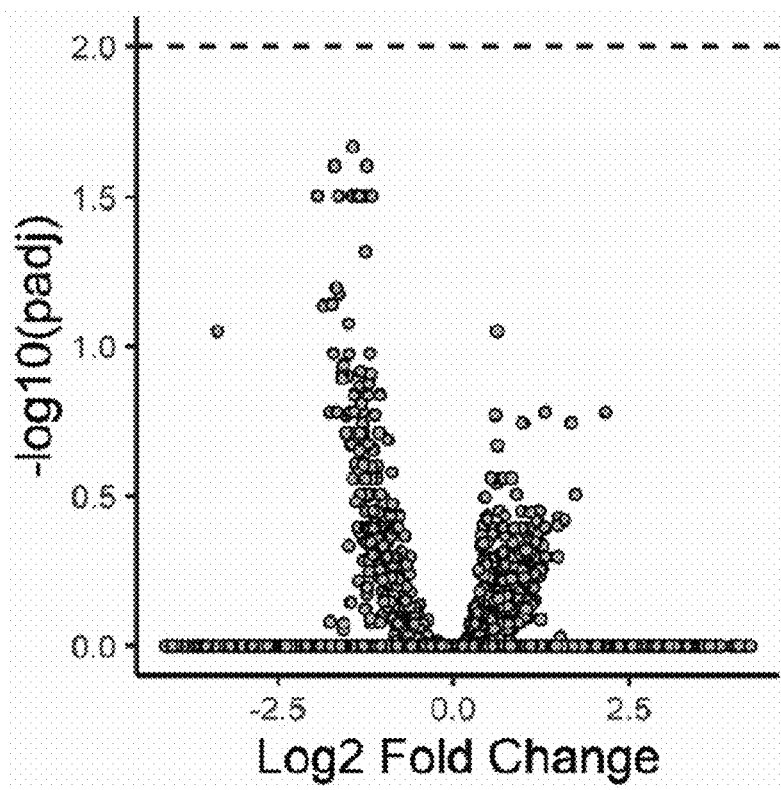

Previous photoactivatable marker-based methods have been limited to two photoactivation levels: activated and unactivated. To test whether this system could encode more than one photoactivation level, and thus more than one phenotype, different cells were exposed in the same well to 405 nm light for 0, 50, 200, or 800 ms. Flow cytometry of the Dendra2 fluorescence distribution by showed four distinct levels of Dendra2 photoactivation, indicating that Visual Cell Sorting can sort four different visual phenotypes or four discrete bins of a continuous phenotype (FIG. 1D). Furthermore, these four photoactivation levels can still be distinguished over 12 hours following activation (FIG. 8B, left panel). To extend the amount of time that the photoactivation levels remain distinct from one another, H3-Dendra2 expression was placed under the control of a doxycycline-inducible promoter. By shutting off Dendra2 expression before the experiment, the 50, 200, and 800 ms photoactivation levels remained distinguishable for up to 24 hours (FIG. 8B, right panel). Finally, the effect of Dendra2 photoactivation on cell viability and function was examined. Activated cells did not exhibit higher rates of apoptosis or cell death even two days after photoactivation, nor were effects of photoactivation on gene expression detected (FIGS. 8C and 8D). These results indicate that Dendra2 photoactivation does not appreciably affect cell survival or gene expression programs.

Visual Cell Sorting Enables Pooled, Image-Based Genetic Screening

Figure 2A:
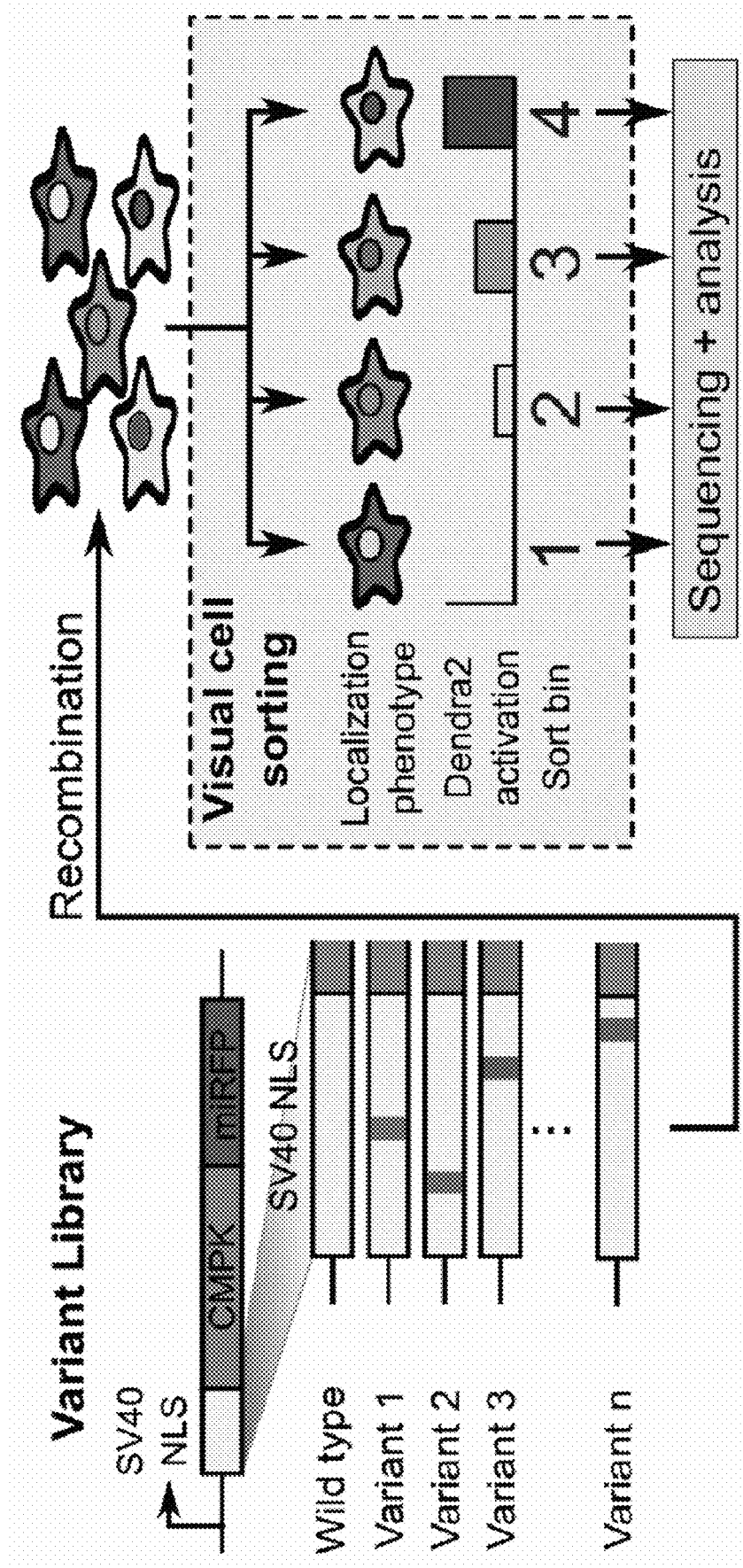
FIGS. 2A-2D. Visual Cell Sorting for pooled, image-based genetic screening. (2A) A mutagenized simian virus (SV) 40 NLS library containing 346 unique nucleotide variants fused to a chicken muscle pyruvate kinase (CMPK) miRFP reporter was recombined into a U-2 OS H3-Dendra2 cell line. Visual Cell Sorting was performed to separate the NLS library expressing cells into four photoactivation bins according to the microscope-derived nucleus-to-cytoplasm ratio of the miRFP reporter. Each bin was deeply sequenced and analyzed to assign each amino acid variant a quantitative nuclear localization score. (2B) U-2 OS H3-Dendra2 cells expressing either the NLS library, a wild type control or a no NLS control were imaged at 20× magnification and nucleus to cytoplasm (N:C) ratios measured. Curves, estimated kernel density of cells (N=1,529, 3,269, and 3,931 cells for no NLS, SV40 NLS, and WT NLS, respectively); dotted lines, Visual Cell Sorting photoactivation gates with associated bin numbers. (2C) Raw variant nuclear localization scores were calculated using a scaled weighted average of variant frequencies across the four sort bins. WT-like variants have a score of 1 and cytoplasm-localized variants a score of 0. Localization score, mean values of normalized scores from 5 replicates (N=637,605 cells); curves, kernel density estimate of variant score distributions. (2D) Nuclear localization scores of missense variants (N=202) displayed as a heatmap. Gray boxes, variants not observed or scored in a single replicate; black dots, WT sequence; dotted gray area on the horizontal axis, SV40 NLS often used to localize recombinant proteins to the nucleus; black box, the five residue K/R-rich region.

To test whether Visual Cell Sorting enables image-based genetic screening, it was asked whether one could separate cells according to the nuclear localization of a fluorescent reporter protein. Nuclear localization sequences (NLS's) are short peptides that direct proteins to the nucleus, and NLS's are critical for the function of thousands of human transcription factors, nuclear structural proteins, and chromatin modifying enzymes. Over 90% of nuclear proteins do not have an annotated nuclear localization sequence in UniProt, and current NLS prediction algorithms cannot sensitively identify known NLS's without drastically decreasing their precision. This shortcoming may arise because these NLS prediction algorithms rely on sequence alignments or amino acid frequencies of naturally observed NLS's, which are subject to discovery bias. Therefore, Visual Cell Sorting was used to evaluate a large library of NLS missense variants; sort cells according to the NLS function; and sequence the sorted cells (FIG. 2A), with the hypothesis that the resulting data could be used to improve NLS prediction.

Figure 2B:
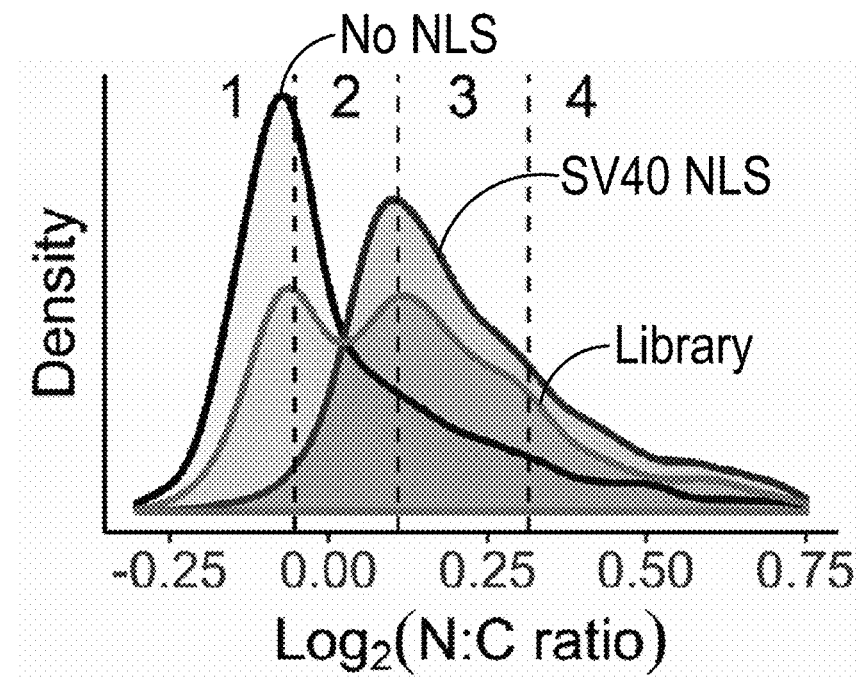
Figure 9A:
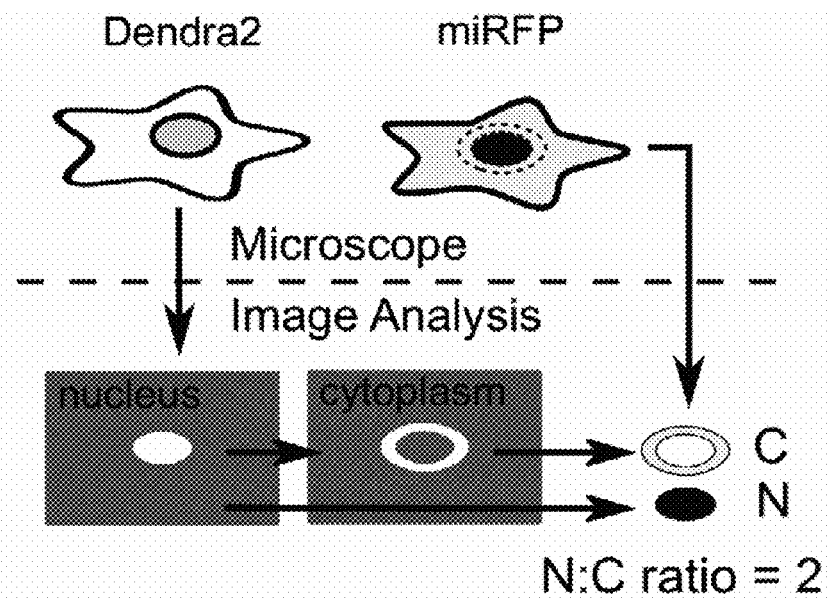
Figure 9B:
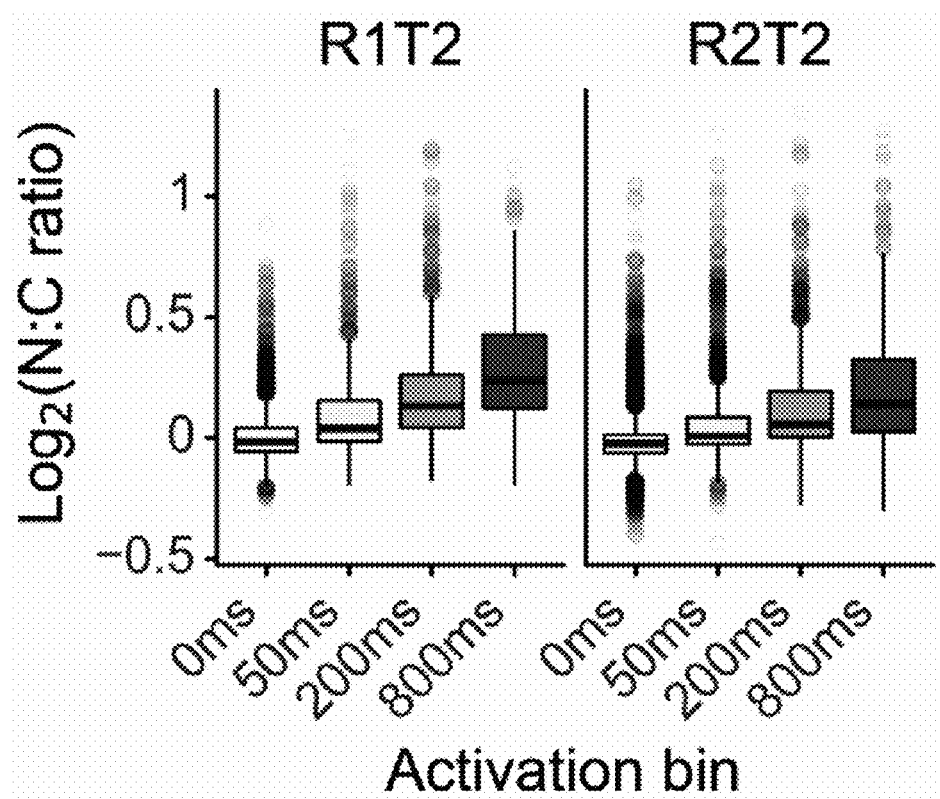

A library was based on the SV40 NLS, a 7-residue sequence containing a lysine and arginine-rich region (K/R motif) that was the first NLS to be discovered. To assess NLS variant function, a fluorescent nuclear localization reporter was constructed similar to one described previously. Cultured U-2 OS H3-Dendra2 cells expressing the wild-type SV40 NLS fused to a CMPK-miRFP reporter had high levels of miRFP in the nucleus, relative to the cytoplasm. The degree of nuclear localization was calculated using a nucleus-to-cytoplasm miRFP intensity ratio (N:C ratio; FIG. 9A). In contrast to the wild-type SV40 NLS-tagged reporter, cells expressing an untagged reporter had a low nucleus-to-cytoplasm ratio (FIG. 2B).

Figure 9C:
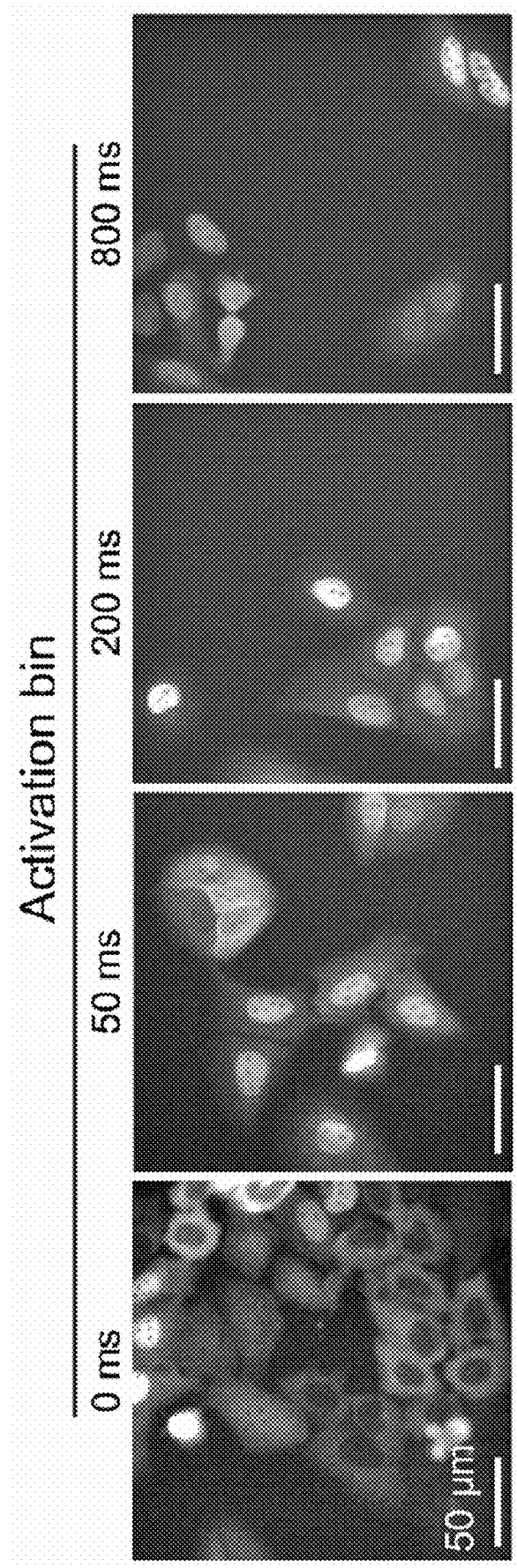
Figure 9D:
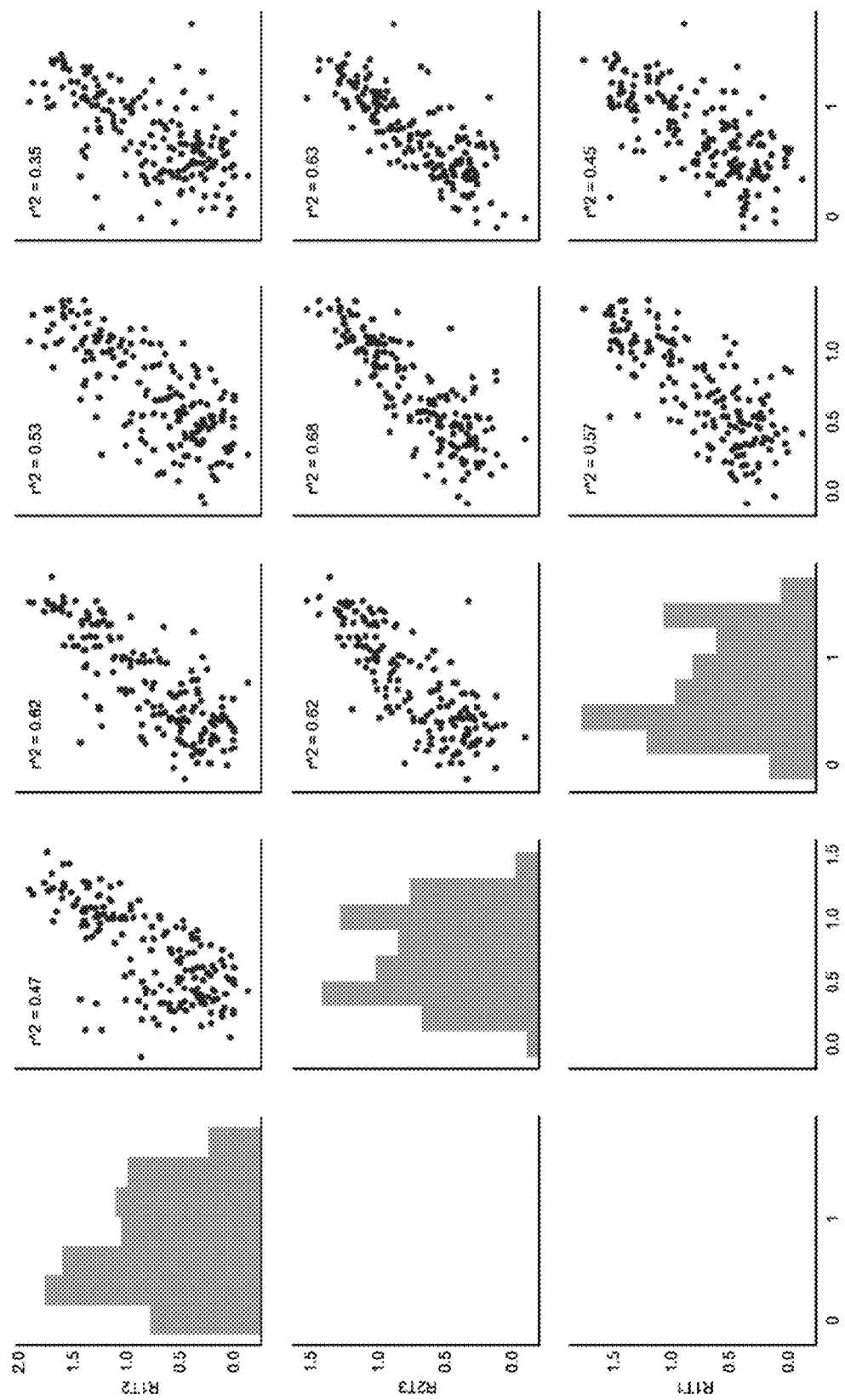
Figure 9D:
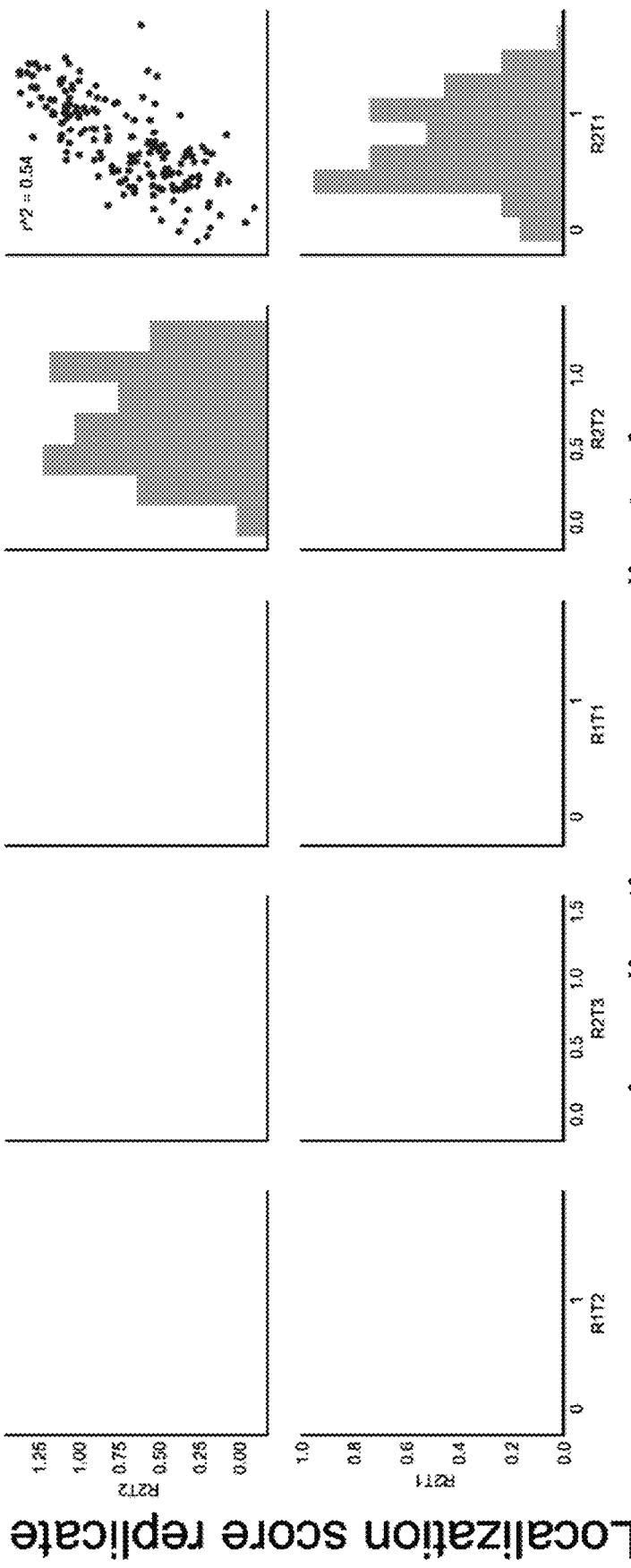

A library of 346 NLS nucleotide variants, corresponding to all possible 209 single amino acid missense variants, was generated. Cells expressing the library had a bimodal nucleus-to-cytoplasm ratio distribution, indicating that some variants preserved reporter nuclear localization while others disrupted its localization to different degrees (FIG. 2B). The library was divided into four photoactivation levels spanning the nucleus-to-cytoplasm ratio range and used Visual Cell Sorting to sort cells into four bins (FIG. 2B, vertical dotted lines). A total of 637,605 cells were sorted across 5 replicates (TABLE 1). Microscopy on the sorted cells revealed that Visual Cell Sorting faithfully separated cells by the nuclear localization phenotype (FIGS. 9C and 9D). Deep sequencing revealed the frequency of each variant in every bin. These frequencies were used to compute a quantitative nuclear localization score for 97% of the 209 possible single missense variants (FIG. 2D) (Rubin A F, et al. (2017) A statistical framework for analyzing deep mutational scanning data. *Genome Biol.* 18: 1-15). Scores were subsequently normalized such that wild-type had a normalized score of 1 and the bottom 10% of scoring variants had a median normalized score of 0.

TABLE 1

Number of cells sorted for each replicate of the image based screen of SV40 NLS variants.

| Replicate | # cells bin 1 (no activation) | # cells bin 2 (50 ms) | # cells bin 3 (200 ms) | # cells bin 4 (800 ms) | Total number of cells sorted | Total microscope time (hr) |
|---|---|---|---|---|---|---|
| R1T1 | 94122 | 16752 | 23761 | 12939 | 147574 | 7.6 |
| R1T2 | 91770 | 23307 | 30495 | 16189 | 161761 | 13.4 |
| R2T1 | 55237 | 9794 | 14636 | 8979 | 88646 | 10.3 |
| R2T2 | 44305 | 6708 | 11721 | 7332 | 70066 | 9.1 |
| R2T3 | 109122 | 15957 | 30135 | 14344 | 169558 | 14.8 |
| | | | | Grand total: | 637605 | 55.1 |

Figure 2C:
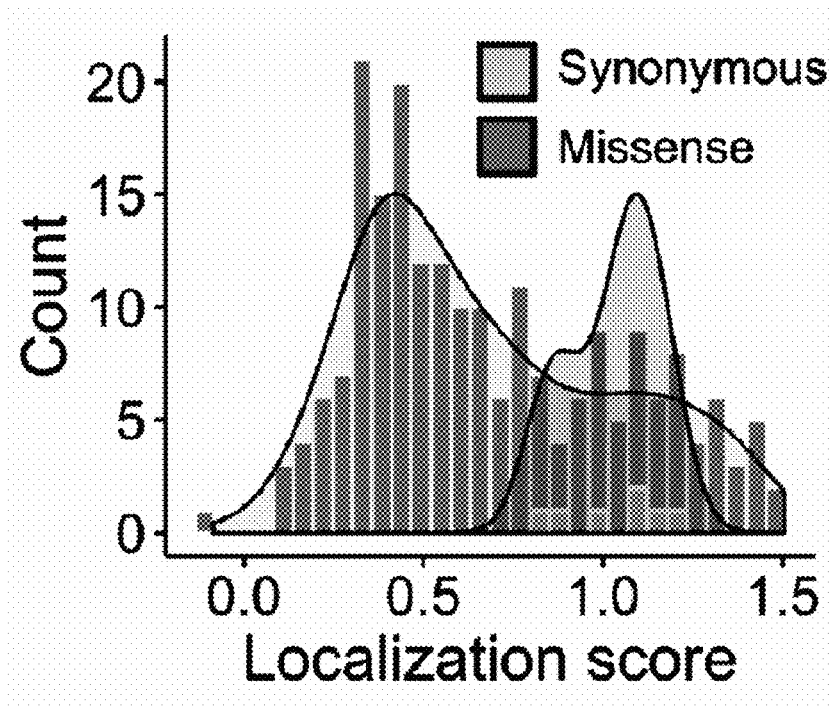
Figure 2D:
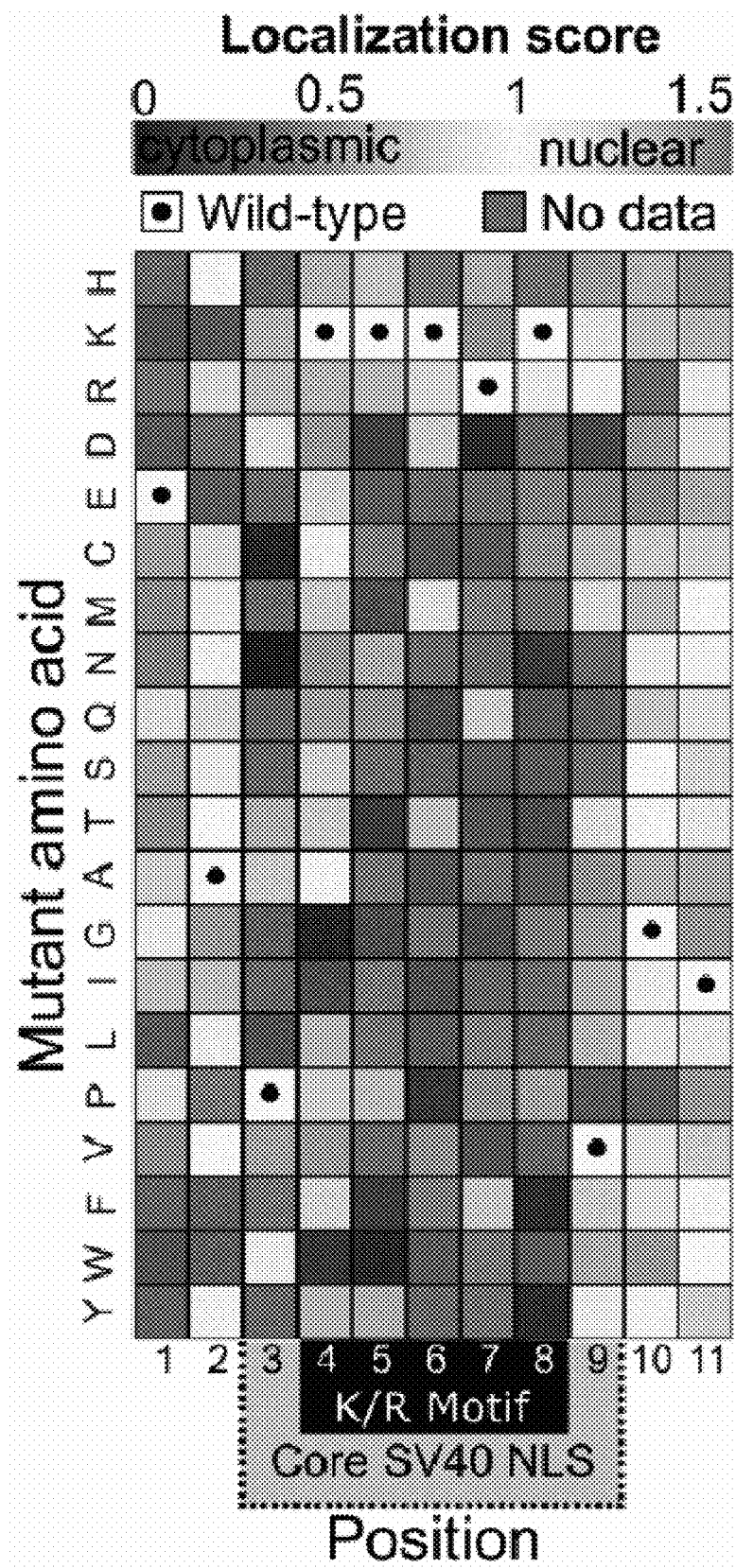
Figure 3A:
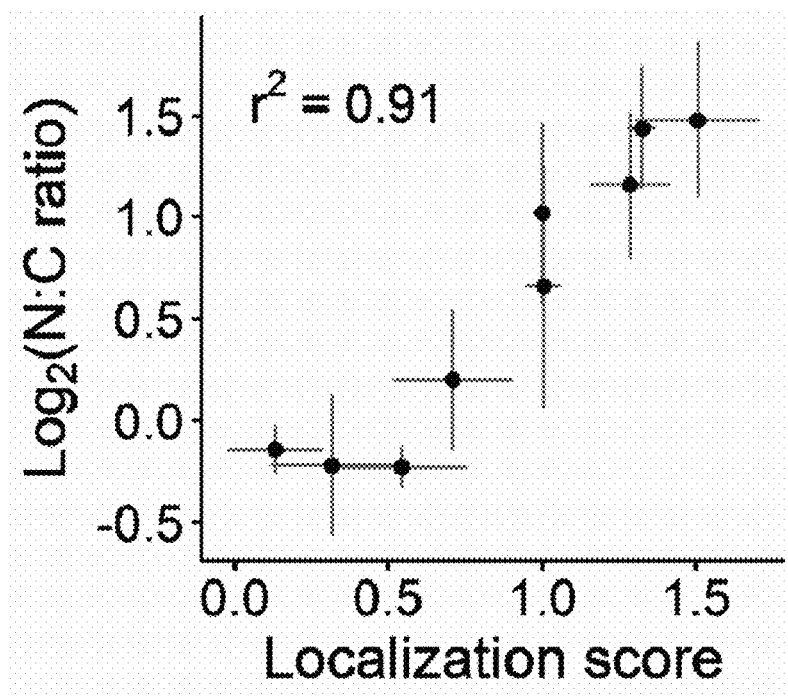

As expected, nuclear localization scores for synonymous variants were close to a wild-type-like score of one, and most missense scores were lower than one, indicating loss of nuclear localization sequence function (FIG. 2C). Furthermore, the SV40 NLS was most sensitive to substitutions in its K/R motif (FIG. 2D). Localization scores were reproducible (mean r=0.73; FIG. 9D), and individually assessed nucleus-to-cytoplasm ratios were highly correlated to the localization scores derived using Visual Cell Sorting ($r^2$=0.91; FIG. 3A). Finally, localization scores of individual variants were correlated with previously reported in vitro $K_d$ values for binding to importin alpha (r=−0.76, FIG. 10A). Thus, Visual Cell Sorting accurately quantified the effect of NLS variants on their nuclear localization function.

Figure 3B:
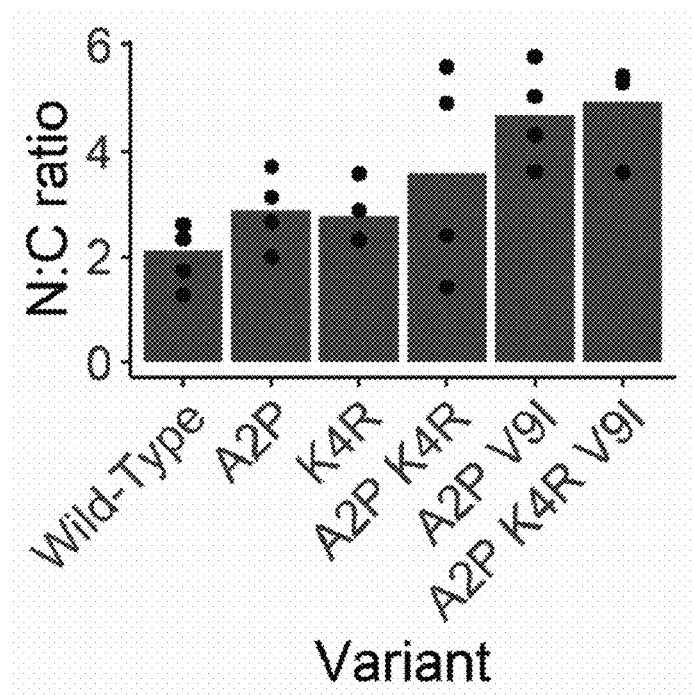
Figure 3C:
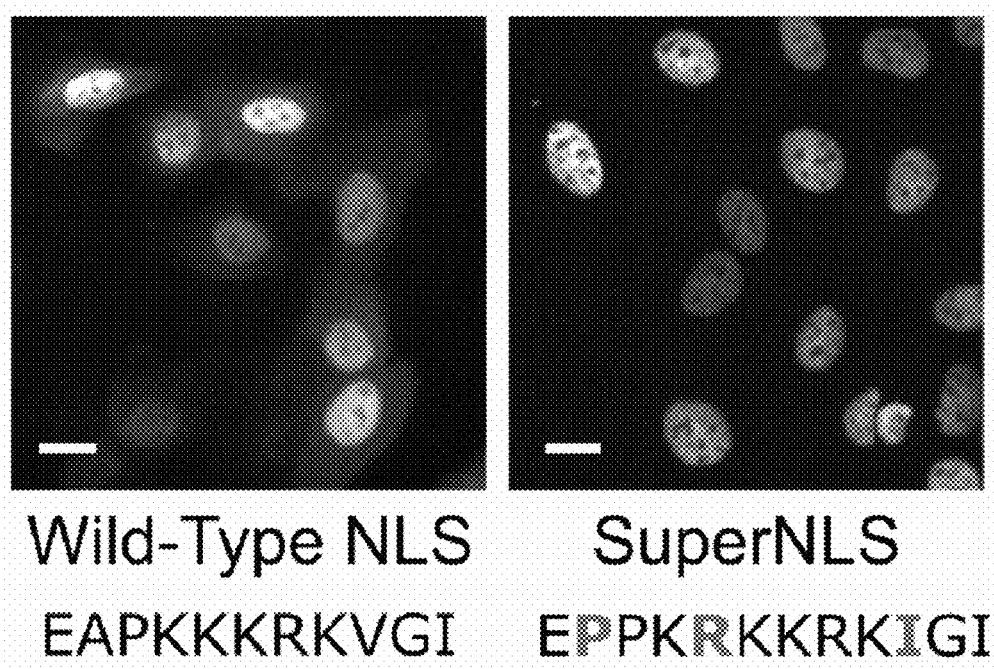

The SV40 NLS is commonly used to localize recombinant proteins to the nucleus and is included in over 10% of all constructs deposited in AddGene (accessed June 2019). Thus, an optimized NLS could improve a wide range of experiments including CRISPR-mediated genome editing. Three variants that appreciably increased nuclear localization of the reporter compared to the wild-type SV40 NLS were then further investigated. Individually, these variants modestly improved nuclear localization, and a "superNLS" with three missense variants increased nuclear localization by 2.3 fold (FIGS. 3B and 3C).

Figure 3D:
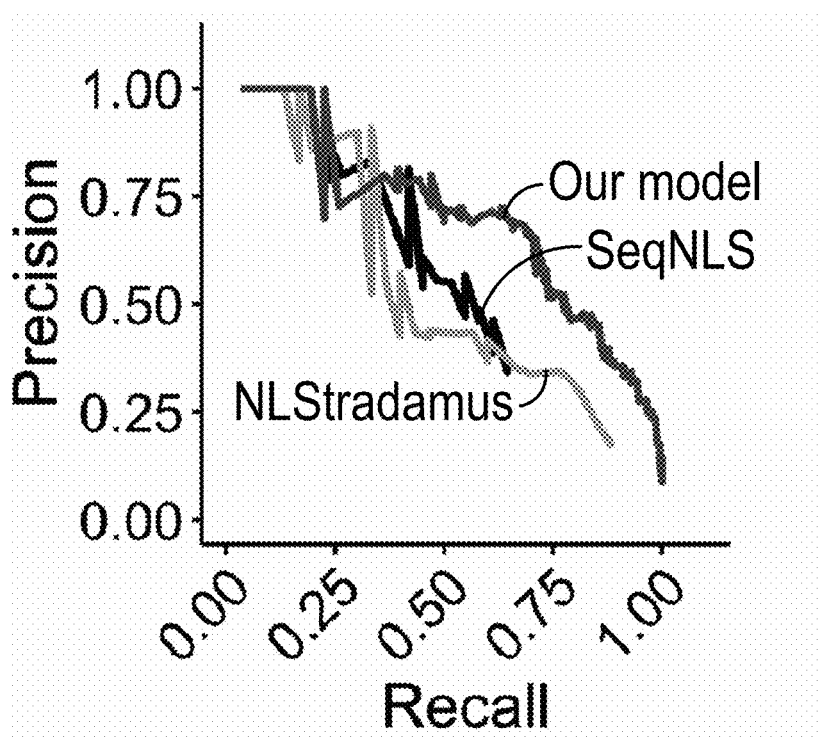

Most NLS prediction algorithms use naturally occurring, individually validated NLS sequences to identify similar sequences in new proteins. By contrast, these data comprise a comprehensive set of NLS-like sequences with variable function. A linear regression model was trained to predict whether any given 11-mer functions as a monopartite NLS by using the experimentally-determined amino acid preferences (Bloom, 2014, An Experimentally Determined Evolutionary Model Dramatically Improves Phylogenetic Fit Article Fast Track. 31: 1956-1978) at each NLS position, which were calculated with the localization score data. The model was evaluated using a test dataset, not used for training, of 30 NLS's in 20 proteins. The resulting model more accurately predicted NLS's than two previously-published linear motif scoring models, particularly at a stringency where the majority of NLS's are detected (FIG. 3D). This model was used to annotate NLS's in nuclear human proteins according to two score thresholds: one for high confidence monopartite NLS (precision 0.88, recall 0.23) and one for candidate monopartite NLS's (precision 0.51, recall 0.76). In total, 3,068 high confidence monopartite NLS's and an additional 30,814 candidate monopartite NLS's across 11,796 human nuclear proteins were annotated (Not shown).

To substantiate that these represent bona-fide NLS sequences, the top-scoring 11-mers were compared in exclusively nuclear proteins to those in exclusively cytoplasmic proteins (FIGS. 10B and 10C). As expected, nuclear proteins had higher top-scoring 11mer sequences than cytoplasmic proteins (Wilcoxon rank sum p-value $<10^{-16}$). Twenty-eight percent of the nucleus-only proteins contained an 11-mer with an NLS score higher than our high-confidence cutoff; only 11% of cytoplasmic proteins contained such a sequence. These results are consistent with the predictor identifying monopartite, SV40-like NLS's in the human proteome.

Visual Cell Sorting Enables Transcriptome Profiling on Image-Based Phenotypes

Figure 4A:
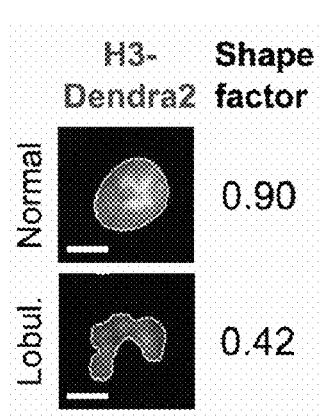
Figure 4B:
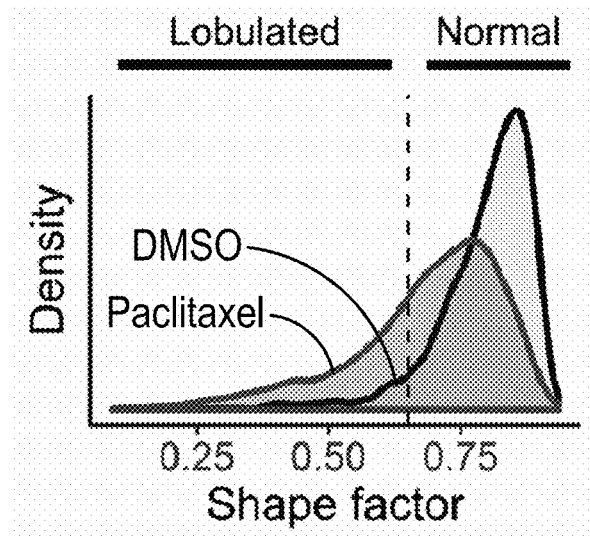

To test whether Visual Cell Sorting enables transcriptomics on cells with distinct image-based phenotypes, single cell RNA sequencing was performed on cells undergoing divergent morphologic responses to paclitaxel. Paclitaxel is a chemotherapeutic agent that stabilizes microtubules and has been used to treat cancer for decades. Even in a clonal population, a subset of cells adopt a lobulated nuclear morphology when treated with a low dose (≤10 nM) of paclitaxel. A telomerase-immortalized cell line derived from human retinal pigment epithelium, hTERT RPE-1, was treated with paclitaxel and observed mitoses that sometimes resulted in nuclear lobulation that persists through the cell cycle. In order to computationally define a cutoff for lobulated nuclei, we measured the shape factor, a circularity metric (FIG. 4A), of nuclei in vehicle-treated cells and found that 95% of these morphologically normal cells have a nuclear shape factor greater than 0.65. Paclitaxel treated cells were then analyzed it was observed that 30% of paclitaxel treated cells had lobulated nuclei, defined by shape factor of less than 0.65 (FIG. 4B).

Figure 4C:
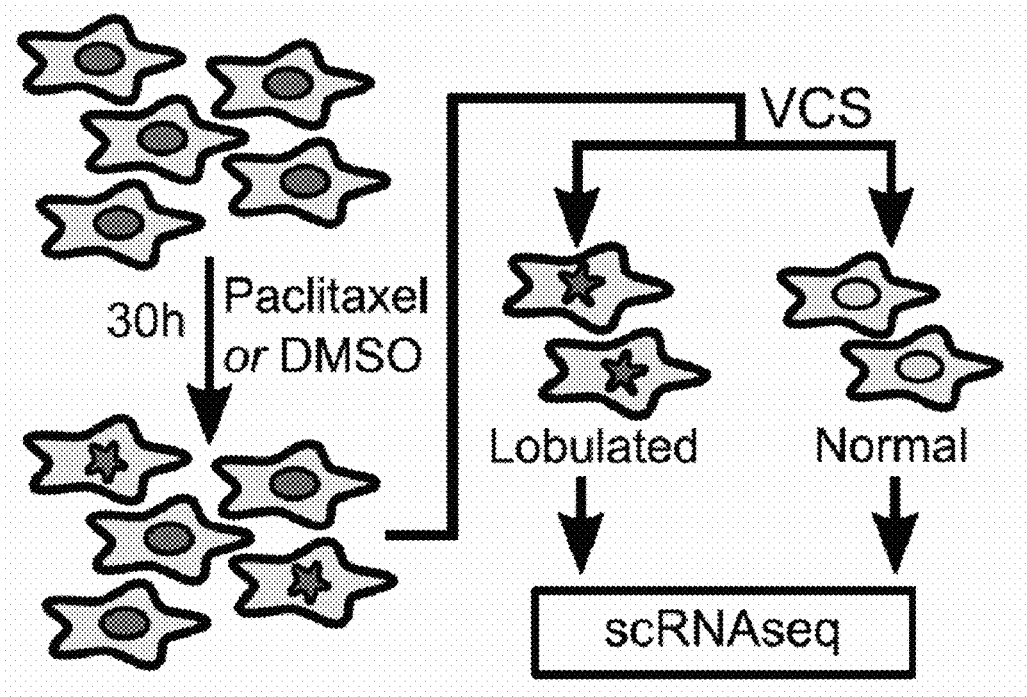

Given that morphologic phenotypes are potent indicators of cell state, it was hypothesized that the change in nuclear morphology was accompanied by a distinct gene expression program. To test this hypothesis, Visual Cell Sorting was used to separate morphologically normal paclitaxel-treated cells (shape factor >0.65) from those with lobulated nuclei (shape factor <0.65). Each population of cells was then subjected to single cell RNA sequencing (FIG. 4C). Imaging, analysis, photoactivation, and FACS-based recovery (FIG. 11A) of 200,000 cells took less than 7 hours. Following FACS, sequencing libraries were prepared for approximately 6,000 single cell transcriptomes from each population. An RNA sequencing batch effect was observed that was completely attributable to different levels of cell-free RNA in the lobulated and morphologically-normal cell sequencing preps (FIG. 11B).

Figure 4D:
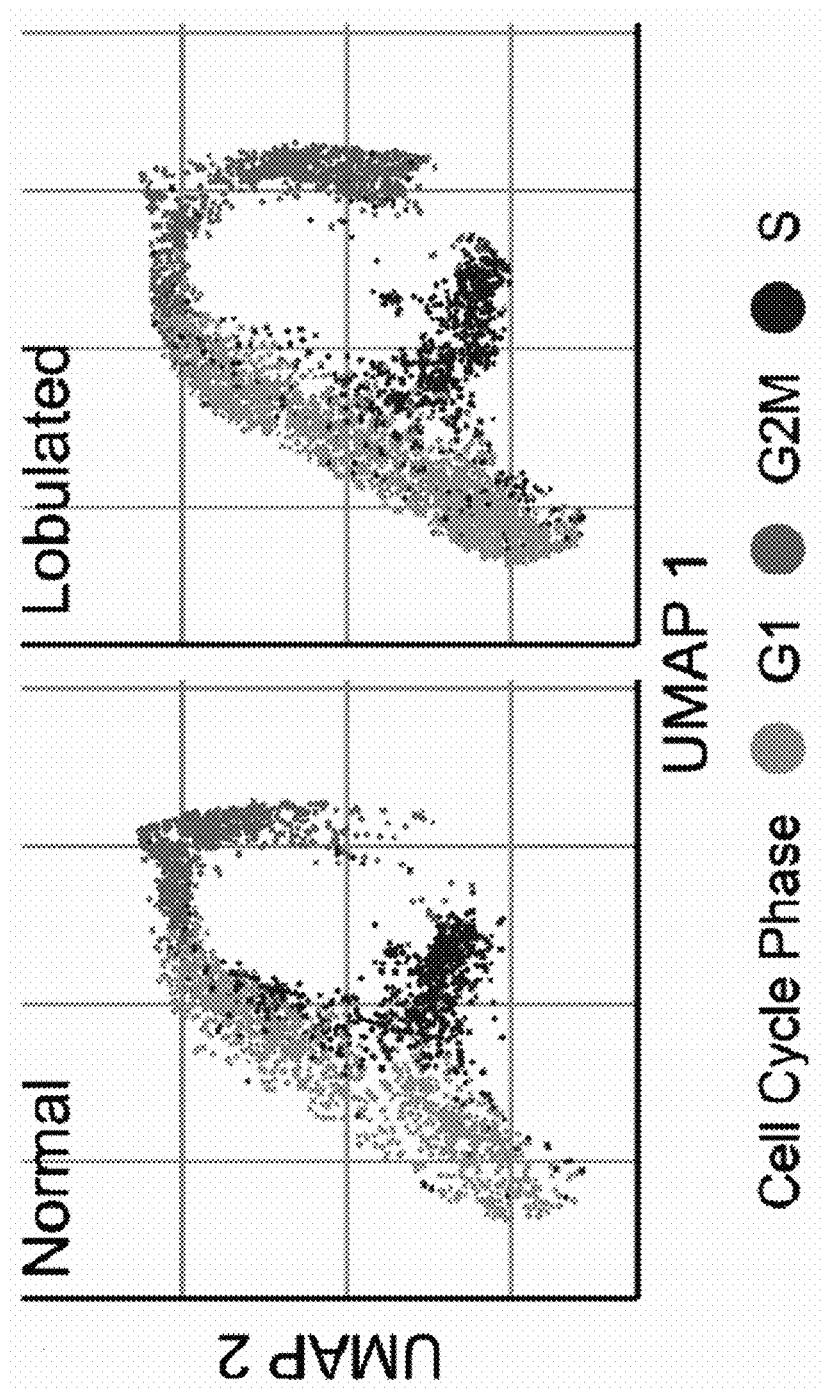

UMAP (McInnes et al, 2018, UMAP: Uniform Manifold Approximation and Projection for Dimension Reduction. ArXiv) was used to visualize a low-dimensional embedding of the single cell transcriptomes. The distributions of normal and lobulated cells in the UMAP embedding were similar, indicating modest differences in their transcriptomic states. Differences in cell-cycle phase (Butler A, et al. (2018) Integrating single-cell transcriptomic data across different conditions, technologies, and species. *Nat. Biotechnol.* 36: 411-420) largely explained transcriptomic variation (FIG. 4D). More lobulated cells than normal cells were in G1 (53% vs. 44%), suggesting that lobulated cells had an increased propensity to arrest in G1. Indeed, G1 arrest is known to occur after paclitaxel treatment in non-transformed cell lines (Trielli M O, et al. (1996) Differential taxol-dependent arrest of transformed and nontransformed cells in the G1 phase of the cell cycle, and specific-related mortality of transformed cells. *J. Cell Biol.* 135: 689-700).

To understand the relationship between transcriptomic variation, lobulation, and cell cycle, the top batch-corrected principal components of the single cell transcriptomes were examined. It was noted that the first four principal components separated cells by nuclear morphology (FIG. 11C). To discover the genes associated with nuclear lobulation while controlling for the cell-free RNA batch effect, an unseparated paclitaxel-treated cell population was sequenced and their transcriptomes were aligned to those from morphologically-normal and lobulated cells. A lobulation score was then derived for each cell via linear combinations of the four principal components that correlate with nuclear morphology (FIG. 11D). Finally, genes associated with this lobulation score, which is higher in cells with lobulated nuclei, were extracted in the unseparated cells by using a differentially expressed gene test (see Methods section).

Figure 4E:
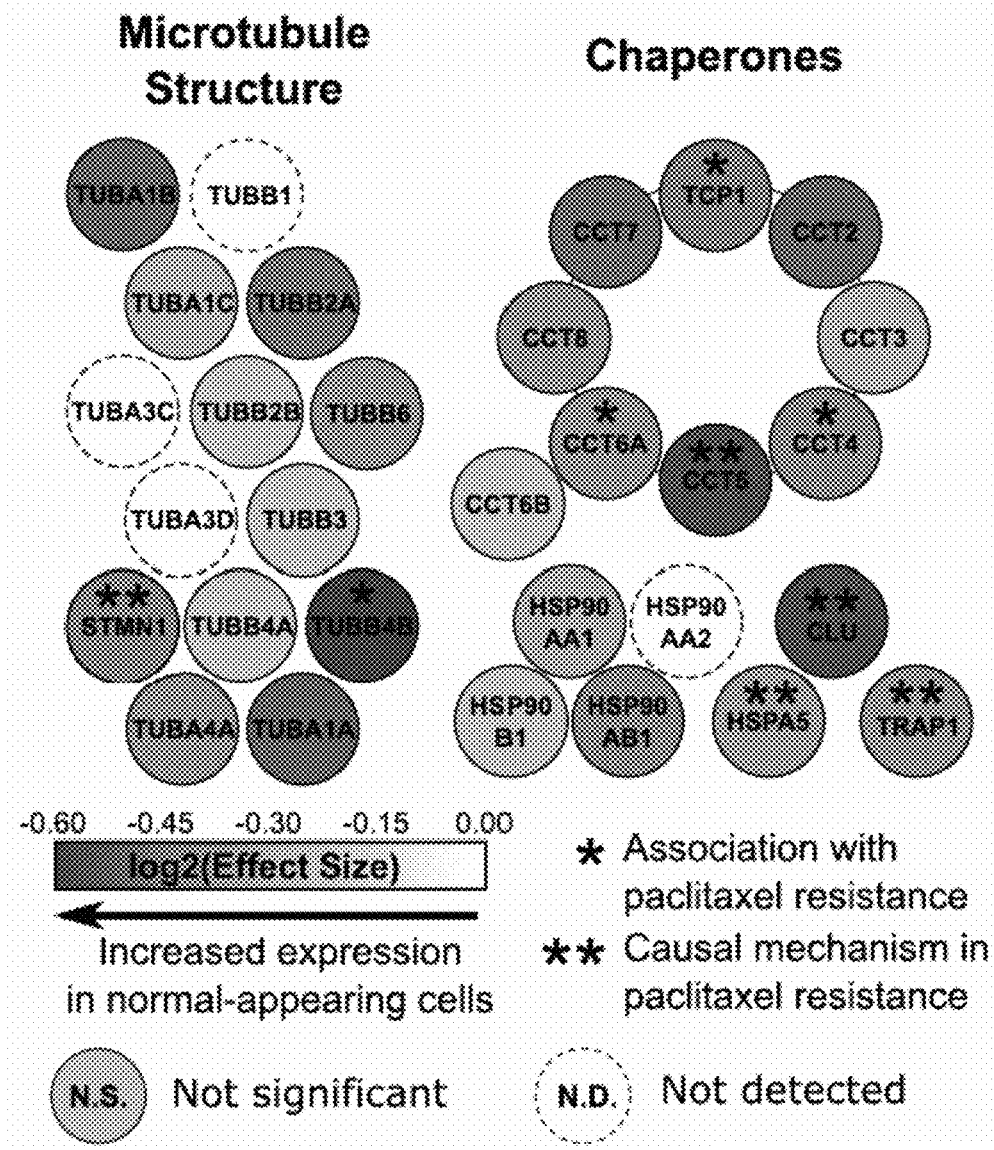
Figure 11E:
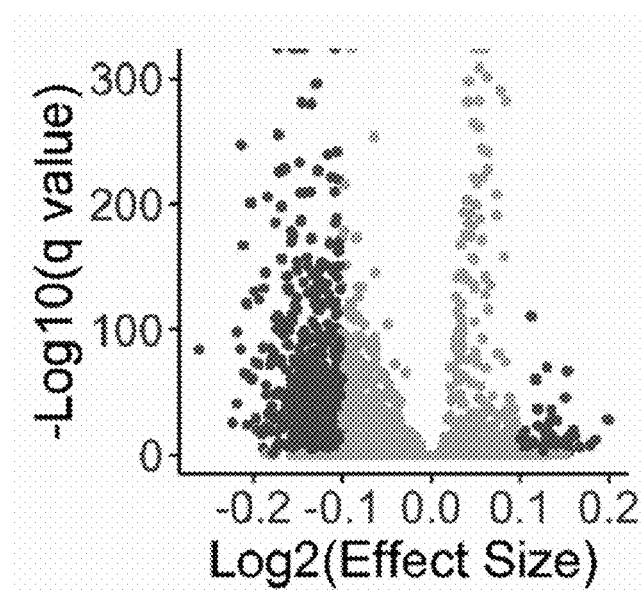
Figure 11F:
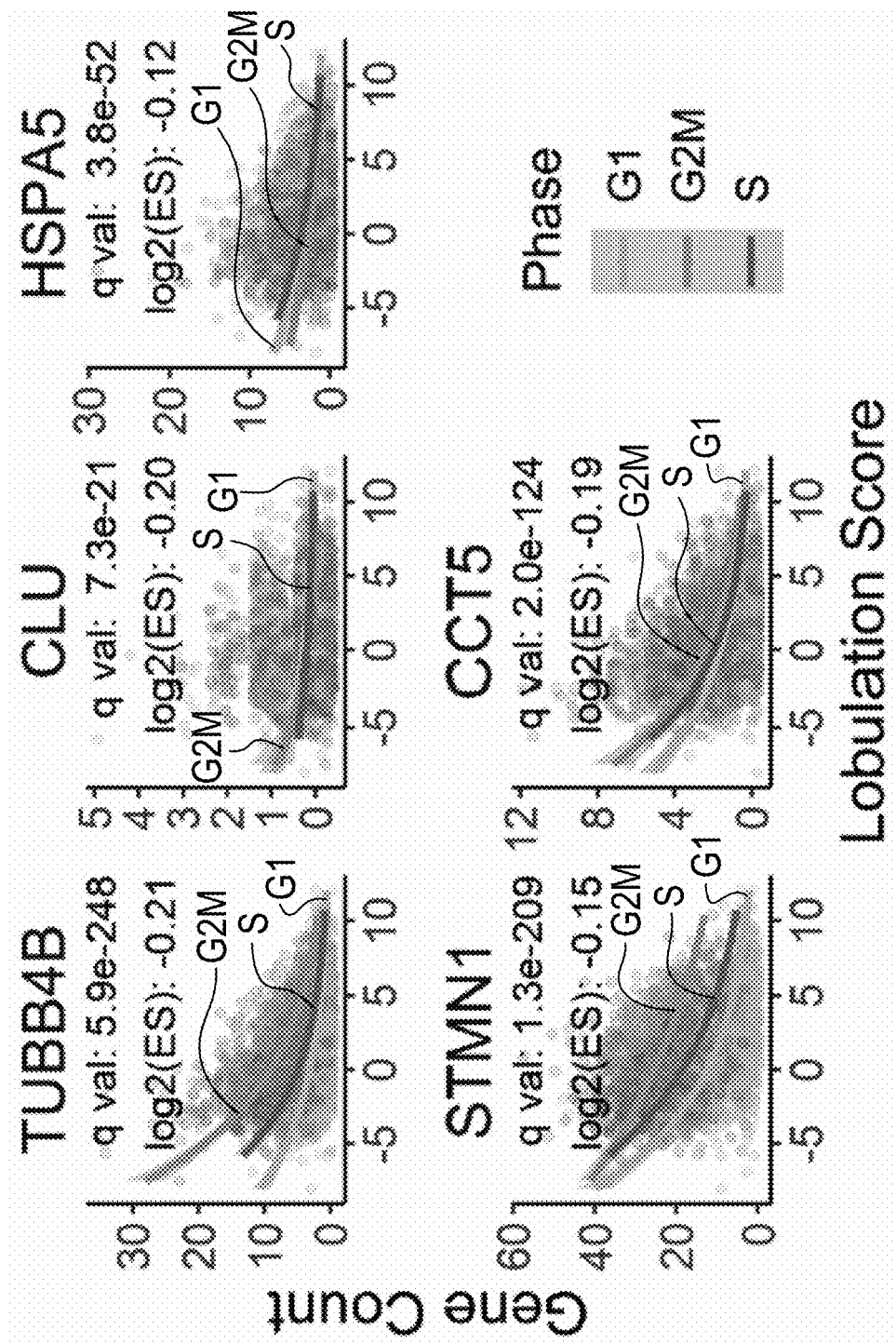
Figure 12B:
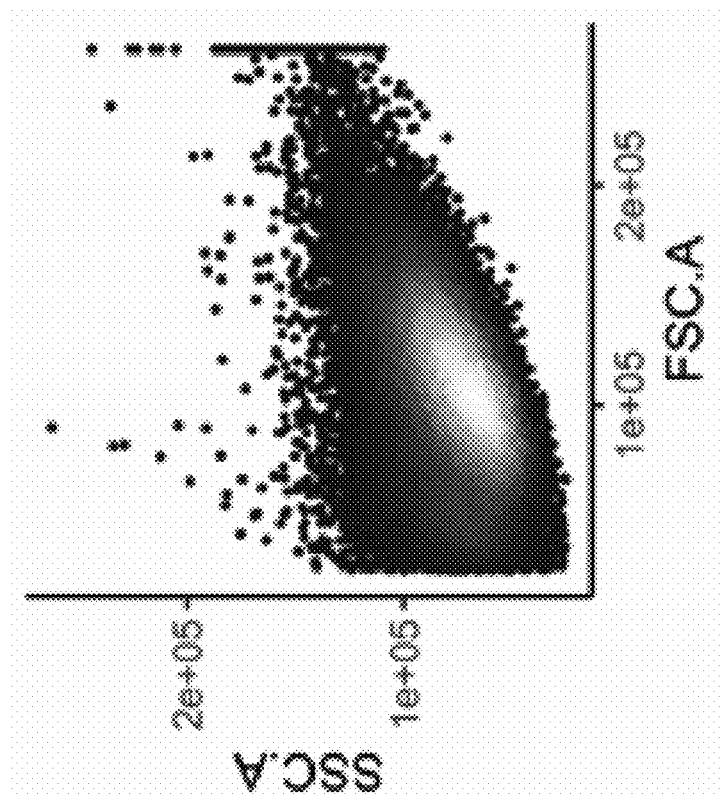
Figure 12A:
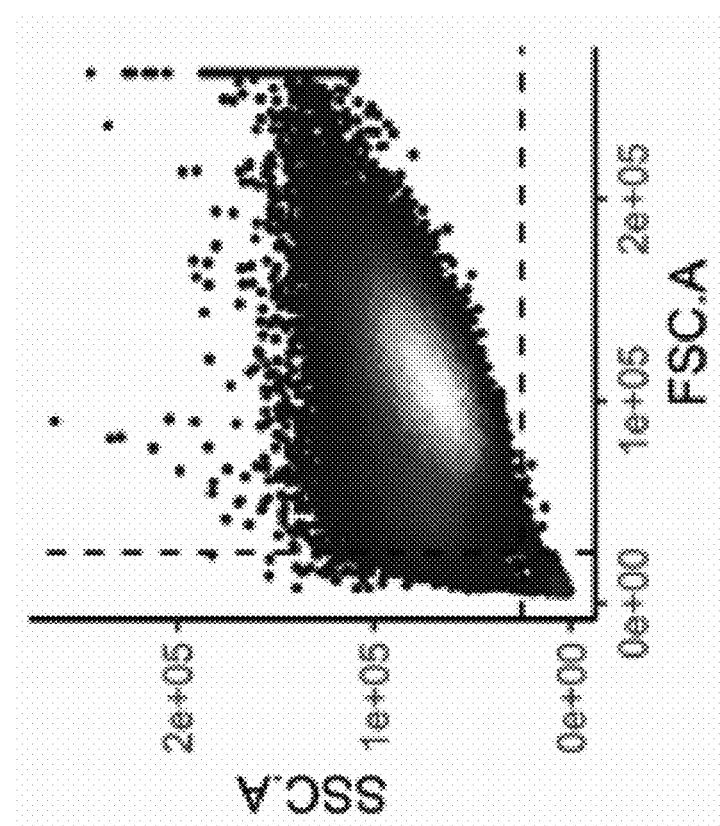
Figure 12D:
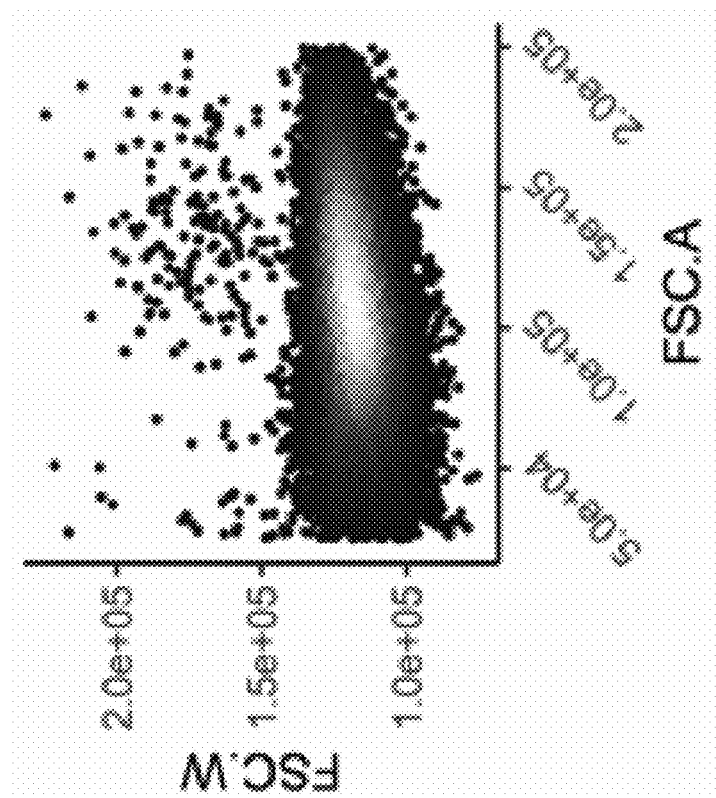
Figure 12C:
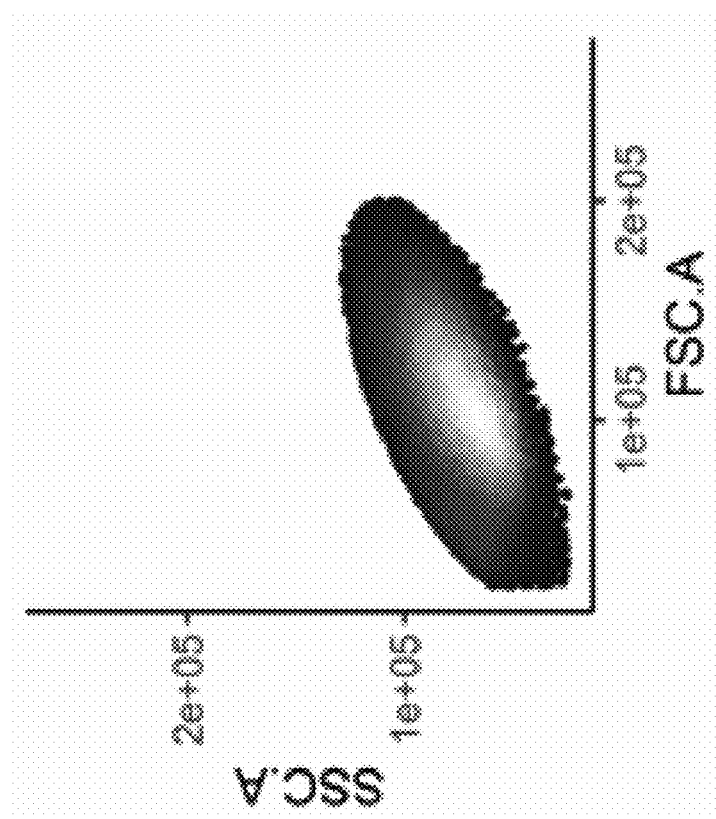
Figure 12F:
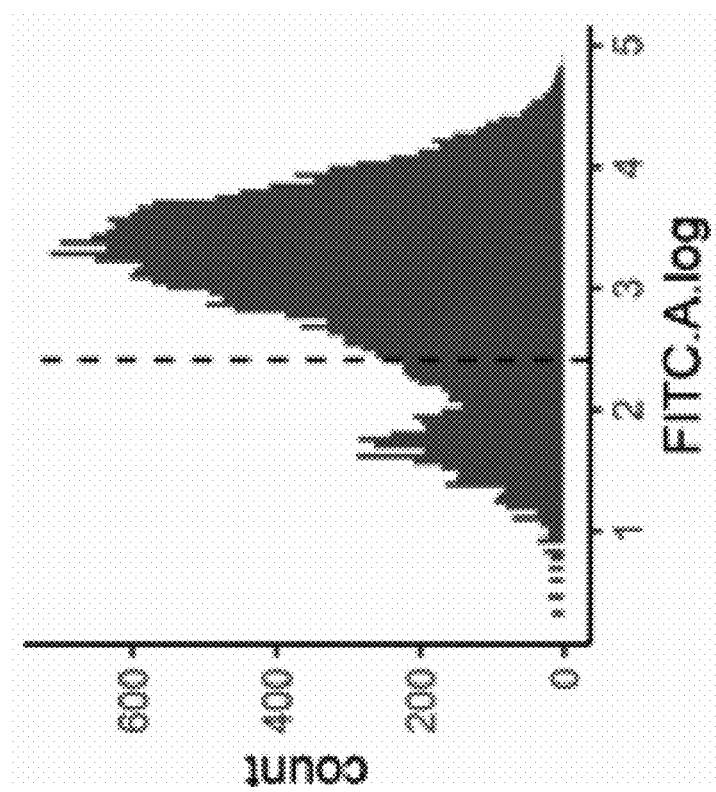
Figure 12E:
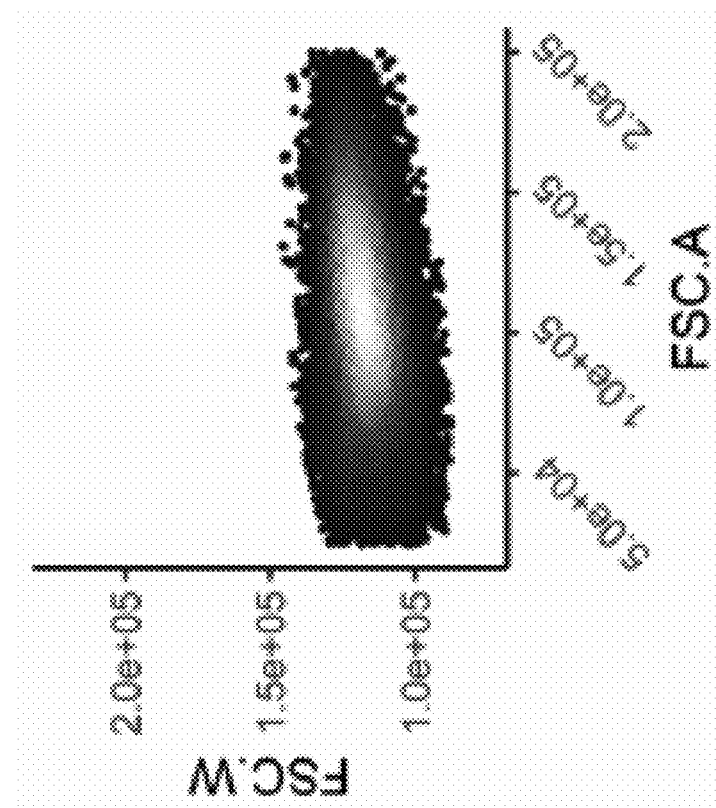
Figure 13B:
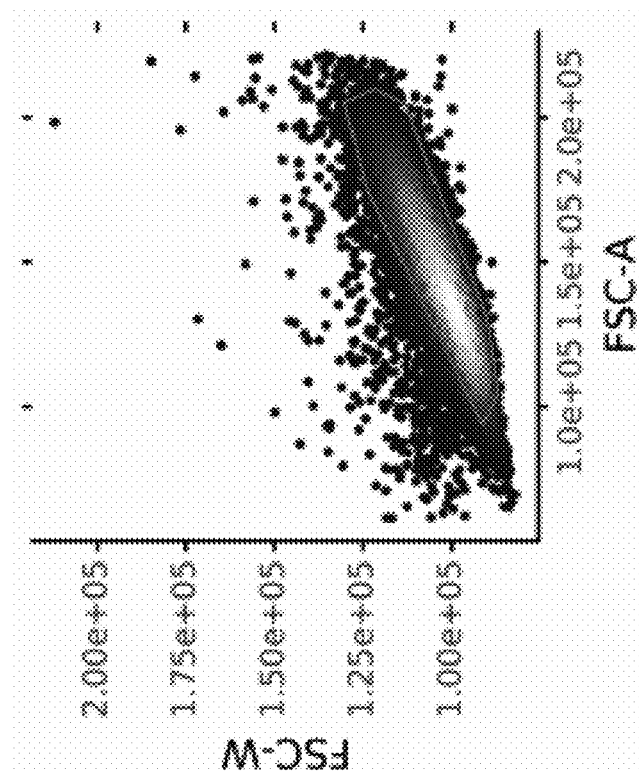
Figure 13A:
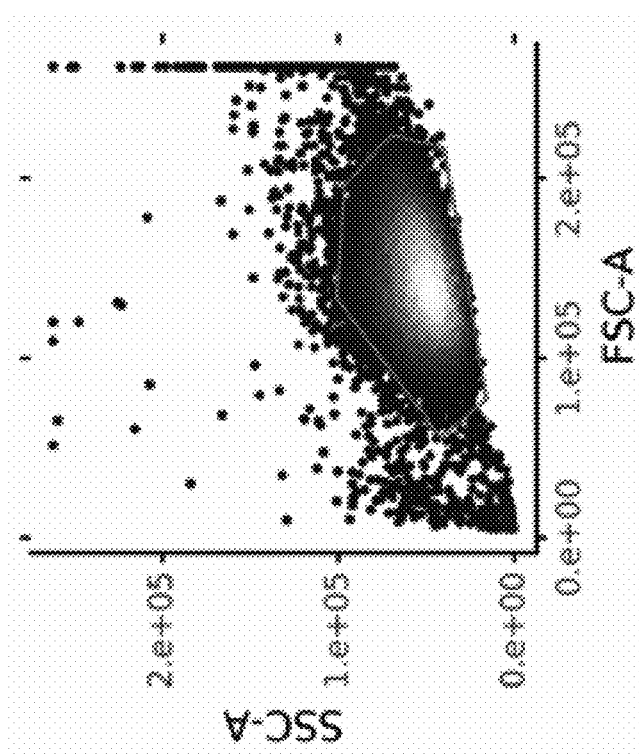
Figure 13D:
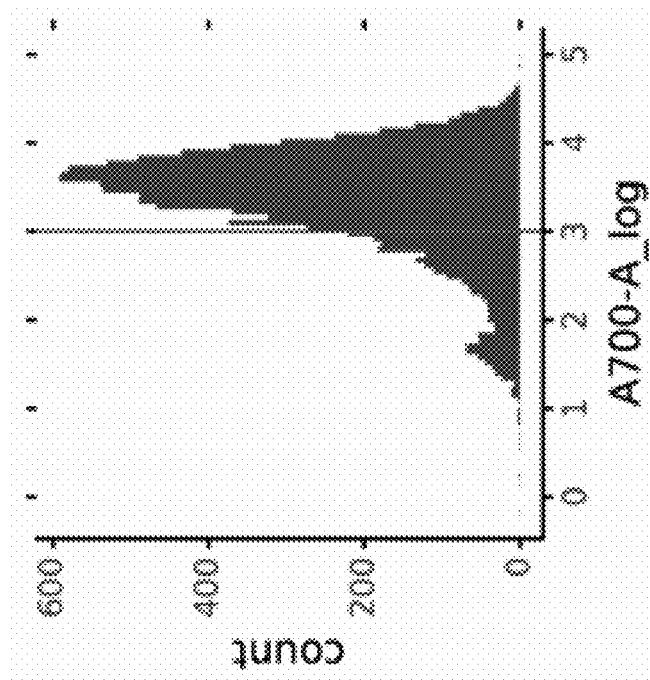
Figure 13C:
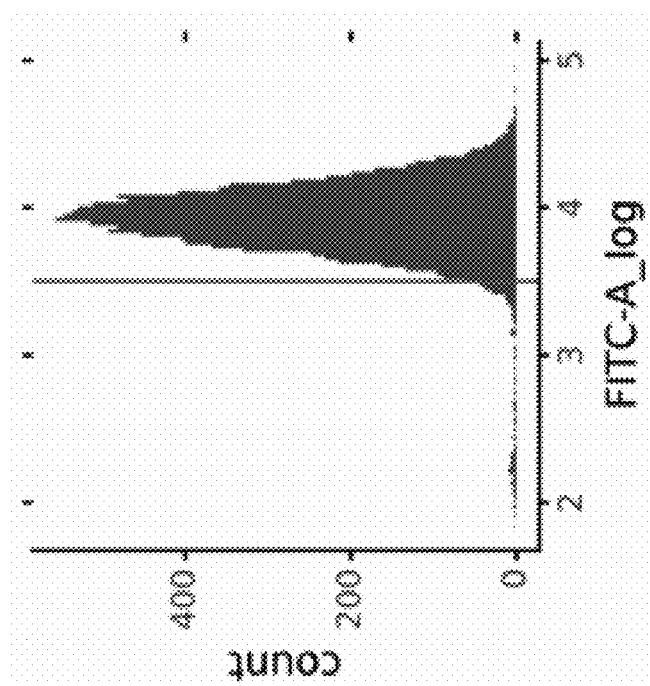
Figure 13E:
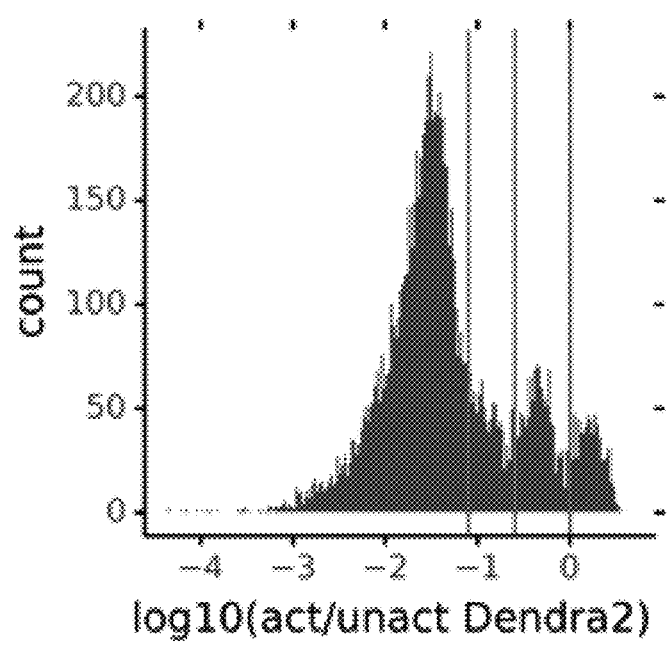
Figure 14A:
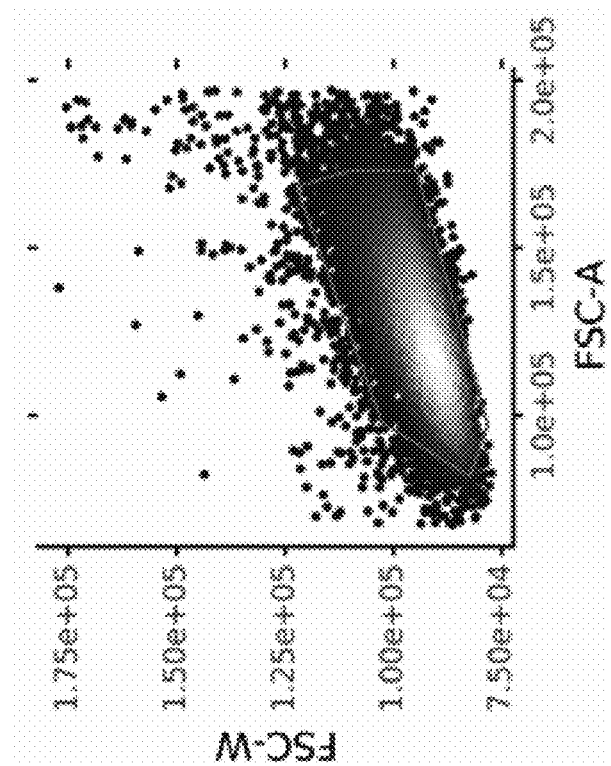
Figure 14B:
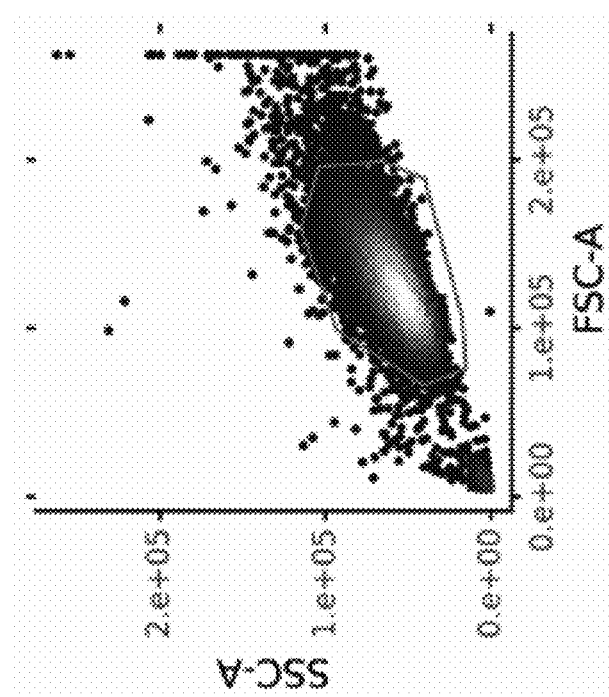
Figure 14D:
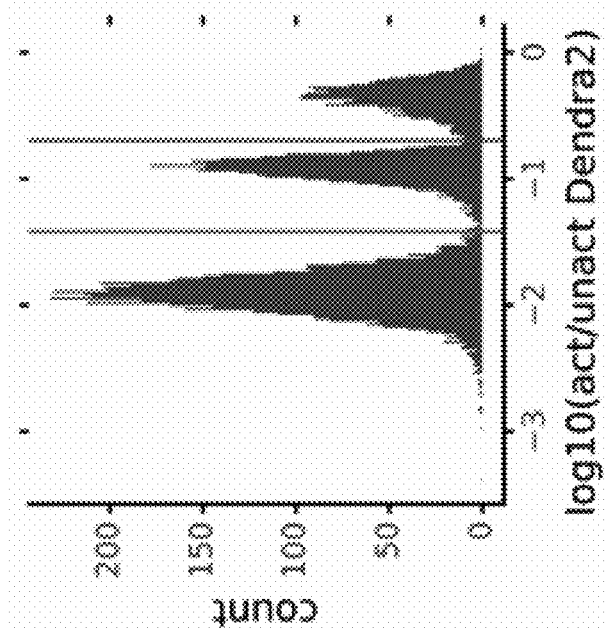
Figure 14C:
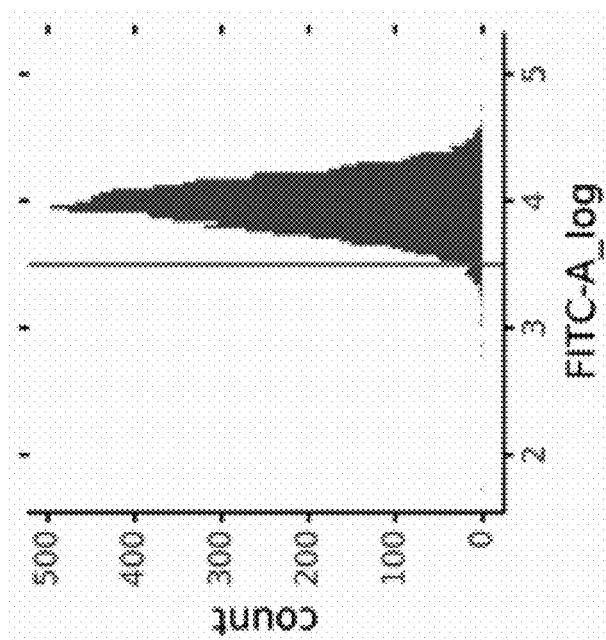

In total, 765 genes were significantly associated with the lobulation score (adjusted p-value <0.01; FIG. 11E). Surprisingly, the vast majority (84%) of these genes were more highly expressed by morphologically normal cells. Morphologically normal cells upregulated the genes encoding actin and microtubules (e.g. ACTB, TUBB4B; FIGS. 4E and 11F), a well-documented response to microtubule damage and paclitaxel treatment (Gasic I, et al. (2019) Tubulin mRNA stability is sensitive to change in microtubule dynamics caused by multiple physiological and toxic cues. *PLoS Biol.* 17: e3000225). It was also noted that these cells upregulated the chaperone clusterin (CLU) and its co-activator HSPA5, which together decrease paclitaxel-mediated apoptosis by stabilizing mitochondrial membrane potential (Li N, et al. (2013) GRP78 regulates clusterin stability, retrotranslocation and mitochondrial localization under ER stress in prostate cancer. *Oncogene* 32: 1933-1942). Intrigued by the notion that morphologically normal cells are resisting the effects of paclitaxel, the literature was searched for other genes upregulated in these cells and found that many of them, including PRMT1 (Cho J H, Lee M K, Yoon K W, Lee J, Cho S G & Choi E J (2012) Arginine methylation-dependent regulation of ASK1 signaling by PRMT1. Cell Death Differ. 19: 859-870), ENO1 (Georges E, et al. (2011) RNAi-mediated knockdown of α-enolase increases the sensitivity of tumor cells to antitubulin chemotherapeutics. *Int. J. Biochem. Mol. Biol.* 2: 303-308), STMN1 Alli E, et al. (2007) Reversal of stathmin-mediated resistance to paclitaxel and vinblastine in human breast carcinoma cells. *Mol. Pharmacol.* 71: 1233-1240), LDHA (Zhou M, et al. (2010) Warburg effect in chemosensitivity: Targeting lactate dehydrogenase-A re-sensitizes Taxol-resistant cancer cells to Taxol. *Mol. Cancer* 9: 1-12), ANXA5 (Di Michele M, et al. (2009) A proteomic approach to paclitaxel chemoresistance in ovarian cancer cell lines. *Biochim. Biophys. Acta—Proteins Proteomics* 1794: 225-236), and HSPA8 (Sugimura M, et al. (2004) Mechanisms of paclitaxel-induced apoptosis in an ovarian cancer cell line and its paclitaxel-resistant clone. Oncology 66: 53-61), are associated with paclitaxel resistance in diverse cancers.

Figure 4F:
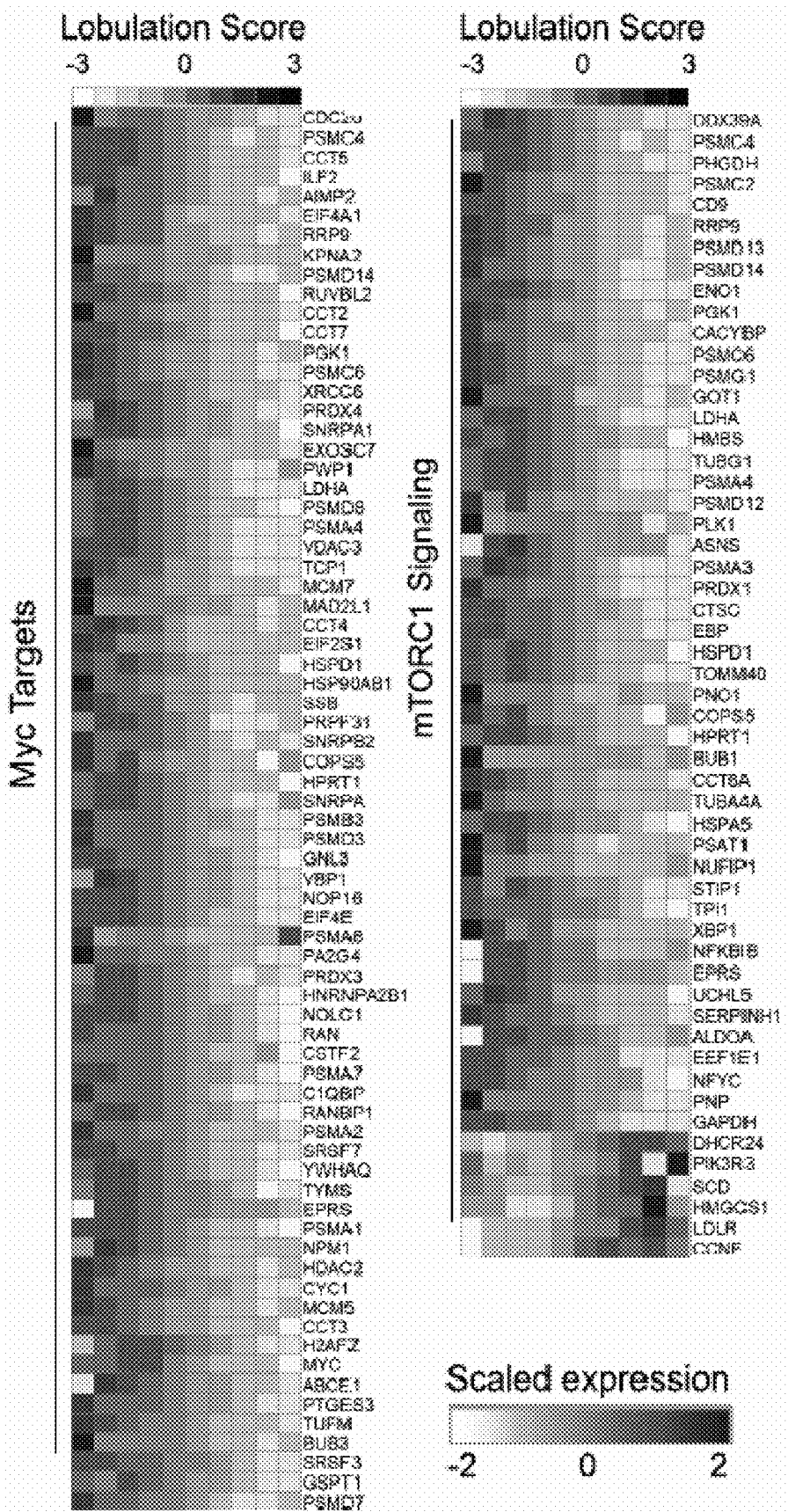

To better understand the gene expression program associated with normal nuclear morphology in the context of paclitaxel treatment, enrichment of genes in previously defined gene sets (Liberzon A, et al. (2015) The Molecular Signatures Database Hallmark Gene Set Collection. *Cell Syst.* 1: 417-425) covering a host of cellular processes was examined. Morphologically normal cells upregulated 7 out of 8 proteins in the chaperonin containing TCP-1 complex (adjusted p value=7.64e-15; FIG. 4E), which is critical for tubulin folding and has been previously associated with paclitaxel resistance in ovarian cancer (Di Michele M, et al. (2009) A proteomic approach to paclitaxel chemoresistance in ovarian cancer cell lines. *Biochim. Biophys. Acta—Proteins Proteomics* 1794: 225-236). Morphologically normal cells also upregulated the transcriptional targets of two paclitaxel resistance-associated signaling pathways (Parasido E, et al. (2019) The Sustained Induction of c-MYC Drives Nab-Paclitaxel Resistance in Primary Pancreatic Ductal Carcinoma Cells. *Mol. Cancer Res.* 17: 1815-1827; Shafer A, et al. (2010) Rapamycin potentiates the effects of paclitaxel in endometrial cancer cells through inhibition of cell proliferation and induction of apoptosis. *Int. J. Cancer* 126: 1144-1154): c-Myc (adjusted p value=1.66e-30) and mTORC1 (adjusted p value=6.19e-17; FIG. 4F). Together, these results indicate that the morphologically normal, paclitaxel-treated cells exhibit a biosynthetic and proteostatic gene expression program, with remarkable similarities to the gene expression profiles observed in paclitaxel resistant cell lines and cancers.

Discussion

A major limitation of current microscopy-based experiments is the inability to isolate hundreds of thousands of phenotypically defined cells for further analysis. Visual Cell Sorting, a microscope-based method that directs a digital micromirror device to irreversibly photoactivate a genetically encoded fluorescent protein in cells of interest, was developed to effectively translate a complex visual phenotype into one that can be sorted by FACS.

To highlight the Visual Cell Sorting's flexibility, two distinct experiments were performed. First, the high throughput was leveraged to quantify the function of hundreds of nuclear localization sequence variants in a pooled, image-based genetic screen. By combining single variants that individually improved NLS function, an eight-residue superNLS (EPPRKKRKIGI (SEQ ID NO:1)) was created that could be used to improve CRISPR-mediated genome editing, fluorescent protein-based nuclear labelling, and other experiments that leverage nuclear recombinant proteins. The variant scores were then used to make an accurate, amino acid preference-based predictor of NLS function, which was applied to the human nuclear proteome and validated by comparing the top-scoring sequences between cytoplasmic and nuclear proteins. Interestingly, some cytoplasmic proteins contain putative NLS's, which could be explained by an NLS that becomes accessible to the nuclear import machinery after a signaling event or a nuclear export signal located on the same protein that overwhelms an otherwise functional NLS. Nuclear proteins without high-scoring sequences may harbor a non-SV40 type NLS or have an interaction partner with a functional NLS enables co-import into the nucleus.

In a second application, Visual Cell Sorting's ability to recover live, phenotypically defined subsets of cells was leveraged to investigate the heterogenous cellular response to paclitaxel treatment using single cell RNA sequencing. Surprisingly, cells that resist the effect of paclitaxel on nuclear morphology appear to be counteracting the drug's effects at the molecular level with a gene expression program similar to paclitaxel-resistant cancers. This phenomenon, whereby a subset of clonal cells resists the effects of drug treatment with a protective gene expression program, is reminiscent of the "pre-resistance" reported in primary melanoma cells. However, the experiment conducted here cannot determine whether this gene expression program pre-exists in the population or is stochastically induced upon paclitaxel addition. To answer this question, live-cell microscopy or cell barcoding could be used to determine whether pre-treatment levels of the genes expressed highly in morphologically normal cells (e.g. TUBB4B expression, c-Myc targets) leads to morphologic responses and survival after paclitaxel treatment.

High throughput is a key advantage of Visual Cell Sorting, compared to other similar methods. In the disclosed pooled image-based screen, approximately one million cultured human cells were analyzed across 60 hours of imaging and sorting time, ultimately recovering 650,000. This throughput is ~1,000-fold more than what could be achieved using other photoconvertible fluorophore-based methods, ~20-fold more than current MERFISH pooled screens, and similar in per-day throughput to in situ sequencing-based screens. Thus, Visual Cell Sorting enables the analysis of thousands of genetic variants in a single experiment. Visual Cell Sorting throughput could be increased even further by analyzing cellular phenotypes at a lower magnification, by applying faster image analysis algorithms, or by shutting off Dendra2 expression before imaging to extend imaging time (FIG. 8B).

A second key advantage of Visual Cell Sorting is that it does not require any expensive dye-based reagents such as oligo libraries or fluorescent-labelled oligos; customized hardware components; or complex workflows. Outfitting an automated wide-field microscope requires just three inexpensive, commercially available components: a live cell incubation chamber, a digital micromirror device, and a 405 nm laser. Finally, Visual Cell Sorting enables recovery of cells with up to four distinct phenotypes in one experiment, unlike other photoconvertible fluorophore-based methods.

Visual Cell Sorting has important requirements. Cells must be genetically engineered to express the fluorophore (e.g., Dendra2, which is photoactivated by blue fluorescent protein (BFP) excitation wavelengths and emits at GFP and RFP wavelengths). This requirement limits the other fluorescent channels are available for imaging. However, miRFP (Shcherbakova et al, 2016, Bright monomeric near-infrared fluorescent proteins as tags and biosensors for multiscale imaging. Nat Commun 7: 1-12) and mBeRFP (Yang et al, 2013, mBeRFP, an Improved Large Stokes Shift Red Fluorescent Protein. PLoS One 8:6-11) can be used in conjunction with Dendra2, allowing two additional compartments or proteins to be marked in each experiment. Moreover, new analytical approaches leveraging brightfield images may reduce the need for fluorescent markers. Another requirement is that, unlike morphological profiling approaches, Visual Cell Sorting requires a pre-defined phenotype of interest and may be limited by FACS hardware to a number (e.g., 4) phenotypic bins. Finally, Visual Cell Sorting experiments are limited to approximately twelve hours to avoid Dendra2 activation signal decay or cell overgrowth. The several hours required to execute a Visual Cell Sorting experiment makes it challenging to study transient phenotypes (e.g. cell-cycle dependent phenotypes). Furthermore, decay of photoactivated Dendra2 may be more pronounced in rapidly dividing bacterial or yeast as activated Dendra2 is diluted by cell division. However, the workflow presented here, with imaging at 20× magnification and image processing times of 3-8 seconds, is sufficient for the analysis of hundreds of thousands of human cells in one experiment.

In summary, Visual Cell Sorting is a robust and flexible method that can be used to separate heterogeneous cultures of cells into up to four morphologically defined subpopulations. The components required for Visual Cell Sorting are already in widespread use, are commercially available and can be adapted to most modern automated widefield fluorescent microscopes. The method will improve in scope and speed as further advances are made in cell segmentation and image analysis. It is demonstrated that Visual Cell Sorting can be used for both image-based pooled genetic screens and image-based transcriptomics experiments. This flexibility should drive the application of Visual Cell Sorting to a wide range of biological problems in diverse fields of research that seek to dissect cellular heterogeneity, including stem cell biology, functional genomics, and cellular pharmacology.

Methods and Materials

TABLE 2

Reagents and Tools

| Reagent/Resource | Source | Identifier or Catalog Number |
|---|---|---|
| Experimental Models | | |
| U-2 OS cells | ATCC | HTB-96 |
| hTERT RPE-1 cells | ATCC | CRL-4000 |
| HEK 293T cells | ATCC | CRL-3216 |
| Recombinant DNA | | |
| Dendra2-Lifeact7 | Addgene | 54694 |
| mEmerald-H3-23 | Addgene | 54115 |
| pH2B-miRFP703 | Addgene | 80001 |

TABLE 2-continued

Reagents and Tools

| Reagent/Resource | Source | Identifier or Catalog Number |
|---|---|---|
| psPAX2 | Addgene | 12260 |
| pMD.2 | Addgene | 12259 |
| pLenti CMV rtTA3 Blast | Addgene | 26429 |
| Other constructs, gBlocks, etc. | This study | Table 3 |
| Antibodies | | |
| None | NA | NA |
| Oligonucleotides and sequence-based reagents | | |
| PCR primers | This study | Table 3 |
| Chemicals, enzymes and other reagents | | |
| KAPA Hifi 2x polymerase | Kapa Biosystems | KK2601 |
| Dulbecco's modified Eage's medium (DMEM) | ThermoFisher | 11965118 |
| DMEM, no phenol red | ThermoFisher | 21063045 |
| DMEM/F12 | ThermoFisher | 11320033 |
| DMEM/F12, no phenol red | ThermoFisher | 21041025 |
| Doxycycline | Sigma | D9891 |
| Trypsin-EDTA 0.25% | ThermoFisher | 25200056 |
| OPTIMEM | Fisher Scientific | 31985070 |
| FuGENE6 | Promega | E2691 |
| 2X Gibson Assembly Master Mix | NEB | E2611L |
| DpnI | NEB | R0176L |
| DNA Clean & Concentrator | Zymo Research | D4013 |
| GenElute HP Plasmid DNA Midiprep Kit | Sigma | NA0200-1KT |
| PEG-it Virus Precipitation Solution | SBI | LV810A-1 |
| Lipofectamine 3000 | ThermoFisher | L3000015 |
| Software | | |
| Metamorph (v7.10.1.161) | Molecular Devices | |
| Other | | |
| LeicaDMi8 with Adaptive Focus | Leica | |
| Incubation i8 chamber | Leica | |
| TempController 2000-1 | PeCon | |
| CO2 regulator | Oko | |
| Spectra X Light Engine LED | Lumencor | |
| Multi-band dichroic filter | Spectra Services | LED-DA-FI-TR-Cy5-4X-A-000 |
| Multi-band dichroic filter | Spectra Services | LED-CFP/YFP/mCherry-3X-A-000 |
| Brightline bandpass filter (DAPI) | Semrock | FF01-433/24-25 |
| Brightline bandpass filter (GFP) | Semrock | FF01-520/35-25 |
| Brightline bandpass filter (RFP) | Semrock | FF01-600/37-25 |
| Brightline bandpass filter (NIR) | Semrock | FF01-680/42-25 |
| 20X 0.8 NA apochromatic objective | Leica | |
| Mosaic 3 Digital Micromirror Device | Andor | |
| Mosaic SS 405/1.1 W laser | Andor | |
| iXon Ultra 888 EMCCD monochrome camera | Andor | |
| Glass bottom black-walled plates | CellVis | P06-1.5H-N |
| LSR-II | BD Biosciences | |
| FACS Aria III | BD Biosciences | |

Methods and Protocols

General Reagents, DNA Oligonucleotides and Plasmids

Unless otherwise noted, all chemicals were obtained from Sigma and all enzymes were obtained from New England Biolabs (Ipswich, MA). KAPA Hifi 2× Polymerase (Kapa Biosystems; Wilmington, USA; cat. no. KK2601) was used for all cloning and library production steps. E. coli were cultured at 37° C. in Luria broth. All cell culture reagents were purchased from ThermoFisher Scientific (Waltham, MA) unless otherwise noted. HEK 293T cells (ATCC; Manassas, VA; CRL-3216) and U-2 OS cells (ATCC HTB-96), and derivatives thereof were cultured in Dulbecco's modified Eagle's medium supplemented with 10% fetal bovine serum, 100 U/mL penicillin, 0.1 mg/mL streptomycin, and 1 ug/mL doxycycline (Sigma; St. Louis, MO), unless otherwise noted. hTERT RPE-1 cells (ATCC CRL-4000) and derivatives thereof were cultured in F12/DMEM supplemented with 10% FBS, 1 mM PenStrep, and 0.01 mg/mL hygromycin B. For Visual Cell Sorting experiments, DMEM without phenol red was used to reduce background fluorescence. Cells were passaged by detachment with trypsin-EDTA 0.25%. All cell lines tested negative for mycoplasma in monthly tests. All synthetic oligonucleotides were obtained from IDT and their sequence reference identifiers can be found in Table 3. All non-library-related plasmid modifications were performed with Gibson assembly. See the Appendix and Table 3 for construction of the vectors used.

TABLE 3

Primer and plasmid sequence identifiers.

| Type | Name | SEQ ID NO: | Purpose | Notes |
|---|---|---|---|---|
| Primer | pNH042_SV40NLS_f_2 | 2 | SV40 NLS Library creation with Gibson | |
| Primer | pNH042_SV40NLS_f_3 | 3 | SV40 NLS Library creation with Gibson | |
| Primer | pNH042_SV40NLS_f_4 | 4 | SV40 NLS Library creation with Gibson | |
| Primer | pNH042_SV40NLS_f_5 | 5 | SV40 NLS Library creation with Gibson | |
| Primer | pNH042_SV40NLS_f_6 | 6 | SV40 NLS Library creation with Gibson | |
| Primer | pNH042_SV40NLS_f_7 | 7 | SV40 NLS Library creation with Gibson | |
| Primer | pNH042_SV40NLS_f_8 | 8 | SV40 NLS Library creation with Gibson | |
| Primer | pNH042_SV40NLS_f_9 | 9 | SV40 NLS Library creation with Gibson | |
| Primer | pNH042_SV40NLS_f_10 | 10 | SV40 NLS Library creation with Gibson | |
| Primer | pNH042_SV40NLS_f_11 | 11 | SV40 NLS Library creation with Gibson | |
| Primer | pNH042_SV40NLS_f_12 | 12 | SV40 NLS Library creation with Gibson | |
| Primer | pNH042_SV40NLS_r_2 | 13 | SV40 NLS Library creation with Gibson | |
| Primer | pNH042_SV40NLS_r_3 | 14 | SV40 NLS Library creation with Gibson | |
| Primer | pNH042_SV40NLS_r_4 | 15 | SV40 NLS Library creation with Gibson | |
| Primer | pNH042_SV40NLS_r_5 | 16 | SV40 NLS Library creation with Gibson | |
| Primer | pNH042_SV40NLS_r_6 | 17 | SV40 NLS Library creation with Gibson | |
| Primer | pNH042_SV40NLS_r_7 | 18 | SV40 NLS Library creation with Gibson | |
| Primer | pNH042_SV40NLS_r_8 | 19 | SV40 NLS Library creation with Gibson | |
| Primer | pNH042_SV4ONLS_r_9 | 20 | SV40 NLS Library creation with Gibson | |
| Primer | pNH042_SV40NLS_r_10 | 21 | SV40 NLS Library creation with Gibson | |
| Primer | pNH042_SV40NLS_r_11 | 22 | SV40 NLS Library creation with Gibson | |
| Primer | pNH042_SV40NLS_r_12 | 23 | SV40 NLS Library creation with Gibson | |
| Primer | SV40_NLS_seq_F | 24 | Amplify NLS library from gDNA | |
| Primer | SV40_NLS_seq_R | 25 | Amplify NLS library from gDNA | |
| Primer | P5(short) | 26 | | |
| Primer | Reverse Index example | 27 | Index samples for sequencing | |
| Primer | SV40_NLS_Read1 | 28 | Read NLS fwd | |
| Primer | SV40_NLS_Read2 | 29 | Read NLS rev | |
| Primer | SV40_NLS_Index1 | 30 | | |
| Plasmid | attB_H3-Dendra2 | 31 | Recombination plasmid to express H3-Dendra2 in U2OS landing pad cells | pNH_039, Clone 3 (C3) sequence-confirmed |
| Primer | NH_213 | 32 | Amplify Dendra2 for attB_H3-Dendra2 | |
| Primer | NH_145 | 33 | Amplify Dendra2 for attB_H3-Dendra2 | |
| Primer | NH_223 | 34 | Amplify H3 for attB_H3-Dendra2 | |
| Primer | NH_212 | 35 | Amplify H3 for attB_H3-Dendra2 | |
| Primer | NH_105 | 36 | Amplify attB backbone for attB_H3-Dendra2 | |
| Primer | NH_116 | 37 | Amplify attB backbone for attB_H3-Dendra2 | |

TABLE 3-continued

Primer and plasmid sequence identifiers.

| Type | Name | SEQ ID NO: | Purpose | Notes |
|---|---|---|---|---|
| Plasmid | attB_H3-Dendra2-P2A-H2B-miRFP | 38 | Recombination plasmid to express H3-Dendra2 and H2B-miRFP in U2OS landing pad cells | pNH_054, Clone 1 (C1) sequence-confirmed |
| Primer | NH_243 | 39 | Amplify H2B-miRFP for attB_H3-Dendra2-P2A-H2B-miRFP | |
| Primer | NH_241 | 40 | Amplify H2B-miRFP for attB_H3-Dendra2-P2A-H2B-miRFP | |
| Primer | NH_116 | 41 | Amplify backbone for attB_H3-Dendra2-P2A-H2B-miRFP | |
| Primer | NH_242 | 42 | Amplify backbone for attB_H3-Dendra2-P2A-H2B-miRFP | |
| Plasmid | pLenti_CMV H3-Dendra2 | 43 | Introduce H3-Dendra2 into U2OS cells expressing the landing pad | pNH_046 Clone 8-2 (C8_2) sequence-confirmed |
| Primer | NH_248 | 44 | Amplify backbone for pLenti_CMV_H3 | |
| Primer | NH_245 | 45 | Amplify backbone for pLenti_CMV_H3 | |
| Primer | NH_246 | 46 | Amplify H3-Dendra2 for pLenti_CMV_H3 | |
| Primer | NH_247 | 47 | Amplify H3-Dendra2 for pLenti_CMV_H3 | |
| Plasmid | attB_Nterm-CMPK-miRFP | 48 | Destination for single variants of the SV40 NLS library | pNH_062 Clone 2 (C2) sequence confirm3ed |
| gBlock | gNH002 | 49 | CMPK fragment | |
| Primer | NH_178 | 50 | Amplify gNH002 gblock for attB_Nterm-CMPK-miRFP_IRES_Dendra2 | |
| Primer | NH_236 | 51 | Amplify gNH002 gblock for attB_Nterm-CMPK-miRFP_IRES_Dendra2 | |
| Primer | NH_235 | 52 | Amplify miRFP for attB_Nterm-CMPK-miRFP_IRES_Dendra2 | |
| Primer | NH_193 | 53 | Amplify miRFP for attB_Nterm-CMPK-miRFP_IRES_Dendra2 | |
| Primer | NH_116 | 54 | Amplify backbone for attB_Nterm-CMPK-miRFP_IRES_Dendra2 | |
| Primer | NH_182 | 55 | Amplify backbone for attB_Nterm-CMPK-miRFP_IRES_Dendra2 | |
| Plasmid | attB-NLS-CMPK-miRFP | 56 | Wild-type NLS construct | pNH_063 Clone 1 (Cl) sequence-confirmed |
| Oligo | SV40-NLS-Oligo | 57 | Create SV40 Wild-type construct | Digest attB_Nterm-CMPK-miRFP with EcoRI + Gibson with oligo |
| Oligo | A2I_SV40-NLS-Oligo | 58 | Create SV40 variant | Digest attB_Nterm-CMPK-miRFP with EcoRI + Gibson with oligo |
| Oligo | A2P_SV40_NLS-Oligo | 59 | Create SV40 variant | Digest attB_Nterm-CMPK-miRFP with EcoRI + Gibson with oligo |
| Oligo | A2P-K4R_SV40_NLS-Oligo | 60 | Create SV40 variant | Digest attB_Nterm-CMPK-miRFP with EcoRI + Gibson with oligo |
| Oligo | A2P-K4R-V91_SV40_NLS-Oligo | 61 | Create SV40 variant | Digest attB_Nterm-CMPK-miRFP with EcoRI + Gibson with oligo |
| Oligo | A2P-V9I_SV40_NLS-Oligo | 62 | Create SV40 variant | Digest attB_Nterm-CMPK-miRFP with EcoRI + Gibson with oligo |
| Oligo | E1I_SV40_NLS-Oligo | 63 | Create SV40 variant | Digest attB_Nterm-CMPK-miRFP with EcoRI + Gibson with oligo |

TABLE 3-continued

Primer and plasmid sequence identifiers.

| Type | Name | SEQ ID NO: | Purpose | Notes |
|---|---|---|---|---|
| Oligo | 11WI_SV40_NLS-Oligo | 64 | Create SV40 variant | Digest attB_Nterm-CMPK-miRFP with EcoRI + Gibson with oligo |
| Oligo | K4G_SV40_NLS-Oligo | 65 | Create SV40 variant | Digest attB_Nterm-CMPK-miRFP with EcoRI + Gibson with oligo |
| Oligo | K4R_SV40_NLS-Oligo | 66 | Create SV40 variant | Digest attB_Nterm-CMPK-miRFP with EcoRI + Gibson with oligo |
| Oligo | K6V_SV40_NLS-Oligo | 67 | Create SV40 variant | Digest attB_Nterm-CMPK-miRFP with EcoRI + Gibson with oligo |
| Oligo | R7V_SV40_NLS-Oligo | 68 | Create SV40 variant | Digest attB_Nterm-CMPK-miRFP with EcoRI + Gibson with oligo |
| Plasmid | attB_NLS-Dendra2x3 | 69 | Intermediate to make pLenti-CMV-NLS-Dendra2x3-P2A-H2B-miRFP | pNH_041, Clone 12 (C12) sequence-confirmed |
| Primer | NH_226 | 70 | Amplify backbone for attB_NLS-Dendra2x3 | |
| Primer | NH_105 | 71 | Amplify backbone for attB_NLS-Dendra2x3 | |
| Primer | NH_225 | 72 | Amplify Dendra2, ORF1 for attB_NLS-Dendra2x3 | |
| Primer | NH_228 | 73 | Amplify Dendra2, ORF1 for attB_NLS-Dendra2x3 | |
| Primer | NH_227 | 74 | Amplify Dendra2, ORF2 for attB_NLS-Dendra2x3 | |
| Primer | NH_230 | 75 | Amplify Dendra2, ORF2 for attB_NLS-Dendra2x3 | |
| Primer | NH_229 | 76 | Amplify Dendra2, ORF3 for attB_NLS-Dendra2x3 | |
| Primer | NH_145 | 77 | Amplify Dendra2, ORF3 for attB_NLS-Dendra2x3 | |
| Plasmid | attB_NLS-Dendra2x3-P2A-H2BmiRFP703 | 78 | Intermediate to make pLenti-CMV-NLS-Dendra2x3-P2A-H2B-miRFP | pNH_045, Clone 2 (C2) sequence-confirmed |
| Primer | NH_105 | 79 | Amplify backbone and Dendra2 for attB_NLS-Dendra2x3-P2A-H2BmiRFP703 | |
| Primer | NH_242 | 80 | Amplify backbone and Dendra2 for attB_NLS-Dendra2x3-P2A-H2BmiRFP703 | |
| Primer | NH_241 | 81 | Amplify H2B-miRFP for attB_NLS-Dendra2x3-P2A-H2BmiRFP703 | |
| Primer | NH_243 | 82 | Amplify H2B-miRFP for attB_NLS-Dendra2x3-P2A-H2BmiRFP703 | |
| Plasmid | pLenti-CMV-NLS-Dendra2x3-P2A-H2B-miRFP | 83 | For creating Dendra2-expressing RPE-I cells | pNH_058 Clone 1 (C1) sequence confirmed |
| Primer | NH_253 | 84 | Amplify backbone for pLenti-CMV-NLS-Dendra2x3-P2A-H2B-miRFP | |
| Primer | NH_245 | 85 | Amplify backbone for pLenti-CMV-NLS-Dendra2x3-P2A-H2B-miRFP | |
| Primer | NH_249 | 86 | Amplify Dendra2x3 insert for pLenti-CMV-NLS-Dendra2x3-P2A-H2B-miRFP | |
| Primer | NH_292 | 87 | Amplify Dendra2x3 insert for pLenti-CMV-NLS-Dendra2x3-P2A-H2B-miRFP | |

TABLE 3-continued

Primer and plasmid sequence identifiers.

| Type | Name | SEQ ID NO: | Purpose | Notes |
|---|---|---|---|---|
| Plasmid | pLenti-CMV-mBeRFP-NES | 88 | For creating mBeRFP-NES expressing RPE-I cells | pNH_067 Clone 1 (C1) sequence-confirmed |
| Primer | NH_253 | 89 | Amplify backbone for pLenti-CMV-mBeRFP-NES | |
| Primer | NH_349 | 90 | Amplify backbone for pLenti-CMV-mBeRFP-NES | |
| Primer | NH_350 | 91 | Amplify mBeRFP for pLenti-CMV-mBeRFP-NES | |
| Primer | NH_348 | 92 | Amplify mBeRFP for pLenti-CMV-mBeRFP-NES | |

Construction of the SV40 NLS Library

A site saturation mutagenesis library of the SV40 NLS upstream of a tetramerizing miRFP reporter (attB-NLS-CMPK-miRFP library) was constructed using Gibson cloning (Gibson D G, et al. (2009) Enzymatic assembly of DNA molecules up to several hundred kilobases. Nat. Methods 6: 343-5). See the Appendix, below, for a detailed description of the construction of the site-saturation mutagenesis library.

Cell Lines

U-2 OS cells (ATCC, HTB-96) expressing the Tet-ON Bxb1 landing pad (U-2 OS AAVS-LP Clone 11) were generated as previously described (Matreyek et al, 2017, A platform for functional assessment of large variant libraries in mammalian cells. Nucleic Acids Res 45:e102). To create H3-Dendra2- and H3-Dendra2/H2B-miRFP-expressing derivative cell lines, attB-H3-Dendra2 or attB-H3-Dendra2-P2A-H2B-miRFP703 were recombined into U-2 OS AAVS-LP Clone 11 cells, as previously described (Matreyek et al, 2017, supra). For the NLS work, a separate clonal U-2 OS cell line expressing the Tet-ON landing pad and CMV-H3-Dendra2 was created by co-transduction of parental U-2 OS cells with the LLP-Blast lentivirus (Matreyek et al, 2020, An improved platform for functional assessment of large protein libraries in mammalian cells. Nucleic Acids Res 48: e1) and another expressing histone H3-Dendra2 (U-2 OS LLP-Blast/H3-Dendra2 Clone 4). A clonal hTERT RPE-1 cell line expressing CMV-NL $S_{SV40}$-Dendra2-GS SG-Dendra2-GS SG-Dendra2 (NL S-Dendra2×3); CMV-H2B-miRFP; and CMV-NES-mBeRFP was generated by transduction of a parental line (ATCC, CRL-4000) with three lentiviral vectors followed by single cell sorting (RPE-1 NLS-Dendra2×3/H2B-miRFP/NES-mBeRFP Clone 3). For more information regarding these lines and for the lentiviral production protocol, see the Appendix.

Recombination of Single-Variant SV40 NLS Clones or the Library into U-2 OS LLP-Blast/H3-Dendra2 Clone 4 Cells The SV40 NLS variant library or single-variant clones were recombined into U-2 OS LLP-Blast/H3-Dendra2 Clone 4 cells, as previously described in HEK 293 Ts (Matreyek et al, 2017, supra). Two recombination replicates were performed. For more information, see Appendix.

Visual Cell Sorting: Equipment and Settings

A Lecia DMi8 Inverted Microscope was outfitted with Adaptive Focus; an Incubator i8 chamber with PeCon Temp-Controller 2000-1 and Oko $CO_2$ regulator set to 5%; a 6-line Lumencor Spectra X Light Engine LED; Semrock multi-band dichroic filters (Spectra Services, Ontario, NY; cat. no. LED-DA-FI-TR-Cy5-4X-A-000, LED-CFP/YFP/mCherry-3X-A-000); BrightLine bandpass emissions filters for DAPI (433/24 nm), GFP (520/35 nm), RFP (600/37 nm), and NIR (680/22 nm); a 20×0.8 NA apochromatic objective; and a Mosaic3 Digital Micromirror Device affixed to a Mosaic SS 405 nm/1.1 W laser and mapped to an Ixon 888 Ultra EMCCD monochrome camera. The microscope and digital micromirror device were controlled with the Metamorph Advanced Image Acquisition software package (v7.10.1.161; Molecular Devices, San Jose, CA). The image size was ~560×495 µm. Image bit depth ranged from 12-16 bits, depending on the brightness of cells in the field of view.

Cells were plated and imaged on glass-bottom, black-walled plates (CellVis, Mountain View, CA; P06-1.5H-N, P24-1.5H-N, P96-1.5H-N) in phenol-red free media at 5% $CO_2$ and 37° C. using the 20×0.8 NA objective. ~50-100 cells were imaged per field of view. To image unactivated Dendra2, 474/24 nm excitation and 482/25 nm emission filters were used. To image activated Dendra2, 554/23 nm excitation and 600/37 nm emission filters were used. To image miRFP, 635/18 nm excitation and 680/22 nm emission filters were used. Prior to imaging, the Auto Focus Control system was activated. Metamorph's Plate Acquisition module was used to collect images and run Metamorph journals that analyzed cells and directed their selective photoactivation by the digital micromirror device. For more information about the Metamorph journals used to image and activate cells, see the Appendix.

Visual Cell Sorting: Cell Preparation, Imaging, Analysis and Photoactivation

An up-to-date version of this protocol can be found at protocols.io (protocols.io/view/visual-cell-sorting-beigjcbw).

1. 24 to 48 hours before imaging, plate cells onto 6-well glass bottom, black walled plates at a density of 50,000 to 200,000 cells per well.

2. Before imaging, wash cells with 1×DPBS and add complete media without phenol red.

3. Turn on the microscope and incubation chamber, set the CO2 regulator to 5%, and open Metamorph.

4. Place cells in microscope and bring cells into focus. Test imaging conditions (LED power, exposure time, etc.) for the desired channels.

5. Turn on Auto Focus Control. Using the Well Plate Acquire dialog box, image ~25-100 sites of experimental conditions (and controls, if applicable). Initialize a log file to collect phenotypic data. Using the Journal >Loop >Loop Through Images in Directory command, run the analysis journal on the images to collect the desired phenotypic information. The journal must include an "Integrated Morphometry—Measure" or a "Region Measurements" command to add phenotypic information for each cell to the log file. Note: these specific images will not be used for activation; rather, this analysis serves to ensure that the phenotypes match what one would expect.

6. Save the imaging conditions used for the Well Plate Acquire dialog box as a state file.

7. Close the log file. Check the distribution of phenotypes in experimental conditions and controls by running custom software (e.g. Python script) with the log file as input.

8. Load the site map. As of Metamorph v7.10.1.161, this can be done by:
   a) Closing Metamorph
   b) Replacing the htacquir.cfg file in the Metamorph application Groups >Metamorph directory with an htacquir.cfg file that contains the site map. htacquir.cfg files that contain various site maps for 6- and 24-well plates used in our experiments can be found on the GitHub repository under the Metamorph directory.
   c) Reopening Metamorph and reloading the saved state file (load everything except for site map settings). Note: in Metamorph v7.10.1.161, the site map can be contaminated by extra sites in the top left corner after this operation. Check the "Sites" tab of the Well Plate Acquire dialog box and remove any extra sites by left clicking.

9. Center the well:
   a) Move the objective to the approximate center of well A1.
   b) Under the Well Plate Acquire "Plate" tab, select "Set A1 Center . . . ">"Set A1 Center to Current".
   c) Under the "Sites" tab, move the objective to the top center site by right clicking.
   Using the eyepiece and brightfield illumination settings, check whether the objective is centered at the top of the well. If not, manually change the A1 center settings (measured in microns) to move it in the desired direction.
   e) Repeat steps (d) and (e) until the top center site of the site map is centered on the top.
   f) Re-check that cells are in focus and that Auto Focus Control in "on". Auto Focus Control can be turned off by the objective moving too far from the plate and hitting the plate holder.

10. Select the wells to be subject to Visual Cell Sorting under the "Plates" tab by left-clicking 11. Select appropriate journals to be run at the Start of Plate, After Imaging, and End of Plate under the "Journals" tab
   a) The "Start of Plate" journals (labelled "startup.jnl" in the GitHub) serve to add a delay to imaging, if necessary; set the 405 nm pulse times for the activations; set any phenotypic threshold values (e.g. NC ratios) for activation; etc.
   b) The "After Imaging" journals contain analysis and activation scripts that are performed after each image is taken
   c) The "End of Plate" journals turn off the laser to increase its lifetime 12. OPTIONAL: Re-align the digital micromirror device:
   a) Under Devices >Mosaic Targeted Illumination, click "Update Settings" in the Configuration tab
   b) Follow the instructions to re-calibrate the device 13. OPTIONAL: Run the experiment without the laser on to check that the correct cells are being identified and activated:
   a) In the Well Plate Acquire dialog box, hit "Acquire"
   b) Watch the first 5-10 sites of imaging, analysis, and marking cells for activation. In the activation journals associated with this publication, nuclei subject to the three activation states (50, 200, and 800 ms) are outlined in three different colors.

14. Turn on the laser

15. Select "Acquire" to begin acquisition, analysis, and activation.

Visual Cell Sorting: FACS on Microscope-Activated Cells
Cells activated on the microscope were analyzed using an LSR II (BD Biosciences; San Jose, CA) or sorted into bins according to their Dendra2 photoactivation state using a FACS Aria III (BD Biosciences). Raw .fcs files and code associated with this work are available on GitHub. For more information, see the Appendix.

1. Trypsinize cells and resuspend in DPBS supplemented with 1-2% FBS or BSA

2. Make a gate for live cells using a SSC-A vs. FSC-A plot.

3. Within the live cell gate, make a gate for single cells using a FSC-W vs. FSC-A plot.

4. Within the single cell gate, make a gate for Dendra2-positive cells using a FITC-A histogram plot. In some clonally derived lines, Dendra2 expression will silence over the course of weeks to months. If Dendra2-negative cells exceed 10%, we recommend resorting the population or returning to a lower passage stock.

5. Create an activated (PE-YG-A) vs. unactivated (FITC-A) Dendra2 scatter plot. Draw gates for the activated populations of interest. Activated populations will appear as diagonal clouds with higher PE-YG-A signals than a negative control.

6. Create a ratio (PE-YG-A/FITC-A) histogram. Show the activated populations of interest (defined in Step 5) within the ratio histogram. Create sorting gates for each population.

7. Sort populations of activated cells according to the gates set on the ratio histogram plot.

8. Spin cells for 5 minutes at 300-500×g, then plate cells in warm, complete media.

9. Analyze data using FlowCytometryTools (v0.5.0) in Python (v3.6.5) or flowCore (v1.11.20) in R (v3.6.0).

Selective Photoactivation of Cells Expressing miRFP
U-2 OS AAVS-LP Clone 11 cells with attB-H3-Dendra2 or attB-H3-Dendra2-P2A-H2B-miRFP recombined into the landing pad were counted and mixed in ratios ranging from 0.5% to 50% miRFP-expressing cells, then 40,000 cells of each mixture were seeded into three wells of a 24-well plate. The next day, cells were placed on the microscope and imaged, analyzed, and activated at 661 sites across each well of the plate, covering ~95% of the total well area. At each site, Dendra2 and miRFP were imaged with 2×2 binning; Metamorph's Count Nuclei module was used on the miRFP image to identify miRFP-expressing cells; and a binary with regions corresponding to miRFP-expressing cells was passed to the digital micromirror device, which subsequently activated the cells. Once all sites were imaged, analyzed, and activated, the cells were subject to flow cytometry to assess unactivated Dendra2, activated Dendra2, and miRFP expression. The experiment was repeated two additional times for a total of three replicates. For the Metamorph journals used to analyze and activate cells, see the GitHub repository. For more information about the gating scheme used for this experiment, see Appendix FIGS. 12A-12F.

Photoactivation of Cells for 0, 50, 200, and 800 Milliseconds

U-2 OS AAVS-LP Clone 11 cells with attB-H3-Dendra2-P2A-H2B-miRFP recombined into the landing pad were seeded at 50,000 cells per well in a 6-well glass bottomed plate. The next day, cells were imaged for unactivated Dendra2 and miRFP at 100 sites (10×10 square) and quartiles of total miRFP intensity were measured using Metamorph. Then, cells across 661 sites in two wells were left unactivated or activated for 50 ms, 200 ms, or 800 ms according to the miRFP intensity quartile to which they belonged (Q1=0-3803, Q2 =3804-5839, Q3=7396-9674, Q4=9674+). For the Metamorph journals used to analyze and activate cells, see the GitHub repository.

Testing for Photoactivation-Induced Toxicity with Annexin V and DAPI

U-2 OS AAVS-LP Clone 11 cells with attB-H3-Dendra2 recombined into the landing pad were seeded at 20,000 cells per well in a 24-well plate. Over the next two days, cells across 400 sites (60% well coverage) in three replicate wells were segmented using the Count Nuclei module in Metamorph and activated for 800 ms. Forty-eight hours after the first well was activated, cells were trypsinized, stained with Annexin V (Thermo, cat. no. A23204) and DAPI (Invitrogen, cat. no. D1306), and subjected to flow cytometry to assess unactivated Dendra2, activated Dendra2, Annexin V, and DAPI. Three wells of unactivated cells were heated at 50° C. for 10 minutes as a cell death positive control. The experiment was repeated two additional times for a total of three replicates. Data was analyzed using FlowJo (v10.5.3).

Testing for Photoactivation-Induced Toxicity with RNA Sequencing

U-2 OS AAVS-LP Clone 11 cells with attB-H3-Dendra2 recombined into the landing pad were seeded at 20,000 cells per well in 8 wells of a 24-well plate. Eighteen hours later, cells across 6 wells (678 sites per well; ~100% well coverage) were activated and then incubated for 0.5, 1.5, 2.5, 3.5, 4.5, or 6 hours (1 well each). Two wells were left unactivated. Dendra2 photoactivation was verified by flow cytometry, with the two unactivated samples were used as negative controls. Bulk RNA sequencing libraries were prepared as described previously (Cao et. al. 2017). Briefly, RNA was extracted from each sample using a Trizol/RNeasy Mini Kit (ThermoFisher, cat. no. 15596026, Qiagen; Germantown, MD; cat. no. 74104) then subjected to SuperScript IV First-Strand Synthesis (Thermo Fisher 18091050) and NEBNext Ultra II Directional RNA Second Strand Synthesis (NEB E7550), according to the manufacturer's instructions. cDNA was then tagmented with Nextera Tn5 (Illumina; San Diego, CA; FC-131-1024) and amplified/indexed by PCR with the NEBNext DNA Library Prep Kit (NEB E6040). Samples were sequenced using a NextSeq 500/550 75 cycle kit (Illumina, cat. no. TG-160-2005). Differential gene expression analysis of RNA sequencing data followed the standard DESeq2 workflow (Love et al, 2014, Moderated estimation of fold change and dispersion for RNA-seq data with DESeq2. *Genome Biol.* 15: 1-21). Briefly, differential gene expression testing was performed using a binary coding of photoactivation status in the DESeq2 design formula. Dispersion estimates, log 2 fold changes and adjusted p-values were all calculated using the DESeq function with default parameters as specified in DESeq2.

Visual Cell Sorting of Cells Expressing SV40 NLS Library

Eighteen hours before imaging, 300,000 U-2 OS LLP-Blast/H3-Dendra2 Clone 4 cells with the attB-NLS-CMPK-miRFP library recombined into the landing pad were seeded into each well of a 6-well plate. The next day, cells were placed onto the microscope and imaged, analyzed, and activated across 2,949 sites (~100% well coverage) across two wells. At each site, Dendra2 and miRFP were imaged with 2×2 binning; Metamorph's Count Nuclei module was used on the Dendra2 image to identify nuclei and create a nuclear binary image; cytoplasm binaries were created by subjecting the nuclear binary to a dilate function and subtracting away the nuclear binary; each nucleus-cytoplasm binary pair was superimposed on the miRFP image and average pixel intensities were measured for each compartment; cells with an average nuclear or cytoplasmic miRFP pixel intensity of less than 11,000 were filtered out; a nucleus-to-cytoplasm (N:C) ratio was calculated by dividing the average nuclear pixel intensity by the average cytoplasmic pixel intensity; nuclei with N:C<0.964 were not activated at all, N:C 0.964-1.079 were activated for 50 ms, N:C 1.079-1.244 were activated for 200 ms, and N:C >1.244 were activated for 800 ms. Once all sites were imaged, analyzed, and activated, the cells were subject to FACS and unactivated Dendra2 (FITC), activated Dendra2 (PE-YG), and miRFP (AlexaFluor-700) fluorescence intensities assessed. Cells were then sorted into four photoactivation bins (FIG. 2B). A total of two Visual Cell Sorting technical replicates were performed on recombination replicate 1, and three were performed on recombination replicate 2. The details of replicate sorts for the NLS library can be found in TABLE 1. For an example of the gating scheme, see Appendix FIGS. 13A-13E.

Sorted SV40 NLS Library Genomic DNA Preparation and Sequencing

After sorting, cells in each Dendra2 photoactivation bin were grown in the absence of doxycycline until confluent in one well of a 6-well plate (~7 days), then pelleted and stored at −20° C. DNA was extracted from cell pellets with the DNEasy kit (Qiagen, cat. no. 69504) using RNAse according to the manufacturer's instructions. gDNA was amplified using SV40_NLS_seq_f and SV40_NLS_seq_r (TABLE 2) primers using Kapa Hifi (Kapa Biosystems, cat. no. KK2602) according to the manufacturer's instructions. Amplicons were cleaned using Ampure XP beads (Beckman Coulter; Brea, CA; cat. no. A63880), then subjected to an indexing PCR step using KAPA2G Robust (Kapa Biosystems, cat. no. KK5705) with primers P5 and an indexing primer (TABLE 2). Amplicons were then run on a 1.5% agarose gel at 130 V for 40 min and the DNA in the 235 bp band extracted using Freeze'N Squeeze DNA Gel Extraction Spin Columns (BioRad, cat. no. 7326165). Extracted DNA was sequenced on an Illumina NextSeq500 using SV40_NLS_Read1, SV40_NLS_Read2, and SV40_NLS_Index1 primers (TABLE 2). Reads were trimmed and merged using PEAR (Zhang et al, 2014, PEAR: A fast and accurate Illumina Paired-End reAd mergeR. *Bioinformatics* 30: 614-620). Sequences were quality-filtered and variants were called and counted by using Enrich2, as previously described (Rubin et al, 2017, A statistical framework for analyzing deep mutational scanning data. *Genome Biol.* 18: 1-15). The Enrich2 configuration file is available on the GitHub repository.

Calculating NLS Variant Localization Scores

Jupyter v5.5.0 running Python v3.6.5 was used for analyses of the Enrich2 output. First, two filters were applied to remove low-quality variants: (1) a minimum nucleotide variant count cutoff of 5 in each bin in each replicate and (2) a requirement that the variant was accessible via NNK codon mutagenesis. After filtering, remaining nucleotide variants encoding the same amino acid substitution were added to yield a sum of counts for that variant within each bin for each replicate. To generate raw quantitative scores ($S_{raw}$), a weighted average approach as previously described (Matreyek et al, 2018, Multiplex assessment of protein variant abundance by massively parallel sequencing. *Nat. Genet.* 50: 874-882) was applied to the variant frequencies ($f_{var}$) across the 4 bins (b1-b4) in each replicate:

$$S_{raw} = \frac{0.25(f_{var_{b1}}) + 0.50(f_{var_{b2}}) + 0.75(f_{var_{b3}}) + f_{var_{b4}}}{f_{var_{b1}} + f_{var_{b2}} + f_{var_{b3}} + f_{var_{b4}}}$$

Raw scores were subsequently normalized such that variants with a wild-type raw score ($S_{WT}$) have a normalized score of 1 and variants with the median raw score of the bottom 10% of variants ($S_{P10}$) have a normalized score of 0:

$$S_{norm} = \frac{S_{raw} - \text{median}(S_{P10})}{S_{WT}}$$

A final round of frequency filtering for variants, which sought to increase score correlations without excluding too many variants, removed variants present at a frequency lower than 0.003% of reads in all bins. Then, the raw and normalized scores were recalculated for each replicate; and the mean and standard error of the normalized scores from the five replicates were calculated to produce final scores. An iPython notebook file with the code used to run the analysis is available on the GitHub repository.

Validation of Single NLS Variants ssDNA oligos (IDT, Newark, NJ) encoding the NLS variants were introduced into EcoRI-digested attB-EcoRI-CMPK-miRFP reporter plasmid via a Gibson reaction (Gibson et al, 2009, Enzymatic assembly of DNA molecules up to several hundred kilobases. *Nat. Methods* 6: 343-5). Variants were validated by Sanger sequencing. Plasmids were recombined into 80,000 U-2 OS cells in a 24 well plate using 1.5 uL of FuGENE6 (Promega; Madison, WI; cat. no. E2691) in 100 uL OPTIMEM (Fisher Scientific; Waltham, MA; cat. no. 31985070) with 100 ng of pCAG-Bxb1 and 295 ng of the attB variant recombination plasmid. After 5 days, recombined cells, which are miRFP+, were isolated using FACS for miRFP+ cells and plated in glass-bottom 24 well plates. Then, recombined cells were imaged for H3-Dendra2 and miRFP. Metamorph was used to segment nuclei and calculate mean nuclear and cytoplasmic miRFP intensity for each cell, as described above ("Visual Cell Sorting on cells expressing SV40 NLS library"). miRFP intensities were background-corrected (see Appendix), and cells with nuclear and cytoplasm miRFP intensities roughly equal to background levels were removed. Then, N:C ratios were calculated for each cell using the cell's mean nuclear ($I_{nuc}$) and cytoplasmic ($I_{cyt}$) miRFP intensities:

$$NC = I_{nuc} / I_{cyt}$$

Each variant was examined in at least three separate imaging replicates. For more information regarding the validation of single NLS variants, see Appendix.

Prediction of Novel Human NLS's

Analysis of the normalized variant localization scores were done in RStudio v1.1.456 running R v3.6.0. Position-wise amino acid preferences were calculated (Bloom, 2014, An Experimentally Determined Evolutionary Model Dramatically Improves Phylogenetic Fit Article Fast Track. 31: 1956-1978):

$$x_{r,a} = \frac{s_{r,a} - \min(s_r)}{\max(s_r) - \min(s_r)}$$

Where $x_{r,a}$ is the amino acid preference for amino acid a at position r, $s_{r,a}$ is the mean raw score of variants with amino acid a at position r, and $s_r$ is the set of all raw scores at position r. The scores of missing variants were estimated using the median score at that variant's position. To train a weighted preference model, NLS sequences (n=573) were downloaded from UniProt using a SPARQL query for all human proteins with a sequence motif annotation that contained the string "Nuclear localization" in its comment. A set of 573 "likely NLS" 11mers were generated by repeating the following for each NLS: (1) scoring every 11mer peptide overlapping the annotated NLS sequence by summing the amino acid preferences of the 11mer peptide (2) annotating the maximum-scoring 11mer as a "likely NLS". All other possible 11mers in the training dataset (333,255 total) were annotated as "no NLS". To account for the fact that some the amino acid preferences at some positions may be more important than others, a linear regression model of the following form was fit to these data:

$$Y = \beta_0 + \sum_{r=1}^{11} \beta_r x_{r,a}$$

Where Y denotes the sequence class ("no NLS"=0, "likely NLS"=1), $\beta_0$ is the intercept, $\beta_r$ is the weight given to the amino acid preferences at position r, and $x_{r,a}$ is the is the preference of amino acid a at position r. Model parameters were determined by 8-fold cross validation before being applied to an independent test dataset (Lin & Hu, 2013, SeqNLS: nuclear localization signal prediction based on frequent pattern mining and linear motif scoring. *PLoS One* 8.) containing 20 protein sequences with 30 NLS's that were not examined during training.

To apply the final model to the nuclear human proteome, the test dataset was used to generate two score cutoffs: one corresponding to a precision of ~0.9 ("high confidence NLS") and one corresponding to a recall of ~0.9 ("candidate NLS"). All 11mers present in proteins annotated as nuclear by the Human Protein Atlas were then subject to scoring by the model. An R-markdown file with the code used to run the analysis is available on the GitHub repository.

Time-Lapse Imaging of Cells Treated with Paclitaxel hTERT-RPE-1 cells expressing Dendra2-NLS, H2B-miRFP703, and mBeRFP-NES were plated at a density of 50,000 cells per well in 2-well μm-slide chambers (ibidi; Martinsried, Germany). Twenty-four hours after plating, the cell media was replaced with media containing 0.25 nM taxol. After the cell media change, the cells were imaged for 24 hours with a pass time of 10 minutes. Imaging was performed on a Leica DMi8/Yokagawa spinning disk confocal microscope with a 20×0.8 NA air objective at 37° C. and 5% CO2. Images were captured with an Andor (Belfast, United Kingdom) iXon Ultra camera using Metamorph software. Videos were cropped and adjusted for brightness and contrast using ImageJ and Photoshop.

Visual Cell Sorting of Cells Treated with Paclitaxel

RPE-1 NLS-Dendra2×3/H2B-miRFP/NES-mBeRFP Clone 3 cells were plated at 50,000 cells per well in a 6-well plate. After 24 hours, cells were treated with paclitaxel at a final concentration of 0.25 nM. After 30 hours of treatment, cells were placed on the microscope and imaged, analyzed, and activated across 2,204 sites (~75% coverage, avoided well edges) in 2 wells. At each site, Dendra2 was imaged with 1×1 binning; a custom nuclear segmentation pipeline that optimized detection of nuclear blebs, herniations, and other abnormalities was employed (see Appendix); Metamorph's MDA analysis was used to compute shape factors for nuclear binaries. Cells with nuclear shape factor <0.65 were activated for 200 ms, and cells with nuclear shape factor >0.65 were activated for 800 ms. Cells from each well were trypsinized and resuspended in DPBS supplemented with 1% BSA and 2% FBS. Using FACS, cells corresponding to 200 ms and 800 ms photoactivation were sorted using FACS (FIG. 11A) into a 1.5 mL tube containing 1 mL DPBS supplemented with 1% BSA. In Experiment 1, cells were sorted according to their nuclear phenotype (i.e. 200 ms cells in bin 1, 800 ms cells in bin 2; FIG. 11A). Cells were imaged, activated, and sorted identically in Experiment 2, except that all activated cells were sorted into one bin (i.e. both 200 ms and 800 ms cells in bin 1; "unseparated paclitaxel-treated population"). For an example of the gating scheme, see FIGS. 14A-14D.

Single Cell RNA Sequencing of Sorted, Paclitaxel-Treated Populations

After sorting, cells were spun at 1,000×g at 4° C. for 5 minutes, then all but 50-100 uL of supernatant was removed. Cells were counted and subjected to 10× Single-Cell RNA sequencing v2 (10× Genomics; Pleasanton, CA; cat. no. 120236, 12037) according to the manufacturer's instructions. 10× Cell Ranger version 2.1.1 was used to process lanes corresponding to the single cell libraries and map reads to the human reference genome build Hg19. Unique molecular identifier (UMI) cutoffs were chosen by 10× Cell Ranger software. Reads and cell numbers were normalized via downsampling by the aggregate function in 10× Cell Ranger. After normalization, cells had a median of 9,249 UMIs (Experiment 1, separated populations) or 16,932 (Experiment 2, unseparated population) per cell.

Analysis of Single Cell RNA Sequencing Data

Analysis of 10× CellRanger output files was done in RStudio v1.1.456 running R 3.6.0. Cell cycle scoring and annotations were performed with Seurat, as previously described (Butler et al, 2018, Integrating single-cell transcriptomic data across different conditions, technologies, and species. *Nat. Biotechnol.* 36: 411-420). UMAP was performed with Monocle3 (Trapnell et al, 2014, The dynamics and regulators of cell fate decisions are revealed by pseudotemporal ordering of single cells. *Nat. Biotechnol.* 32: 381-386; Qiu et al, 2017, Single-cell mRNA quantification and differential analysis with Census. *Nat. Methods* 14: 309-315). Mutual-nearest neighbors batch correction was performed using the Batchelor package (Haghverdi et al, 2018, Batch effects in single cell RNA-sequencing data are corrected by matching mutual nearest neighbors. *Nat Biotechnol* 36: 421-427) in the following order: unseparated cells from Experiment 2 were batch corrected with morphologically-normal cells from Experiment 1, and then lobulated cells from Experiment 1 were batch corrected. An R-markdown file with the code used to run the analysis is available on the GitHub repository.

Differentially Expressed Genes Analysis

Mutual nearest neighbors batch correction (Haghverdi et al, 2018, Batch effects in single cell RNA-sequencing data are corrected by matching mutual nearest neighbors. *Nat Biotechnol* 36: 421-427) was used to align cells from Experiment 2 (normal and lobulated cells sorted into the same tube, one 10× lane) to cells from Experiment 1 (normal and lobulated cells sorted into separate tubes, two 10× lanes). Principal components 1 through 4, which were output by the batch correction algorithm, were used to train a logistic regression model for nuclear lobulation on the cells in Experiment 1. This model was applied to Experiment 2, resulting in each cell being assigned a lobulation score, which is high in lobulated cells in Experiment 1 and low in normal cells in Experiment 1. Then, a differentially expressed gene test was performed on the cells in Experiment 2 using lobulation score, Seurat-computed G1 score, and Seurat-computed G2/M score as covariates. For a detailed discussion of this analysis, see the Appendix.

Gene Set Enrichment Analysis

Gene set enrichment analysis was performed using the piano package (Väremo et al, 2013, Enriching the gene set analysis of genome-wide data by incorporating directionality of gene expression and combining statistical hypotheses and methods. *Nucleic Acids Res.* 41: 4378-4391) in R on differentially expressed genes with a log 2-normalized effect value (equivalent to the expected log 2-fold change per unit increase in lobulation score) less than −0.1 and a q-value less than 0.01. The MSigDB Hallmarks and Canonical Pathways gene sets were used (Subramanian et al, 2005, Gene set enrichment analysis: A knowledge-based approach for interpreting genome-wide expression profiles. *Proc. Natl. Acad. Sci.* 102: 15545-15550; Liberzon et al, 2015, Molecular Signatures Database Hallmark Gene Set Collection. *Cell Syst.* 1: 417-425).

APPENDIX

Extended Description of General Reagents, DNA Oligonucleotides and Plasmids

To create attB-H3-Dendra2, the Dendra2 open reading frame was obtained from Dendra2-Lifeact7 (Addgene #54694) and cloned downstream of the H3 open reading frame from mEmerald-H3-23 (Addgene #54115) and into the backbone of attB-EGFP-PTEN-IRES-mCherry.

To create attB-H3-Dendra2-P2A-H2B-miRFP703, attB-H3-Dendra2 and pH2B-miRFP703 (a gift from Vladislav Verkhusha, Addgene #80001) were combined and a P2A sequence included in the Gibson overhang regions between Dendra2 and miRFP.

To create pLenti-CMV-H3-Dendra2, the H3-Dendra2 reading frame in attB-H3-Dendra2 replaced the open reading frame in pLenti CMV rtTA3 Blast (w756-1) (Addgene #26429).

To create attB-Nterm-CMPK-miRFP (the destination vector for the NLS library), a gBlock encoding an EcoRI site in-frame and upstream of CMPK (IDT; based off a previously published SV40 NLS construct[21]) was combined with the miRFP open reading frame from pH2B-miRFP703 and inserted into the backbone of attB-H3-Dendra2-P2A-H2B-miRFP703.

To create attB-NLS-CMPK-miRFP and all single, double, and triple amino acid variants, the attB-Nterm-CMPK-miRFP vector was digested with EcoRI for 2 hours at 37° C. Then, the digested plasmid and an oligo that contained the NLS (wild-type or variant of interest) and 55° C. overhangs complementary to the edges of the cut site were incubated in a Gibson reaction in a one to three molar ratio and transformed, as per manufacturer's instructions.

To create pLenti-CMV-NLS-Dendra2×3-P2A-H2B-miRFP, three PCRs of Dendra2 (template derived from Dendra2-Lifeact7) were performed: one with an N-terminal NLS appended on the forward primer and a Gly-rich linker on the reverse; one with the Gly-rich linker on the forward primer and a second, non-identical Gly-rich linker on the reverse primer; and one with the second Gly-rich linker on the forward primer and a stop codon on the reverse primer. These were combined with an attB construct backbone53 to create attB-NLS-Dendra2×3. In a second cloning step, H2B-miRFP from pH2B-miRFP703 was appended downstream to create attB-NLS-Dendra2×3-P2A-miRFP. Finally, the Dendra2×3-P2A-H2B-miRFP open reading frame was cloned into pLenti CMV rtTA3 Blast (w756-1).

To create pLenti-CMV-mBeRFP-NLS, a gBlock encoding codon-optimized mBeRFP (IDT) was cloned into pLenti CMV rtTA3 Blast (w756-1) with an NES encoded into Gibson overhangs.

Extended Description of the Construction of Site-Saturation Mutagenesis Library for the SV40 NLS The library of all possible SV40 NLS missense variants was constructed using a Gibson cloning approach. Eleven primer pairs—1 for each NLS codon, plus 2 codons upstream and 2 codons downstream of the NLS—were designed (TABLE 2). For each pair, the forward primer contained a 3' annealing region (Tm ~55C), an NNK codon, and a 5' Gibson homology region (Tm ~55° C.). The reverse primer comprised of the reverse complement of the forward primer Gibson homology region. Each primer pair was used in a separate PCR reaction that included attB-NLS-CMPK-miRFP as the template, and 5 ul of each reaction were run on a 1% gel to check for product. The remaining 20 ul was DpnI digested for 2 hours at 37 C to remove template plasmid, cleaned using DNA Clean & Concentrator-5 (Zymo Research D4013), subject to a 1-piece Gibson reaction, and transformed into chemically competent *E. coli*. Bulk transformant cultures were grown overnight and harvested using GenElute HP Plasmid DNA Midiprep Kit (Sigma, NA0200-1KT). DNA preps containing single codon variant were subsequently mixed such that each prep contributed an equal amount of DNA. The final library contained 346 NNK nucleotide variants which, due to codon degeneracy in the genetic code, encode for 209 single amino acid variants.

Extended Description of Lentivirus Production

To produce lentivirus, HEK293T cells were plated in clear plastic 6 well plates (VWR, cat. no. 10062-892) at 4.5e5 cells per well. The next day, cells in each well were transfected with 1,125 ng psPAX2 (AddGene #12260), 375 ng pMD2.G (AddGene #12259), and 1,500 ng of pLenti transfer vector using 6 ul of FuGENE6 (Promega, cat. no. E2691) according to manufacturer's instructions. Media was replaced 24 hours after transfection and collected at 48 hours and 72 hours after transfection. Collected media was spun at 1000 g for 5 minutes, then the viral supernatant was decanted and filtered using a 0.45 um filter (VWR, cat. no. 28145-481). Finally, the virus was concentrated using PEG-it Virus Precipitation Solution (SBI, cat. no. LV810A-1) and stored at −80° C.

Extended Description of the Creation of Clonal Cell Lines

To create the clonal U-2 OS landing pad and H3-Dendra2 expressing line, parental U-2 OS cells were transduced with lentivirus encoding the landing pad and lentivirus encoding H3-Dendra2. Five days after transduction, BFP+ve/Dendra2+ve cells were sorted using an Aria III (Pacific Blue and FITC Channels). Three days later, cells were sorted directly into 96 well plates containing 75 ul of conditioned U-2 OS media. Every week, 50 ul of normal media was added to the well. Wells were checked for surviving clones at 2 weeks and 3 weeks post-sorting.

To create the hTERT RPE-1 clonal line expressing NLS-Dendra2×3, mBeRFP-NES, and H2B-miRFP, lentiviruses encoding these constructs were added to the parental line, and single cell clones were similarly sorted and expanded in conditioned media in 96 well plates.

Extended Description of the Recombination of Single-Variant SV40 NLS Clones or the Library into the U-2 OS-Landing Pad Line Expressing H3-Dendra2

To recombine NLS variants or the NLS library into cells, H3-Dendra2 expressing U-2 OS cells with the landing pad were subject to Lipofectamine 3000 (Thermo Fisher L3000015) transfections in 6 well plates, T-25 flasks, or T-75 flasks, according to manufacturer instructions, with the following specifications: plated cells at 0.1e5 cells/well (24 well plate), 0.6e5 cells/well (6 well plate), 1.4e6 cells/flask (T-25), or 4.2e6/flask (T-75); transfected with 0.75 ul/3.75 ul/10.4 ul/31.2 ul Lipofectamine 3000, 1 ul/5 ul/13.9 ul/41.7 ul P3000 reagent, 500 ng/2500 ng/7000 ng/21000 ng total DNA at a by-weight ratio of 1/3 pCAG Bxb1 and 2/3 attB plasmid(s). Cells were transfected immediately after plating. Twenty-four hours after transfection, media was replaced. Doxycycline was added 48h after transfection. BFP negative, miRFP positive, Dendra2 positive cells were sorted 5-8 days after transfection.

Extended Description of the Metamorph Journals Used for Imaging, Analysis, and Photoactivation Visual Cell Sorting experiments have three Metamorph journals specified in the Metamorph high-throughput acquisition dialog box: a startup journal that initializes global variables accessed by other journals; an after-image journal that analyzes and activates cells; and an end of plate journal that turns off the laser. The microscope was directed to leave no overlap between images. In all experiments, nuclei touching the image border were removed. Site maps were customized by altering the htacquir.cfg configuration file. See the GitHub repository for the Metamorph journals and configuration files used.

Extended Description of Validation of Single NLS Variants

Analysis of Metamorph-calculated nucleus and cytoplasm mean intensity values was done using Python (v3.6.5). To correct for differences in background intensity between wells and replicates, each image's miRFP background intensity was estimated using the 10th percentile of image pixel intensity values and this value was subtracted from each cell's mean nucleus and cytoplasmic miRFP intensity. Cells with no miRFP expression were removed with a gate that was determined by examination of the histogram of the mean miRFP intensity values for cells in each well. An iPython notebook file with the code used to run the analysis is available on the GitHub repository.

Extended Description of the Visual Cell Sorting on Cells Treated with Paclitaxel To identify morphologically-normal and lobulated cells were imaged for unactivated Dendra2 (FITC channel; 100 ms). Then, a custom nuclear segmentation pipeline that optimizes detection of nuclear blebs, herniations, and other abnormalities was employed. First, a top hat filter with a maximum object area threshold of 5,000 pixels was applied to remove large autofluorescent objects, and a 3×3 low pass filter was applied to smooth nuclear fluorescence. To find nuclei, a flatten background filter (removal of objects <20 pixels in size), Sobel edge detection kernel, and a sharpening kernel were used before applying Metamorph's "legacy heuristic" thresholding algorithm to create nuclear binaries. To clean the nuclear binaries, holes were filled; tunnels 1 pixel in width were filled in using a dilate function; holes were filled again; and then an erode function was used to reverse the enlarging effect of the dilate and edge detection steps. Finally, objects less than 20 pixels in size and greater than 400 pixels in size were discarded. Shape factors were computed for each remaining object. See the GitHub repository for the Metamorph journal that was used.

Extended Description of the Differentially Expressed Genes Analysis

It was noted that the Visual Cell Sorting-derived lobulated and normal single cell RNA transcriptomes appeared to be confounded by a batch effect, despite the fact that cells were derived from a single well, sorted on the same day, and processed side by side (Experiment 1). Using SoupX, which applies a linear PCA transformation that is determined by the RNA in empty 10× emulsion droplets, it was found that cell-free RNA was responsible for this effect (FIG. 11B). To confirm this hypothesis, the experiment were repeated but lobulated (800 ms activated) and morphologically normal (200 ms activated cells) cells were sorted into the same bin (Experiment 2, "unseparated" population) and these cells were processed in a single 10× lane. A UMAP embedding of the single cell transcriptomes derived from these unseparated cells showed a single cluster, confirming the batch effect in Experiment 1.

Although both SoupX and the mutual nearest neighbors algorithm applied to cells in Experiments 1 corrected the batch effect (FIG. 11B), it is not statistically appropriate to use batch-corrected gene expression values to conduct a differentially-expressed gene test. As such, it was sought to use mutual nearest neighbors batch-corrected principal components to label the unseparated cells in Experiment 2 according to their similarity to the known lobulated or morphologically-normal cells in Experiment 1; and then use the raw gene expression values in Experiment 2 to conduct a differentially-expressed gene test. It was noted that the first four principal components in the MNN batch correction output correlated with the visual phenotype (i.e. morphologically normal vs. lobulated) in Experiment 1. So, a logistic regression was performed on the cells in Experiment 1 to devise a score that distinguishes between morphologically normal and lobulated cells:

$$\text{lobulation score} \sim PC1 + PC2 + PC3 + PC4$$

This regression model was then applied to cells in Experiment 2 (unseparated cells, single 10× lane) and the model predictions, which we called the "lobulation scores", were extracted for each cell. Using Moncole3, a DEG test was performed on the Experiment 2 gene expression matrix using the lobulation scores and Seurat-computed cell cycle scores as covariates:

$$\text{Gene} \sim \text{lobulation score} + S \text{ score} + G2M \text{ score}$$

By doing the differentially expressed gene test using Experiment 2, in which lobulated and normal cells were sequenced together, any batch-related artifacts were avoided. This operation is analogous to the cluster-based analysis originally discussed by Haghverdi and colleagues, but uses a principal component-derived score rather than principal component-derived clusters as cell labels.

Example 2

Introduction

This Example described an assay that illustrates utility for further embodiments of the Visual Cells Sorting method. This assay was performed on primary cells and incorporated z-stacking images, which can enhance the assessment of cell phenotype.

Results

Murine embryonic stem cells were obtained and were stained for histone 2B using a primary antibody and a secondary antibody conjugated to photoactivatable PA-JF-549 and Alexa 488. The cells were mixed into a heterogenous population and then imaged. The microscope set up incorporated a Piezo Z stage that allowed z-stacking, i.e., the layering of multiples images of different z planes into a single image, which provides additional resolution and detail of the cells. The z-stacked image permits a more precise and sensitive analysis of cell phenotype. See FIG. 15A. With the assessment, the cells were successfully sorted. See FIG. 15B. The Visual Cell Sorting procedure can be facilitated by incorporation of hardware triggering, which coordinates the control of the image capture, image processing, illumination, and other steps in the process, thus reducing lag time between the components and improving overall efficiency.

This assay demonstrates the versatility of the Visual Cell Sorting approach for sorting not just cultured cell lines, but primary cells obtained from tissue and other biological samples as well. Furthermore, it demonstrates that the incorporation of system features such as z-stacking (e.g., using a Piezo Z stage) and hardware triggering can enhance the functionality and throughput of the Visual Cell Sorting process.

Example 3

Introduction

This Example describes development of a method to release fixed, adherent cells to form single nuclear suspension for subsequence analysis and sorting.

Results and Discussion

Fixed Adherent Cells can be Dissociated into Single Nuclear Suspension

In brief, adherent cells that are fixed with paraformaldehyde can be easily detached with the combination of trypLE Express (Gibco) treatment and manual pipetting and scraping with a pipette tip. The trypLE incubation time can be tuned accordingly based on the degree of fixation. For example, three minutes of trypLE incubation is recommend at 37° C. for cells that were fixed with 4% PFA, whereas one minute incubation is recommend for 1% PFA fixed cells. The trypsinized cells then can be detached via pipetting and scraping. TrypLE was chosen over standard trypsin because trypLE is more gentle on the cells and reduces nuclear lysis due to prolonged trypsinization.

To validate this pipeline, U-2 OS cells separately expressing green and red nuclear markers were co-cultured, fixed adherently, and dissociated off the plate (FIG. 5A). Fluorescence activated cell sorting (FACS) analysis of single nuclear suspensions showed low doublet rate (FIG. 5B). The visualization of sorted FITC+ and miRFP+U-2 OS nuclei further verified that the disclosed dissociation protocol produces single nuclei suspension (FIG. 5C).

Visual Cell Sorting is Compatible with Fixed Cells and Immunostaining

With the disclosed fixed cell dissociation protocol, a fixed-cell VCS pipeline was developed where imaging and photoactivation are done on fixed cells/nuclei. The fixed cell VCS pipeline can be run for extended time periods (up to several weeks), which was not feasible with the original VCS pipeline due to degradation of the photoactivated Dendra2 in live cells. Additionally, the use of small molecule dyes and fluorescently labeled antibodies is now possible with cell fixation.

The fixed cell VCS pipeline was applied on a mixture of U-2 OS cells expressing WT or known pathogenic N195K LMNA mutants. Lamin A forms intranuclear aggregates in U-2 OS cells expressing N195K LAMA mutants but not in cells expressing WT LMNA. VCS was used to separate nuclei based on the lamin A aggregation phenotype and verified its performance by visualizing the sorted nuclei (FIG. 6A).

Visual Cell Sorting utilizes the transgenic expression of Dendra2 for encoding of phenotypes, which requires additional cell engineering. A photo-activatable antibody compatible with fixed cell VCS was created by conjugating Alexa 488 and the photo-activatable Janelia Fluor PA-JF-549 dye to an anti-Rabbit IgG antibody (FIG. 6B). This photo-activatable antibody mimics Dendra2, in which Alexa 488 and photo-activated PA-JF-549 serve as unactivated and activated Dendra2, respectively. Immunofluorescence using primary anti-H2A antibody and the photo-activatable secondary antibody enables separation of up to four distinct populations (FIG. 6C).

While illustrative embodiments have been illustrated and described, it will be appreciated that various changes can be made therein without departing from the spirit and scope of the disclosure.

The embodiments of the invention in which an exclusive property or privilege is claimed are defined as follows:

1. A method of high-throughput cell sorting, comprising:
    providing a plurality of cells with at least one photo-activatable detectable marker in their respective nuclei;
    imaging the plurality of cells;
    determining the phenotype status for a plurality of phenotypes of individual cells in the plurality of cells based on the imaging of the plurality of cells;
    exposing the individual cells exhibiting a desired phenotype status for each of the plurality of phenotypes to a light wavelength for a plurality of times sufficient to activate the at least one photo-activatable detectable marker in the individual cells with the desired phenotype status to a plurality of unique photoactivation levels; and
    isolating individual cells or nuclei thereof based on each of the plurality of unique levels of photoactivation of the at least one photo-activatable detectable marker, wherein each level of the plurality of unique levels of photoactivation of the at least one photo-activatable detectable marker is associated with at least one phenotype status for each of the plurality of phenotypes.

2. The method of claim 1, wherein the at least one photo-activatable detectable marker is a photo-activatable protein and the plurality of cells are engineered to express the photo-activatable protein.

3. The method of claim 2, wherein the photo-activatable protein is Dendra2.

4. The method of claim 1, wherein the at least one photo-activatable detectable marker is an affinity reagent conjugated to at least one dye and/or fluorophore, wherein the affinity reagent is optionally an antibody or antibody fragment or derivative.

5. The method of claim 4, wherein the affinity reagent is conjugated to two dye(s) and/or fluorophore(s) that emit different light wavelengths upon exposure to the light wavelength in the exposing step.

6. The method of claim 4, wherein the method further comprises contacting the plurality of cells with the affinity reagent.

7. The method of claim 1, wherein the plurality of cells are in culture.

8. The method of claim 7, wherein the plurality of cells are fixed to a surface.

9. The method of claim 8, further comprising extracting intact nuclei from the fixed cells.

10. The method of claim 1, wherein the plurality of cells are primary cells obtained from a subject.

11. The method of claim 1, wherein the imaging, determining, and exposing steps are automated by a programmable microscope system containing instructions to discriminate phenotypic states for one or more phenotypes of interest.

12. The method of claim 11, wherein the programmable microscope system is configured for z-stack imaging.

13. The method of claim 1, wherein the individual cells or nuclei thereof are isolated and/or sorted using fluorescence activated cell sorting (FACS).

14. The method of claim 1, wherein the individual cells with each of the plurality of phenotypes has a uniquely activated photo-activatable detectable marker that emits a different detectable light wavelength.

* * * * *

SEQUENCE LISTING

```
<160> NUMBER OF SEQ ID NOS: 92

<210> SEQ ID NO 1
<211> LENGTH: 11
<212> TYPE: PRT
<213> ORGANISM: Artificial Sequence
<220> FEATURE:
<223> OTHER INFORMATION: Synthetic

<400> SEQUENCE: 1

Glu Pro Pro Arg Lys Lys Arg Lys Ile Gly Ile
1               5                   10

<210> SEQ ID NO 2
<211> LENGTH: 51
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (22)..(23)
<223> OTHER INFORMATION: n is a, c, g, or t

<400> SEQUENCE: 2
atggacaagg ccgaattcct tnnkgctcct aaaaagaaga gaaaggtagg t         51

<210> SEQ ID NO 3
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (23)..(24)
<223> OTHER INFORMATION: n is a, c, g, or t

<400> SEQUENCE: 3
ggacaaggcc gaattccttg agnnkcctaa aaagaagaga aggtaggta tccc        54

<210> SEQ ID NO 4
<211> LENGTH: 50
<212> TYPE: DNA
```

```
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: n is a, c, g, or t

<400> SEQUENCE: 4
ggccgaattc cttgaggctn nkaaaaagaa gagaaaggta ggtatcccag            50

<210> SEQ ID NO 5
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (22)..(23)
<223> OTHER INFORMATION: n is a, c, g, or t

<400> SEQUENCE: 5
gccgaattcc ttgaggctcc tnnkaagaag agaaaggtag gtatcccaga            50

<210> SEQ ID NO 6
<211> LENGTH: 53
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(25)
<223> OTHER INFORMATION: n is a, c, g, or t

<400> SEQUENCE: 6
ccgaattcct tgaggctcct aaannkaaga gaaaggtagg tatcccagaa ttc        53

<210> SEQ ID NO 7
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (26)..(27)
<223> OTHER INFORMATION: n is a, c, g, or t

<400> SEQUENCE: 7
cgaattcctt gaggctccta aaagnnkag aaaggtaggt atcccagaat tcca         54

<210> SEQ ID NO 8
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (28)..(29)
<223> OTHER INFORMATION: n is a, c, g, or t

<400> SEQUENCE: 8
gaattccttg aggctcctaa aagaagnnk aaggtaggta tcccagaatt ccacg        55

<210> SEQ ID NO 9
<211> LENGTH: 51
```

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (26)..(27)
<223> OTHER INFORMATION: n is a, c, g, or t

<400> SEQUENCE: 9
ccttgaggct cctaaaaaga agagannkgt aggtatccca gaattccacg c         51

<210> SEQ ID NO 10
<211> LENGTH: 52
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (28)..(29)
<223> OTHER INFORMATION: n is a, c, g, or t

<400> SEQUENCE: 10
cttgaggctc ctaaaagaa gagaaagnnk ggtatcccag aattccacgc tg          52

<210> SEQ ID NO 11
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (28)..(29)
<223> OTHER INFORMATION: n is a, c, g, or t

<400> SEQUENCE: 11
gaggctccta aaagaagag aaaggtannk atcccagaat tccacgctgc              50

<210> SEQ ID NO 12
<211> LENGTH: 49
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (28)..(29)
<223> OTHER INFORMATION: n is a, c, g, or t

<400> SEQUENCE: 12
gctcctaaaa agaagagaaa ggtaggtnnk ccagaattcc acgctgcca              49

<210> SEQ ID NO 13
<211> LENGTH: 21
<212> TYPE: DNA
<213> ORGANISM: Artificial Sequence
<220> FEATURE:
<223> OTHER INFORMATION: Synthetic

<400> SEQUENCE: 13
aaggaattcg gccttgtcca t                                             21

<210> SEQ ID NO 14
<211> LENGTH: 22
<212> TYPE: DNA
<213> ORGANISM: Artificial Sequence
<220> FEATURE:
```

```
<223> OTHER INFORMATION: Synthetic

<400> SEQUENCE: 14
ctcaaggaat tcggccttgt cc                                              22

<210> SEQ ID NO 15
<211> LENGTH: 19
<212> TYPE: DNA
<213> ORGANISM: Artificial Sequence
<220> FEATURE:
<223> OTHER INFORMATION: Synthetic

<400> SEQUENCE: 15
agcctcaagg aattcggcc                                                  19

<210> SEQ ID NO 16
<211> LENGTH: 21
<212> TYPE: DNA
<213> ORGANISM: Artificial Sequence
<220> FEATURE:
<223> OTHER INFORMATION: Synthetic

<400> SEQUENCE: 16
aggagcctca aggaattcgg c                                               21

<210> SEQ ID NO 17
<211> LENGTH: 23
<212> TYPE: DNA
<213> ORGANISM: Artificial Sequence
<220> FEATURE:
<223> OTHER INFORMATION: Synthetic

<400> SEQUENCE: 17
tttaggagcc tcaaggaatt cgg                                             23

<210> SEQ ID NO 18
<211> LENGTH: 25
<212> TYPE: DNA
<213> ORGANISM: Artificial Sequence
<220> FEATURE:
<223> OTHER INFORMATION: Synthetic

<400> SEQUENCE: 18 cttttagga gcctcaagga attcg                                            25

<210> SEQ ID NO 19
<211> LENGTH: 27
<212> TYPE: DNA
<213> ORGANISM: Artificial Sequence
<220> FEATURE:
<223> OTHER INFORMATION: Synthetic

<400> SEQUENCE: 19
cttcttttta ggagcctcaa ggaattc                                         27

<210> SEQ ID NO 20
<211> LENGTH: 25
<212> TYPE: DNA
<213> ORGANISM: Artificial Sequence
<220> FEATURE:
<223> OTHER INFORMATION: Synthetic

<400> SEQUENCE: 20
tctcttcttt ttaggagcct caagg                                           25
```

```
<210> SEQ ID NO 21
<211> LENGTH: 27
<212> TYPE: DNA
<213> ORGANISM: Artificial Sequence
<220> FEATURE:
<223> OTHER INFORMATION: Synthetic

<400> SEQUENCE: 21
ctttctcttc tttttaggag cctcaag                                           27

<210> SEQ ID NO 22
<211> LENGTH: 27
<212> TYPE: DNA
<213> ORGANISM: Artificial Sequence
<220> FEATURE:
<223> OTHER INFORMATION: Synthetic

<400> SEQUENCE: 22
tacctttctc ttcttttag gagcctc                                            27

<210> SEQ ID NO 23
<211> LENGTH: 27
<212> TYPE: DNA
<213> ORGANISM: Artificial Sequence
<220> FEATURE:
<223> OTHER INFORMATION: Synthetic

<400> SEQUENCE: 23
acctaccttt ctcttctttt taggagc                                           27

<210> SEQ ID NO 24
<211> LENGTH: 49
<212> TYPE: DNA
<213> ORGANISM: Artificial Sequence
<220> FEATURE:
<223> OTHER INFORMATION: Synthetic

<400> SEQUENCE: 24
aatgatacgg cgaccaccga gatctacacc cgcagattat accgcaact                   49

<210> SEQ ID NO 25
<211> LENGTH: 39
<212> TYPE: DNA
<213> ORGANISM: Artificial Sequence
<220> FEATURE:
<223> OTHER INFORMATION: Synthetic

<400> SEQUENCE: 25
gggttagcaa gtggcagcct ttcgctgtca atgtcgagt                              39

<210> SEQ ID NO 26
<211> LENGTH: 18
<212> TYPE: DNA
<213> ORGANISM: Artificial Sequence
<220> FEATURE:
<223> OTHER INFORMATION: Synthetic

<400> SEQUENCE: 26
aatgatacgg cgaccacc                                                     18

<210> SEQ ID NO 27
<211> LENGTH: 52
<212> TYPE: DNA
<213> ORGANISM: Artificial Sequence
<220> FEATURE:
<223> OTHER INFORMATION: Synthetic
<220> FEATURE:
```

```
<221> NAME/KEY: misc_feature
<222> LOCATION: (25)..(32)
<223> OTHER INFORMATION: n is a, c, g, or t

<400> SEQUENCE: 27
caagcagaag acggcatacg agatnnnnnn nngggttagc aagtggcagc ct            52

<210> SEQ ID NO 28
<211> LENGTH: 38
<212> TYPE: DNA
<213> ORGANISM: Artificial Sequence
<220> FEATURE:
<223> OTHER INFORMATION: Synthetic

<400> SEQUENCE: 28
cgcaactaca cgccaccatg gacaaggccg aattcctt                            38

<210> SEQ ID NO 29
<211> LENGTH: 43
<212> TYPE: DNA
<213> ORGANISM: Artificial Sequence
<220> FEATURE:
<223> OTHER INFORMATION: Synthetic

<400> SEQUENCE: 29
tgtgttccag aaaagtgtct gccatggcag cgtggaattc tgg                      43

<210> SEQ ID NO 30
<211> LENGTH: 41
<212> TYPE: DNA
<213> ORGANISM: Artificial Sequence
<220> FEATURE:
<223> OTHER INFORMATION: Synthetic

<400> SEQUENCE: 30
cgactcgaca ttgacagcga aaggctgcca cttgctaacc c                        41

<210> SEQ ID NO 31
<211> LENGTH: 4273
<212> TYPE: DNA
<213> ORGANISM: Artificial Sequence
<220> FEATURE:
<223> OTHER INFORMATION: Synthetic

<400> SEQUENCE: 31
aaagggagcc cccgatttag agcttgacgg ggaaagccgg cgaacgtggc gagaaaggaa    60
gggaagaaag cgaaaggagc gggcgctagg gcgctggcaa gtgtagcggt cacgctgcgc   120
gtaaccacca cacccgccgc gcttaatgcg ccgctacagg gcgcgtccca ttcgccattc   180
aggctgcgca actgttggga agggcgatcg gtgcgggcct cttcgctatt acgccagctg   240
gcgaaagggg gatgtgctgc aaggcgatta agttgggtaa cgccagggtt ttcccagtca   300
cgacgttgta aaacgacggc cagtgaattg taatacgact cactataggg cgaattgggt   360
accgggcccc ccctcgaggt cgacgatgta ggtcacggca ttccggactc agcgctcgag   420
ccggcttgtc gacgacggcg gtctccgtcg tcaggatcat ccgcagatta taccgcaact   480
acacgccacc atggctcgta ctaaacagac agctcggaaa tccaccggcg gtaaagcgcc   540
acgcaagcag ctggctacca aggctgctcg caagagcgcg ccggctaccg gcggcgtgaa   600
aaagcctcac cgttaccgcc cgggcactgt ggctctgcgc gagatccgcc gctaccaaaa   660
gtcgaccgag ttgctgattc ggaagctgcc gttccagcgc ctggtgcgag aaatcgccca   720
agacttcaag accgatcttc gcttccagag ctctgcggtg atggcgctgc aggaggcttg   780
```

```
tgaggcctac ttggtagggc tctttgagga cacaaacctt tgcgccatcc atgctaagcg      840
agtgactatt atgcccaaag acatccagct cgctcgccgc attcgcggag aaagagcgag      900
tagaccaccc gtcgcaacca tgaacacccc gggaattaac ctgatcaagg aggacatgcg      960
cgtgaaggtg cacatggagg gcaacgtgaa cggccacgcc ttcgtgatcg agggcgaggg     1020
caagggcaag ccctacgagg gcacccagac cgccaacctg accgtgaagg agggcgcccc     1080
cctgcccttc agctacgaca tcctgaccac cgccgtgcac tacggcaacc gggtgttcac     1140
caagtacccc gaggacatcc ccgactactt caagcagagc ttccccgagg gctacagctg     1200
ggagcgcacc atgaccttcg aggacaaggg catctgcacc atccgcagcg acatcagcct     1260
ggagggcgac tgcttcttcc agaacgtgcg cttcaagggc accaacttcc cccccaacgg     1320
ccccgtgatg cagaagaaga ccctgaagtg ggagcccagc accgagaagc tgcacgtgcg     1380
cgacggcctg ctggtgggca acatcaacat ggccctgctg ctggagggcg gcggccacta     1440
cctgtgcgac ttcaagacca cctacaaggc caagaaggtg gtgcagctgc ccgacgccca     1500
cttcgtggac caccgcatcg agatcctggg caacgacagc gactacaaca aggtgaagct     1560
gtacgagcac gccgtggccc gctacagccc cctgcccagc caggtgtggt aatagggatc     1620
ctgatcataa tcagccatac cacatttgta gaggttttac ttgctttaaa aaacctccca     1680
cacctccccc tgaacctgaa acataaaatg aatgcaattg ttgttgttaa cttgtttatt     1740
gcagcttata atggttacaa ataaagcaat agcatcacaa atttcacaaa taaagcattt     1800
ttttcactgc attctagttg tggtttgtcc aaactcatca atgtatctta ggagatcccc     1860
tttagtgagg gttaatttcg agcttggcgt aatcatggtc atagctgttt cctgtgtgaa     1920
attgttatcc gctcacaatt ccacacaaca tacgagccgg aagcataaag tgtaaagcct     1980
ggggtgccta atgagtgagc taactcacat taattgcgtt gcgctcactg cccgctttcc     2040
agtcgggaaa cctgtcgtgc cagctgcatt aatgaatcgg ccaacgcgcg gggagaggcg     2100
gtttgcgtat tgggcgctct tccgcttcct cgctcactga ctcgctgcgc tcggtcgttc     2160
ggctgcggcg agcggtatca gctcactcaa aggcggtaat acggttatcc acagaatcag     2220
gggataacgc aggaaagaac atgtgagcaa aaggccagca aaaggccagg aaccgtaaaa     2280
aggccgcgtt gctggcgttt ttccataggc tccgcccccc tgacgagcat cacaaaaatc     2340
gacgctcaag tcagaggtgg cgaaacccga caggactata agataccagg cgtttccccc     2400
ctggaagctc cctcgtgcgc tctcctgttc cgaccctgcc gcttaccgga tacctgtccg     2460
cctttctccc ttcgggaagc gtggcgcttt ctcatagctc acgctgtagg tatctcagtt     2520
cggtgtaggt cgttcgctcc aagctgggct gtgtgcacga accccccgtt cagcccgacc     2580
gctgcgcctt atccggtaac tatcgtcttg agtccaaccc ggtaagacac gacttatcgc     2640
cactggcagc agccactggt aacaggatta gcagagcgag gtatgtaggc ggtgctacag     2700
agttcttgaa gtggtggcct aactacggct acactagaag aacagtattt ggtatctgcg     2760
ctctgctgaa gccagttacc ttcggaaaaa gagttggtag ctcttgatcc ggcaaacaaa     2820
ccaccgctgg tagcggtggt ttttttgttt gcaagcagca gattacgcgc agaaaaaaag     2880
gatctcaaga agatcctttg atcttttcta cggggtctga cgctcagtgg aacgaaaact     2940
cacgttaagg gattttggtc atgagattat caaaaaggat cttcacctag atccttttaa     3000
attaaaaatg aagttttaaa tcaatctaaa gtatatatga gtaaacttgg tctgacagtt     3060
agaagaactc gtcaagaagg cgatagaagg cgatgcgctg cgaatcggga gcggcgatac     3120
```

```
cgtaaagcac gaggaagcgg tcagcccatt cgccgccaag ctcttcagca atatcacggg      3180
tagccaacgc tatgtcctga tagcggtccg ccacacccag ccggccacag tcgatgaatc      3240
cagaaaagcg gccatttccc accatgatat tcggcaagca ggcatcgcca tgggtcacga      3300
cgagatcctc gccgtcgggc atgctcgcct tgagcctggc gaacagttcg gctggcgcga      3360 gccctgatg ctcttcgtcc agatcatcct gatcgacaag accggcttcc atccgagtac      3420
gtgctcgctc gatgcgatgt ttcgcttggt ggtcgaatgg gcaggtagcc ggatcaagcg      3480
tatgcagccg ccgcattgca tcagccatga tggatacttt ctcggcagga gcaaggtgag      3540
atgacaggag atcctgcccc ggcacttcgc ccaatagcag ccagtcccct tccgcttcag      3600
tgacaacgtc gagcacagct cgcaaggaa cgcccgtcgt ggccagccac gatagccgcg      3660
ctgcctcgtc ttgcagttca ttcagggcac cggacaggtc ggtcttgaca aaaagaaccg      3720
ggcgcccctg cgctgacagc cggaacacgg cggcatcaga gcagccgatt gtctgttgtg      3780
cccagtcata gccgaatagc ctctccaccc aagcggccgg agaacctgcg tgcaatccat      3840
cttgttcaat catactcttc cttttcaat attattgaag catttatcag ggttattgtc        3900
tcatgagcgg atacatattt gaatgtattt agaaaaataa acaaataggg gttccgcgca      3960
catttccccg aaaagtgcca cctaaattgt aagcgttaat attttgttaa aattcgcgtt      4020 aaattttgt taaatcagct catttttta ccaataggcc gaaatcggca aaatccctta        4080
taaatcaaaa gaatagaccg agatagggt gagtgttgtt ccagtttgga acaagagtcc      4140
actattaaag aacgtggact ccaacgtcaa agggcgaaaa accgtctatc agggcgatgg      4200
cccactacgt gaaccatcac cctaatcaag ttttttgggg tcgaggtgcc gtaaagcact      4260
aaatcggaac cct                                                         4273

<210> SEQ ID NO 32
<211> LENGTH: 42
<212> TYPE: DNA
<213> ORGANISM: Artificial Sequence
<220> FEATURE:
<223> OTHER INFORMATION: Synthetic

<400> SEQUENCE: 32
agtagaccac ccgtcgcaac catgaacacc ccgggaatta ac                          42

<210> SEQ ID NO 33
<211> LENGTH: 35
<212> TYPE: DNA
<213> ORGANISM: Artificial Sequence
<220> FEATURE:
<223> OTHER INFORMATION: Synthetic

<400> SEQUENCE: 33
ctgattatga tcaggatccc cacacctggc tgggc                                  35

<210> SEQ ID NO 34
<211> LENGTH: 39
<212> TYPE: DNA
<213> ORGANISM: Artificial Sequence
<220> FEATURE:
<223> OTHER INFORMATION: Synthetic

<400> SEQUENCE: 34
cgcaactaca cgccaccatg gctcgtacta aacagacag                              39

<210> SEQ ID NO 35
<211> LENGTH: 40
```

```
<212> TYPE: DNA
<213> ORGANISM: Artificial Sequence
<220> FEATURE:
<223> OTHER INFORMATION: Synthetic

<400> SEQUENCE: 35
ggttgcgacg ggtggtctac tcgctctttc tccgcgaatg                           40

<210> SEQ ID NO 36
<211> LENGTH: 24
<212> TYPE: DNA
<213> ORGANISM: Artificial Sequence
<220> FEATURE:
<223> OTHER INFORMATION: Synthetic

<400> SEQUENCE: 36
tagggatcct gatcataatc agcc                                            24

<210> SEQ ID NO 37
<211> LENGTH: 17
<212> TYPE: DNA
<213> ORGANISM: Artificial Sequence
<220> FEATURE:
<223> OTHER INFORMATION: Synthetic

<400> SEQUENCE: 37
ggtggcgtgt agttgcg                                                    17

<210> SEQ ID NO 38
<211> LENGTH: 5680
<212> TYPE: DNA
<213> ORGANISM: Artificial Sequence
<220> FEATURE:
<223> OTHER INFORMATION: Synthetic

<400> SEQUENCE: 38
aaagggagcc cccgatttag agcttgacgg ggaaagccgg cgaacgtggc gagaaaggaa     60
gggaagaaag cgaaaggagc gggcgctagg gcgctggcaa gtgtagcggt cacgctgcgc    120
gtaaccacca cacccgccgc gcttaatgcg ccgctacagg gcgcgtccca ttcgccattc    180
aggctgcgca actgttggga agggcgatcg gtgcgggcct cttcgctatt acgccagctg    240
gcgaaagggg gatgtgctgc aaggcgatta agttgggtaa cgccagggtt ttcccagtca    300
cgacgttgta aaacgacggc cagtgaattg taatacgact cactataggg cgaattgggt    360
accgggcccc cctcgaggt cgacgatgta ggtcacggca ttccggactc agcgctcgag    420
ccggcttgtc gacgacggcg gtctccgtcg tcaggatcat ccgcagatta taccgcaact    480
acacgccacc atggctcgta ctaaacagac agctcggaaa tccaccggcg gtaaagcgcc    540
acgcaagcag ctggctacca aggctgctcg caagagcgcg ccggctaccg gcggcgtgaa    600
aaagcctcac cgttaccgcc cgggcactgt ggctctgcgc gagatccgcc gctaccaaaa    660
gtcgaccgag ttgctgattc ggaagctgcc gttccagcgc ctggtgcgag aaatcgccca    720
agacttcaag accgatcttc gcttccagag ctctgcggtg atggcgctgc aggaggcttg    780
tgaggcctac ttggtagggc tctttgagga cacaaacctt tgcgccatcc atgctaagcg    840
agtgactatt atgcccaaag acatccagct cgctcgccgc attcgcggag aaagagcgag    900
tagaccaccc gtcgcaacca tgaacacccc gggaattaac ctgatcaagg aggacatgcg    960
cgtgaaggtg cacatggagg gcaacgtgaa cggccacgcc ttcgtgatcg agggcgaggg   1020
caagggcaag ccctacgagg gcacccagac cgccaacctg accgtgaagg agggcgcccc   1080
```

```
cctgcccttc agctacgaca tcctgaccac cgccgtgcac tacggcaacc gggtgttcac    1140
caagtacccc gaggacatcc ccgactactt caagcagagc ttccccgagg gctacagctg    1200
ggagcgcacc atgaccttcg aggacaaggg catctgcacc atccgcagcg acatcagcct    1260
ggagggcgac tgcttcttcc agaacgtgcg cttcaagggc accaacttcc cccccaacgg    1320
ccccgtgatg cagaagaaga ccctgaagtg ggagcccagc accgagaagc tgcacgtgcg    1380
cgacggcctg ctggtgggca acatcaacat ggccctgctg ctggagggcg gcggccacta    1440
cctgtgcgac ttcaagacca cctacaaggc caagaaggtg gtgcagctgc ccgacgccca    1500
cttcgtggac caccgcatcg agatcctggg caacgacagc gactacaaca aggtgaagct    1560
gtacgagcac gccgtggccc gctacagccc cctgcccagc caggtgtggg ggagcggcgc    1620
aacgaatttt tccctcctta acaggctgg cgacgtagag gaaaaccctg gtcccatgcc    1680
agagccagcg aagtctgctc ccgccccgaa aaagggctcc aagaaggcgg tgactaaggc    1740
gcagaagaaa ggcggcaaga gcgcaagcg cagccgcaag gagagctatt ccatctatgt    1800
gtacaaggtt ctgaagcagg tccacccctga caccggcatt tcgtccaagg ccatgggcat    1860
catgaattcg tttgtgaacg acatttttcga gcgcatcgca ggtgaggctt cccgcctggc    1920
gcattacaac aagcgctcga ccatcacctc cagggagatc cagacggccg tgcgcctgct    1980
gctgcctggg gagttggcca agcacgccgt gtccgagggt actaaggcca tcaccaagta    2040
caccagcgct aaggatccac cggtcgccac catggtagca ggtcatgcct ctggcagccc    2100
cgcattcggg accgcctctc attcgaattg cgaacatgaa gagatccacc tcgccggctc    2160
gatccagccg catggcgcgc ttctggtcgt cagcgaacat gatcatcgcg tcatccaggc    2220
cagcgccaac gccgcggaat ttctgaatct cggaagcgta ctcggcgttc cgctcgccga    2280
gatcgacggg gatctgttga tcaagatcct gccgcatctc gatcccaccg ccgaaggcat    2340
gccggtcgcg gtgcgctgcc ggatcggcaa tccctctacg gagtactgcg gtctgatgca    2400
tcggcctccg gaaggcgggc tgatcatcga actcgaacgt gccggccgt cgatcgatct    2460 gtcaggcacg ctggcgccgg cgctggagcg gatccgcacg gcgggttcac tgcgcgcgct    2520
gtgcgatgac accgtgctgc tgtttcagca gtgcaccggc tacgaccggg tgatggtgta    2580
tcgtttcgat gagcaaggcc acggcctggt attctccgag tgccatgtgc ctgggctcga    2640
atcctatttc ggcaaccgct atccgtcgtc gctggtcccg cagatggcgc ggcagctgta    2700
cgtgcggcag cgcgtccgcg tgctggtcga cgtcacctat cagccggtgc cgctggagcc    2760
gcggctgtcg ccgctgaccg ggcgcgatct cgacatgtcg ggctgcttcc tgcgctcgat    2820
gtcgccgatc catctgcagt tcctgaagga catgggcgtg cgcgccaccc tggcggtgtc    2880
gctggtggtc ggcggcaagc tgtggggcct ggttgtctgt caccattatc tgccgcgctt    2940
catccgtttc gagctgcggg cgatctgcaa acggctcgcc gaaaggatcg cgacgcggat    3000
caccgcgctt gagagctaat agggatcctg atcataatca gccataccac atttgtagag    3060
gttttacttg cttttaaaaaa cctcccacac ctcccctga acctgaaaca taaaatgaat    3120
gcaattgttg ttgttaactt gtttattgca gcttataatg gttacaaata aagcaatagc    3180
atcacaaatt tcacaaataa agcattttttt tcactgcatt ctagttgtgg tttgtccaaa    3240
ctcatcaatg tatcttagga gatccccttt agtgagggtt aatttcgagc ttggcgtaat    3300
catggtcata gctgtttcct gtgtgaaatt gttatccgct cacaattcca cacaacatac    3360
gagccggaag cataaagtgt aaagcctggg gtgcctaatg agtgagctaa ctcacattaa    3420
ttgcgttgcg ctcactgccc gctttccagt cgggaaacct gtcgtgccag ctgcattaat    3480
```

```
gaatcggcca acgcgcgggg agaggcggtt tgcgtattgg gcgctcttcc gcttcctcgc    3540
tcactgactc gctgcgctcg gtcgttcggc tgcggcgagc ggtatcagct cactcaaagg    3600
cggtaatacg gttatccaca gaatcagggg ataacgcagg aaagaacatg tgagcaaaag    3660
gccagcaaaa ggccaggaac cgtaaaaagg ccgcgttgct ggcgtttttc cataggctcc    3720
gcccccctga cgagcatcac aaaaatcgac gctcaagtca gaggtggcga acccgacag    3780 gactataaag ataccaggcg tttccccctg gaagctccct cgtgcgctct cctgttccga    3840
ccctgccgct taccggatac ctgtccgcct ttctcccttc gggaagcgtg gcgctttctc    3900
atagctcacg ctgtaggtat ctcagttcgg tgtaggtcgt tcgctccaag ctgggctgtg    3960
tgcacgaacc ccccgttcag cccgaccgct gcgccttatc cggtaactat cgtcttgagt    4020
ccaacccggt aagacacgac ttatcgccac tggcagcagc cactggtaac aggattagca    4080
gagcgaggta tgtaggcggt gctacagagt tcttgaagtg gtggcctaac tacggctaca    4140
ctagaagaac agtatttggt atctgcgctc tgctgaagcc agttaccttc ggaaaaagag    4200
ttggtagctc ttgatccggc aaacaaacca ccgctggtag cggtggtttt tttgtttgca    4260
agcagcagat tacgcgcaga aaaaaaggat ctcaagaaga tcctttgatc ttttctacgg    4320
ggtctgacgc tcagtggaac gaaaactcac gttaagggat tttggtcatg agattatcaa    4380
aaaggatctt cacctagatc cttttaaatt aaaaatgaag ttttaaatca atctaaagta    4440
tatatgagta aacttggtct gacagttaga gaactcgtc aagaaggcga tagaaggcga     4500
tgcgctgcga atcgggagcg gcgataccgt aaagcacgag gaagcggtca gcccattcgc    4560
cgccaagctc ttcagcaata tcacgggtag ccaacgctat gtcctgatag cggtccgcca    4620
cacccagccg gccacagtcg atgaatccag aaaagcggcc attttccacc atgatattcg    4680
gcaagcaggc atcgccatgg gtcacgacga gatcctcgcc gtcgggcatg ctcgccttga    4740
gcctggcgaa cagttcggct ggcgcgagcc cctgatgctc ttcgtccaga tcatcctgat    4800
cgacaagacc ggcttccatc cgagtacgtg ctcgctcgat gcgatgtttc gcttggtggt    4860
cgaatgggca ggtagccgga tcaagcgtat gcagccgccg cattgcatca gccatgatgg    4920
atactttctc ggcaggagca aggtgagatg acaggagatc ctgccccggc acttcgccca    4980
atagcagcca gtcccttccc gcttcagtga caacgtcgag cacagctgcg caaggaacgc    5040
ccgtcgtggc cagccacgat agccgcgctg cctcgtcttg cagttcattc agggcaccgg    5100
acaggtcggt cttgacaaaa agaaccgggc gcccctgcgc tgacagccgg aacacggcgg    5160
catcagagca gccgattgtc tgttgtgccc agtcatagcc gaatagcctc tccacccaag    5220
cggccggaga acctgcgtgc aatccatctt gttcaatcat actcttcctt tttcaatatt    5280
attgaagcat ttatcagggt tattgtctca tgagcggata catatttgaa tgtatttaga    5340
aaaataaaca ataggggtt ccgcgcacat ttccccgaaa agtgccacct aaattgtaag     5400
cgttaatatt ttgttaaaat tcgcgttaaa ttttttgttaa atcagctcat ttttaacca    5460 ataggccgaa atcggcaaaa tcccttataa atcaaaagaa tagaccgaga taggagttgag  5520 tgttgttcca gtttgaaaca agagtccact attaaagaac gtggactcca acgtcaaagg    5580
gcgaaaaacc gtctatcagg gcgatggccc actacgtgaa ccatcaccct aatcaagttt    5640
tttggggtcg aggtgccgta aagcactaaa tcggaacccct                         5680
```

<210> SEQ ID NO 39  
<211> LENGTH: 60  
<212> TYPE: DNA

<213> ORGANISM: Artificial Sequence
<220> FEATURE:
<223> OTHER INFORMATION: Synthetic

<400> SEQUENCE: 39

```
ctccttaaac aggctggcga cgtagaggaa aaccctggtc ccatgccaga gccagcgaag    60
```

<210> SEQ ID NO 40
<211> LENGTH: 30
<212> TYPE: DNA
<213> ORGANISM: Artificial Sequence
<220> FEATURE:
<223> OTHER INFORMATION: Synthetic

<400> SEQUENCE: 40

```
atcaggatcc ctattagctc tcaagcgcgg                                     30
```

<210> SEQ ID NO 41
<211> LENGTH: 17
<212> TYPE: DNA
<213> ORGANISM: Artificial Sequence
<220> FEATURE:
<223> OTHER INFORMATION: Synthetic

<400> SEQUENCE: 41

```
ggtggcgtgt agttgcg                                                   17
```

<210> SEQ ID NO 42
<211> LENGTH: 60
<212> TYPE: DNA
<213> ORGANISM: Artificial Sequence
<220> FEATURE:
<223> OTHER INFORMATION: Synthetic

<400> SEQUENCE: 42

```
tcgccagcct gtttaaggag ggaaaaattc gttgcgccgc tcccccacac ctggctgggc    60
```

<210> SEQ ID NO 43
<211> LENGTH: 7269
<212> TYPE: DNA
<213> ORGANISM: Artificial Sequence
<220> FEATURE:
<223> OTHER INFORMATION: Synthetic

<400> SEQUENCE: 43

```
ttctttcctg cgttatcccc tgattctgtg gataaccgta ttaccgcctt tgagtgagct    60
gataccgctc gccgcagccg aacgaccgag cgcagcgagt cagtgagcga ggaagcggaa   120
gagcgcccaa tacgcaaacc gcctctcccc gcgcgttggc cgattcatta atgcagctgg   180
cacgacaggt ttcccgactg gaaagcgggc agtgagcgca acgcaattaa tgtgagttag   240
ctcactcatt aggcaccccca ggctttacac tttatgcttc cggctcgtat gttgtgtgga   300
attgtgagcg gataacaatt tcacacagga aacagctatg accatgatta cgccaagcgc   360
gcaattaacc ctcactaaag ggaacaaaag ctggagctgc aagcttaatg tagtcttatg   420
caatactctt gtagtcttgc aacatggtaa cgatgagtta gcaacatgcc ttacaaggag   480
agaaaaagca ccgtgcatgc cgattggtgg aagtaaggtg gtacgatcgt gccttattag   540
gaaggcaaca gacgggtctg acatggattg gacgaaccac tgaattgccg cattgcagag   600
atattgtatt taagtgccta gctcgataca taaacgggtc tctctggtta gaccagatct   660
gagcctggga gctctctggc taactaggga acccactgct taagcctcaa taaagcttgc   720
cttgagtgct tcaagtagtg tgtgcccgtc tgttgtgtga ctctggtaac tagagatccc   780
```

```
tcagacccttt ttagtcagtg tggaaaatct ctagcagtgg cgcccgaaca gggacttgaa    840
agcgaaaggg aaaccagagg agctctctcg acgcaggact cggcttgctg aagcgcgcac    900
ggcaagaggc gaggggcggc gactggtgag tacgccaaaa attttgacta gcggaggcta    960
gaaggagaga gatgggtgcg agagcgtcag tattaagcgg gggagaatta gatcgcgatg   1020
ggaaaaaatt cggttaaggc caggggggaaa gaaaaaatat aaattaaaac atatagtatg   1080
ggcaagcagg gagctagaac gattcgcagt taatcctggc ctgttagaaa catcagaagg   1140
ctgtagacaa atactgggac agctacaacc atcccttcag acaggatcag aagaacttag   1200
atcattatat aatacagtag caaccctcta ttgtgtgcat caaggatag agataaaaga   1260 caccaaggaa gctttagaca agatagagga agagcaaaac aaaagtaaga ccaccgcaca   1320
gcaagcggcc gctgatcttc agacctggag gaggagatat gagggacaat ggagaagtg    1380 aattatataa atataaagta gtaaaaattg aaccattagg agtagcaccc accaaggcaa   1440
agagaagagt ggtgcagaga gaaaaaagag cagtgggaat aggagctttg ttccttgggt   1500
tcttgggagc agcaggaagc actatgggcg cagcgtcaat gacgctgacg gtacaggcca   1560
gacaattatt gtctggtata gtgcagcagc agaacaattt gctgagggct attgaggcgc   1620
aacagcatct gttgcaactc acagtctggg gcatcaagca gctccaggca gaatcctgg    1680 ctgtggaaag atacctaaag gatcaacagc tcctggggat ttggggttgc tctggaaaac   1740
tcatttgcac cactgctgtg ccttggaatg ctagttggag taataaatct ctggaacaga   1800
tttggaatca cacgacctgg atggagtggg acagagaaat taacaattac acaagcttaa   1860
tacactcctt aattgaagaa tcgcaaaacc agcaagaaaa gaatgaacaa gaattattgg   1920
aattagataa atgggcaagt ttgtggaatt ggtttaacat aacaaattgg ctgtggtata   1980
taaaattatt cataatgata gtaggaggct tggtaggttt aagaatagtt tttgctgtac   2040
tttctatagt gaatagagtt aggcagggat attcaccatt atcgtttcag acccacctcc   2100
caaccccgag gggacccgac aggcccgaag gaatagaaga agaaggtgga gagagagaca   2160
gagacagatc cattcgatta gtgaacggat ctcgacggta tcggttaact tttaaaagaa   2220
aaggggggat tggggggtac agtgcagggg aaagaatagt agacataata gcaacagaca   2280
tacaaactaa agaattacaa aaacaaatta caaaattcaa aatttatcg ataagcttgg    2340 gagttccgcg ttacataact tacggtaaat ggcccgcctg gctgaccgcc caacgacccc   2400
cgcccattga cgtcaataat gacgtatgtt cccatagtaa cgccaatagg gactttccat   2460
tgacgtcaat gggtggagta tttacggtaa actgcccact tggcagtaca tcaagtgtat   2520
catatgccaa gtacgccccc tattgacgtc aatgacggta aatggcccgc ctggcattat   2580
gcccagtaca tgaccttatg ggactttcct acttggcagt acatctacgt attagtcatc   2640
gctattacca tggtgatgcg gttttggcag tacatcaatg ggcgtggata gcggtttgac   2700
tcacggggat ttccaagtct ccaccccatt gacgtcaatg ggagtttgtt ttggcaccaa   2760
aatcaacggg actttccaaa atgtcgtaac aactccgccc cattgacgca atgggcggt    2820 aggcgtgtac ggtgggaggt ctatataagc agagctcgtt tagtgaaccg tcagatcgcc   2880
tggagacgcc atccacgctg ttttgacctc catagaagac accgactcta gtccagtgtg   2940
gtggaattct gcagatatca acaagtttgt acaaaaaagt tggcaccatg gctcgtacta   3000
aacagacagc tcggaaatcc accggcggta aagcgccacg caagcagctg gctaccaagg   3060
ctgctcgcaa gagcgcgccg gctaccggcg gcgtgaaaaa gcctcaccgt taccgcccgg   3120
```

```
gcactgtggc tctgcgcgag atccgccgct accaaaagtc gaccgagttg ctgattcgga   3180
agctgccgtt ccagcgcctg gtgcgagaaa tcgcccaaga cttcaagacc gatcttcgct   3240
tccagagctc tgcggtgatg gcgctgcagg aggcttgtga ggcctacttg gtagggctct   3300
ttgaggacac aaacctttgc gccatccatg ctaagcgagt gactattatg cccaaagaca   3360
tccagctcgc tcgccgcatt cgcggagaaa gagcgagtag accaccgtc gcaaccatga    3420 acaccccggg aattaacctg atcaaggagg acatgcgcgt gaaggtgcac atggagggca   3480
acgtgaacgg ccacgccttc gtgatcgagg gcagggcaa gggcaagccc tacgagggca    3540
cccagaccgc caacctgacc gtgaaggagg gcgcccccct gcccttcagc tacgacatcc   3600
tgaccaccgc cgtgcactac ggcaaccggg tgttcaccaa gtaccccgag gacatccccg   3660
actacttcaa gcagagcttc cccgagggct acagctggga gcgcaccatg accttcgagg   3720
acaagggcat ctgcaccatc gcagcgaca tcagcctgga gggcgactgc ttcttccaga    3780
acgtgcgctt caagggcacc aacttccccc ccaacggccc cgtgatgcag aagaagaccc   3840
tgaagtggga gcccagcacc gagaagctgc acgtgcgcga cggcctgctg gtgggcaaca   3900
tcaacatggc cctgctgctg gagggcggcg gccactacct gtgcgacttc aagaccacct   3960
acaaggccaa gaaggtggtg cagctgcccg acgcccactt cgtggaccac cgcatcgaga   4020
tcctgggcaa cgacagcgac tacaacaagg tgaagctgta cgagcacgcc gtggcccgct   4080
acagccccct gcccagccag gtgtggtaag cacaattcga gctcggtacc tttaagacca   4140
atgacttaca aggcagctgt agatcttagc cacttttttaa aagaaaaggg gggactggaa   4200
gggctagctc actcccaacg aagacaagat ctgcttttttg cttgtactgg gtctctctgg   4260
ttagaccaga tctgagcctg ggagctctct ggctaactag ggaacccact gcttaagcct   4320
caataaagct tgccttgagt gcttcaagta gtgtgtgccc gtctgttgtg tgactctggt   4380
aactagagat ccctcagacc cttttagtca gtgtggaaaa tctctagcag tagtagttca   4440
tgtcatctta ttattcagta tttataactt gcaaagaaat gaatatcaga gagtgagagg   4500
aacttgttta ttgcagctta taatggttac aaataaagca atagcatcac aaatttcaca   4560
aataaagcat ttttttcact gcattctagt tgtggtttgt ccaaactcat caatgtatct   4620
tatcatgtct ggctctagct atcccgcccc taactccgcc catcccgccc ctaactccgc   4680
ccagttccgc ccattctccg ccccatggct gactaatttt ttttatttat gcagaggccg   4740
aggccgcctc ggcctctgag ctattccaga agtagtgagg aggcttttttt ggaggcctag   4800 ggacgtaccc aattcgccct atagtgagtc gtattacgcg cgctcactgg ccgtcgtttt   4860
acaacgtcgt gactgggaaa accctggcgt tacccaactt aatcgccttg cagcacatcc   4920 cccttttcgcc agctggcgta atagcgaaga ggcccgcacc gatcgccctt cccaacagtt   4980
gcgcagcctg aatggcgaat gggacgcgcc ctgtagcggc gcattaagcg cggcgggtgt   5040
ggtggttacg cgcagcgtga ccgctacact tgccagcgcc ctagcgcccg ctcctttcgc   5100
tttcttccct tcctttctcg ccacgttcgc cggctttccc cgtcaagctc taaatcgggg   5160
gctcccttta gggttccgat ttagtgcttt acggcacctc gaccccaaaa aacttgatta   5220
gggtgatggt tcacgtagtg gccatcgccc tgatagacg ttttttcgcc ctttgacgtt    5280
ggagtccacg ttctttaata gtggactctt gttccaaact ggaacaacac tcaaccctat   5340
ctcggtctat tcttttgatt tataagggat tttgccgatt tcggcctatt ggttaaaaaa   5400
tgagctgatt taacaaaaat ttaacgcgaa ttttaacaaa atattaacgc ttacaattta   5460
ggtggcactt ttcggggaaa tgtgcgcgga accctatt  gtttatttt ctaaatacat    5520
```

```
tcaaatatgt atccgctcat gagacaataa ccctgataaa tgcttcaata atattgaaaa    5580
aggaagagta tgagtattca acatttccgt gtcgcccttta ttcccttttt tgcggcattt    5640
tgccttcctg tttttgctca cccagaaacg ctggtgaaag taaaagatgc tgaagatcag    5700
ttgggtgcac gagtgggtta catcgaactg gatctcaaca gcggtaagat ccttgagagt    5760
tttcgccccg aagaacgttt tccaatgatg agcacttttta agttctgct atgtggcgcg    5820
gtattatccc gtattgacgc cgggcaagag caactcggtc gccgcataca ctattctcag    5880
aatgacttgg ttgagtactc accagtcaca gaaaagcatc ttacggatgg catgacagta    5940
agagaattat gcagtgctgc cataaccatg agtgataaca ctgcggccaa cttacttctg    6000
acaacgatcg gaggaccgaa ggagctaacc gcttttttgc acaacatggg ggatcatgta    6060
actcgccttg atcgttggga accggagctg aatgaagcca taccaaacga cgagcgtgac    6120
accacgatgc ctgtagcaat ggcaacaacg ttgcgcaaac tattaactgg cgaactactt    6180
actctagctt cccggcaaca attaatagac tggatggagg cggataaagt tgcaggacca    6240
cttctgcgct cggcccttcc ggctggctgg tttattgctg ataaatctgg agccggtgag    6300
cgtgggtctc gcggtatcat tgcagcactg gggccagatg gtaagccctc ccgtatcgta    6360
gttatctaca cgacggggag tcaggcaact atggatgaac gaaatagaca gatcgctgag    6420
ataggtgcct cactgattaa gcattggtaa ctgtcagacc aagttactc atatatactt    6480
tagattgatt taaaacttca ttttaatttt aaaaggatct aggtgaagat cctttttgat    6540
aatctcatga ccaaaatccc ttaacgtgag ttttcgttcc actgagcgtc agaccccgta    6600
gaaaagatca aaggatcttc ttgagatcct ttttttctgc gcgtaatctg ctgcttgcaa    6660
acaaaaaaac caccgctacc agcggtggtt tgtttgccgg atcaagagct accaactctt    6720
tttccgaagg taactggctt cagcagagcg cagataccaa atactgttct tctagtgtag    6780
ccgtagttag gccaccactt caagaactct gtagcaccgc ctacatacct cgctctgcta    6840
atcctgttac cagtggctgc tgccagtggc gataagtcgt gtcttaccgg gttggactca    6900
agacgatagt taccggataa ggcgcagcgg tcggctgaa cggggggttc gtgcacacag    6960
cccagcttgg agcgaacgac ctacaccgaa ctgagatacc tacagcgtga gctatgagaa    7020
agcgccacgc ttcccgaagg gagaaaggcg gacaggtatc cggtaagcgg cagggtcgga    7080
acaggagagc gcacgaggga gcttccaggg ggaaacgcct ggtatcttta tagtcctgtc    7140
gggtttcgcc acctctgact tgagcgtcga ttttttgtgat gctcgtcagg ggggcggagc    7200
ctatggaaaa acgccagcaa cgcggccttt ttacggttcc tggccttttg ctggcctttt    7260
gctcacatg                                                             7269
```

<210> SEQ ID NO 44
<211> LENGTH: 38
<212> TYPE: DNA
<213> ORGANISM: Artificial Sequence
<220> FEATURE:
<223> OTHER INFORMATION: Synthetic
<400> SEQUENCE: 44

```
cccagccagg tgtggtaagc acaattcgag ctcggtac                              38
```

<210> SEQ ID NO 45
<211> LENGTH: 26
<212> TYPE: DNA
<213> ORGANISM: Artificial Sequence
<220> FEATURE:

<223> OTHER INFORMATION: Synthetic

<400> SEQUENCE: 45

| ggtgccaact tttttgtaca aacttg | 26 |

<210> SEQ ID NO 46
<211> LENGTH: 48
<212> TYPE: DNA
<213> ORGANISM: Artificial Sequence
<220> FEATURE:
<223> OTHER INFORMATION: Synthetic

<400> SEQUENCE: 46

| caagtttgta caaaaaagtt ggcaccatgg ctcgtactaa acagacag | 48 |

<210> SEQ ID NO 47
<211> LENGTH: 18
<212> TYPE: DNA
<213> ORGANISM: Artificial Sequence
<220> FEATURE:
<223> OTHER INFORMATION: Synthetic

<400> SEQUENCE: 47

| ttaccacacc tggctggg | 18 |

<210> SEQ ID NO 48
<211> LENGTH: 5671
<212> TYPE: DNA
<213> ORGANISM: Artificial Sequence
<220> FEATURE:
<223> OTHER INFORMATION: Synthetic

<400> SEQUENCE: 48

| acatatttga atgtatttag aaaaataaac aaataggggt tccgcgcaca tttccccgaa | 60 |
| aagtgccacc taaattgtaa gcgttaatat tttgttaaaa ttcgcgttaa attttttgtta | 120 |
| aatcagctca ttttttaacc aataggccga atcggcaaa atcccttata aatcaaaaga | 180 |
| atagaccgag atagggttga gtgttgttcc agtttggaac aagagtccac tattaaagaa | 240 |
| cgtggactcc aacgtcaaag ggcgaaaaac cgtctatcag ggcgatggcc cactacgtga | 300 |
| accatcaccc taatcaagtt ttttggggtc gaggtgccgt aaagcactaa atcggaaccc | 360 |
| taaagggagc ccccgattta gagcttgacg gggaaagccg cgaacgtgg cgagaaagga | 420 |
| agggaagaaa gcgaaaggag cgggcgctag ggcgctggca agtgtagcgg tcacgctgcg | 480 |
| cgtaaccacc acacccgccg cgcttaatgc gccgctacag ggcgcgtccc attcgccatt | 540 |
| caggctgcgc aactgttggg aagggcgatc ggtgcgggcc tcttcgctat tacgccagct | 600 |
| ggcgaaaggg ggatgtgctg caaggcgatt aagttgggta acgccaggt tttcccagtc | 660 |
| acgacgttgt aaaacgacgg ccagtgaatt gtaatacgac tcactatagg gcgaattggg | 720 |
| taccgggccc cccctcgagg tcgacgatgt aggtcacggc attccggact cagcgctcga | 780 |
| gccggcttgt cgacgacggc ggtctccgtc gtcaggatca tccgcagatt ataccgcaac | 840 |
| tacacgccac catggacaag gccgaattcc acgctgccat ggcagacact tttctggaac | 900 |
| acatgtgtcg actcgacatt gacagcgaac caactatagc tcgcaatacg ggatcatat | 960 |
| gcactatagg acccgcgagc aggtccgttg ataaactgaa ggagatgatc aagagcggca | 1020 |
| tgaacgttgc gcgccttaac ttctcccacg ggacccatga gtatcacgaa ggaacgatta | 1080 |
| agaacgtgcg ggaggcgaca gaaagttttg caagtgaccc gataacgtac cgaccagtcg | 1140 |
| ctattgccct ggacactaag ggtccagaga tccggacagg gctgataaag ggctctggta | 1200 |

```
cagcagaagt agaattgaaa aaaggggcag ccctgaaagt taccctcgac aatgctttta    1260
tggaaaattg tgacgaaaat gtactttggg ttgactacaa aaatttgatc aaggtcattg    1320
atgtcggaag caaatctat gttgacgatg ggctcatatc actccttgta aaagaaaaag     1380
gcaaagactt tgtaatgacg gaggttgaga acggtgggat gcttggcagc aaaaaaggtg    1440
tcaatctccc cggcgccgcc gttgacctgc cggccgtatc agagaaggac atacaggatc    1500
tcaaattcgg cgtcgaacaa aacgtagaca tggtgttcgc atctttcatc cgaaaggcag    1560
ccgacgttca cgctgtgaga aaagtcttgg gtgagaaggg taagcatata aagataatct    1620
ccaagataga gaaccatgag ggcgtcagaa gattcgacga aataatggaa gcatcagacg    1680
gtatcatggt cgctaggggg gacctgggta ttgagatccc cgctgagaag gtctttttgg    1740
cgcaaaagat gatgatcggt cgatgcaacc gcgcggggaa acctatcatt tgtgcgaccc    1800
agatgcttga gtctatgatc aagaagccaa gaccaactag agccgaaggg tccgatgtgg    1860
ctaatgcggt gctggatgga gctgattgca ttatgctcag tggcgaaacg gcgaaagggg    1920
attatccatt ggaagccgtg aggatgcagc atgccatagc gcgcgaagcc gaagctgcga    1980
tgtttcacag gcagcagttc gaagaaatcc tgcgccatag cgtgcaccac agggagcccg    2040
ctgacgcgat ggctgcaggt gcagtggaag cgagctttaa atgcctggca gccgctttga    2100
tagtcatgac agagagtggg cgctcagccc accttgttag ccggtaccga ccgcgcgcac    2160
ctattattgc cgtcacgaga aatgaccaga cggcccgaca agcccatttg tatagagggg    2220
tgttcccggt actctgtaag cagcctgcac acgatgcttg ggccgaggat gtggatttgc    2280
gagtaaactt gggaatgaat gtgggtaaag cgcgggttt cttcaagact ggggatttgg     2340
tcattgtcct cacgggctgg cgacctggta gcggatatac taataccatg agggttgtgc    2400
cggtcccagg aggtagcggt ggaagtatgg tagcaggtca tgcctctggc agccccgcat    2460
tcgggaccgc ctctcattcg aattgcgaac atgaagagat ccacctcgcc ggctcgatcc    2520
agccgcatgg cgcgcttctg gtcgtcagcg aacatgatca tcgcgtcatc caggccagcg    2580
ccaacgccgc ggaatttctg aatctcggaa gcgtactcgg cgttccgctc gccgagatcg    2640
acggcgatct gttgatcaag atcctgccgc atctcgatcc caccgccgaa ggcatgccgg    2700
tcgcggtgcg ctgccggatc ggcaatccct ctacggagta ctgcggtctg atgcatcggc    2760
ctccggaagg cgggctgatc atcgaactcg aacgtgccgg cccgtcgatc gatctgtcag    2820
gcacgctggc gccggcgctg gagcggatcc gcacggcggg ttcactgcgc gcgctgtgcg    2880
atgacaccgt gctgctgttt cagcagtgca ccggctacga ccgggtgatg gtgtatcgtt    2940
tcgatgagca aggccacggc ctggtattct ccgagtgcca tgtgcctggg ctcgaatcct    3000
atttcggcaa ccgctatccg tcgtcgctgg tcccgcagat ggcgcggcag ctgtacgtgc    3060
ggcagcgcgt ccgcgtgctg gtcgacgtca cctatcagcc ggtgccgctg gagccgcggc    3120
tgtcgccgct gaccgggcgc gatctcgaca tgtcggctg cttcctgcgc tcgatgtcgc    3180
cgatccatct gcagttcctg aaggacatgg gcgtgcgcgc caccctggcg gtgtcgctgg    3240
tggtcggcgg caagctgtgg ggcctggttg tctgtcacca ttatctgccg cgcttcatcc    3300
gtttcgagct gcgggcgatc tgcaaacggc tcgccgaaag gatcgcgacg cggatcaccg    3360
cgcttgagag ctagggatcc tgatcataat cagccatacc acatttgtag aggttttact    3420
tgctttaaaa aacctcccac acctcccct gaacctgaaa cataaaatga atgcaattgt     3480
tgttgttaac ttgtttattg cagcttataa tggttacaaa taaagcaata gcatcacaaa    3540
```

```
tttcacaaat aaagcatttt tttcactgca ttctagttgt ggtttgtcca aactcatcaa    3600
tgtatcttag gagatcccct ttagtgaggg ttaatttcga gcttggcgta atcatggtca    3660
tagctgtttc ctgtgtgaaa ttgttatccg ctcacaattc cacacaacat acgagccgga    3720
agcataaagt gtaaagcctg gggtgcctaa tgagtgagct aactcacatt aattgcgttg    3780
cgctcactgc ccgctttcca gtcgggaaac ctgtcgtgcc agctgcatta atgaatcggc    3840
caacgcgcgg ggagaggcgg tttgcgtatt gggcgctctt ccgcttcctc gctcactgac    3900
tcgctgcgct cggtcgttcg gctgcggcga gcggtatcag ctcactcaaa ggcggtaata    3960
cggttatcca cagaatcagg ggataacgca ggaaagaaca tgtgagcaaa aggccagcaa    4020
aaggccagga accgtaaaaa ggccgcgttg ctggcgtttt tccataggct ccgcccccct    4080
gacgagcatc acaaaaatcg acgctcaagt cagaggtggc gaaacccgac aggactataa    4140
agataccagg cgtttccccc tggaagctcc ctcgtgcgct ctcctgttcc gaccctgccg    4200
cttaccggat acctgtccgc ctttctccct tcgggaagcg tggcgctttc tcatagctca    4260
cgctgtaggt atctcagttc ggtgtaggtc gttcgctcca agctgggctg tgtgcacgaa    4320
ccccccgttc agcccgaccg ctgcgcctta tccggtaact atcgtcttga gtccaacccg    4380
gtaagacacg acttatcgcc actggcagca gccactggta acaggattag cagagcgagg    4440
tatgtaggcg gtgctacaga gttcttgaag tggtggccta actacggcta cactagaaga    4500
acagtatttg gtatctgcgc tctgctgaag ccagttacct tcggaaaaag agttggtagc    4560
tcttgatccg gcaaacaaac caccgctggt agcggtggtt ttttgtttg caagcagcag    4620 attacgcgca gaaaaaagg atctcaagaa gatcctttga tcttttctac ggggtctgac    4680
gctcagtgga acgaaaactc acgttaaggg attttggtca tgagattatc aaaaaggatc    4740
ttcacctaga tccttttaaa ttaaaaatga agttttaaat caatctaaag tatatatgag    4800
taaacttggt ctgacagtta agaacctcg tcaagaaggc gatagaaggc gatgcgctgc    4860
gaatcgggag cggcgatacc gtaaagcacg aggaagcggt cagcccattc gccgccaagc    4920
tcttcagcaa tatcacgggt agccaacgct atgtcctgat agcggtccgc cacacccagc    4980
cggccacagt cgatgaatcc agaaaagcgg ccattttcca ccatgatatt cggcaagcag    5040
gcatcgccat gggtcacgac gagatcctcg ccgtcgggca tgctcgcctt gagcctggcg    5100
aacagttcgg ctggcgcgag cccctgatgc tcttcgtcca gatcatcctg atcgacaaga    5160
ccggcttcca tccgagtacg tgctcgctcg atgcgatgtt tcgcttggtg gtcgaatggg    5220
caggtagccg gatcaagcgt atgcagccgc cgcattgcat cagccatgat ggatactttc    5280
tcggcaggag caaggtgaga tgacaggaga tcctgccccg gcacttcgcc caatagcagc    5340
cagtcccttc ccgcttcagt gacaacgtcg agcacagctg cgcaaggaac gcccgtcgtg    5400
gccagccacg atagccgcgc tgcctcgtct tgcagttcat tcagggcacc ggacaggtcg    5460
gtcttgacaa aaagaaccgg gcgcccctgc gctgacagcc ggaacacggc ggcatcagag    5520
cagccgattg tctgttgtgc ccagtcatag ccgaatagcc tctccaccca gcggccgga    5580 gaacctgcgt gcaatccatc ttgttcaatc atactcttcc tttttcaata ttattgaagc    5640
atttatcagg gttattgtct catgagcgga t                                   5671
```

<210> SEQ ID NO 49
<211> LENGTH: 1575
<212> TYPE: DNA
<213> ORGANISM: Artificial Sequence
<220> FEATURE:
<223> OTHER INFORMATION: Synthetic

<400> SEQUENCE: 49

```
atggacaagg ccgaattcca cgctgccatg gcagacactt ttctggaaca catgtgtcga      60
ctcgacattg acagcgaacc aactatagct cgcaatacgg ggatcatatg cactatagga     120
cccgcgagca ggtccgttga taaactgaag gagatgatca agagcggcat gaacgttgcg     180
cgccttaact tctcccacgg gacccatgag tatcacgaag gaacgattaa gaacgtgcgg     240
gaggcgacag aaagttttgc aagtgacccg ataacgtacc gaccagtcgc tattgccctg     300
gacactaagg gtccagagat ccggacaggg ctgataaagg gctctggtac agcagaagta     360
gaattgaaaa aaggggcagc cctgaaagtt accctcgaca atgctttat ggaaaattgt      420
gacgaaaatg tactttgggt tgactacaaa aatttgatca aggtcattga tgtcggaagc     480
aaaatctatg ttgacgatgg gctcatatca ctccttgtaa aagaaaaagg caaagacttt     540
gtaatgacgg aggttgagaa cggtgggatg cttggcagca aaaaaggtgt caatctcccc     600
ggcgccgccg ttgacctgcc ggccgtatca gagaaggaca tacaggatct caaattcggc     660
gtcgaacaaa acgtagacat ggtgttcgca tctttcatcc gaaaggcagc cgacgttcac     720
gctgtgagaa aagtcttggg tgagaagggt aagcatataa agataatctc caagatagag     780
aaccatgagg gcgtcagaag attcgacgaa ataatggaag catcagacgg tatcatggtc     840
gctagggggg acctgggtat tgagatcccc gctgagaagg tcttttttggc gcaaaagatg     900
atgatcggtc gatgcaaccg cgcggggaaa cctatcattt gtgcgaccca gatgcttgag     960
tctatgatca gaagccaag accaactaga gccgaagggt ccgatgtggc taatgcggtg    1020
ctggatggag ctgattgcat tatgctcagt ggcgaaacgg cgaaagggga ttatccattg    1080
gaagccgtga ggatgcagca tgccatagcg cgcgaagccg aagctgcgat gtttcacagg    1140
cagcagttcg aagaaatcct gcgccatagc gtgcaccaca gggagcccgc tgacgcgatg    1200
gctgcaggtg cagtggaagc gagctttaaa tgcctggcag ccgctttgat agtcatgaca    1260
gagagtgggc gctcagccca ccttgttagc cggtaccgac cgcgcgcacc tattattgcc    1320
gtcacgagaa atgaccagac ggcccgacaa gcccatttgt atagagggg gttcccggta    1380
ctctgtaagc agcctgcaca cgatgcttgg gccgaggatg tggatttgcg agtaaacttg    1440
ggaatgaatg tgggtaaagc gcggggtttc ttcaagactg gggatttggt cattgtcctc    1500
acgggctggc gacctggtag cggatatact aataccatga gggttgtgcc ggtcccagga    1560
ggtagcggtg gaagt                                                      1575
```

<210> SEQ ID NO 50
<211> LENGTH: 36
<212> TYPE: DNA
<213> ORGANISM: Artificial Sequence
<220> FEATURE:
<223> OTHER INFORMATION: Synthetic

<400> SEQUENCE: 50

```
ggaattcggc cttgtccatg gtggcgtgta gttgcg                                36
```

<210> SEQ ID NO 51
<211> LENGTH: 17
<212> TYPE: DNA
<213> ORGANISM: Artificial Sequence
<220> FEATURE:
<223> OTHER INFORMATION: Synthetic

<400> SEQUENCE: 51

```
ccggcacaac cctcatg                                                17
```

<210> SEQ ID NO 52
<211> LENGTH: 60
<212> TYPE: DNA
<213> ORGANISM: Artificial Sequence
<220> FEATURE:
<223> OTHER INFORMATION: Synthetic

<400> SEQUENCE: 52

```
catgagggtt gtgccggtcc caggaggtag cggtggaagt atggtagcag gtcatgcctc    60
```

<210> SEQ ID NO 53
<211> LENGTH: 39
<212> TYPE: DNA
<213> ORGANISM: Artificial Sequence
<220> FEATURE:
<223> OTHER INFORMATION: Synthetic

<400> SEQUENCE: 53

```
gagaaggagg tcagaccggt ttagctctca agcgcggtg                            39
```

<210> SEQ ID NO 54
<211> LENGTH: 17
<212> TYPE: DNA
<213> ORGANISM: Artificial Sequence
<220> FEATURE:
<223> OTHER INFORMATION: Synthetic

<400> SEQUENCE: 54

```
ggtggcgtgt agttgcg                                                   17
```

<210> SEQ ID NO 55
<211> LENGTH: 20
<212> TYPE: DNA
<213> ORGANISM: Artificial Sequence
<220> FEATURE:
<223> OTHER INFORMATION: Synthetic

<400> SEQUENCE: 55

```
accggtctga cctccttctc                                                20
```

<210> SEQ ID NO 56
<211> LENGTH: 5716
<212> TYPE: DNA
<213> ORGANISM: Artificial Sequence
<220> FEATURE:
<223> OTHER INFORMATION: Synthetic

<400> SEQUENCE: 56

```
acatatttga atgtatttag aaaaataaac aaatagggt tccgcgcaca tttccccgaa     60
aagtgccacc taaattgtaa gcgttaatat tttgttaaaa ttcgcgttaa attttttgtta  120
aatcagctca ttttttaacc aataggccga atcggcaaa atcccttata aatcaaaaga    180
atagaccgag atagggttga gtgttgttcc agtttggaac aagagtccac tattaaagaa   240
cgtggactcc aacgtcaaag ggcgaaaaac cgtctatcag ggcgatggcc cactacgtga   300
accatcaccc taatcaagtt ttttggggtc gaggtgccgt aaagcactaa atcggaaccc   360
taaagggagc ccccgattta gagcttgacg gggaaagccg gcgaacgtgg cgagaaagga   420
agggaagaaa gcgaaaggag cgggcgctag ggcgctggca agtgtagcgg tcacgctgcg   480
cgtaaccacc acacccgccg cgcttaatgc gccgctacag ggcgcgtccc attcgccatt   540
caggctgcgc aactgttggg aagggcgatc ggtgcgggcc tcttcgctat tacgccagct   600
```

```
ggcgaaaggg ggatgtgctg caaggcgatt aagttgggta acgccagggt tttcccagtc    660
acgacgttgt aaaacgacgg ccagtgaatt gtaatacgac tcactatagg gcgaattggg    720
taccgggccc ccctcgagg tcgacgatgt aggtcacggc attccggact cagcgctcga    780
gccggcttgt cgacgacggc ggtctccgtc gtcaggatca tccgcagatt ataccgcaac    840
tacacgccac catggacaag gccgaattcc ttgaggctcc taaaaagaag agaaaggtag    900
gtatcccaga attccacgct gccatggcag acacttttct ggaacacatg tgtcgactcg    960
acattgacag cgaaccaact atagctcgca atacgggat catatgcact ataggacccg   1020
cgagcaggtc cgttgataaa ctgaaggaga tgatcaagag cggcatgaac gttgcgcgcc   1080
ttaacttctc ccacgggacc catgagtatc acgaaggaac gattaagaac gtgcgggagg   1140
cgacagaaag ttttgcaagt gacccgataa cgtaccgacc agtcgctatt gccctggaca   1200
ctaagggtcc agagatccgg acagggctga taaagggctc tggtacagca gaagtagaat   1260
tgaaaaaagg ggcagccctg aaagttaccc tcgacaatgc ttttatggaa aattgtgacg   1320
aaaatgtact ttgggttgac tacaaaaatt tgatcaaggt cattgatgtc ggaagcaaaa   1380
tctatgttga cgatgggctc atatcactcc ttgtaaaaga aaaaggcaaa gactttgtaa   1440
tgacggaggt tgagaacggt gggatgcttg gcagcaaaaa aggtgtcaat ctccccggcg   1500
ccgccgttga cctgccggcc gtatcagaga aggacataca ggatctcaaa ttcggcgtcg   1560
aacaaaacgt agacatggtg ttcgcatctt tcatccgaaa ggcagccgac gttcacgctg   1620
tgagaaaagt cttgggtgag aagggtaagc atataaagat aatctccaag atagagaacc   1680
atgagggcgt cagaagattc gacgaaataa tggaagcatc agacggtatc atggtcgcta   1740
gggggaccct gggtattgag atccccgctg agaaggtctt tttggcgcaa agatgatga   1800 tcggtcgatg caaccgcgcg gggaaaccta tcatttgtgc gacccagatg cttgagtcta   1860
tgatcaagaa gccaagacca actagagccg aagggtccga tgtggctaat gcggtgctgg   1920
atggagctga ttgcattatg ctcagtggcg aaacggcgaa aggggattat ccattggaag   1980
ccgtgaggat gcagcatgcc atagcgcgcg aagccgaagc tgcgatgttt cacaggcagc   2040
agttcgaaga aatcctgcgc catagcgtgc accacaggga gcccgctgac gcgatggctg   2100
caggtgcagt ggaagcgagc tttaaatgcc tggcagccgc tttgatagtc atgacagaga   2160
gtgggcgctc agcccacctt gttagccggt accgaccgcg cgcacctatt attgccgtca   2220
cgagaaatga ccagacggcc cgacaagccc atttgtatag aggggtgttc ccggtactct   2280
gtaagcagcc tgcacacgat gcttgggccg aggatgtgga tttgcgagta aacttgggaa   2340
tgaatgtggg taaagcgcgg ggtttcttca agactgggga tttggtcatt gtcctcacgg   2400
gctggcgacc tggtagcgga tatactaata ccatgagggt tgtgccggtc ccaggaggta   2460
gcggtggaag tatggtagca ggtcatgcct ctggcagccc cgcattcggg accgcctctc   2520
attcgaattg cgaacatgaa gagatccacc tcgccggctc gatccagccg catggcgcgc   2580
ttctggtcgt cagcgaacat gatcatcgcg tcatccaggc cagcgccaac gccgcggaat   2640
ttctgaatct cggaagcgta ctcggcgttc cgctcgccga gatcgacggc gatctgttga   2700
tcaagatcct gccgcatctc gatcccaccg ccgaaggcat gccggtcgcg gtgcgctgcc   2760
ggatcggcaa tccctctacg gagtactgcg gtctgatgca tcggcctccg gaaggcgggc   2820
tgatcatcga actcgaacgt gccggcccgt cgatcgatct gtcaggcacg ctggcgccgg   2880
cgctggagcg gatccgcacg gcgggttcac tgcgcgcgct gtgcgatgac accgtgctgc   2940
```

```
tgtttcagca gtgcaccggc tacgaccggg tgatggtgta tcgtttcgat gagcaaggcc    3000
acggcctggt attctccgag tgccatgtgc ctgggctcga atcctatttc ggcaaccgct    3060
atccgtcgtc gctggtcccg cagatggcgc ggcagctgta cgtgcggcag cgcgtccgcg    3120
tgctggtcga cgtcacctat cagccggtgc cgctggagcc gcggctgtcg ccgctgaccg    3180
ggcgcgatct cgacatgtcg ggctgcttcc tgcgctcgat gtcgccgatc catctgcagt    3240
tcctgaagga catgggcgtg cgcgccaccc tggcggtgtc gctggtggtc ggcggcaagc    3300
tgtggggcct ggttgtctgt caccattatc tgccgcgctt catccgtttc gagctgcggg    3360
cgatctgcaa acggctcgcc gaaaggatcg cgacgcggat caccgcgctt gagagctagg    3420
gatcctgatc ataatcagcc ataccacatt tgtagaggtt ttacttgctt taaaaaacct    3480
cccacacctc cccctgaacc tgaaacataa aatgaatgca attgttgttg ttaacttgtt    3540
tattgcagct tataatggtt acaaataaag caatagcatc acaaatttca caaataaagc    3600
atttttttca ctgcattcta gttgtggttt gtccaaactc atcaatgtat cttaggagat    3660
cccctttagt gagggttaat ttcgagcttg gcgtaatcat ggtcatagct gtttcctgtg    3720
tgaaattgtt atccgctcac aattccacac aacatacgag ccggaagcat aaagtgtaaa    3780
gcctggggtg cctaatgagt gagctaactc acattaattg cgttgcgctc actgcccgct    3840
ttccagtcgg gaaacctgtc gtgccagctg cattaatgaa tcggccaacg cgcggggaga    3900
ggcggtttgc gtattgggcg ctcttccgct tcctcgctca ctgactcgct gcgctcggtc    3960
gttcggctgc ggcgagcggt atcagctcac tcaaaggcgg taatacggtt atccacagaa    4020
tcagggggata acgcaggaaa gaacatgtga gcaaaaggcc agcaaaaggc caggaaccgt    4080
aaaaaggccg cgttgctggc gtttttccat aggctccgcc cccctgacga gcatcacaaa    4140
aatcgacgct caagtcagag gtggcgaaac ccgacaggac tataaagata ccaggcgttt    4200
ccccctggaa gctccctcgt gcgctctcct gttccgaccc tgccgcttac cggatacctg    4260
tccgcctttc tcccttcggg aagcgtggcg ctttctcata gctcacgctg taggtatctc    4320
agttcggtgt aggtcgttcg ctccaagctg ggctgtgtgc acgaacccccc cgttcagccc    4380
gaccgctgcg ccttatccgg taactatcgt cttgagtcca acccggtaag acacgactta    4440
tcgccactgg cagcagccac tggtaacagg attagcagag cgaggtatgt aggcggtgct    4500
acagagttct tgaagtggtg gcctaactac ggctacacta agaacagt atttggtatc    4560
tgcgctctgc tgaagccagt taccttcgga aaaagagttg gtagctcttg atccggcaaa    4620
caaaccaccg ctggtagcgg tggttttttt gtttgcaagc agcagattac gcgcagaaaa    4680
aaaggatctc aagaagatcc tttgatcttt tctacggggt ctgacgctca gtggaacgaa    4740
aactcacgtt aagggatttt ggtcatgaga ttatcaaaaa ggatcttcac ctagatcctt    4800
ttaaattaaa aatgaagttt taaatcaatc taaagtatat atgagtaaac ttggtctgac    4860
agttagaaga actcgtcaag aaggcgatag aaggcgatgc gctgcgaatc gggagcggcg    4920
ataccgtaaa gcacgaggaa gcggtcagcc cattcgccgc caagctcttc agcaatatca    4980
cgggtagcca acgctatgtc ctgatagcgg tccgccacac ccagccggcc acagtcgatg    5040
aatccagaaa agcggccatt ttccaccatg atattcggca agcaggcatc gccatgggtc    5100
acgacgagat cctcgccgtc gggcatgctc gccttgagcc tggcgaacag ttcggctggc    5160
gcgagcccct gatgctcttc gtccagatca tcctgatcga caagaccggc ttccatccga    5220
gtacgtgctc gctcgatgcg atgtttcgct tggtggtcga atgggcaggt agccggatca    5280
agcgtatgca gccgccgcat tgcatcagcc atgatggata cttctctcggc aggagcaagg    5340
```

```
tgagatgaca ggagatcctg ccccggcact tcgcccaata gcagccagtc ccttcccgct    5400
tcagtgacaa cgtcgagcac agctgcgcaa ggaacgcccg tcgtggccag ccacgatagc    5460
cgcgctgcct cgtcttgcag ttcattcagg gcaccggaca ggtcggtctt gacaaaaaga    5520
accgggcgcc cctgcgctga cagccggaac acggcggcat cagagcagcc gattgtctgt    5580
tgtgcccagt catagccgaa tagcctctcc acccaagcgg ccggagaacc tgcgtgcaat    5640
ccatcttgtt caatcatact cttccttttt caatattatt gaagcattta tcagggttat    5700
tgtctcatga gcggat                                                   5716

<210> SEQ ID NO 57
<211> LENGTH: 84
<212> TYPE: DNA
<213> ORGANISM: Artificial Sequence
<220> FEATURE:
<223> OTHER INFORMATION: Synthetic

<400> SEQUENCE: 57
ccaccatgga caaggccgaa ttccttgagg ctcctaaaaa gaagagaaag gtaggtatcc      60
cagaattcca cgctgccatg gcag                                            84

<210> SEQ ID NO 58
<211> LENGTH: 5671
<212> TYPE: DNA
<213> ORGANISM: Artificial Sequence
<220> FEATURE:
<223> OTHER INFORMATION: Synthetic

<400> SEQUENCE: 58
acatatttga atgtatttag aaaaataaac aaatagggt tccgcgcaca tttccccgaa      60
aagtgccacc taaattgtaa gcgttaatat tttgttaaaa ttcgcgttaa attttttgtta    120 aatcagctca ttttttaacc aataggccga atcggcaaa atcccttata atcaaaaga      180 atagaccgag ataggggttga gtgttgttcc agtttggaac aagagtccac tattaaagaa    240
cgtggactcc aacgtcaaag ggcgaaaaac cgtctatcag ggcgatggcc cactacgtga    300
accatcaccc taatcaagtt ttttggggtc gaggtgccgt aaagcactaa atcggaaccc    360
taaagggagc cccgatttta gagcttgacg gggaaagccg gcgaacgtgg cgagaaagga    420
agggaagaaa gcgaaaggag cgggcgctag ggcgctggca agtgtagcgg tcacgctgcg    480
cgtaaccacc acacccgccg cgcttaatgc gccgctacag ggcgcgtccc attcgccatt    540
caggctgcgc aactgttggg aagggcgatc ggtgcgggcc tcttcgctat tacgccagct    600
ggcgaaaggg ggatgtgctg caaggcgatt aagttgggta acgccagggt tttcccagtc    660
acgacgttgt aaaacgacgg ccagtgaatt gtaatacgac tcactatagg gcgaattggg    720
taccgggccc cccctcgagg tcgacgatgt aggtcacggc attccggact cagcgctcga    780
gccggcttgt cgacgacggc ggtctccgtc gtcaggatca tccgcagatt ataccgcaac    840
tacacgccac catggacaag gccgaattcc acgctgccat ggcagacact tttctggaac    900
acatgtgtcg actcgacatt gacagcgaac caactatagc tcgcaatacg ggatcatat    960 gcactatagg acccgcgagc aggtccgttg ataaactgaa ggagatgatc aagagcggca    1020
tgaacgttgc gcgccttaac ttctcccacg ggacccatga gtatcacgaa ggaacgatta    1080
agaacgtgcg ggaggcgaca gaaagttttg caagtgaccc gataacgtac cgaccagtcg    1140
ctattgccct ggacactaag ggtccagaga tccggacagg gctgataaag ggctctggta    1200
```

-continued

```
cagcagaagt agaattgaaa aaaggggcag ccctgaaagt taccctcgac aatgctttta      1260
tggaaaattg tgacgaaaat gtactttggg ttgactacaa aaatttgatc aaggtcattg      1320
atgtcggaag caaaatctat gttgacgatg ggctcatatc actccttgta aaagaaaaag      1380
gcaaagactt tgtaatgacg gaggttgaga acggtgggat gcttggcagc aaaaaaggtg      1440
tcaatctccc cggcgccgcc gttgacctgc cggccgtatc agagaaggac atacaggatc      1500
tcaaattcgg cgtcgaacaa aacgtagaca tggtgttcgc atctttcatc cgaaaggcag      1560
ccgacgttca cgctgtgaga aaagtcttgg gtgagaaggg taagcatata aagataatct      1620
ccaagataga gaaccatgag ggcgtcagaa gattcgacga aataatggaa gcatcagacg      1680
gtatcatggt cgctaggggg gacctgggta ttgagatccc cgctgagaag gtcttttttgg     1740 cgcaaaagat gatgatcggt cgatgcaacc gcgcggggaa acctatcatt tgtgcgaccc      1800
agatgcttga gtctatgatc aagaagccaa gaccaactag agccgaaggg tccgatgtgg      1860
ctaatgcggt gctggatgga gctgattgca ttatgctcag tggcgaaacg gcgaaagggg      1920
attatccatt ggaagccgtg aggatgcagc atgccatagc gcgcgaagcc gaagctgcga      1980
tgtttcacag gcagcagttc gaagaaatcc tgcgccatag cgtgcaccac agggagcccg      2040
ctgacgcgat ggctgcaggt gcagtggaag cgagctttaa atgcctggca gccgctttga      2100
tagtcatgac agagagtggg cgctcagccc accttgttag ccggtaccga ccgcgcgcac      2160
ctattattgc cgtcacgaga aatgaccaga cggcccgaca agcccatttg tatagagggg      2220
tgttcccggt actctgtaag cagcctgcac acgatgcttg ggccgaggat gtggatttgc      2280
gagtaaactt gggaatgaat gtgggtaaag cgcggggttt cttcaagact ggggatttgg      2340
tcattgtcct cacgggctgg cgacctggta gcggatatac taataccatg agggttgtgc      2400
cggtcccagg aggtagcggt ggaagtatgg tagcaggtca tgcctctggc agccccgcat      2460
tcgggaccgc ctctcattcg aattgcgaac atgaagagat ccacctcgcc ggctcgatcc      2520
agccgcatgg cgcgcttctg gtcgtcagcg aacatgatca tcgcgtcatc caggccagcg      2580
ccaacgccgc ggaatttctg aatctcggaa gcgtactcgg cgttccgctc gccgagatcg      2640
acggcgatct gttgatcaag atcctgccgc atctcgatcc caccgccgaa ggcatgccgg      2700
tcgcggtgcg ctgccggatc ggcaatccct ctacggagta ctgcggtctg atgcatcggc      2760
ctccggaagg cgggctgatc atcgaactcg aacgtgccgg cccgtcgatc gatctgtcag      2820
gcacgctggc gccggcgctg gagcggatcc gcacggcggg ttcactgcgc gcgctgtgcg      2880
atgacaccgt gctgctgttt cagcagtgca ccggctacga ccgggtgatg gtgtatcgtt      2940
tcgatgagca aggccacggc ctggtattct ccgagtgcca tgtgcctggg ctcgaatcct      3000
atttcggcaa ccgctatccg tcgtcgctgg tcccgcagat ggcgcggcag ctgtacgtgc      3060
ggcagcgcgt ccgcgtgctg gtcgacgtca cctatcagcc ggtgccgctg gagccgcggc      3120
tgtcgccgct gaccgggcgc gatctcgaca tgtcgggctg cttcctgcgc tcgatgtcgc      3180
cgatccatct gcagttcctg aaggacatgg gcgtgcgcgc caccctggcg gtgtcgctgg      3240
tggtcggcgg caagctgtgg ggcctggttg tctgtcacca ttatctgccg cgcttcatcc      3300
gtttcgagct gcgggcgatc tgcaaacggc tcgccgaaag gatcgcgacg cggatcaccg      3360
cgcttgagag ctagggatcc tgatcataat cagccatacc acatttgtag aggttttact      3420
tgctttaaaa aacctcccac acctcccct gaacctgaaa cataaaatga atgcaattgt      3480
tgttgttaac ttgtttattg cagcttataa tggttacaaa taaagcaata gcatcacaaa      3540
tttcacaaat aaagcatttt tttcactgca ttctagttgt ggtttgtcca aactcatcaa      3600
```

```
tgtatcttag gagatcccct ttagtgaggg ttaatttcga gcttggcgta atcatggtca   3660
tagctgtttc ctgtgtgaaa ttgttatccg ctcacaattc cacacaacat acgagccgga   3720
agcataaagt gtaaagcctg gggtgcctaa tgagtgagct aactcacatt aattgcgttg   3780
cgctcactgc ccgctttcca gtcgggaaac ctgtcgtgcc agctgcatta atgaatcggc   3840
caacgcgcgg ggagaggcgg tttgcgtatt gggcgctctt ccgcttcctc gctcactgac   3900
tcgctgcgct cggtcgttcg gctgcggcga gcggtatcag ctcactcaaa ggcggtaata   3960
cggttatcca cagaatcagg ggataacgca ggaaagaaca tgtgagcaaa aggccagcaa   4020
aaggccagga accgtaaaaa ggccgcgttg ctggcgtttt tccataggct ccgcccccct   4080
gacgagcatc acaaaaatcg acgctcaagt cagaggtggc gaaacccgac aggactataa   4140
agataccagg cgtttccccc tggaagctcc ctcgtgcgct ctcctgttcc gaccctgccg   4200
cttaccggat acctgtccgc ctttctccct tcgggaagcg tggcgctttc tcatagctca   4260
cgctgtaggt atctcagttc ggtgtaggtc gttcgctcca agctgggctg tgtgcacgaa   4320
ccccccgttc agcccgaccg ctgcgcctta tccggtaact atcgtcttga gtccaacccg   4380
gtaagacacg acttatcgcc actggcagca gccactggta acaggattag cagagcgagg   4440
tatgtaggcg gtgctacaga gttcttgaag tggtggccta actacggcta cactagaaga   4500
acagtatttg gtatctgcgc tctgctgaag ccagttacct tcggaaaaag agttggtagc   4560
tcttgatccg gcaaacaaac caccgctggt agcggtggtt tttttgtttg caagcagcag   4620
attacgcgca gaaaaaaagg atctcaagaa gatcctttga tcttttctac ggggtctgac   4680
gctcagtgga acgaaaactc acgttaaggg attttggtca tgagattatc aaaaaggatc   4740
ttcacctaga tccttttaaa ttaaaaatga agttttaaat caatctaaag tatatatgag   4800
taaacttggt ctgacagtta agaactcg tcaagaaggc gatagaaggc gatgcgctgc   4860
gaatcgggag cggcgatacc gtaaagcacg aggaagcggt cagcccattc gccgccaagc   4920
tcttcagcaa tatcacgggt agccaacgct atgtcctgat agcggtccgc cacacccagc   4980
cggccacagt cgatgaatcc agaaaagcgg ccattttcca ccatgatatt cggcaagcag   5040
gcatcgccat gggtcacgac gagatcctcg ccgtcgggca tgctcgcctt gagcctggcg   5100
aacagttcgg ctggcgcgag cccctgatgc tcttcgtcca gatcatcctg atcgacaaga   5160
ccggcttcca tccgagtacg tgctcgctcg atgcgatgtt tcgcttggtg gtcgaatggg   5220
caggtagccg gatcaagcgt atgcagccgc cgcattgcat cagccatgat ggatactttc   5280
tcggcaggag caaggtgaga tgacaggaga tcctgccccg gcacttcgcc caatagcagc   5340
cagtcccttc ccgcttcagt gacaacgtcg agcacagctg cgcaaggaac gcccgtcgtg   5400
gccagccacg atagccgcgc tgcctcgtct tgcagttcat tcagggcacc ggacaggtcg   5460
gtcttgacaa aaagaaccgg gcgcccctgc gctgacagcc ggaacacggc ggcatcagag   5520
cagccgattg tctgttgtgc ccagtcatag ccgaatagcc tctccaccca gcggccgga   5580 gaacctgcgt gcaatccatc ttgttcaatc atactcttcc tttttcaata ttattgaagc   5640
atttatcagg gttattgtct catgagcgga t                                 5671
```

<210> SEQ ID NO 59
<211> LENGTH: 84
<212> TYPE: DNA
<213> ORGANISM: Artificial Sequence
<220> FEATURE:
<223> OTHER INFORMATION: Synthetic

<400> SEQUENCE: 59
ccaccatgga caaggccgaa ttccttgagc cacctaaaaa gaagagaaag gtaggtatcc    60
cagaattcca cgctgccatg gcag    84

<210> SEQ ID NO 60
<211> LENGTH: 84
<212> TYPE: DNA
<213> ORGANISM: Artificial Sequence
<220> FEATURE:
<223> OTHER INFORMATION: Synthetic

<400> SEQUENCE: 60
ccaccatgga caaggccgaa ttccttgagc cacctagaaa gaagagaaag gtaggtatcc    60
cagaattcca cgctgccatg gcag    84

<210> SEQ ID NO 61
<211> LENGTH: 84
<212> TYPE: DNA
<213> ORGANISM: Artificial Sequence
<220> FEATURE:
<223> OTHER INFORMATION: Synthetic

<400> SEQUENCE: 61
ccaccatgga caaggccgaa ttccttgagc cacctagaaa gaagagaaag ataggtatcc    60
cagaattcca cgctgccatg gcag    84

<210> SEQ ID NO 62
<211> LENGTH: 84
<212> TYPE: DNA
<213> ORGANISM: Artificial Sequence
<220> FEATURE:
<223> OTHER INFORMATION: Synthetic

<400> SEQUENCE: 62
ccaccatgga caaggccgaa ttccttgagc cacctaaaaa gaagagaaag ataggtatcc    60
cagaattcca cgctgccatg gcag    84

<210> SEQ ID NO 63
<211> LENGTH: 84
<212> TYPE: DNA
<213> ORGANISM: Artificial Sequence
<220> FEATURE:
<223> OTHER INFORMATION: Synthetic

<400> SEQUENCE: 63
ccaccatgga caaggccgaa ttccttatcg ctcctaaaaa gaagagaaag gtaggtatcc    60
cagaattcca cgctgccatg gcag    84

<210> SEQ ID NO 64
<211> LENGTH: 84
<212> TYPE: DNA
<213> ORGANISM: Artificial Sequence
<220> FEATURE:
<223> OTHER INFORMATION: Synthetic

<400> SEQUENCE: 64
ccaccatgga caaggccgaa ttccttgagg ctcctaaaaa gaagagaaag gtaggttggc    60
cagaattcca cgctgccatg gcag    84

<210> SEQ ID NO 65
<211> LENGTH: 84

```
<212> TYPE: DNA
<213> ORGANISM: Artificial Sequence
<220> FEATURE:
<223> OTHER INFORMATION: Synthetic

<400> SEQUENCE: 65
ccaccatgga caaggccgaa ttccttgagg ctcctggaaa gaagagaaag gtaggtatcc    60
cagaattcca cgctgccatg gcag                                           84

<210> SEQ ID NO 66
<211> LENGTH: 84
<212> TYPE: DNA
<213> ORGANISM: Artificial Sequence
<220> FEATURE:
<223> OTHER INFORMATION: Synthetic

<400> SEQUENCE: 66
ccaccatgga caaggccgaa ttccttgagg ctcctagaaa gaagagaaag gtaggtatcc    60
cagaattcca cgctgccatg gcag                                           84

<210> SEQ ID NO 67
<211> LENGTH: 84
<212> TYPE: DNA
<213> ORGANISM: Artificial Sequence
<220> FEATURE:
<223> OTHER INFORMATION: Synthetic

<400> SEQUENCE: 67
ccaccatgga caaggccgaa ttccttgagg ctcctaaaaa ggtgagaaag gtaggtatcc    60
cagaattcca cgctgccatg gcag                                           84

<210> SEQ ID NO 68
<211> LENGTH: 84
<212> TYPE: DNA
<213> ORGANISM: Artificial Sequence
<220> FEATURE:
<223> OTHER INFORMATION: Synthetic

<400> SEQUENCE: 68
ccaccatgga caaggccgaa ttccttgagg ctcctaaaaa gaaggtaaag gtaggtatcc    60
cagaattcca cgctgccatg gcag                                           84

<210> SEQ ID NO 69
<211> LENGTH: 5344
<212> TYPE: DNA
<213> ORGANISM: Artificial Sequence
<220> FEATURE:
<223> OTHER INFORMATION: Synthetic

<400> SEQUENCE: 69
aaagggagcc cccgatttag agcttgacgg ggaaagccgg cgaacgtggc gagaaaggaa    60
gggaagaaag cgaaaggagc gggcgctagg gcgctggcaa gtgtagcggt cacgctgcgc   120
gtaaccacca cacccgccgc gcttaatgcg ccgctacagg gcgcgtccca ttcgccattc   180
aggctgcgca actgttggga agggcgatcg gtgcgggcct cttcgctatt acgccagctg   240
gcgaaagggg gatgtgctgc aaggcgatta agttgggtaa cgccagggtt ttcccagtca   300
cgacgttgta aaacgacggc cagtgaattg taatacgact cactataggg cgaattgggt   360
accgggcccc cctcgaggt cgacgatgta ggtcacggca ttccggactc agcgctcgag   420
ccggcttgtc gacgacggcg gtctccgtcg tcaggatcat ccgcagatta taccgcaact   480
```

-continued

```
acacgccacc atggctccaa agaagaagcg taaggtacgg tacccagctt tcttgtacaa     540
agtggccacc atgaacaccc cgggaattaa cctgatcaag gaggacatgc gcgtgaaggt     600
gcacatggag ggcaacgtga acggccacgc cttcgtgatc gagggcgagg gcaagggcaa     660
gccctacgag ggcacccaga ccgccaacct gaccgtgaag gagggcgccc ccctgccctt     720
cagctacgac atcctgacca ccgccgtgca ctacggcaac cgggtgttca ccaagtaccc     780
cgaggacatc cccgactact tcaagcagag cttccccgag ggctacagct gggagcgcac     840
catgaccttc gaggacaagg gcatctgcac catccgcagc gacatcagcc tggagggcga     900
ctgcttcttc cagaacgtgc gcttcaaggg caccaacttc cccccaacg gccccgtgat     960
gcagaagaag accctgaagt gggagcccag caccgagaag ctgcacgtgc gcgacggcct    1020
gctggtgggc aacatcaaca tggccctgct gctggagggc ggcggccact acctgtgcga    1080
cttcaagacc acctacaagg ccaagaaggt ggtgcagctg cccgacgccc acttcgtgga    1140
ccaccgcatc gagatcctgg gcaacgacag cgactacaac aaggtgaagc tgtacgagca    1200
cgccgtggcc cgctacagcc ccctgcccag ccaggtgtgg ggaggtggtg gctcaggcgg    1260
tggtggatct atgaacaccc cgggaattaa cctgatcaag gaggacatgc gcgtgaaggt    1320
gcacatggag ggcaacgtga acggccacgc cttcgtgatc gagggcgagg gcaagggcaa    1380
gccctacgag ggcacccaga ccgccaacct gaccgtgaag gagggcgccc ccctgccctt    1440
cagctacgac atcctgacca ccgccgtgca ctacggcaac cgggtgttca ccaagtaccc    1500
cgaggacatc cccgactact tcaagcagag cttccccgag ggctacagct gggagcgcac    1560
catgaccttc gaggacaagg gcatctgcac catccgcagc gacatcagcc tggagggcga    1620
ctgcttcttc cagaacgtgc gcttcaaggg caccaacttc cccccaacg gccccgtgat    1680
gcagaagaag accctgaagt gggagcccag caccgagaag ctgcacgtgc gcgacggcct    1740
gctggtgggc aacatcaaca tggccctgct gctggagggc ggcggccact acctgtgcga    1800
cttcaagacc acctacaagg ccaagaaggt ggtgcagctg cccgacgccc acttcgtgga    1860
ccaccgcatc gagatcctgg gcaacgacag cgactacaac aaggtgaagc tgtacgagca    1920
cgccgtggcc cgctacagcc ccctgcccag ccaggtgtgg ggtggcggag gatccggtgg    1980
gggaggttca atgaacaccc cgggaattaa cctgatcaag gaggacatgc gcgtgaaggt    2040
gcacatggag ggcaacgtga acggccacgc cttcgtgatc gagggcgagg gcaagggcaa    2100
gccctacgag ggcacccaga ccgccaacct gaccgtgaag gagggcgccc ccctgccctt    2160
cagctacgac atcctgacca ccgccgtgca ctacggcaac cgggtgttca ccaagtaccc    2220
cgaggacatc cccgactact tcaagcagag cttccccgag ggctacagct gggagcgcac    2280
catgaccttc gaggacaagg gcatctgcac catccgcagc gacatcagcc tggagggcga    2340
ctgcttcttc cagaacgtgc gcttcaaggg caccaacttc cccccaacg gccccgtgat    2400
gcagaagaag accctgaagt gggagcccag caccgagaag ctgcacgtgc gcgacggcct    2460
gctggtgggc aacatcaaca tggccctgct gctggagggc ggcggccact acctgtgcga    2520
cttcaagacc acctacaagg ccaagaaggt ggtgcagctg cccgacgccc acttcgtgga    2580
ccaccgcatc gagatcctgg gcaacgacag cgactacaac aaggtgaagc tgtacgagca    2640
cgccgtggcc cgctacagcc ccctgcccag ccaggtgtgg taatagggat cctgatcata    2700
atcagccata ccacatttgt agaggtttta cttgctttaa aaaacctccc acacctcccc    2760
ctgaacctga aacataaaat gaatgcaatt gttgttgtta acttgtttat tgcagcttat    2820
aatggttaca ataaagcaa tagcatcaca aatttcacaa ataaagcatt ttttcactg    2880
```

```
cattctagtt gtggtttgtc caaactcatc aatgtatctt aggagatccc ctttagtgag   2940
ggttaatttc gagcttggcg taatcatggt catagctgtt tcctgtgtga aattgttatc   3000
cgctcacaat tccacacaac atacgagccg aagcataaa gtgtaaagcc tggggtgcct    3060
aatgagtgag ctaactcaca ttaattgcgt tgcgctcact gcccgctttc cagtcgggaa   3120
acctgtcgtg ccagctgcat taatgaatcg gccaacgcgc ggggagaggc ggtttgcgta   3180
ttgggcgctc ttccgcttcc tcgctcactg actcgctgcg ctcggtcgtt cggctgcggc   3240
gagcggtatc agctcactca aaggcggtaa tacggttatc cacagaatca ggggataacg   3300
caggaaagaa catgtgagca aaaggccagc aaaaggccag gaaccgtaaa aaggccgcgt   3360
tgctggcgtt tttccatagg ctccgccccc ctgacgagca tcacaaaaat cgacgctcaa   3420
gtcagaggtg gcgaaacccg acaggactat aaagatacca ggcgtttccc cctggaagct   3480
ccctcgtgcg ctctcctgtt ccgaccctgc cgcttaccgg atacctgtcc gcctttctcc   3540
cttcgggaag cgtggcgctt tctcatagct cacgctgtag gtatctcagt tcggtgtagg   3600
tcgttcgctc caagctgggc tgtgtgcacg aaccccccgt tcagcccgac cgctgcgcct   3660
tatccggtaa ctatcgtctt gagtccaacc cggtaagaca cgacttatcg ccactggcag   3720
cagccactgg taacaggatt agcagagcga ggtatgtagg cggtgctaca gagttcttga   3780
agtggtggcc taactacggc tacactagaa gaacagtatt tggtatctgc gctctgctga   3840
agccagttac cttcggaaaa agagttggta gctcttgatc cggcaaacaa accaccgctg   3900
gtagcggtgg tttttttgtt tgcaagcagc agattacgcg cagaaaaaaa ggatctcaag   3960
aagatccttt gatcttttct acggggtctg acgctcagtg gaacgaaaac tcacgttaag   4020 ggatttggt catgagatta tcaaaaagga tcttcaccta gatccttta aattaaaaat    4080 gaagttttaa atcaatctaa agtatatatg agtaaacttg gtctgacagt tagaagaact   4140
cgtcaagaag gcgatagaag gcgatgcgct gcgaatcggg agcggcgata ccgtaaagca   4200
cgaggaagcg gtcagcccat tcgccgccaa gctcttcagc aatatcacgg gtagccaacg   4260
ctatgtcctg atagcggtcc gccacaccca gccggccaca gtcgatgaat ccagaaaagc   4320
ggccattttc caccatgata ttcggcaagc aggcatcgcc atgggtcacg acgagatcct   4380
cgccgtcggg catgctcgcc ttgagcctgg cgaacagttc ggctggcgcg agccctgat    4440 gctcttcgtc cagatcatcc tgatcgacaa gaccggcttc catccgagta cgtgctcgct   4500
cgatgcgatg tttcgcttgg tggtcgaatg ggcaggtagc cggatcaagc gtatgcagcc   4560
gccgcattgc atcagccatg atggatactt tctcggcagg agcaaggtga gatgacagga   4620
gatcctgccc cggcacttcg cccaatagca gccagtccct tcccgcttca gtgacaacgt   4680
cgagcacagc tgcgcaagga acgcccgtcg tggccagcca cgatagccgc gctgcctcgt   4740
cttgcagttc attcagggca ccggacaggt cggtcttgac aaaaagaacc gggcgcccct   4800
gcgctgacag ccggaacacg gcggcatcag agcagccgat tgtctgttgt gcccagtcat   4860
agccgaatag cctctccacc caagcggccg gagaacctgc gtgcaatcca tcttgttcaa   4920
tcatactctt ccttttcaa tattattgaa gcatttatca gggttattgt ctcatgagcg    4980
gatacatatt tgaatgtatt tagaaaaata acaaataggg gttccgcgc acatttcccc     5040 gaaaagtgcc acctaaattg taagcgttaa tattttgtta aaattcgcgt taaattttg     5100 ttaaatcagc tcattttta accaataggc cgaaatcggc aaaatccctt ataaatcaaa    5160
agaatagacc gagatagggt tgagtgttgt tccagtttgg aacaagagtc cactattaaa   5220
```

-continued

```
gaacgtggac tccaacgtca aagggcgaaa aaccgtctat cagggcgatg gcccactacg    5280
tgaaccatca ccctaatcaa gttttttggg gtcgaggtgc cgtaaagcac taaatcggaa    5340
ccct                                                                 5344
```

<210> SEQ ID NO 70
<211> LENGTH: 60
<212> TYPE: DNA
<213> ORGANISM: Artificial Sequence
<220> FEATURE:
<223> OTHER INFORMATION: Synthetic

<400> SEQUENCE: 70

```
agaaagctgg gtaccgtacc ttacgcttct tctttggagc catggtggcg tgtagttgcg      60
```

<210> SEQ ID NO 71
<211> LENGTH: 24
<212> TYPE: DNA
<213> ORGANISM: Artificial Sequence
<220> FEATURE:
<223> OTHER INFORMATION: Synthetic

<400> SEQUENCE: 71

```
tagggatcct gatcataatc agcc                                             24
```

<210> SEQ ID NO 72
<211> LENGTH: 60
<212> TYPE: DNA
<213> ORGANISM: Artificial Sequence
<220> FEATURE:
<223> OTHER INFORMATION: Synthetic

<400> SEQUENCE: 72

```
aaggtacggt acccagcttt cttgtacaaa gtggccacca tgaacacccc gggaattaac      60
```

<210> SEQ ID NO 73
<211> LENGTH: 40
<212> TYPE: DNA
<213> ORGANISM: Artificial Sequence
<220> FEATURE:
<223> OTHER INFORMATION: Synthetic

<400> SEQUENCE: 73

```
accaccgcct gagccaccac ctccccacac ctggctgggc                            40
```

<210> SEQ ID NO 74
<211> LENGTH: 45
<212> TYPE: DNA
<213> ORGANISM: Artificial Sequence
<220> FEATURE:
<223> OTHER INFORMATION: Synthetic

<400> SEQUENCE: 74

```
ggtggctcag gcggtggtgg atctatgaac accccgggaa ttaac                      45
```

<210> SEQ ID NO 75
<211> LENGTH: 40
<212> TYPE: DNA
<213> ORGANISM: Artificial Sequence
<220> FEATURE:
<223> OTHER INFORMATION: Synthetic

<400> SEQUENCE: 75

```
tcccccaccg gatcctccgc caccccacac ctggctgggc                            40
```

```
<210> SEQ ID NO 76
<211> LENGTH: 45
<212> TYPE: DNA
<213> ORGANISM: Artificial Sequence
<220> FEATURE:
<223> OTHER INFORMATION: Synthetic

<400> SEQUENCE: 76
ggaggatccg gtgggggagg ttcaatgaac ccccgggaa ttaac            45

<210> SEQ ID NO 77
<211> LENGTH: 35
<212> TYPE: DNA
<213> ORGANISM: Artificial Sequence
<220> FEATURE:
<223> OTHER INFORMATION: Synthetic

<400> SEQUENCE: 77
ctgattatga tcaggatccc cacacctggc tgggc                       35

<210> SEQ ID NO 78
<211> LENGTH: 6751
<212> TYPE: DNA
<213> ORGANISM: Artificial Sequence
<220> FEATURE:
<223> OTHER INFORMATION: Synthetic

<400> SEQUENCE: 78
aaagggagcc cccgatttag agcttgacgg ggaaagccgg cgaacgtggc gagaaaggaa    60
gggaagaaag cgaaaggagc gggcgctagg gcgctggcaa gtgtagcggt cacgctgcgc   120
gtaaccacca cacccgccgc gcttaatgcg ccgctacagg gcgcgtccca ttcgccattc   180
aggctgcgca actgttggga agggcgatcg gtgcgggcct cttcgctatt acgccagctg   240
gcgaaagggg gatgtgctgc aaggcgatta agttgggtaa cgccagggtt ttcccagtca   300
cgacgttgta aaacgacggc cagtgaattg taatacgact cactataggg cgaattgggt   360
accgggcccc ccctcgaggt cgacgatgta ggtcacggca ttccggactc agcgctcgag   420
ccggcttgtc gacgacggcg gtctccgtcg tcaggatcat ccgcagatta taccgcaact   480
acacgccacc atggctccaa agaagaagcg taaggtacgg tacccagctt tcttgtacaa   540
agtggccacc atgaacaccc cgggaattaa cctgatcaag gaggacatgc gcgtgaaggt   600
gcacatggag ggcaacgtga acggccacgc cttcgtgatc gagggcgagg caagggcaa    660 gccctacgag ggcacccaga ccgccaacct gaccgtgaag gagggcgccc cctgcccttt   720
cagctacgac atcctgacca ccgccgtgca ctacggcaac cgggtgttca ccaagtaccc   780
cgaggacatc cccgactact tcaagcagag cttccccgag ggctacagct gggagcgcac   840
catgaccttc gaggacaagg gcatctgcac catccgcagc gacatcagcc tggagggcga   900
ctgcttcttc cagaacgtgc gcttcaaggg caccaacttc cccccaacg ccccgtgat    960 gcagaagaag accctgaagt gggagcccag caccgagaag ctgcacgtgc gcgacggcct  1020
gctggtgggc aacatcaaca tggccctgct gctggagggc ggcggccact acctgtgcga  1080
cttcaagacc acctacaagg ccaagaaggt ggtgcagctg cccgacgccc acttcgtgga  1140
ccaccgcatc gagatcctgg gcaacgacag cgactacaac aaggtgaagc tgtacgagca  1200
cgccgtggcc cgctacagcc ccctgcccag ccaggtgtgg ggaggtggtg gctcaggcgg  1260
tggtggatct atgaacaccc cgggaattaa cctgatcaag gaggacatgc gcgtgaaggt  1320
gcacatggag ggcaacgtga acggccacgc cttcgtgatc gagggcgagg caagggcaa  1380
```

```
gccctacgag ggcacccaga ccgccaacct gaccgtgaag gagggcgccc ccctgccctt    1440
cagctacgac atcctgacca ccgccgtgca ctacggcaac cgggtgttca ccaagtaccc    1500
cgaggacatc cccgactact tcaagcagag cttccccgag ggctacagct gggagcgcac    1560
catgaccttc gaggacaagg gcatctgcac catccgcagc gacatcagcc tggagggcga    1620
ctgcttcttc cagaacgtgc gcttcaaggg caccaacttc ccccccaacg gccccgtgat    1680
gcagaagaag accctgaagt gggagcccag caccgagaag ctgcacgtgc gcgacggcct    1740
gctggtgggc aacatcaaca tggccctgct gctggagggc ggcggccact acctgtgcga    1800
cttcaagacc acctacaagg ccaagaaggt ggtgcagctg cccgacgccc acttcgtgga    1860
ccaccgcatc gagatcctgg gcaacgacag cgactacaac aaggtgaagc tgtacgagca    1920
cgccgtggcc cgctacagcc ccctgcccag ccaggtgtgg ggtggcggag gatccggtgg    1980
gggaggttca atgaacaccc cgggaattaa cctgatcaag gaggacatgc gcgtgaaggt    2040
gcacatggag ggcaacgtga acggccacgc cttcgtgatc gagggcgagg gcaagggcaa    2100
gccctacgag ggcacccaga ccgccaacct gaccgtgaag gagggcgccc ccctgccctt    2160
cagctacgac atcctgacca ccgccgtgca ctacggcaac cgggtgttca ccaagtaccc    2220
cgaggacatc cccgactact tcaagcagag cttccccgag ggctacagct gggagcgcac    2280
catgaccttc gaggacaagg gcatctgcac catccgcagc gacatcagcc tggagggcga    2340
ctgcttcttc cagaacgtgc gcttcaaggg caccaacttc ccccccaacg gccccgtgat    2400
gcagaagaag accctgaagt gggagcccag caccgagaag ctgcacgtgc gcgacggcct    2460
gctggtgggc aacatcaaca tggccctgct gctggagggc ggcggccact acctgtgcga    2520
cttcaagacc acctacaagg ccaagaaggt ggtgcagctg cccgacgccc acttcgtgga    2580
ccaccgcatc gagatcctgg gcaacgacag cgactacaac aaggtgaagc tgtacgagca    2640
cgccgtggcc cgctacagcc ccctgcccag ccaggtgtgg gggagcggcg caacgaattt    2700
ttccctcctt aaacaggctg cgacgtaga ggaaaaccct ggtccatgc cagagccagc    2760
gaagtctgct cccgccccga aaaagggctc aagaaggcg gtgactaagg cgcagaagaa    2820
aggcggcaag aagcgcaagc gcagccgcaa ggagagctat tccatctatg tgtacaaggt    2880
tctgaagcag gtccaccctg acaccggcat ttcgtccaag gccatgggca tcatgaattc    2940
gtttgtgaac gacatttttcg agcgcatcgc aggtgaggct tcccgcctgg cgcattacaa    3000
caagcgctcg accatcacct ccagggagat ccagacggcc gtgcgcctgc tgctgcctgg    3060
ggagttggcc aagcacgccg tgtccgaggg tactaaggcc atcaccaagt acaccagcgc    3120
taaggatcca ccggtcgcca ccatggtagc aggtcatgcc tctggcagcc ccgcattcgg    3180
gaccgcctct cattcgaatt gcgaacatga agagatccac ctcgccggct cgatccagcc    3240
gcatggcgcg cttctggtcg tcagcgaaca tgatcatcgc gtcatccagg ccagcgccaa    3300
cgccgcggaa tttctgaatc tcggaagcgt actcggcgtt ccgctcgccg agatcgacgg    3360
cgatctgttg atcaagatcc tgccgcatct cgatcccacc gccgaaggca tgccggtcgc    3420
ggtgcgctgc cggatcggca atccctctac ggagtactgc ggtctgatgc atcggcctcc    3480
ggaaggcggg ctgatcatcg aactcgaacg tgccggcccg tcgatcgatc tgtcaggcac    3540
gctggcgccg gcgctggagc ggatccgcac ggcgggttca ctgcgcgcgc tgtgcgatga    3600
caccgtgctg ctgtttcagc agtgcaccgg ctacgaccgg gtgatggtgt atcgtttcga    3660
tgagcaaggc cacggcctgg tattctccga gtgccatgtg cctgggctcg aatcctattt    3720
cggcaaccgc tatccgtcgt cgctggtccc gcagatggcg cggcagctgt acgtgcggca    3780
```

-continued

```
gcgcgtccgc gtgctggtcg acgtcaccta tcagccggtg ccgctggagc cgcggctgtc    3840
gccgctgacc gggcgcgatc tcgacatgtc gggctgcttc ctgcgctcga tgtcgccgat    3900
ccatctgcag ttcctgaagg acatgggcgt gcgcgccacc ctggcggtgt cgctggtggt    3960
cggcggcaag ctgtggggcc tggttgtctg tcaccattat ctgccgcgct tcatccgttt    4020
cgagctgcgg gcgatctgca acggctcgc cgaaggatc gcgacgcgga tcaccgcgct    4080
tgagagctaa tagggatcct gatcataatc agccatacca catttgtaga ggttttactt    4140
gctttaaaaa acctcccaca cctccccctg aacctgaaac ataaaatgaa tgcaattgtt    4200
gttgttaact tgtttattgc agcttataat ggttacaaat aaagcaatag catcacaaat    4260
ttcacaaata aagcattttt ttcactgcat tctagttgtg gtttgtccaa actcatcaat    4320
gtatcttagg agatccccct tagtgagggt taatttcgag cttggcgtaa tcatggtcat    4380
agctgtttcc tgtgtgaaat tgttatccgc tcacaattcc acacaacata cgagccggaa    4440
gcataaagtg taaagcctgg ggtgcctaat gagtgagcta actcacatta attgcgttgc    4500
gctcactgcc cgctttccag tcgggaaacc tgtcgtgcca gctgcattaa tgaatcggcc    4560
aacgcgcggg gagaggcggt ttgcgtattg ggcgctcttc cgcttcctcg ctcactgact    4620
cgctgcgctc ggtcgttcgg ctgcggcgag cggtatcagc tcactcaaag gcggtaatac    4680
ggttatccac agaatcaggg gataacgcag gaaagaacat gtgagcaaaa ggccagcaaa    4740
aggccaggaa ccgtaaaaag gccgcgttgc tggcgttttt ccataggctc cgcccccctg    4800
acgagcatca aaaaatcga cgctcaagtc agaggtggcg aaacccgaca ggactataaa    4860
gataccaggc gtttccccct ggaagctccc tcgtgcgctc tcctgttccg accctgccgc    4920
ttaccggata cctgtccgcc tttctccctt cgggaagcgt ggcgctttct catagctcac    4980
gctgtaggta tctcagttcg gtgtaggtcg ttcgctccaa gctgggctgt gtgcacgaac    5040
cccccgttca gcccgaccgc tgcgccttat ccggtaacta tcgtcttgag tccaacccgg    5100
taagacacga cttatcgcca ctggcagcag ccactggtaa caggattagc agagcgaggt    5160
atgtaggcgg tgctacagag ttcttgaagt ggtggcctaa ctacggctac actagaagaa    5220
cagtatttgg tatctgcgct ctgctgaagc cagttacctt cggaaaaaga gttggtagct    5280
cttgatccgg caaacaaacc accgctggta gcggtggttt ttttgtttgc aagcagcaga    5340
ttacgcgcag aaaaaaagga tctcaagaag atcctttgat cttttctacg ggtctgacg    5400
ctcagtggaa cgaaaactca cgttaaggga ttttggtcat gagattatca aaaaggatct    5460
tcacctagat ccttttaaat taaaatgaa gttttaaatc aatctaaagt atatatgagt    5520
aaacttggtc tgacagttag aagaactcgt caagaaggcg atagaaggcg atgcgctgcg    5580
aatcgggagc ggcgataccg taaagcacga ggaagcggtc agcccattcg ccgccaagct    5640
cttcagcaat atcacgggta gccaacgcta tgtcctgata gcggtccgcc acacccagcc    5700
ggccacagtc gatgaatcca gaaaagcggc cattttccac catgatattc ggcaagcagg    5760
catcgccatg ggtcacgacg agatcctcgc cgtcgggcat gctcgccttg agcctggcga    5820
acagttcggc tggcgcgagc ccctgatgct cttcgtccag atcatcctga tcgacaagac    5880
cggcttccat ccgagtacgt gctcgctcga tgcgatgttt cgcttggtgg tcgaatgggc    5940
aggtagccgg atcaagcgta tgcagccgcc gcattgcatc agccatgatg gatactttct    6000
cggcaggagc aaggtgagat gacaggagat cctgccccgg cacttcgccc aatagcagcc    6060
agtcccttcc cgcttcagtg acaacgtcga gcacagctgc gcaaggaacg cccgtcgtgg    6120
```

```
ccagccacga tagccgcgct gcctcgtctt gcagttcatt cagggcaccg gacaggtcgg    6180
tcttgacaaa aagaaccggg cgcccctgcg ctgacagccg gaacacggcg gcatcagagc    6240
agccgattgt ctgttgtgcc cagtcatagc cgaatagcct ctccacccaa gcggccggag    6300
aacctgcgtg caatccatct tgttcaatca tactcttcct ttttcaatat tattgaagca    6360
tttatcaggg ttattgtctc atgagcggat acatatttga atgtatttag aaaaataaac    6420 aaatagggt tccgcgcaca tttccccgaa aagtgccacc taaattgtaa gcgttaatat    6480
tttgttaaaa ttcgcgttaa attttttgtta aatcagctca ttttttaacc aataggccga    6540
aatcggcaaa atcccttata aatcaaaaga atagaccgag atagggttga gtgttgttcc    6600
agtttggaac aagagtccac tattaaagaa cgtggactcc aacgtcaaag ggcgaaaaac    6660
cgtctatcag ggcgatggcc cactacgtga accatcaccc taatcaagtt ttttgggtc    6720 gaggtgccgt aaagcactaa atcggaaccc t                                   6751
```

<210> SEQ ID NO 79
<211> LENGTH: 24
<212> TYPE: DNA
<213> ORGANISM: Artificial Sequence
<220> FEATURE:
<223> OTHER INFORMATION: Synthetic

<400> SEQUENCE: 79
tagggatcct gatcataatc agcc                                           24

<210> SEQ ID NO 80
<211> LENGTH: 60
<212> TYPE: DNA
<213> ORGANISM: Artificial Sequence
<220> FEATURE:
<223> OTHER INFORMATION: Synthetic

<400> SEQUENCE: 80
tcgccagcct gtttaaggag ggaaaaattc gttgcgccgc tcccccacac ctggctgggc    60

<210> SEQ ID NO 81
<211> LENGTH: 30
<212> TYPE: DNA
<213> ORGANISM: Artificial Sequence
<220> FEATURE:
<223> OTHER INFORMATION: Synthetic

<400> SEQUENCE: 81
atcaggatcc ctattagctc tcaagcgcgg                                     30

<210> SEQ ID NO 82
<211> LENGTH: 60
<212> TYPE: DNA
<213> ORGANISM: Artificial Sequence
<220> FEATURE:
<223> OTHER INFORMATION: Synthetic

<400> SEQUENCE: 82
ctccttaaac aggctggcga cgtagaggaa aaccctggtc ccatgccaga gccagcgaag    60

<210> SEQ ID NO 83
<211> LENGTH: 9747
<212> TYPE: DNA
<213> ORGANISM: Artificial Sequence
<220> FEATURE:
<223> OTHER INFORMATION: Synthetic

<400> SEQUENCE: 83

```
ttctttcctg cgttatcccc tgattctgtg gataaccgta ttaccgcctt tgagtgagct    60
gataccgctc gccgcagccg aacgaccgag cgcagcgagt cagtgagcga ggaagcggaa   120
gagcgcccaa tacgcaaacc gcctctcccc gcgcgttggc cgattcatta atgcagctgg   180
cacgacaggt ttcccgactg gaaagcgggc agtgagcgca acgcaattaa tgtgagttag   240
ctcactcatt aggcacccca ggctttacac tttatgcttc cggctcgtat gttgtgtgga   300
attgtgagcg gataacaatt tcacacagga aacagctatg accatgatta cgccaagcgc   360
gcaattaacc ctcactaaag ggaacaaaag ctggagctgc aagcttaatg tagtcttatg   420
caatactctt gtagtcttgc aacatggtaa cgatgagtta gcaacatgcc ttacaaggag   480
agaaaaagca ccgtgcatgc cgattggtgg aagtaaggtg gtacgatcgt gccttattag   540
gaaggcaaca gacgggtctg acatggattg gacgaaccac tgaattgccg cattgcagag   600
atattgtatt taagtgccta gctcgataca taaacgggtc tctctggtta gaccagatct   660
gagcctggga gctctctggc taactaggga acccactgct taagcctcaa taaagcttgc   720
cttgagtgct tcaagtagtg tgtgcccgtc tgttgtgtga ctctggtaac tagagatccc   780
tcagaccctt ttagtcagtg tggaaaatct ctagcagtgg cgcccgaaca gggacttgaa   840
agcgaaaggg aaaccagagg agctctctcg acgcaggact cggcttgctg aagcgcgcac   900
ggcaagaggc gaggggcggc gactggtgag tacgccaaaa attttgacta gcggaggcta   960
gaaggagaga gatgggtgcg agagcgtcag tattaagcgg gggagaatta gatcgcgatg  1020
ggaaaaaatt cggttaaggc cagggggaaa gaaaaaatat aaattaaaac atatagtatg  1080
ggcaagcagg gagctagaac gattcgcagt taatcctggc ctgttagaaa catcagaagg  1140
ctgtagacaa atactgggac agctacaacc atcccttcag acaggatcag aagaacttag  1200
atcattatat aatacagtag caaccctcta ttgtgtgcat caaaggatag agataaaaga  1260
caccaaggaa gctttagaca agatagagga agagcaaaac aaaagtaaga ccaccgcaca  1320
gcaagcggcc gctgatcttc agacctggag gaggagatat gagggacaat ggagaagtg   1380 aattatataa atataaagta gtaaaaattg aaccattagg agtagcaccc accaaggcaa  1440
agagaagagt ggtgcagaga gaaaaaagag cagtgggaat aggagctttg ttccttgggt  1500
tcttgggagc agcaggaagc actatgggcg cagcgtcaat gacgctgacg gtacaggcca  1560
gacaattatt gtctggtata gtgcagcagc agaacaattt gctgagggct attgaggcgc  1620
aacagcatct gttgcaactc acagtctggg gcatcaagca gctccaggca agaatcctgg  1680
ctgtggaaag atacctaaag gatcaacagc tcctggggat ttggggttgc tctggaaaac  1740
tcatttgcac cactgctgtg ccttggaatg ctagttggag taataaatct ctggaacaga  1800
tttggaatca cacgacctgg atggagtggg acagagaaat taacaattac acaagcttaa  1860
tacactcctt aattgaagaa tcgcaaaacc agcaagaaaa gaatgaacaa gaattattgg  1920
aattagataa atgggcaagt ttgtggaatt ggtttaacat aacaaattgg ctgtggtata  1980
taaaattatt cataatgata gtaggaggct tggtaggttt aagaatagtt tttgctgtac  2040
tttctatagt gaatagagtt aggcagggat attcaccatt atcgtttcag acccacctcc  2100
caaccccgag gggacccgac aggcccgaag gaatagaaga agaaggtgga gagagagaca  2160
gagacagatc cattcgatta gtgaacggat ctcgacggta tcggttaact tttaaaagaa  2220 aagggggat tgggggtac agtgcagggg aagaatagt agacataata gcaacagaca  2280
tacaaactaa agaattacaa aaacaaatta caaaattcaa aattttatcg ataagcttgg  2340
```

-continued

```
gagttccgcg ttacataact tacggtaaat ggcccgcctg gctgaccgcc caacgacccc    2400
cgcccattga cgtcaataat gacgtatgtt cccatagtaa cgccaatagg gactttccat    2460
tgacgtcaat gggtggagta tttacggtaa actgcccact tggcagtaca tcaagtgtat    2520
catatgccaa gtacgccccc tattgacgtc aatgacggta aatggcccgc ctggcattat    2580
gcccagtaca tgaccttatg ggactttcct acttggcagt acatctacgt attagtcatc    2640
gctattacca tggtgatgcg gttttggcag tacatcaatg ggcgtggata gcggtttgac    2700
tcacggggat ttccaagtct ccaccccatt gacgtcaatg ggagtttgtt ttggcaccaa    2760
aatcaacggg actttccaaa atgtcgtaac aactccgccc cattgacgca aatgggcggt    2820
aggcgtgtac ggtgggaggt ctatataagc agagctcgtt tagtgaaccg tcagatcgcc    2880
tggagacgcc atccacgctg ttttgacctc catagaagac accgactcta gtccagtgtg    2940
gtggaattct gcagatatca acaagtttgt acaaaaaagt tggcaccatg gctccaaaga    3000
agaagcgtaa ggtacggtac ccagcttttct tgtacaaagt ggccaccatg aacaccccgg    3060
gaattaacct gatcaaggag gacatgcgcg tgaaggtgca catggagggc aacgtgaacg    3120
gccacgcctt cgtgatcgag ggcgagggca agggcaagcc ctacgagggc acccagaccg    3180
ccaacctgac cgtgaaggag ggcgccccc tgcccttcag ctacgacatc ctgaccaccg    3240
ccgtgcacta cggcaaccgg gtgttcacca agtaccccga ggacatcccc gactacttca    3300
agcagagctt ccccgagggc tacagctggg agcgcaccat gaccttcgag gacaagggca    3360
tctgcaccat ccgcagcgac atcagcctgg agggcgactg cttcttccag aacgtgcgct    3420
tcaagggcac caacttcccc cccaacggcc ccgtgatgca gaagaagacc ctgaagtggg    3480
agcccagcac cgagaagctg cacgtgcgcg acggcctgct ggtgggcaac atcaacatgg    3540
ccctgctgct ggagggcggc ggccactacc tgtgcgactt caagaccacc tacaaggcca    3600
agaaggtggt gcagctgccc gacgcccact cgtggacca ccgcatcgag atcctgggca    3660
acgacagcga ctacaacaag gtgaagctgt acgagcacgc cgtggcccgc tacagccccc    3720
tgcccagcca ggtgtggggga ggtggtggct caggcggtgg tggatctatg aacacccgg    3780 gaattaacct gatcaaggag gacatgcgcg tgaaggtgca catggagggc aacgtgaacg    3840
gccacgcctt cgtgatcgag ggcgagggca agggcaagcc ctacgagggc acccagaccg    3900
ccaacctgac cgtgaaggag ggcgccccc tgcccttcag ctacgacatc ctgaccaccg    3960
ccgtgcacta cggcaaccgg gtgttcacca agtaccccga ggacatcccc gactacttca    4020
agcagagctt ccccgagggc tacagctggg agcgcaccat gaccttcgag gacaagggca    4080
tctgcaccat ccgcagcgac atcagcctgg agggcgactg cttcttccag aacgtgcgct    4140
tcaagggcac caacttcccc cccaacggcc ccgtgatgca gaagaagacc ctgaagtggg    4200
agcccagcac cgagaagctg cacgtgcgcg acggcctgct ggtgggcaac atcaacatgg    4260
ccctgctgct ggagggcggc ggccactacc tgtgcgactt caagaccacc tacaaggcca    4320
agaaggtggt gcagctgccc gacgcccact cgtggacca ccgcatcgag atcctgggca    4380
acgacagcga ctacaacaag gtgaagctgt acgagcacgc cgtggcccgc tacagccccc    4440
tgcccagcca ggtgtgggggt ggcggaggat ccggtggggg aggttcaatg aacacccgg    4500 gaattaacct gatcaaggag gacatgcgcg tgaaggtgca catggagggc aacgtgaacg    4560
gccacgcctt cgtgatcgag ggcgagggca agggcaagcc ctacgagggc acccagaccg    4620
ccaacctgac cgtgaaggag ggcgccccc tgcccttcag ctacgacatc ctgaccaccg    4680
ccgtgcacta cggcaaccgg gtgttcacca agtaccccga ggacatcccc gactacttca    4740
```

```
agcagagctt ccccgagggc tacagctggg agcgcaccat gaccttcgag gacaagggca    4800
tctgcaccat ccgcagcgac atcagcctgg agggcgactg cttcttccag aacgtgcgct    4860
tcaagggcac caacttcccc cccaacggcc ccgtgatgca gaagaagacc ctgaagtggg    4920
agcccagcac cgagaagctg cacgtgcgcg acggcctgct ggtgggcaac atcaacatgg    4980
ccctgctgct ggagggcggc ggccactacc tgtgcgactt caagaccacc tacaaggcca    5040
agaaggtggt gcagctgccc gacgcccact cgtggacca ccgcatcgag atcctgggca    5100
acgacagcga ctacaacaag gtgaagctgt acgagcacgc cgtggcccgc tacagccccc    5160
tgcccagcca ggtgtggggg agcggcgcaa cgaattttc cctccttaaa caggctggcg    5220
acgtagagga aaaccctggt cccatgccag agccagcgaa gtctgctccc gccccgaaaa    5280
agggctccaa gaaggcggtg actaaggcgc agaagaaagg cggcaagaag cgcaagcgca    5340
gccgcaagga gagctattcc atctatgtgt acaaggttct gaagcaggtc caccctgaca    5400
ccggcatttc gtccaaggcc atgggcatca tgaattcgtt tgtgaacgac attttcgagc    5460
gcatcgcagg tgaggcttcc cgcctggcgc attacaacaa gcgctcgacc atcacctcca    5520
gggagatcca gacggccgtg cgcctgctgc tgcctgggga gttggccaag cacgccgtgt    5580
ccgagggtac taaggccatc accaagtaca ccagcgctaa ggatccaccg gtcgccacca    5640
tggtagcagg tcatgcctct ggcagccccg cattcgggac cgcctctcat tcgaattgcg    5700
aacatgaaga gatccacctc gccggctcga tccagccgca tggcgcgctt ctggtcgtca    5760
gcgaacatga tcatcgcgtc atccaggcca gcgccaacgc cgcggaattt ctgaatctcg    5820
gaagcgtact cggcgttccg ctcgccgaga tcgacggcga tctgttgatc aagatcctgc    5880
cgcatctcga tccaaccgcc gaaggcatgc cggtcgcggt gcgctgccgg atcggcaatc    5940
cctctacgga gtactgcggt ctgatgcatc ggcctccgga aggcgggctg atcatcgaac    6000
tcgaacgtgc cggcccgtcg atcgatctgt caggcacgct ggcgccggcg ctggagcgga    6060
tccgcacggc gggttcactg cgcgcgctgt gcgatgacac cgtgctgttg tttcagcagt    6120
gcaccggcta cgaccgggtg atggtgtatc gtttcgatga gcaaggccac ggcctggtat    6180
tctccgagtg ccatgtgcct gggctcgaat cctatttcgg caaccgctat ccgtcgtcgc    6240
tggtcccgca gatggcgcgg cagctgtacg tgcggcagcg cgtccgcgtg ctggtcgacg    6300
tcacctatca gccggtgccg ctggagccgc ggctgtcgcc gctgaccggg cgcgatctcg    6360
acatgtcggg ctgcttcctg cgctcgatgt cgccgatcca tctgcagttc ctgaaggaca    6420
tgggcgtgcg cgccacctg gcggtgtcgc tggtggtcgg cggcaagctg tggggcctgg    6480
ttgtctgtca ccattatctg ccgcgcttca tccgtttcga gctgcgggcg atctgcaaac    6540
ggctcgccga aaggatcgcg acgcggatca ccgcgcttga gagctaagca caattcgagc    6600
tcggtacctt taagaccaat gacttacaag gcagctgtag atcttagcca ctttttaaaa    6660
gaaaagggg gactggaagg gctagctcac tcccaacgaa gacaagatct gcttttttgct    6720
tgtactgggt ctctctggtt agaccagatc tgagcctggg agctctctgg ctaactaggg    6780
aacccactgc ttaagcctca ataaagcttg ccttgagtgc ttcaagtagt gtgtgcccgt    6840
ctgttgtgtg actctggtaa ctagagatcc ctcagaccct ttagtcagt gtggaaaatc    6900
tctagcagta gtagttcatg tcatcttatt attcagtatt tataacttgc aaagaaatga    6960
atatcagaga gtgagaggaa cttgtttatt gcagcttata atggttacaa ataaagcaat    7020
agcatcacaa atttcacaaa taaagcattt ttttcactgc attctagttg tggtttgtcc    7080
```

```
aaactcatca atgtatctta tcatgtctgg ctctagctat cccgcccta actccgccca    7140 tcccgcccct aactccgccc agttccgccc attctccgcc ccatggctga ctaatttttt    7200
ttatttatgc agaggccgag gccgcctcgg cctctgagct attccagaag tagtgaggag    7260
gcttttttgg aggcctaggg acgtacccaa ttcgccctat agtgagtcgt attacgcgcg    7320
ctcactggcc gtcgttttac aacgtcgtga ctgggaaaac cctggcgtta cccaacttaa    7380
tcgccttgca gcacatcccc ctttcgccag ctggcgtaat agcgaagagg cccgcaccga    7440
tcgcccttcc caacagttgc gcagcctgaa tggcgaatgg gacgcgccct gtagcggcgc    7500
attaagcgcg gcgggtgtgg tggttacgcg cagcgtgacc gctacacttg ccagcgccct    7560
agcgcccgct cctttcgctt tcttcccttc ctttctcgcc acgttcgccg gctttccccg    7620
tcaagctcta atcggggc tcctttagg gttccgattt agtgctttac ggcacctcga    7680
ccccaaaaaa cttgattagg gtgatggttc acgtagtggg ccatcgccct gatagacggt    7740
ttttcgccct tgacgttgg agtccacgtt ctttaatagt ggactcttgt tccaaactgg    7800
aacaacactc aaccctatct cggtctattc ttttgattta aagggatttt gccgatttc    7860 ggcctattgg ttaaaaaatg agctgattta acaaaaattt aacgcgaatt ttaacaaaat    7920
attaacgctt acaatttagg tggcacttt cggggaaatg tgcgcggaac ccctatttgt    7980
ttatttttct aaatacattc aaatatgtat ccgctcatga gaacaataacc ctgataaatg    8040 cttcaataat attgaaaaag gaagagtatg agtattcaac atttccgtgt cgcccttatt    8100 ccctttttg cggcattttg ccttcctgtt tttgctcacc cagaaacgct ggtgaaagta    8160
aaagatgctg aagatcagtt gggtgcacga gtgggttaca tcgaactgga tctcaacagc    8220
ggtaagatcc ttgagagttt tcgccccgaa gaacgttttc caatgatgag cacttttaaa    8280
gttctgctat gtggcgcggt attatcccgt attgacgccg ggcaagagca actcggtcgc    8340
cgcatacact attctcagaa tgacttggtt gagtactcac cagtcacaga aaagcatctt    8400
acggatggca tgacagtaag agaattatgc agtgctgcca taaccatgag tgataacact    8460
gcggccaact tacttctgac aacgatcgga ggaccgaagg agctaaccgc ttttttgcac    8520
aacatggggg atcatgtaac tcgccttgat cgttgggaac cggagctgaa tgaagccata    8580
ccaaacgacg agcgtgacac cacgatgcct gtagcaatgg caacaacgtt gcgcaaacta    8640
ttaactggcg aactacttac tctagcttcc cggcaacaat taatagactg gatggaggcg    8700
gataaagttg caggaccact tctgcgctcg gcccttccgg ctggctggtt tattgctgat    8760
aaatctggag ccggtgagcg tgggtctcgc ggtatcattg cagcactggg gccagatggt    8820
aagccctccc gtatcgtagt tatctacacg acggggagtc aggcaactat ggatgaacga    8880
aatagacaga tcgctgagat aggtgcctca ctgattaagc attggtaact gtcagaccaa    8940
gtttactcat atatacttta gattgattta aaacttcatt tttaatttaa aaggatctag    9000
gtgaagatcc tttttgataa tctcatgacc aaaatccctt aacgtgagtt ttcgttccac    9060
tgagcgtcag accccgtaga aaagatcaaa ggatcttctt gagatccttt ttttctgcgc    9120
gtaatctgct gcttgcaaac aaaaaaacca ccgctaccag cggtggtttg tttgccggat    9180
caagagctac caactctttt tccgaaggta actggcttca gcagagcgca gataccaaat    9240
actgttcttc tagtgtagcc gtagttaggc caccacttca agaactctgt agcaccgcct    9300
acatacctcg ctctgctaat cctgttacca gtggctgctg ccagtggcga taagtcgtgt    9360
cttaccgggt tggactcaag acgatagtta ccggataagg cgcagcggtc gggctgaacg    9420
gggggttcgt gcacacagcc cagcttggag cgaacgacct acaccgaact gagataccta    9480
```

| | |
|---|---:|
| cagcgtgagc tatgagaaag cgccacgctt cccgaaggga gaaaggcgga caggtatccg | 9540 |
| gtaagcggca gggtcggaac aggagagcgc acgagggagc ttccaggggg aaacgcctgg | 9600 |
| tatctttata gtcctgtcgg gtttcgccac ctctgacttg agcgtcgatt tttgtgatgc | 9660 |
| tcgtcagggg ggcggagcct atggaaaaac gccagcaacg cggccttttt acggttcctg | 9720 |
| gccttttgct ggccttttgc tcacatg | 9747 |

<210> SEQ ID NO 84
<211> LENGTH: 20
<212> TYPE: DNA
<213> ORGANISM: Artificial Sequence
<220> FEATURE:
<223> OTHER INFORMATION: Synthetic

<400> SEQUENCE: 84

| | |
|---|---:|
| gcacaattcg agctcggtac | 20 |

<210> SEQ ID NO 85
<211> LENGTH: 26
<212> TYPE: DNA
<213> ORGANISM: Artificial Sequence
<220> FEATURE:
<223> OTHER INFORMATION: Synthetic

<400> SEQUENCE: 85

| | |
|---|---:|
| ggtgccaact tttttgtaca aacttg | 26 |

<210> SEQ ID NO 86
<211> LENGTH: 46
<212> TYPE: DNA
<213> ORGANISM: Artificial Sequence
<220> FEATURE:
<223> OTHER INFORMATION: Synthetic

<400> SEQUENCE: 86

| | |
|---|---:|
| caagtttgta caaaaaagtt ggcaccatgg ctccaaagaa gaagcg | 46 |

<210> SEQ ID NO 87
<211> LENGTH: 37
<212> TYPE: DNA
<213> ORGANISM: Artificial Sequence
<220> FEATURE:
<223> OTHER INFORMATION: Synthetic

<400> SEQUENCE: 87

| | |
|---|---:|
| gtaccgagct cgaattgtgc ttagctctca agcgcgg | 37 |

<210> SEQ ID NO 88
<211> LENGTH: 6897
<212> TYPE: DNA
<213> ORGANISM: Artificial Sequence
<220> FEATURE:
<223> OTHER INFORMATION: Synthetic

<400> SEQUENCE: 88

| | |
|---|---:|
| ttctttcctg cgttatcccc tgattctgtg gataaccgta ttaccgcctt tgagtgagct | 60 |
| gataccgctc gccgcagccg aacgaccgag cgcagcgagt cagtgagcga ggaagcggaa | 120 |
| gagcgcccaa tacgcaaacc gcctctcccc gcgcgttggc cgattcatta atgcagctgg | 180 |
| cacgacaggt ttcccgactg gaaagcgggc agtgagcgca acgcaattaa tgtgagttag | 240 |
| ctcactcatt aggcacccca ggctttacac tttatgcttc cggctcgtat gttgtgtgga | 300 |

```
attgtgagcg ataacaatt tcacacagga aacagctatg accatgatta cgccaagcgc    360
gcaattaacc ctcactaaag ggaacaaaag ctggagctgc aagcttaatg tagtcttatg    420
caatactctt gtagtcttgc aacatggtaa cgatgagtta gcaacatgcc ttacaaggag    480
agaaaaagca ccgtgcatgc cgattggtgg aagtaaggtg gtacgatcgt gccttattag    540
gaaggcaaca gacgggtctg acatggattg gacgaaccac tgaattgccg cattgcagag    600
atattgtatt taagtgccta gctcgataca taaacgggtc tctctggtta gaccagatct    660
gagcctggga gctctctggc taactaggga acccactgct taagcctcaa taaagcttgc    720
cttgagtgct tcaagtagtg tgtgcccgtc tgttgtgtga ctctggtaac tagagatccc    780
tcagaccctt ttagtcagtg tggaaaatct ctagcagtgg cgcccgaaca gggacttgaa    840
agcgaaaggg aaaccagagg agctctctcg acgcaggact cggcttgctg aagcgcgcac    900
ggcaagaggc gaggggcggc gactggtgag tacgccaaaa attttgacta gcggaggcta    960
gaaggagaga gatgggtgcg agagcgtcag tattaagcgg gggagaatta gatcgcgatg    1020
ggaaaaaatt cggttaaggc caggggggaaa gaaaaaatat aaattaaaac atatagtatg    1080
ggcaagcagg gagctagaac gattcgcagt taatcctggc ctgttagaaa catcagaagg    1140
ctgtagacaa atactgggac agctacaacc atcccttcag acaggatcag aagaacttag    1200
atcattatat aatacagtag caaccctcta ttgtgtgcat caaaggatag agataaaaga    1260
caccaaggaa gctttagaca agatagagga gagcaaaaac aaaagtaaga ccaccgcaca    1320
gcaagcggcc gctgatcttc agacctggag gaggagatat gagggacaat tggagaagtg    1380
aattatataa atataaagta gtaaaaattg aaccattagg agtagcaccc accaaggcaa    1440
agagaagagt ggtgcagaga gaaaaaagag cagtgggaat aggagctttg ttccttgggt    1500
tcttgggagc agcaggaagc actatgggcg cagcgtcaat gacgctgacg gtacaggcca    1560
gacaattatt gtctggtata gtgcagcagc agaacaattt gctgagggct attgaggcgc    1620
aacagcatct gttgcaactc acagtctggg gcatcaagca gctccaggca agaatcctgg    1680
ctgtggaaag atacctaaag gatcaacagc tcctggggat ttggggttgc tctggaaaac    1740
tcatttgcac cactgctgtg ccttggaatg ctagttggag taataaatct ctggaacaga    1800
tttggaatca cacgacctgg atggagtggg acagagaaat taacaattac acaagcttaa    1860
tacactcctt aattgaagaa tcgcaaaacc agcaagaaaa gaatgaacaa gaattattgg    1920
aattagataa atgggcaagt ttgtggaatt ggtttaacat aacaaattgg ctgtggtata    1980
taaaattatt cataatgata gtaggaggct tggtaggttt aagaatagtt tttgctgtac    2040
tttctatagt gaatagagtt aggcagggat attcaccatt atcgtttcag acccacctcc    2100 caacccgag gggaccccgac aggcccgaag gaatagaaga agaaggtgga gagagagaca    2160
gagacagatc cattcgatta gtgaacggat ctcgacggta tcggttaact tttaaaagaa    2220
aaggggggat tggggggtac agtgcagggg aaagaatagt agacataata gcaacagaca    2280
tacaaactaa agaattacaa aaacaaatta caaaattcaa aattttatcg ataagcttgg    2340
gagttccgcg ttacataact acggtaaat ggcccgcctg gctgaccgcc caacgacccc    2400
cgcccattga cgtcaataat gacgtatgtt cccatagtaa cgccaatagg gactttccat    2460
tgacgtcaat gggtggagta tttacggtaa actgcccact tggcagtaca tcaagtgtat    2520
catatgccaa gtacgcccc tattgacgtc aatgacggta aatggcccgc ctggcattat    2580
gcccagtaca tgaccttatg ggactttcct acttggcagt acatctacgt attagtcatc    2640
gctattacca tggtgatgcg gttttggcag tacatcaatg ggcgtggata gcggtttgac    2700
```

```
tcacggggat ttccaagtct ccaccccatt gacgtcaatg ggagtttgtt ttggcaccaa    2760
aatcaacggg actttccaaa atgtcgtaac aactccgccc cattgacgca aatgggcggt    2820
aggcgtgtac ggtgggaggt ctatataagc agagctcgtt tagtgaaccg tcagatcgcc    2880
tggagacgcc atccacgctg ttttgacctc catagaagac accgactcta gtccagtgtg    2940
gtggaattct gcagatatca acaagtttgt acaaaaaagt tggcaccatg gtatcaaagg    3000
gtgaagaatt gataaaggag aacatgcaca tgaaactcta catggagggg accgtaaata    3060
atcaccattt caaatgcaca tcagaaggcg aaggaaaacc atatgagggg actcagacca    3120
tgcgaataaa ggtagttgaa ggtggtcccc tcccgtttgc cttttgacatc cttgcaacga    3180 gtttcatgta tggctccaaa acgttcataa atcatacgca aggcatacct gacttcttca    3240
agcagagttt tccggaagga tttacctggg agcgcagtac aacatacgaa gacggcgggg    3300
ttctgactgc gactcaagac accagccttc aagatgggtg cttgatttac aatgtaaaga    3360
tacgaggggt aattttccc tctaacggtc ccgtgatgca aaaaaaacg cttggttggg    3420 aagccagtac agaaatgctg tacccagcgg atgggggact tgaagggcgg gattacatgg    3480
ctctcaaact ggttggtggg ggtcatctta tttgcaatgc aaagacgacc tacagatcta    3540 aaaaaccgc aaaaaacttg aaggtgccgg gagtatatta cgttgaccgg cgcttggaac    3600
ggatcaaaga agctgacaaa gaaacatcag ttgagcaaca tgaggtagct gtggccaggt    3660
actgcgatct gccttcaaaa cttggtcata agctcaatct gcagctgcca cctctggagc    3720 gcctgacccct ggactaggca caattcgagc tcggtacctt taagaccaat gacttacaag    3780
gcagctgtag atcttagcca ctttttaaaa gaaaaggggg gactggaagg gctagctcac    3840
tcccaacgaa gacaagatct gcttttttgct tgtactgggt ctctctggtt agaccagatc    3900
tgagcctggg agctctctgg ctaactaggg aaccccactgc ttaagcctca ataaagcttg    3960
ccttgagtgc ttcaagtagt gtgtgcccgt ctgttgtgtg actctggtaa ctagagatcc    4020 ctcagacccct tttagtcagt gtggaaaatc tctagcagta gtagttcatg tcatcttatt    4080
attcagtatt tataacttgc aaagaaatga atatcagaga gtgagaggaa cttgttattt    4140
gcagcttata atggttacaa ataaagcaat agcatcacaa atttcacaaa taaagcatttt   4200 ttttcactgc attctagttg tggtttgtcc aaactcatca atgtatctta tcatgtctgg    4260
ctctagctat cccgcccctta actccgccca tcccgcccct aactccgccc agttccgccc   4320
attctccgcc ccatggctga ctaattttttt ttatttatgc agaggccgag gccgcctcgg   4380
cctctgagct attccagaag tagtgaggag gcttttttgg aggcctaggg acgtacccaa    4440
ttcgccctat agtgagtcgt attacgcgcg ctcactggcc gtcgttttac aacgtcgtga    4500
ctgggaaaac cctggcgtta cccaacttaa tcgccttgca gcacatcccc ctttcgccag    4560
ctggcgtaat agcgaagagg cccgcaccga tcgcccttcc caacagttgc gcagcctgaa    4620
tggcgaatgg gacgcgccct gtagcggcgc attaagcgcg gcgggtgtgg tggttacgcg    4680
cagcgtgacc gctacacttg ccagcgccct agcgcccgct cctttcgctt tcttcccttc    4740
ctttctcgcc acgttcgccg gctttccccg tcaagctcta aatcggggc tccctttagg    4800 gttccgattt agtgctttac ggcacctcga ccccaaaaaa cttgattagg gtgatggttc    4860
acgtagtggg ccatcgccct gatagacggt ttttcgccct ttgacgttgg agtccacgtt    4920
ctttaatagt ggactcttgt tccaaactgg aacaacactc aaccctatct cggtctattc    4980 ttttgatttta aagggatttt tgccgatttc ggcctattgg ttaaaaaatg agctgattta   5040
```

```
acaaaaattt aacgcgaatt ttaacaaaat attaacgctt acaatttagg tggcactttt     5100
cggggaaatg tgcgcggaac ccctatttgt ttatttttct aaatacattc aaatatgtat     5160
ccgctcatga gacaataacc ctgataaatg cttcaataat attgaaaaag gaagagtatg     5220
agtattcaac atttccgtgt cgcccttatt ccctttttg cggcattttg ccttcctgtt      5280
tttgctcacc cagaaacgct ggtgaaagta aaagatgctg aagatcagtt gggtgcacga     5340
gtgggttaca tcgaactgga tctcaacagc ggtaagatcc ttgagagttt cgccccgaa      5400 gaacgttttc caatgatgag cacttttaaa gttctgctat gtggcgcggt attatcccgt     5460
attgacgccg ggcaagagca actcggtcgc cgcatacact attctcagaa tgacttggtt     5520
gagtactcac cagtcacaga aaagcatctt acggatggca tgacagtaag agaattatgc     5580
agtgctgcca taaccatgag tgataacact gcggccaact tacttctgac aacgatcgga     5640
ggaccgaagg agctaaccgc ttttttgcac aacatggggg atcatgtaac tcgccttgat     5700
cgttgggaac cggagctgaa tgaagccata ccaaacgacg agcgtgacac cacgatgcct     5760
gtagcaatgg caacaacgtt gcgcaaacta ttaactggcg aactacttac tctagcttcc     5820
cggcaacaat taatagactg gatggaggcg gataaagttg caggaccact tctgcgctcg     5880
gcccttccgg ctggctggtt tattgctgat aaatctggag ccggtgagcg tgggtctcgc     5940
ggtatcattg cagcactggg gccagatggt aagccctccc gtatcgtagt tatctacacg     6000
acggggagtc aggcaactat ggatgaacga atagacaga tcgctgagat aggtgcctca     6060
ctgattaagc attggtaact gtcagaccaa gtttactcat atatacttta gattgattta     6120
aaacttcatt tttaatttaa aaggatctag gtgaagatcc tttttgataa tctcatgacc     6180
aaaatccctt aacgtgagtt ttcgttccac tgagcgtcag accccgtaga aaagatcaaa     6240
ggatcttctt gagatccttt ttttctgcgc gtaatctgct gcttgcaaac aaaaaaacca     6300
ccgctaccag cggtggtttg tttgccggat caagagctac caactctttt tccgaaggta     6360
actggcttca gcagagcgca gataccaaat actgttcttc tagtgtagcc gtagttaggc     6420
caccacttca agaactctgt agcaccgcct acatacctcg ctctgctaat cctgttacca     6480
gtggctgctg ccagtggcga taagtcgtgt cttaccgggt tggactcaag acgatagtta     6540
ccggataagg cgcagcggtc gggctgaacg gggggttcgt gcacacagcc cagcttggag     6600
cgaacgacct acaccgaact gagatacccta cagcgtgagc tatgagaaag cgccacgctt     6660
cccgaaggga gaaaggcgga caggtatccg gtaagcggca gggtcggaac aggagagcgc     6720
acgagggagc ttccagggg aaacgcctgg tatctttata gtcctgtcgg gtttcgccac      6780
ctctgacttg agcgtcgatt tttgtgatgc tcgtcagggg gcggagcct atggaaaaac       6840 gccagcaacg cggccttttt acggttcctg gccttttgct ggccttttgc tcacatg         6897
```

<210> SEQ ID NO 89
<211> LENGTH: 20
<212> TYPE: DNA
<213> ORGANISM: Artificial Sequence
<220> FEATURE:
<223> OTHER INFORMATION: Synthetic

<400> SEQUENCE: 89
gcacaattcg agctcggtac                                                    20

<210> SEQ ID NO 90
<211> LENGTH: 50
<212> TYPE: DNA
<213> ORGANISM: Artificial Sequence

```
<220> FEATURE:
<223> OTHER INFORMATION: Synthetic

<400> SEQUENCE: 90
ccacctctgg agcgcctgac cctggactag gcacaattcg agctcggtac            50

<210> SEQ ID NO 91
<211> LENGTH: 50
<212> TYPE: DNA
<213> ORGANISM: Artificial Sequence
<220> FEATURE:
<223> OTHER INFORMATION: Synthetic

<400> SEQUENCE: 91
caagtttgta caaaaaagtt ggcaccatgg tatcaaaggg tgaagaattg            50

<210> SEQ ID NO 92
<211> LENGTH: 51
<212> TYPE: DNA
<213> ORGANISM: Artificial Sequence
<220> FEATURE:
<223> OTHER INFORMATION: Synthetic

<400> SEQUENCE: 92
ggcgctccag aggtggcagc tgcagattga gcttatgacc aagttttgaa g          51
```